US010947563B2

(12) United States Patent
Wu et al.

(10) Patent No.: US 10,947,563 B2
(45) Date of Patent: Mar. 16, 2021

(54) TERPENE SYNTHASES FOR BIOFUEL PRODUCTION AND METHODS THEREOF

(71) Applicant: National Technology & Engineering Solutions of Sandia, LLC, Albuquerque, NM (US)

(72) Inventors: Weihua Wu, San Francisco, CA (US); John Michael Gladden, Alameda, CA (US); Benjamin Chiau-Pin Wu, San Ramon, CA (US); Ryan Wesley Davis, San Jose, CA (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 0 days.

(21) Appl. No.: 16/512,072

(22) Filed: Jul. 15, 2019

(65) Prior Publication Data
US 2020/0017885 A1 Jan. 16, 2020

Related U.S. Application Data

(62) Division of application No. 15/066,651, filed on Mar. 10, 2016, now Pat. No. 10,400,254.

(60) Provisional application No. 62/132,093, filed on Mar. 12, 2015.

(51) Int. Cl.
*C12P 5/00* (2006.01)
*C12N 9/88* (2006.01)
*C12N 15/52* (2006.01)

(52) U.S. Cl.
CPC ............... *C12P 5/007* (2013.01); *C12N 9/88* (2013.01); *C12N 15/52* (2013.01); *C12Y 402/03014* (2013.01); *C12Y 402/03057* (2013.01); *C12Y 402/03072* (2013.01); *C12Y 402/03076* (2013.01); *C12Y 402/03078* (2013.01)

(58) Field of Classification Search
None
See application file for complete search history.

(56) References Cited

U.S. PATENT DOCUMENTS

| 6,030,587 | A | 2/2000 | Haroldsen et al. |
| 8,047,978 | B1 | 11/2011 | Haroldsen et al. |
| 8,481,974 | B1 | 7/2013 | Davis et al. |
| 8,753,851 | B2 | 6/2014 | Stephen et al. |
| 10,077,454 | B1 | 9/2018 | Davis et al. |

OTHER PUBLICATIONS

U.S. Appl. No. 14/750,960, filed Jun. 25, 2015, Davis et al.
U.S. Appl. No. 14/750,993, filed Jun. 25, 2015, Hewson et al.
U.S. Appl. No. 15/447,567, filed Mar. 2, 2017, Davis et al.
U.S. Appl. No. 16/438,763, filed Jun. 12, 2019, Davis et al.
U.S. Appl. No. 16/388,385, filed Apr. 18, 2019, Davis et al.
Adams, C et al., "Understanding precision nitrogen stress to optimize the growth and lipid content tradeoff in oleaginous green microalgae," *Bioresour. Technol.* 2013;131:188-94.
Adey, WH et al., "Algal turf scrubbing: cleaning surface waters with solar energy while producing a biofuel," *BioScience* 2011;61(6):434-41.
Agger, S et al., "Diversity of sesquiterpene synthases in the basidiomycete *Coprinus cinereusmmi*," *Mol. Microbiol.* 2009;72(5):1181-95.
Agger, S et al., Supplementary Information for "Diversity of sesquiterpene synthases in the basidiomycete *Coprinus cinereusmmi*," *Mol. Microbiol.* 2009;72(5):1307-8.
Ajikumar, PK et al., "Terpenoids: opportunities for biosynthesis of natural product drugs using engineered microorganisms," *Mol. Pharm.* 2008;5(2):167-90.
Al Mansouri, S et al., "The cannabinoid receptor 2 agonist, β-caryophyllene, reduced voluntary alcohol intake and attenuated ethanol-induced place preference and sensitivity in mice," *Pharmacol. Biochem. Behav.* 2014;124:260-8.
Alonso-Gutierrez, J et al., "Metabolic engineering of *Escherichia coli* for limonene and perillyl alcohol production," *Metab. Eng.* 2013;19:33-41.
Amslinger, S et al., "Biosynthesis of terpenes: preparation of (E)-1-hydroxy-2-methyl-but-2-enyl 4-diphosphate, an intermediate of the deoxyxylulose phosphate pathway," *J. Org. Chem.* 2002;67(13):4590-4.
Anderson, JC et al., "BglBricks: A flexible standard for biological part assembly," *J. Biol. Eng.* 2010;20;4(1):1 (12 pp.).
Anon, "Researchers convert algae to butanol," *Marine Pollution Bull.* 2011;62(4):658.
Anthony, JR et al., "Optimization of the mevalonate-based isoprenoid biosynthetic pathway in *Escherichia coli* for production of the anti-malarial drug precursor amorpha-4,11-diene," *Metab. Eng.* 2009;11(1):13-9.
Babujanarthanama, R et al., "Simultaneous saccharification and fermentation of dilute acid pretreated red algae (*Gelidiella acerosa*) for bioethanol production," *Energy Sources A* 2014;36(12):1305-14.
Banerjee, D et al., "*Muscodor albus* MOW12 an Endophyte of *Piper nigrum* L. (Piperaceae) collected from north east India produces volatile antimicrobials," *Indian J. Microbiol.* 2014;54(1):27-32.
Bogorad, IW et al., "Building carbon-carbon bonds using a biocatalytic methanol condensation cycle," *Proc. Nat'l Acad. Sci. USA* 2014;111(45):15928-33.
Bohlmann, J et al., "Monoterpene synthases from grand fir (*Abies grandis*): cDNA isolation, characterization, and functional expression of myrcene synthase, (-)-(4S)-limonene synthase, and (-)-(1S,5S)-pinene synthase," *J. Biol. Chem.* 1997;272(35):21784-92.
Bohlmann, J et al., "Terpenoid biomaterials," *Plant J.* 2008;54(4):656-69.
Bombarda, I et al., "Spectrometric identifications of sesquiterpene alcohols from niaouli (*Melaleuca quinquenervia*) essential oil," *Anal. Chim. Acta* 2001;447:113-23.

(Continued)

*Primary Examiner* — Anand U Desai
(74) *Attorney, Agent, or Firm* — Helen S. Baca

(57) ABSTRACT

The present invention relates to terpene synthases capable of degrading precursors into biofuel compounds, such as terpenoid compounds. In one instance, a transformed organism can include such terpene synthases, as well as vectors encoding such synthases. Methods of employing such synthases and organisms are also described herein.

20 Claims, 44 Drawing Sheets

Specification includes a Sequence Listing.

(56) References Cited

OTHER PUBLICATIONS

Burke, C et al., "Geranyl diphosphate synthase from *Abies grandis*: cDNA isolation, functional expression, and characterization," *Arch. Biochem. Biophys.* 2002;405(1):130-6.
Cane, DE et al., "Exploration and mining of the bacterial terpenome," *Acc. Chem. Res.* 2012;45(3):463-72.
Carothers, JM et al., "Selecting RNA aptamers for synthetic biology: investigating magnesium dependence and predicting binding affinity," *Nucleic Acids Res.* 2010;38(8):2736-47.
Chang, MC et al., "Production of isoprenoid pharmaceuticals by engineered microbes," *Nat. Chem. Biol.* 2006;2(12):674-81.
Chappell, J et al., "Unraveling the catalytic specificity of terpene biosynthetic enzymes and engineering the biosynthesis of novel terpenes in yeast and plants," *In Vitro Cell. Dev. Biol.—Animal* 2008;44:S27 (Abstract P-26).
Chen, CY et al., "Microalgae-based carbohydrates for biofuel production," *Biochem. Eng. J.* 2013;78:1-10.
Chen, W et al., "Anti-tumor effect of $\alpha$-pinene on human hepatoma cell lines through inducing G2/M cell cycle arrest," *J. Pharmacol. Sci.* 2015;127(3):332-8.
Chen, Y et al., "Inhibition of anaerobic digestion process: a review," *Bioresour. Technol.* 2008;99(10):4044-64.
Cheng, AX et al., "The rice (E)-beta-caryophyllene synthase (OsTPS3) accounts for the major inducible volatile sesquiterpenes," *Phytochemistry* 2007;68(12):1632-41.
Christianson, DW, "Structural biology and chemistry of the terpenoid cyclases," *Chemical Reviews* 2006;106(8):3412-42.
Croteau, R et al., "[44] Monoterpene and sesquiterpene cyclases," *Methods in Enzymology* 1985;110:383-405.
Davis, EM et al., "Cyclization enzymes in the biosynthesis of monoterpenes, sesquiterpenes, and diterpenes," *Topics Curr. Chem.* 2000;209:53-95.
Davis, R et al., "Techno-economic analysis of autotrophic microalgae for fuel production," *Appl. Energy* 2011;88(10):3524-31.
Davis, RW et al., "Multiplex fluorometric assessment of nutrient limitation as a strategy for enhanced lipid enrichment and harvesting of *Neochloris oleoabundans*," *Biotechnol. Bioeng.* 2012;109(10):2503-12.
De La Cruz, V et al., "Integrated synthesis of biodiesel, bioethanol, isobutene, and glycerol ethers from algae," *Ind. Eng. Chem. Res.* 2014;53:14397-407.
Degenhardt, J et al., "Monoterpene and sesquiterpene synthases and the origin of terpene skeletal diversity in plants," *Phytochemistry* 2009;70(15-16):1621-37.
Dewick, PM, "The biosynthesis of $C_5$—$C_{25}$ terpenoid compounds," *Nat. Prod. Rep.* 2002;19(2):181-222.
Edwards, T et al., "Evaluation of combustion performance of alternative aviation fuels," *46th AIAA/ASME/SAE/ASEE Joint Propulsion Conference & Exhibit*, held on Jul. 25-28, 2010 in Nashville, TN, Art. No. AIAA 2010-7155 (21 pp.).
El-Mashad, HM, "Biomethane and ethanol production potential of *Spirulina platensis* algae and enzymatically saccharified switchgrass," *Biochem. Eng. J.* 2015;93:119-27.
Fasahati, P et al., "Industrial-scale bioethanol production from brown algae: effects of pretreatment processes on plant economics," *Appl. Energy* 2015;139:175-87.
Fischbach, RJ et al., "Monoterpene synthase activities in leaves of *Picea abies* (L.) Karst. and *Quercus ilex* L.," *Phytochemistry* 2000;54(3):257-65.
Fujisaki, S et al., "Cloning and nucleotide sequence of the ispA gene responsible for farnesyl diphosphate synthase activity in *Escherichia coli*," *J. Biochem.* 1990;108(6):995-1000.
Gambliel, H et al., "Pinene cyclases I and II: two enzymes from sage (*Salvia officinalis*) which catalyze stereospecific cyclizations of geranyl pyrophosphate to monoterpene olefins of opposite configuration," *J. Biol. Chem.* 1984;259(2):740-8.
Gladden, JM et al., "Tailoring next-generation biofuels and their combustion in next-generation engines," *Sandia Report No. SAND2013-10094*, 2013 (100 pp.).

Gong, CMS et al., "Metabolic engineering Deinococcus radiodurans for actinide bioprecipitation," *227th ACS National Meeting*, held on Mar. 28 to Apr. 1, 2004 in Anaheim, CA, Abstract NUCL 61 (1 p.).
Gong, HY et al., "Analysis of essential oils of *Origanum vulgare* from six production areas of China and Pakistan," *Revista Brasileira de Farmacognosia [Braz. J. Pharmacognosy]* 2014;24(1):25-32.
Grawert, T et al., "Biochemistry of the non-mevalonate isoprenoid pathway," *Cell. Mol. Life Sci.* 2011;68(23):3797-814.
Griffin, MA et al., "Volatile organic compound production by organisms in the genus *Ascocoryne* and a re-evaluation of mycodiesel production by NRRL 50072," *Microbiology* 2010;156(Pt 12):3814-29.
Gunnewich, N et al., "Functional expression and characterization of trichome-specific (−)-limonene synthase and (+)-$\alpha$-pinene synthase from *Cannabis sativa*," *Natural Prod. Commun.* 2007;2(3):223-32 (2006 preprint, 10 pp).
Guo, K et al., "Trans-caryophyllene suppresses hypoxia-induced neuroinflammatory responses by inhibiting NF-$\kappa$B activation in microglia," *J. Mol. Neurosci.* 2014;54(1):41-8.
Guzman-Gutierrez, SL et al., "Linalool and $\beta$-pinene exert their antidepressant-like activity through the monoaminergic pathway," *Life Sci.* 2015;128:24-9.
Haehnel-Taguchi, M et al., "Afferent and motoneuron activity in response to single neuromast stimulation in the posterior lateral line of larval zebrafish," *J. Neurophysiol.* 2014;112(6):1329-39.
Han, L et al., "Trans-caryophyllene suppresses tumor necrosis factor (TNF$\alpha$)-induced inflammation in human chondrocytes," *Eur. Food Res. Technol.* 2014;239(6):1061-6.
Harvey, BG et al., "High-density renewable diesel and jet fuels prepared from multicyclic sesquiterpanes and a 1-hexene-derived synthetic paraffinic kerosene," *Energy Fuels* 2015;29(4):2431-6.
Harvey, BG et al., "High-density renewable fuels based on the selective dimerization of pinenes," *Energy Fuels* 2010;24:267-73.
He, Z et al., "Global transcriptional, physiological, and metabolite analyses of the responses of *Desulfovibrio vulgaris* Hildenborough to salt adaptation," *Appl. Environ. Microbiol.* 2010;76(5):1574-86.
Huang, X et al., "Identification and characterization of (E)-$\beta$-caryophyllene synthase and $\alpha/\beta$-pinene synthase potentially involved in constitutive and herbivore-induced terpene formation in cotton," *Plant Physiol. Biochem.* 2013;73:302-8.
Huo, YX et al., "Conversion of proteins into biofuels by engineering nitrogen flux," *Nat. Biotechnol.* 2011;29(4):346-51.
Hyatt, DC et al., "Mutational analysis of a monoterpene synthase reaction: altered catalysis through directed mutagenesis of (−)-pinene synthase from *Abies grandis*," *Arch. Biochem. Biophys.* 2005;439(2):222-33.
Iijima, Y et al., "The biochemical and molecular basis for the divergent patterns in the biosynthesis of terpenes and phenylpropenes in the peltate glands of three cultivars of basil," *Plant Physiol.* 2004;136(3):3724-36.
Illarionova, V et al., "Nonmevalonate terpene biosynthesis enzymes as antiinfective drug targets: substrate synthesis and high-throughput screening methods," *J. Org. Chem.* 2006;71(23):8824-34.
Jacobson, MZ, "Review of solutions to global warming, air pollution, and energy security," *Energy Environ. Sci.* 2009;2:148-73.
Katoh, S et al., "Altering product outcome in *Abies grandis* (−)-limonene synthase and (−)-limonene/(−)-alpha-pinene synthase by domain swapping and directed mutagenesis," *Arch. Biochem. Biophys.* 2004;425(1):65-76.
Khodayari, A et al., "A kinetic model of *Escherichia coli* core metabolism satisfying multiple sets of mutant flux data," *Metab. Eng.* 2014;25:50-62.
Kim, SW et al., "Metabolic engineering of the nonmevalonate isopentenyl diphosphate synthesis pathway in *Escherichia coli* enhances lycopene production," *Biotechnol. Bioeng.* 2001;72(4):408-15.
Klauke, AL et al., "The cannabinoid $CB_2$ receptor-selective phytocannabinoid beta-caryophyllene exerts analgesic effects in mouse models of inflammatory and neuropathic pain," *Eur. NeuropsychopharmacoL* 2014;24(4):608-20.

(56) References Cited

OTHER PUBLICATIONS

Koksal, M et al., "Taxadiene synthase structure and evolution of modular architecture in terpene biosynthesis," *Nature* 2011;469(7328):116-20.

Kolewe, ME et al., "Pharmaceutically active natural product synthesis and supply via plant cell culture technology," *Mol. Pharm.* 2008;5(2):243-56.

Kollner, TG et al., "A maize (E)-beta-caryophyllene synthase implicated in indirect defense responses against herbivores is not expressed in most American maize varieties," *Plant Cell* 2008;20(2):482-94.

Kovac, J et al., "Antibiotic resistance modulation and modes of action of (-)-α-pinene in *Campylobacter jejuni*," *PLoS One* 2015;10(4):e0122871 (14 pp.).

Kpadonou Kpoviessi, BG et al., "Chemical variation of essential oil constituents of Ocimum gratissimum L. from Benin, and impact on antimicrobial properties and toxicity against Artemia salina leach," *Chem. Biodivers.* 2012;9(1):139-50.

Kudalkar, P et al., "*Muscodor sutura*, a novel endophytic fungus with volatile antibiotic activities," *Mycoscience* 2012;53(4):319-25.

Kumar, S et al., "MEGA-CC: computing core of molecular evolutionary genetics analysis program for automated and iterative data analysis," *Bioinformatics* 2012;28(20):2685-6.

Kumeta, Y et al., "Characterization of δ-guaiene synthases from cultured cells of *Aquilaria*, responsible for the formation of the sesquiterpenes in agarwood," *Plant Physiol.* 2010;154(4):1998-2007.

Kumeta, Y et al., "Genomic organization of δ-guaiene synthase genes in *Aquilaria crassna* and its possible use for the identification of *Aquilaria* species," *J. Nat. Med.* 2011;65(3-4):508-13.

Lane, J, "9 advanced molecules that could revolutionize jet and missile fuel," *Biofuels Digest*, Jun. 18, 2014 (4 pp.), available at http://www.biofuelsdigest.com/bdigest/2014/06/18/9-advanced-molecules-that-could-revolutionize-jet-and-missile-fuel/ (last accessed Feb. 15, 2016).

Lee, JB et al., "Induction, cloning and functional expression of a sesquiterpene biosynthetic enzyme, δ-guaiene synthase, of *Aquilaria microcarpa* cell cultures," *Natural Prod. Commun.* 2014;9(9):1231-5.

Lee, TS et al., "BglBrick vectors and datasheets: A synthetic biology platform for gene expression," *J. Biol. Eng.* 2011;5:Art. No. 12 (14 pp.).

Lee, TS et al., "Metabolic engineering of mevalonate pathway," 239th ACS National Meeting & Exposition, held on Mar. 21-25, 2010 in San Francisco, CA (abstract, 1 p.).

Li, K et al., "An overview of algae bioethanol production," *Int'l J. Energy Res.* 2014;38(8):965-77.

Lin, PP et al., "Isobutanol production at elevated temperatures in thermophilic *Geobacillus thermoglucosidasius*," *Metab. Eng.* 2014;24:1-8 (erratum in *Metab. Eng.* 2014;24:192).

Liu, H et al., "Neuroprotective effects of trans-caryophyllene against kainic acid induced seizure activity and oxidative stress in mice," *Neurochem. Res.* 2015;40(1):118-23.

Lu, S et al., "Cloning and functional characterization of a beta-pinene synthase from *Artemisia annua* that shows a circadian pattern of expression," *Plant Physiol.* 2002;130(1):477-86.

Luque, R et al., "Algal biofuels: the eternal promise?," *Energy Environ. Sci.* 2010;3:254-7.

Lynd, LR et al., "Consolidated bioprocessing of cellulosic biomass: an update," *Curr. Opin. Biotechnol.* 2005;16(5):577-83.

Ma, Y et al., "Genome-wide identification and characterization of novel genes involved in terpenoid biosynthesis in *Salvia miltiorrhiza*," *J. Exp. Bot.* 2012;63(7):2809-23.

Ma, SM et al., "Optimization of a heterologous mevalonate pathway through the use of variant HMG-CoA reductases," *Metab. Eng.* 2011;13(5):588-97.

Malingre, T et al., "The essential oil of *Cannabis sativa*," *Planta Med.* 1975;28(1):56-61.

Martin, DM et al., "Functional annotation, genome organization and phylogeny of the grapevine (*Vitis vinifera*) terpene synthase gene family based on genome assembly, FLcDNA cloning, and enzyme assays," *BMC Plant Biol.* 2010;10:226 (22 pp.).

Martin, M et al., "Design of an optimal process for enhanced production of bioethanol and biodiesel from algae oil via glycerol fermentation," *Appl. Energy* 2014;135:108-14.

Martin, VJ et al., "Engineering a mevalonate pathway in *Escherichia coli* for production of terpenoids," *Nat. Biotechnol.* 2003;21(7):796-802.

Maury, J et al., "Reconstruction of a bacterial isoprenoid biosynthetic pathway in *Saccharomyces cerevisiae*," *FEBS Lett.* 2008;582(29):4032-8.

Meccia, G et al., "Chemical composition and antibacterial activity of the essential oil of *Cordia verbenacea* from the Venezuelan Andes," *Nat. Prod. Commun.* 2009;4(8):1119-22.

Miller, DJ et al., "Sesquiterpene synthases: passive catalysts or active players?," *Nat. Prod. Rep.* 2012;29(1):60-71.

Miziorko, HM, "Enzymes of the mevalonate pathway of isoprenoid biosynthesis," *Arch. Biochem. Biophys.* 2011;505(2):131-43.

Moncada, J et al., "Techno-economic and environmental assessment of essential oil extraction from Oregano (*Origanum vulgare*) and Rosemary (*Rosmarinus officinalis*) in Colombia," *J. Cleaner Production* 2016;112(1):172-81.

Moody, JW et al., "Global evaluation of biofuel potential from microalgae," *Proc. Nat'l Acad. Sci. USA* 2014;111(23):8691-6.

Myburg, AA et al., "The genome of *Eucalyptus grandis*," *Nature* 2014;510(7505):356-62.

Nagegowda, DA et al., "Two nearly identical terpene synthases catalyze the formation of nerolidol and linalool in snapdragon flowers," *Plant J.* 2008;55(2):224-39.

Nakano, C et al., "Identification of the first bacterial monoterpene cyclase, a 1,8-cineole synthase, that catalyzes the direct conversion of geranyl diphosphate," *Chembiochem* 2011;12(13):1988-91.

Oldfield, E et al., "Terpene biosynthesis: modularity rules," *Angew. Chem. Int. Ed. Engl.* 2012;51(5):1124-37.

Ouyang, Z et al., "Identification and quantification of sesquiterpenes and polyacetylenes in *Atractylodes lancea* from various geographical origins using GC-MS analysis," *Revista Brasileira de Farmacognosia* [*Braz. J. Pharmacognosy*] 2012;22(5):957-63.

Pant, A et al., "Beta-caryophyllene modulates expression of stress response genes and mediates longevity in *Caenorhabditis elegans*," *Exp. Gerontol.* 2014;57:81-95.

Paula-Freire, L et al., "The oral administration of trans-caryophyllene attenuates acute and chronic pain in mice," *Phytomedicine* 2014;21(3):356-62.

Peralta-Yahya, PP et al., "Identification and microbial production of a terpene-based advanced biofuel," *Nat. Commun.* 2011;2:Art. No. 483 (8 pp.).

Peralta-Yahya, PP et al., "Microbial engineering for the production of advanced biofuels," *Nature* 2012;488(7411):320-8.

Petersen, TN et al., "SignalP 4.0: discriminating signal peptides from transmembrane regions," *Nat. Methods* 2011;8(10):785-6.

Phillips, MA et al., "cDNA isolation, functional expression, and characterization of (+)-alpha-pinene synthase and (-)-alpha-pinene synthase from loblolly pine (*Pinus taeda*): stereocontrol in pinene biosynthesis," *Arch. Biochem. Biophys.* 2003;411(2):267-76.

Pitera, DJ et al., "Balancing a heterologous mevalonate pathway for improved isoprenoid production in *Escherichia coli*," *Metab. Eng.* 2007;9(2):193-207.

Rabe, p. et al., "Volatile terpenes from actinomycetes: a biosynthetic study correlating chemical analyses to genome data," *Chembiochem* 2013;14(17):2345-54.

Razeghifard, R, "Algal biofuels," *Photosynth. Res.* 2013;117(1-3):207-19.

Riyaz-Ul-Hassan, S et al., "An endophytic *Nodulisporium* sp. from Central America producing volatile organic compounds with both biological and fuel potential," *J. Microbiol. Biotechnol.* 2013;23(1):29-35.

Rodrigues, FF et al., "Chemical composition, antibacterial and antifungal activities of essential oil from *Cordia verbenacea* DC leaves," *Pharmacognosy Res.* 2012;4(3):161-5.

(56) References Cited

OTHER PUBLICATIONS

Rodriguez, S et al., "Production and quantification of sesquiterpenes in *Saccharomyces cerevisiae*, including extraction, detection and quantification of terpene products and key related metabolites," *Nat. Protoc.* 2014;9(8):1980-96.

Rohdich, F et al., "Deoxyxylulose phosphate pathway of isoprenoid biosynthesis: discovery and function of ispDEFGH genes and their cognate enzymes," *Pure Appl. Chem.* 2003;75(2-3):393-405.

Rohdich, F et al., "Studies on the nonmevalonate terpene biosynthetic pathway: metabolic role of IspH (LytB) protein," *Proc. Nat'l Acad. Sci. USA* 2002;99(3):1158-63.

Rosano, GL et al., "Recombinant protein expression in *Escherichia coli*: advances and challenges," *Front. Microbiol.* 2014;5:Art. No. 172 (17 pp.).

Rufino, AT et al., "Evaluation of the anti-inflammatory, anti-catabolic and pro-anabolic effects of E-caryophyllene, myrcene and limonene in a cell model of osteoarthritis," *Eur. J. Pharmacol.* 2015;750:141-50.

Saranya, J et al., "Chemical composition of leaf essential oil of *Syzygium densiflorum* wall. ex wt. & arn.—a vulnerable tree species," *J. Essential Oil Bearing Plants* 2012;15(2):283-7.

Schmidt, Co et al., "Isolation, characterization, and mechanistic studies of (-)-alpha-gurjunene synthase from Solidago canadensis," *Arch. Biochem. Biophys.* 1999;364(2):167-77.

Schwab, W et al., "Mechanism of monoterpene cyclization: stereochemical aspects of the transformation of noncyclizable substrate analogs by recombinant (-)-limonene synthase, (+)-bornyl diphosphate synthase, and (-)-pinene synthase," *Arch. Biochem. Biophys.* 2001;392(1):123-36.

Scott, SA et al., "Biodiesel from algae: challenges and prospects," *Curr. Opin. Biotechnol.* 2010;21(3):277-86.

Scullin, C et al., "Optimization of renewable pinene production from the conversion of macroalgae *Saccharina latissimi*," *Bioresour. Technol.* 2015;184:415-20.

Sharma, KK et al., "High lipid induction in microalgae for biodiesel production," *Energies* 2012;5(5):1532-53.

Shaw, JJ et al., "Identification of a fungal 1,8-cineole synthase from *Hypoxylon* sp. with specificity determinants in common with the plant synthases," *J. Biol. Chem.* 2015;290(13):8511-26.

Shen, HY et al., "Advances in sesquiterpene synthases (cyclases) of *Artemisia annua*," *Sheng Wu Gong Cheng Xue Bao* [*Chinese J. Biotechnol.*] 2007;23(6):976-81.

Singh, J et al., "Commercialization potential of microalgae for biofuels production," *Renew. Sust. Energy Rev.* 2010;14(9):2596-610.

Singh, R, "Facts, growth, and opportunities in industrial biotechnology," *Org. Process Res. Dev.* 2011;15(1):175-9.

Singh, SK et al., "An endophytic *Phomopsis* sp. possessing bioactivity and fuel potential with its volatile organic compounds," *Microb. Ecol.* 2011;61(4):729-39.

Sosa, ME et al., "Insecticidal and nematicidal essential oils from Argentinean *Eupatorium* and *Baccharis* spp.," *Biochem. Syst Ecol.* 2012;43:132-8.

Steele, CL et al., "Sesquiterpene synthases from grand fir (*Abies grandis*): comparison of constitutive and wound-induced activities, and cDNA isolation, characterization, and bacterial expression of delta-selinene synthase and gamma-humulene synthase," *J. Biol. Chem.* 1998;273(4):2078-89.

Stolle, A et al., "Thermal rearrangements of monoterpenes and monoterpenoids," *Helvetica Chim. Acta* 2009;92(9):1673-719.

Strobel, G et al., "An endophytic/pathogenic *Phoma* sp. from creosote bush producing biologically active volatile compounds having fuel potential," *FEMS Microbiol. Lett.* 2011;320(2):87-94.

Strobel, G et al., "Natural products from endophytic microorganisms," *J. Nat. Prod.* Feb. 2004;67(2):257-68.

Strobel, G, "The story of mycodiesel," *Curr. Opin. Microbiol.* 2014;19:52-8.

Strobel, GA et al., "Endophytic microbes embody pharmaceutical potential: specific associations of fungal endophytes with plant hosts represent a large untapped area for discovery," *ASM News* 1998;64(5):263-8.

Strobel, GA et al., "Taxol from fungal endophytes and the issue of biodiversity," *J. Indus. Microbiol.* 1996;17(5-6):417-23.

Strobel, GA et al., "The production of myco-diesel hydrocarbons and their derivatives by the endophytic fungus *Gliocladium roseum* (NRRL 50072)," *Microbiology-Sgm* 2008;154(11):3319-28.

Strobel, GA et al., Corrigendum for "The production of myco-diesel hydrocarbons and their derivatives by the endophytic fungus *Gliocladium roseum* (NRRL 50072)," *Microbiology-Sgm* 2010;156:3830-3.

Subhadra, B et al., "An integrated renewable energy park approach for algal biofuel production in United States," *Energy Policy* 2010;38(9):4897-902.

Suijun, W et al., "A role for trans-caryophyllene in the moderation of insulin secretion," *Biochem. Biophys. Res. Commun.* 2014;444(4):451-4.

Tang, YJ et al., "Investigation of carbon metabolism in 'Dehalococcoides ethenogenes' strain 195 by use of isotopomer and transcriptomic analyses," *J. Bacteriol.* 2009;191(16):5224-31.

Tholl, D et al., "Two sesquiterpene synthases are responsible for the complex mixture of sesquiterpenes emitted from *Arabidopsis* flowers," *Plant J.* 2005;42(5):757-71.

Tippmann, S et al., "From flavors and pharmaceuticals to advanced biofuels: production of isoprenoids in *Saccharomyces cerevisiae*," *Biotechnol. J.* 2013;8(12):1435-44.

Tomsheck, Ar et al., "*Hypoxylon* sp., an endophyte of *Persea indica*, producing 1,8-cineole and other bioactive volatiles with fuel potential," *Microb. Ecol.* 2010;60(4):903-14.

Trapp, SC et al., "Genomic organization of plant terpene synthases and molecular evolutionary implications," *Genetics* 2001;158(2):811-32.

Ul-Hassan, SR et al., "Modulation of volatile organic compound formation in the Mycodiesel-producing endophyte *Hypoxylon* sp. CI-4," *Microbiology* 2012;158(Pt 2):465-73.

U.S. Department of Energy, "MycoCosm: the fungal genomics resource—Group name: Xylariales," available //genome.jgi.doe.gov/Xylariales/Xylariales.info.html (last accessed Feb. 15, 2016).

U.S. Department of Energy, "National algal biofuels technology roadmap," May 2010 (140 pp.), available www1.eere.energy.gov/bioenergy/pdfs/algal_biofuels_roadmap.pdf (last accessed Feb. 15, 2016).

Van Dien, SJ et al., "Manipulation of independent synthesis and degradation of polyphosphate in *Escherichia coli* for investigation of phosphate secretion from the cell," *Appl. Environ. Microbiol.* 1997;63(5):1689-95.

Wang, H et al., "Growth and biochemical composition of filamentous microalgae *Tribonema* sp. as potential biofuel feedstock," *Bioprocess Biosyst. Eng.* 2014;37(12):2607-13.

Wawrzyn, GT et al., "Discovery and characterization of terpenoid biosynthetic pathways of fungi," *Methods Enzymol.* 2012;515:83-105.

Weaver, LJ et al., "A kinetic-based approach to understanding heterologous mevalonate pathway function in *E. coli*," *Biotechnol. Bioeng.* 2015;112(1):111-9.

Wu, S et al., "Surrogate splicing for functional analysis of sesquiterpene synthase genes," *Plant Physiol.* 2005;138(3):1322-33.

Wu, W et al., "A general inhibition kinetics model for ethanol production using a novel carbon source: sodium gluconate," *Bioprocess Biosyst. Eng.* 2013;36(11):1631-40.

Wu, W, "Fuel ethanol production using novel carbon sources and fermentation medium optimization with response surface methodology," *Int. J. Agric. Biol. Eng.* 2013;6(2):42-53.

Wu, W et al., "Rapid discovery and functional characterization of terpene synthases from four endophytic Xylariaceae," *PLoS One* 2016;11(2):e0146983 (19 pp.).

Yamada, Y et al., "Diversity and analysis of bacterial terpene synthases," *Methods Enzymol.* 2012;515:123-62.

Yen, HW et al., "Microalgae-based biorefinery—from biofuels to natural products," *Bioresour. Technol.* 2013;135:166-74.

(56) References Cited

OTHER PUBLICATIONS

Zhang, H et al., "Microbial production of sabinene—a new terpene-based precursor of advanced biofuel," *Microb. Cell Fact.* 2014;13:Art. No. 20 (10 pp.).

Zhang, Z et al., "Synergistic antitumor effect of α-pinene and β-pinene with paclitaxel against non-small-cell lung carcinoma (NSCLC)," *Drug Res.* (Stuttg.) 2015;65(4):214-8.

U.S. Department of Energy, "MycoCosm: the fungal genomics resource—Group name: Xylariales," available at genome.jgi.doe.gov/Xylariales/Xylariales.info.html (last accessed Feb. 15, 2016).

U.S. Department of Energy, "National algal biofuels technology roadmap," May 2010 (140 pp.), available at www1.eere.energy.gov/bioenergy/pdfs/algal_biofuels_roadmap.pdf (last accessed Feb. 15, 2016).

CLUSTER 1
\>1:HypCI4A-20984 (SEQ ID NO:11)
MAYSEKKLLVKRLEGQRYTIPDMRPIFAHWPSGQNEHYSEVKEIIDQRLASQSMDEEARKAFDDMNPTLL
AASRYSALVDFVIWFGYWDDLSEKLVSEPTAGADLRSTTKLFVRQSLQLANPGKENIAMPDSLIHGFKSI
AEKVLVAYDEEQRGVLISNFERYIDSTELEAEADISEELPSLKRYWETRIMTSGMDALLAFTEFAAEVKL
PLRLVNSTLYQTLWTTTIMINSIVNDLISFKKEMKAGSVLSSVAILYQQVNNLDAAVQMSLAHLRIMVDE
YDYTANTILSEFSLNSEETDAVTKVIDTLRTVNTGNLEWSLQAKRYGVSPFITQAGHIELTL

\>1:HypCO27-269219 (SEQ ID NO:12)
MIMSDYNEKELLAKRLKGQRLVIPDMRPIFAHWPSERNENYQAVKDAIDERLAKQTMTDEARTSFNFMNP
ALFAATWWPTSSKDHYRILVDYVIWFLYWDDLVEGLAHDASAAEDLRSETKTLVRRSLGLGGLEEKMTIS
NPFILGIKDIAKGLCSFYDEEQRKVLLGHFDRYIDSTLLEAEADLNDKLPSLKRYWEVRILTSGMGTLLG
VTEYAAHAKLPSRLVHSAAYETLWVSTIMINSIVNDLVSFKKEMKAGSVLSSVAILYQQVDNLDAAVQMS
LAHLRILVDEFDRTATTILSKFSLAPNEIEPVSKVINALRMVNTGNLEWRSVLPLKDTYSAVAHLLTSYT
A

\>1:HypEC38-3887 (SEQ ID NO:13)
MSDYNEKELLAKRLKGQRLVIPDMRSIFAHWPSARNENYQAVKDAVDERLAKQTMTDEARTSFHYMNPAL
YAATWWPTSSKDHYRILVDYVIWFLHWDDLVEGLADDPSAAEDLRSETKTLVRRSLGLGGLDEKMTISNP
FILGFKDIAKGLCSFYDEEQRKVLLGHFDRYIDSTLLEAEADLSDKLPSLKRYWEVRILTSGMGTLLGVT
EYAAHAKLPSRLVHSAAYETLWVSTIVINSIVNDLISFKKEMKAGSVLSSVAILYQQVDNLDAAVQMSLA
HLRILVDEFDRTATTILSKFSLAPNEIEPVSKVINALRMVNTGNLEWSLSVKRYGVGQFMNHNGQIEIIL

\>1:DalEC12-25458 (SEQ ID NO:14)
MPNSNEKELVANSLKGQRLVIPDIRPIFAHWPSEEHEQYQTVKEIIDKQITEQPMSDEARKAFFNMDPSL
LAARWWPRASKDNYQVLVDLIIWFGYWDDLSESLAVDPVAAENLRGATKVLGRQALGLATSEEEVAISNP
LILDFKRIGEKIRAAYNEEQRRTFLGHFERYVDSTVLEAAADLSDTLPSLKRYWEVRILTSGMGILLGVT
EFAAGVKLPTSVVTSAAYDTLWTTAIVINSIVNDLISFKKEMKAGSVLSSVAILYSQVNNLDAAVQMSLA
HLKILVAEFDRTANLLLTKFPLSPEEVEPVSKVIDTLRLVNTGNLEWRFLASKALWGLRLHLTDRTDRSN
SMTAELAGGYTILNSGKWYTKEWQT

FIG. 4A

```
CONSENSUS 1          --MsdynEKe  LlakrLkGQR  lvIPDmRpIF  AHWPSXrnEX  YqaVKXXiDX
1:HypCI4A-20984      --MA-YSEKK  LLVKRLEGQR  YTIPDMRPIF  AHWPSGQNEH  YSEVKEIIDQ
1:HypCO27-269219     MIMSDYNEKE  LLAKRLKGQR  LVIPDMRPIF  AHWPSERNEN  YQAVKDAIDE
1:HypEC38-3887       --MSDYNEKE  LLAKRLKGQR  LVIPDMRSIF  AHWPSARNEN  YQAVKDAVDE
1:DalEC12-25458      --MPNSNEKE  LVANSLKGQR  LVIPDIRPIF  AHWPSEEHEQ  YQTVKEIIDK CONSENSUS 1          rlakQtMtdE  ARXXFXXMnP  aLXAAtwwpt  sskdhYXiLV  DyvIWFXyWD
1:HypCI4A-20984      RLASQSMDEE  ARKAFDDMNP  TLLAAS----  ----RYSALV  DFVIWFGYWD
1:HypCO27-269219     RLAKQTMTDE  ARTSFNFMNP  ALFAATWWPT  SSKDHYRILV  DYVIWFLYWD
1:HypEC38-3887       RLAKQTMTDE  ARTSFHYMNP  ALYAATWWPT  SSKDHYRILV  DYVIWFLHWD
1:DalEC12-25458      QITEQPMSDE  ARKAFFNMDP  SLLAARWWPR  ASKDNYQVLV  DLIIWFGYWD CONSENSUS 1          DLZEXLaXdp  sAaedLRsXT  KtlvRXsLgL  XXX-XEkmXi  snpXIlgfKd
1:HypCI4A-20984      DLSEKLVSEP  TAGADLRSTT  KLFVRQSLQL  ANPGKENIAM  PDSLIHGFKS
1:HypCO27-269219     DLVEGLAHDA  SAAEDLRSET  KTLVRRSLGL  GGL-EEKMTI  SNPFILGIKD
1:HypEC38-3887       DLVEGLADDP  SAAEDLRSET  KTLVRRSLGL  GGL-DEKMTI  SNPFILGFKD
1:DalEC12-25458      DLSESLAVDP  VAAENLRGAT  KVLGRQALGL  ATS-EEEVAI  SNPLILDFKR CONSENSUS 1          IaXXlcsXYd  EEQRkvllgh  FXRYiDSTlL  EAeADlsdkL  PSLKRYWEvR
1:HypCI4A-20984      IAEKVLVAYD  EEQRGVLISN  FERYIDSTEL  EAEADISEEL  PSLKRYWETR
1:HypCO27-269219     IAKGLCSFYD  EEQRKVLLGH  FDRYIDSTLL  EAEADLNDKL  PSLKRYWEVR
1:HypEC38-3887       IAKGLCSFYD  EEQRKVLLGH  FDRYIDSTLL  EAEADLSDKL  PSLKRYWEVR
1:DalEC12-25458      IGEKIRAAYN  EEQRRTFLGH  FERYVDSTVL  EAAADLSDTL  PSLKRYWEVR CONSENSUS 1          IlTSGMgtLL  gvTEXAAhXK  LPsrlVhSaa  YXTLWXXtIX  INSIVNDLZS
1:HypCI4A-20984      IMTSGMDALL  AFTEFAAEVK  LPLRLVNSTL  YQTLWTTTIM  INSIVNDLIS
1:HypCO27-269219     ILTSGMGTLL  GVTEYAAHAK  LPSRLVHSAA  YETLWVSTIM  INSIVNDLVS
1:HypEC38-3887       ILTSGMGTLL  GVTEYAAHAK  LPSRLVHSAA  YETLWVSTIV  INSIVNDLIS
1:DalEC12-25458      ILTSGMGILL  GVTEFAAGVK  LPTSVVTSAA  YDTLWTTAIV  INSIVNDLIS CONSENSUS 1          FKKEMKAGSV  LSSVAILYqQ  VXNLDAAVQM  SLAHLrIlVd  EfDrTAXtIL
1:HypCI4A-20984      FKKEMKAGSV  LSSVAILYQQ  VNNLDAAVQM  SLAHLRIMVD  EYDYTANTIL
1:HypCO27-269219     FKKEMKAGSV  LSSVAILYQQ  VDNLDAAVQM  SLAHLRILVD  EFDRTATTIL
1:HypEC38-3887       FKKEMKAGSV  LSSVAILYQQ  VDNLDAAVQM  SLAHLRILVD  EFDRTATTIL
1:DalEC12-25458      FKKEMKAGSV  LSSVAILYSQ  VNNLDAAVQM  SLAHLKILVA  EFDRTANLLL CONSENSUS 1          skFsLapXEi  epVsKVIXXL  RmVNTGNLEW  XXXaXrXXvX  pXX-------
1:HypCI4A-20984      SEFSLNSEET  DAVTKVIDTL  RTVNTGNLEW  SLQAKRYGVS  PFI-------
1:HypCO27-269219     SKFSLAPNEI  EPVSKVINAL  RMVNTGNLEW  R------SVL  PLK-------
1:HypEC38-3887       SKFSLAPNEI  EPVSKVINAL  RMVNTGNLEW  SLSVKRYGVG  QFM-------
1:DalEC12-25458      TKFPLSPEEV  EPVSKVIDTL  RLVNTGNLEW  RFLASK-ALW  GLRLHLTDRT CONSENSUS 1          -XXnXXiXXX  l--XX-----  ----------  (SEQ ID NO:10)
1:HypCI4A-20984      -TQAGHIELT  L---------  ----------  (SEQ ID NO:11)
1:HypCO27-269219     -DTYSAVAHL  LTSYTA----  ----------  (SEQ ID NO:12)
1:HypEC38-3887       -NHNGQIEII  L---------  ----------  (SEQ ID NO:13)
1:DalEC12-25458      DRSNSMTAEL  AGGYTILNSG  KWYTKEWQT   (SEQ ID NO:14)
```

FIG. 4B

CLUSTER 2

\>2:HypCI4A-216497 (SEQ ID NO:21)
MARSKRVTTTLLNLARRTHSKLSSILFPCPLPAEASSDAVVQYAPEKKKKPSAQQHGLCGEALVLASQLD
GQTFRLPDLWKVLADWPMAANPHAERLEGLVNSILERHITSEKKLKALKQANFARLISLWYPDAEWPELE
AATAYSVWIFVWDDEVDAGDTDVSLDEELSRAYYKKSLSTIHRLLGLDSTSGDDVSGEAEEEALHPNMRE
RFYREMESFMIQVGVEHSHRMRGSIPTVDKYMEIRSGSVGCAPQIAITDFMLKIRLPESVMESAAMKALW
RETVVICLILNDVYSVQKEIAQGSLLNLVPVIFKNCDPKEQNLDTVTADIEVALQGSIRGFEDAAASLGQ
MVSDDAQLDKDVQSFVRWCRYFITGVQQWSIESARYGMAQCLQEDGSLSIVL

\>2:HypCO27-31178 (SEQ ID NO:22)
MKSSKMMRTTLLRLAQRTRLRLLSILFPHSLPAAQEDQRAPEKASAQQGLCGEALVLASQLDGKTFHLPD
LWKVFSDWPLAANPHAQRLDALVDSLLERIITNEKKLKALKQANFGRLISLWYPNAEWSELEIAAAYSVW
IFVWDDEIDAGDTDVSNDEELSRAYYQKSLSTIHNLLGLDPVEDGQEPVYEDDESLHPNMALFADVGRGM
RATTDRIQRERFYRELEHFMIQVGVEHVHRMRGSIPSVEKYIEIRSGSVGCAPQIAITDAMLKIRLPESI
MESAAMKALWRETVVICFILNDVYSVQKEIAQGSLLNLVPVMYKNCDPEKQSLDTVTRDIEVLLQKSLKG
FEDAATSLTGTAEKHENMTYHNAQVFSKTGSRCNSKVVTATVGSHSMKQPQTSYKIFPTEDF

\>2:DalEC12-17536 (SEQ ID NO:23)
MKSQTLSPLFRLAELVHYKLLSIFPRKPLAQTVEPTANPDLRGDASILAAQLDGKTFRLPDLWKVFSEWP
LAANPHAKRLEGLVDSMLERIITNEKKLKALKKADFGRLMSLWYPDAEWPELEIATAYSVWIFVWDDEVD
AGDTDVSNDEELARAYYRKSLSTVHCLLGLDESEGAEERIAREEASLHPNMALFADVGRGLRNSTDRIQR
ERFYRELENFMISVGVEHGHRMRGSIPTVEKYLHIRSGSVGCAPQIALTDHMLKIRLPESIMECAPMKEL
WKETVVMCLILNDVYSVQKEIAQASLFNLVPVMYKNCSPEKQTLDTVTRGVEAALQESMRGFEDAAKALG
EMASDDAQVSRDVQAFIKWCRYFITGVLQWSLESKRYGMADCRHKDGSLSIVL

\>2:HypEC38-200002.1 (SEQ ID NO:24)
MMRTTLLRLAQRTRLRLLSILFPHSLPAAQEDQRAPEKASAQQGLCGEALVLASQLDGKTFHLPDLWKVF
SDWPLAANPHAQRLDALVDSLLERIITNEKKLKALKQANFGRLISLWYPNAEWSELEIAAAYSVWIFVWD
DEIDAGDTDVSNDEELSRAYYQKSLSTIHNLLGLDPVEDGQEPVYEDDESLHPNMALFADVGRGMRATTD
RIQRERFYRELEHFMIQVGVEHVHRMRGSIPSVEKYIEIRSGSVGCAPQIAITDAMLKIRLPESIMESAA
MKALWRETVVICFILNDVYSVQKEIAQGSLLNLVPVMYKNCDPEKQSLDTVTRDIEVLLQKSLKGFEDAA
TSLSEMTSSDAKLSQDTQSFIKWCRYFITGVQQWSLESRRYGMAECLNEDGSLSIVL

\>2:HypEC38-200002.2 (SEQ ID NO:25)
MMRTTLLRLAQRTRLRLLSILFPHSLPAAQEDQRAPEKASAQQGLCGEALVLASQLDGKTFHLPDLWKVF
SDWPLAANPHAQRLDALVDSLLERIITNEKKLKALKQANFGRLISLWYPNAEWSELEIAAAYSVWIFVWD
DEIDAGDTDVSNDEELSRAYYQKSLSTIHNLLGLDPVEDGQEPVYEDDESLHPNMALFADVGRGMRATTD
RIQRERFYRELEHFMIQVGVEHVHRMRGSIPSVEKYIEIRSGSVGCAPQIAITDAMLKIRLPESIMESAA
MKALWRETVVICFILNDVYSVAQGSLLNLVPVMYKNCDPEKQSLDTVTRDIEVLLQKSLKGFEDAATSLS
EMTSSDAKLSQDTQSFIKWCRYFITGVQQWSLESRRYGMAECLNEDGSLSIVL

FIG. 5A

```
CONSENSUS 2              mXsXXmmrtt  LlrLAqrtXX  XLlSIlFPhs  lpAaqed---  -qrapek---
2:HypCI4A-216497         MARSKRVTTT  LLNLARRTHS  KLSSILFPCP  LPAEASSDAV  VQYAPEKKKK
2:HypCO27-31178          MKSSKMMRTT  LLRLAQRTRL  RLLSILFPHS  LPAAQED---  -QRAPEK---
2:DalEC12-17536          MKS--QTLSP  LFRLAELVHY  KLLSI-FPRK  PLAQTVE---  ----------
2:HypEC38-200002.1       -----MMRTT  LLRLAQRTRL  RLLSILFPHS  LPAAQED---  -QRAPEK---
2:HypEC38-200002.2       -----MMRTT  LLRLAQRTRL  RLLSILFPHS  LPAAQED---  -QRAPEK---

CONSENSUS 2              -asaqqgLcG  eAlvLAsQLD  GkTFXLPDLW  KVfsdWPlAA  NPHAqRLXXL
2:HypCI4A-216497         PSAQQHGLCG  EALVLASQLD  GQTFRLPDLW  KVLADWPMAA  NPHAERLEGL
2:HypCO27-31178          -ASAQQGLCG  EALVLASQLD  GKTFHLPDLW  KVFSDWPLAA  NPHAQRLDAL
2:DalEC12-17536          -PTANPDLRG  DASILAAQLD  GKTFRLPDLW  KVFSEWPLAA  NPHAKRLEGL
2:HypEC38-200002.1       -ASAQQGLCG  EALVLASQLD  GKTFHLPDLW  KVFSDWPLAA  NPHAQRLDAL
2:HypEC38-200002.2       -ASAQQGLCG  EALVLASQLD  GKTFHLPDLW  KVFSDWPLAA  NPHAQRLDAL CONSENSUS 2              VdSXLERiIT  nEKKLKALKq  AnFgRLiSLW  YPXAEWXELE  iAXAYSVWIF
2:HypCI4A-216497         VNSILERHIT  SEKKLKALKQ  ANFARLISLW  YPDAEWPELE  AATAYSVWIF
2:HypCO27-31178          VDSLLERIIT  NEKKLKALKQ  ANFGRLISLW  YPNAEWSELE  IAAAYSVWIF
2:DalEC12-17536          VDSMLERIIT  NEKKLKALKK  ADFGRLMSLW  YPDAEWPELE  IATAYSVWIF
2:HypEC38-200002.1       VDSLLERIIT  NEKKLKALKQ  ANFGRLISLW  YPNAEWSELE  IAAAYSVWIF
2:HypEC38-200002.2       VDSLLERIIT  NEKKLKALKQ  ANFGRLISLW  YPNAEWSELE  IAAAYSVWIF CONSENSUS 2              VWDDEZDAGD  TDVSnDEELs  RAYYqKSLST  iHnLLGLDpX  eXXqeXXXXX
2:HypCI4A-216497         VWDDEVDAGD  TDVSLDEELS  RAYYKKSLST  IHRLLGLDST  SGDDVSGEAE
2:HypCO27-31178          VWDDEIDAGD  TDVSNDEELS  RAYYQKSLST  IHNLLGLDPV  EDGQEPVYED
2:DalEC12-17536          VWDDEVDAGD  TDVSNDEELA  RAYYRKSLST  VHCLLGLDES  EGAEERIARE
2:HypEC38-200002.1       VWDDEIDAGD  TDVSNDEELS  RAYYQKSLST  IHNLLGLDPV  EDGQEPVYED
2:HypEC38-200002.2       VWDDEIDAGD  TDVSNDEELS  RAYYQKSLST  IHNLLGLDPV  EDGQEPVYED CONSENSUS 2              XesLHPNMal  fadvgrgmra  XtdriqRERF  YRElEhFMIq  VGVEHXHRMR
2:HypCI4A-216497         EEALHPNM--  ----------  ------RERF  YREMESFMIQ  VGVEHSHRMR
2:HypCO27-31178          DESLHPNMAL  FADVGRGMRA  TTDRIQRERF  YRELEHFMIQ  VGVEHVHRMR
2:DalEC12-17536          EASLHPNMAL  FADVGRGLRN  STDRIQRERF  YRELENFMIS  VGVEHGHRMR
2:HypEC38-200002.1       DESLHPNMAL  FADVGRGMRA  TTDRIQRERF  YRELEHFMIQ  VGVEHVHRMR
2:HypEC38-200002.2       DESLHPNMAL  FADVGRGMRA  TTDRIQRERF  YRELEHFMIQ  VGVEHVHRMR CONSENSUS 2              GSIPXVeKYi  eIRSGSVGCA  PQIAiTDXML  KIRLPESiME  sAaMKaLWrE
2:HypCI4A-216497         GSIPTVDKYM  EIRSGSVGCA  PQIAITDFML  KIRLPESVME  SAAMKALWRE
2:HypCO27-31178          GSIPSVEKYI  EIRSGSVGCA  PQIAITDAML  KIRLPESIME  SAAMKALWRE
2:DalEC12-17536          GSIPTVEKYL  HIRSGSVGCA  PQIALTDHML  KIRLPESIME  CAPMKELWKE
2:HypEC38-200002.1       GSIPSVEKYI  EIRSGSVGCA  PQIAITDAML  KIRLPESIME  SAAMKALWRE
2:HypEC38-200002.2       GSIPSVEKYI  EIRSGSVGCA  PQIAITDAML  KIRLPESIME  SAAMKALWRE CONSENSUS 2              TVViCXILND  VYSVQKEIAQ  gSLlNLVPVm  yKNCdPekQs  LDTVTrdiEv
2:HypCI4A-216497         TVVICLILND  VYSVQKEIAQ  GSLLNLVPVI  FKNCDPKEQN  LDTVTADIEV
2:HypCO27-31178          TVVICFILND  VYSVQKEIAQ  GSLLNLVPVM  YKNCDPEKQS  LDTVTRDIEV
2:DalEC12-17536          TVVMCLILND  VYSVQKEIAQ  ASLFNLVPVM  YKNCSPEKQT  LDTVTRGVEA
2:HypEC38-200002.1       TVVICFILND  VYSVQKEIAQ  GSLLNLVPVM  YKNCDPEKQS  LDTVTRDIEV
2:HypEC38-200002.2       TVVICFILND  VYSV----AQ  GSLLNLVPVM  YKNCDPEKQS  LDTVTRDIEV
```

FIG. 5B-1

```
CONSENSUS 2          XLQkSXXGFE  DAAtsLXXma  sddaqls-Xd  XQsFik---w  C--ryfitgV
2:HypCI4A-216497     ALQGSIRGFE  DAAASLGQMV  SDDAQLD-KD  VQSFVR---W  C--RYFITGV
2:HypCO27-31178      LLQKSLKGFE  DAATSLTGTA  EKHENMTYHN  AQVFSKTGSR  CNSKVVTATV
2:DalEC12-17536      ALQESMRGFE  DAAKALGEMA  SDDAQVS-RD  VQAFIK---W  C--RYFITGV
2:HypEC38-200002.1   LLQKSLKGFE  DAATSLSEMT  SSDAKLS-QD  TQSFIK---W  C--RYFITGV
2:HypEC38-200002.2   VDSLLERIIT  NEKKLKALKQ  ANFGRLISLW  YPNAEWSELE  IAAAYSVWIF CONSENSUS 2          qqwSXesXry  gmaXcXXeDg  slsivl      (SEQ ID NO:20)
2:HypCI4A-216497     QQWSIESARY  GMAQCLQEDG  SLSIVL      (SEQ ID NO:21)
2:HypCO27-31178      GSHSMKQPQT  SYKIFPTED-  -----F      (SEQ ID NO:22)
2:DalEC12-17536      LQWSLESKRY  GMADCRHKDG  SLSIVL      (SEQ ID NO:23)
2:HypEC38-200002.1   QQWSLESRRY  GMAECLNEDG  SLSIVL      (SEQ ID NO:24)
2:HypEC38-200002.2   QQWSLESRRY  GMAECLNEDG  SLSIVL      (SEQ ID NO:25)
```

FIG. 5B-2

CLUSTER 3
```
>3:HypCI4A-6706 (SEQ ID NO:31)
MAPDIDQIWASTSDVPASAVDERKALINRALNQKVLVPNILSLMPTWTSALQPDLDEINKEIDEWLPTVN
VAEAKKAKHRARGNYAFLTAVYYPHCKKDKMLTLSKFLYWIFFWDDEIDNGGELTDDEEGTQQCCDETNK
CIDDCLGPNPNYTPPSNARGTVEMFYPILRDLRAGLSPISTERLRLELHDYVNGVGRQQKVRQGDHLPDP
WYHFQIRSDDVGVIPSITQNEYAMEFELPEYVRRHEAMEAIVQECTKLTVLLNDVLSLQKEFRVSQLENI
VLLFMNKYDLSLQAAIDKILDLIREHYQICVAAEERLPWSKDDEKLNEDIREYVRGCQRLATGTAYWSYS
CERYFKQTQVNDKWEVLLDLSYE

>3:HypCO27-397991 (SEQ ID NO:32)
MAPDIDHIWSTTSDVATSSIDERKNLIKRALNQKVLVPSILSLMPEWPSDVQPDVDEINKEIDEWLPTVN
VAEKKKVKHRARGNYTLLAAIYYPHCKKDKMLTLSKFLYWIFFWDDEIDTGGDLTEDEEGTLQCCQETLN
CVDDCLGPNPNYTPPPNSRGTVEMFYPILRDLRAGLGPVSTERLRLELHDYVNGVGKQQQVRQGDHLPDP
WYHFQIRSDDVGVIPSITQNEYAMEFELPEYVRRHEAMEFIVQECTKITVLLNDVLSLQKEFRVSQLENI
VLLFMNKYNISLSKAIDKVLQLIREHYAICVEAEERLPWSKDDEKLNDNIREYVRGCHRLATGTAFWSYS
CERYFKQTQVNDKWEVLLDLSYE

>3:DalEC12-24764 (SEQ ID NO:33)
MAVEVQQAPSAVKDAASLFKTERDNIVNRVLNQKLRLPNVMSLTPEFWFNEIQPDLDEVNTEIDKWLPSV
DVAEEKKAKHRSRGNYALLAAVTYPRCKKEKLLTISKFLYWIFFWDDEIDTGGDLTEDREATLQCCKETN
ECIEDCFVAIPNYTPPPNTRGTISMLYPILKECREGLGPVSNARLQSELHAFINGVGKQQQVRQESLLPD
PWYHFQIRSNDVGALPCITLTEYAMEFELPEYVRRHEAMEVIIDECVKLTTLLNDVLSFQKEFRVSQLEN
IVFLFMNKYNITLQAAIDKTLELIREHYNICIEAEKRLPWSKEDEKLNENIREYVKGCHLVPAGMVDWSY
SCERYFNKSQVDDNWEVQLDMSYA

>3:HypEC38-373976 (SEQ ID NO:34)
MAPDIDHIWSTTSDVATSSIDERKNLIKRALNQKVLVPSILSLMPEWPSDVQPDVDEINKEIDKWLPTVN
VAEKKKAKHRARGNYTLLAAIYYPHCKKDKMLTLSKFLYWIFFWDDEIDTGGELTEDEEGTLQCCQETLN
CVDDCLGPNPNYTPPPNSRGTVEMFYPILRDLRAGLGPVSTERLRLELHDYINGVGKQQQVRQGDRLPDP
WYHFQIRSDDVGVIPSITQNEYAMEFELPEYVRRHEAMEFIVQECTKITVLLNDVLSLQKEFRVSQLENI
VLLFMNKYNISLSKAIDKVLQLIREHYAICVAAEERLPWSKDDEKLNDNIREYVRGCHRLATGTAFWSYS
CERYFKQTQVNDKWEVLLDLSYE
```

FIG. 6A

```
CONSENSUS 3          MApdidXiws XtsDvaXsXi dERknliXRa LNQKvlvPXi lSLmPe-WXs
3:HypCI4A-6706       MAPDIDQIWA STSDVPASAV DERKALINRA LNQKVLVPNI LSLMPT-WTS
3:HypCO27-397991     MAPDIDHIWS TTSDVATSSI DERKNLIKRA LNQKVLVPSI LSLMPE-WPS
3:DalEC12-24764      MAVEVQQAPS AVKDAASLFK TERDNIVNRV LNQKLRLPNV MSLTPEFWFN
3:HypEC38-373976     MAPDIDHIWS TTSDVATSSI DERKNLIKRA LNQKVLVPSI LSLMPE-WPS CONSENSUS 3          dXQPDXDEiN kEIDXWLPtV nVAEkKKaKH RaRGNYXlLa AXyYPhCKKd
3:HypCI4A-6706       ALQPDLDEIN KEIDEWLPTV NVAEAKKAKH RARGNYAFLT AVYYPHCKKD
3:HypCO27-397991     DVQPDVDEIN KEIDEWLPTV NVAEKKKVKH RARGNYTLLA AIYYPHCKKD
3:DalEC12-24764      EIQPDLDEVN TEIDKWLPSV DVAEEKKAKH RSRGNYALLA AVTYPRCKKE
3:HypEC38-373976     DVQPDVDEIN KEIDKWLPTV NVAEKKKAKH RARGNYTLLA AIYYPHCKKD CONSENSUS 3          KmLT1SKFLY WIFFWDDEID tGGXLTeDeE gTlQCCqETX nCXdDClgpn
3:HypCI4A-6706       KMLTLSKFLY WIFFWDDEID NGGELTDDEE GTQQCCDETN KCIDDCLGPN
3:HypCO27-397991     KMLTLSKFLY WIFFWDDEID TGGDLTEDEE GTLQCCQETL NCVDDCLGPN
3:DalEC12-24764      KLLTISKFLY WIFFWDDEID TGGDLTEDRE ATLQCCKETN ECIEDCFVAI
3:HypEC38-373976     KMLTLSKFLY WIFFWDDEID TGGELTEDEE GTLQCCQETL NCVDDCLGPN CONSENSUS 3          PNYTPPpNsR GTveMfYPIL rdlRaGLgPv SteRLrlELH dyXNGVGkQQ
3:HypCI4A-6706       PNYTPPSNAR GTVEMFYPIL RDLRAGLSPI STERLRLELH DYVNGVGRQQ
3:HypCO27-397991     PNYTPPPNSR GTVEMFYPIL RDLRAGLGPV STERLRLELH DYVNGVGKQQ
3:DalEC12-24764      PNYTPPPNTR GTISMLYPIL KECREGLGPV SNARLQSELH AFINGVGKQQ
3:HypEC38-373976     PNYTPPPNSR GTVEMFYPIL RDLRAGLGPV STERLRLELH DYINGVGKQQ CONSENSUS 3          qVRQgdhLPD PWYHFQIRSd DVGviPsITq nEYAMEFELP EYVRRHEAME
3:HypCI4A-6706       KVRQGDHLPD PWYHFQIRSD DVGVIPSITQ NEYAMEFELP EYVRRHEAME
3:HypCO27-397991     QVRQGDHLPD PWYHFQIRSD DVGVIPSITQ NEYAMEFELP EYVRRHEAME
3:DalEC12-24764      QVRQESLLPD PWYHFQIRSN DVGALPCITL TEYAMEFELP EYVRRHEAME
3:HypEC38-373976     QVRQGDRLPD PWYHFQIRSD DVGVIPSITQ NEYAMEFELP EYVRRHEAME CONSENSUS 3          fIvqECtKXT vLLNDVLSZQ KEFRVSQLEN IVlLFMNKYn isLXXAIDKX
3:HypCI4A-6706       AIVQECTKLT VLLNDVLSLQ KEFRVSQLEN IVLLFMNKYD LSLQAAIDKI
3:HypCO27-397991     FIVQECTKIT VLLNDVLSLQ KEFRVSQLEN IVLLFMNKYN ISLSKAIDKV
3:DalEC12-24764      VIIDECVKLT TLLNDVLSFQ KEFRVSQLEN IVFLFMNKYN ITLQAAIDKT
3:HypEC38-373976     FIVQECTKIT VLLNDVLSLQ KEFRVSQLEN IVLLFMNKYN ISLSKAIDKV CONSENSUS 3          LqLIREHYaI CvXAEeRLPW SKdDEKLNXn IREYVrGChr latGtafWSY
3:HypCI4A-6706       LDLIREHYQI CVAAEERLPW SKDDEKLNED IREYVRGCQR LATGTAYWSY
3:HypCO27-397991     LQLIREHYAI CVEAEERLPW SKDDEKLNDN IREYVRGCHR LATGTAFWSY
3:DalEC12-24764      LELIREHYNI CIEAEKRLPW SKEDEKLNEN IREYVKGCHL VPAGMVDWSY
3:HypEC38-373976     LQLIREHYAI CVAAEERLPW SKDDEKLNDN IREYVRGCHR LATGTAFWSY CONSENSUS 3          SCERYFkqtQ VnDkWEV1LD lSYe       (SEQ ID NO:30)
3:HypCI4A-6706       SCERYFKQTQ VNDKWEVLLD LSYE       (SEQ ID NO:31)
3:HypCO27-397991     SCERYFKQTQ VNDKWEVLLD LSYE       (SEQ ID NO:32)
3:DalEC12-24764      SCERYFNKSQ VDDNWEVQLD MSYA       (SEQ ID NO:33)
3:HypEC38-373976     SCERYFKQTQ VNDKWEVLLD LSYE       (SEQ ID NO:34)
```

FIG. 6B

CLUSTER 4
>4:HypCI4A-322581 (SEQ ID NO:41)
MSLAPSSGDYPSSHWTPLIHPLSEKVTREVDGYYLQHWPFPDERSRKKFVAAGFSRVTCFYFPKALNDRI
HFACRLLTVLFLIDDLLEYMSLEDGKAYNEKLIPISRGDVLPDRSVPVEYITYDLWESMRAHDRIMADDI
LEPVFTFMRAQTDSVRLEAMDLGRYLEYRERDVGKALLGALMRFSMGLVVPPEDLAIVRPIDFNCSRHLS
VINDIWSFEKELLASKNAHEEGGVLCSAVSVLADQVGISIDGSKRILYYLCREWEHRHETLVKEMLQVRD
TPALRSYVKGLEYQMSGNEMWSRTTMRYLAPKD

>4:HypCO27-392541 (SEQ ID NO:42)
MAPMAEECVSASPNQGHAKPVATPMRRAVHIPSSEWTAQIHPLHEKVIAEVDGYFLQHWPFPSEKTRKKF
VAAGFSRVTCLYFPKALDDRIHFACRLLTLLFLVDDILEHMSLEDGRAYNERLMPLFRGSVLPDRSVPVE
WISYDLWESMRAHDRDMADEIIEPVFTFMWAQTDPARLTEMGLGQYLEYRERDVGKALLAALMRFSMALI
VSPSDLEMVRPVDRNCSKHLSVINDIWSYEKEVLAAQTLHEEGGMLCTAVAVLSKEAEISTDASKRVLYH
LCREWEDEHRILVADILAQNDTPVLRAYLQGLEFQMSGNELWSRTTLRYVQPRP

>4:DalEC12-12539 (SEQ ID NO:43)
MEYAQSTFTLLCHPRFEVVERETNEYFIANWPFPDVNSRDKFLKAGFSRCTCVYFPKAKDDRIHFACRLL
TLLFLIDDVLEDMSFEEGTAYNGRLMSIIRGDEVPDRSIPVQYISHDLWQSMRAHDQRLADGILEPLFIF
MQAQTDKRRAHSMSLGQYIEYRDKDIGQALLCALMRFCLDIKLTQHELDLVRPADVNCGIHIAIMNDIWS
FEKEALTAARGHDEGGVLCNSVAILSTETSLSTASSKRVLYCMCREWETKHRRFVDELGGGRDTTLWTYL
QGLEYQMSGNEAWSKLTPRYQIQESEKL

>4:HypEC38-328361 (SEQ ID NO:44)
MAPMVEEYVPTSPTQDYAKPVATPIQRAVHIPASEWTAQIHPLHEKVIVEVDGYFLQHWPFPNEKARKKF
VAAGFSRVTCLYFPKALDDRIHFACRLLTLLFLVDDILEHMSLEDGRAYNERLMPLFRGSVLPDRSVPVE
WISYDLWESMRAHDRDMADEIIEPVFTFMRAQTDPARLTDMGLGQYLEYRERDVGKALLAALMRFSMALT
VSPSDLEMVRPVDRNCSKHLSVINDIWSYEKEVLAAQTLHEEGGMLCTAVAVLSKEAEISTDASKRVLYH
LCREWEDEHRILVADILAQNDTPVLRAYLQGLEFQMSGNELWSRTTLRYVQPRP

>4:HypEC38-80361 (SEQ ID NO:45)
MEYAQSTFSLLRHPRFEEVERETNEYFLANWPFPDLNSRDKFLKAGFTRCTCMYFPKAKDDRIQFACRLL
TLLFLIDDVLENMSFEEGTAYNGKLMPIIRGDEVPNCSVPVQKISYDLWQSMRANDRELADGILEPLFIF
MRAQTDKRRAHSMSLGQYLEYRDKDIGQALLCALMRFCLDIKLTQHELDIVRPANVNCGNHIAVINDIWS
FEKEALTATHAHDEGGVLCNSVAILSAETALSTASSKRVLYCLCREWETKHQQFVDGLGDGHDAETLRAY
LQGLEYQMSGNEAWSKITPRYQIHESDRL

>4:HypCI4A-59230 (SEQ ID NO:46)
MSVAVETITAPTVTLSTSKPLVKETWKIPASGWTPMIHPRAEEVSREVDNYFLEHWNFPDDNARSTFLKA
GFSRVTCLYFPLAKDDRIHFACRLLTVLFLIDDILEEMSFADGEALNNRLIELSKGPEYATPDRSIPAEY
VIYDLWESMRKHDLDLANEVLEPTFVFMRSQTDRVRLSIKELGEYLRYREKDVGKALLSALMRYSMELRP
TAEELAALRPLEENCSKHISIVNDIYSFEKEVIAAKTGHKEGSFLCSAVKVVATETALGISATKRVLWSM
VREWELVHDAMCDALLLAASGAGTNSQTVRDYMRGLQYQMSGNELWSCTTPRYIEAIDQAAR

FIG. 7A

```
CONSENSUS 4         X----X--XX  -XpXXX--XX  --------XX  XpXSXwtXli  HPXXEkVXrE
4:HypCI4A-322581    --------MS  LAPSSG----  ---------D  YPSSHWTPLI  HPLSEKVTRE
4:HypCO27-392541    MAPMAEECVS  ASPNQGHAKP  VATPMRRAVH  IPSSEWTAQI  HPLHEKVIAE
4:DalEC12-12539     ----------  ----------  --------ME  YAQSFTLLC   HPRFEVVERE
4:HypEC38-328361    MAPMVEEYVP  TSPTQDYAKP  VATPIQRAVH  IPASEWTAQI  HPLHEKVIVE
4:HypEC38-80361     ----------  ----------  --------ME  YAQSFSLLR   HPRFEEVERE
4:HypCI4A-59230     MSVAVETITA  PTVTLSTSKP  L---VKETWK  IPASGWTPMI  HPRAEEVSRE

CONSENSUS 4         vdgYflqhWp  FPdensRkkF  XXAGFsRvTC  XYFPkAXdDR  IhFACRLLTl
4:HypCI4A-322581    VDGYYLQHWP  FPDERSRKKF  VAAGFSRVTC  FYFPKALNDR  IHFACRLLTV
4:HypCO27-392541    VDGYFLQHWP  FPSEKTRKKF  VAAGFSRVTC  LYFPKALDDR  IHFACRLLTL
4:DalEC12-12539     TNEYFIANWP  FPDVNSRDKF  LKAGFSRCTC  VYFPKAKDDR  IHFACRLLTL
4:HypEC38-328361    VDGYFLQHWP  FPNEKARKKF  VAAGFSRVTC  LYFPKALDDR  IHFACRLLTL
4:HypEC38-80361     TNEYFLANWP  FPDLNSRDKF  LKAGFTRCTC  MYFPKAKDDR  IQFACRLLTL
4:HypCI4A-59230     VDNYFLEHWN  FPDDNARSTF  LKAGFSRVTC  LYFPLAKDDR  IHFACRLLTV CONSENSUS 4         LFLiDDZLEh  MSXedGXAyN  erLmpXXrGd  Xl--PdrSvP  veyisyDLWe
4:HypCI4A-322581    LFLIDDLIEY  MSLEDGKAYN  EKLIPISRGD  VL--PDRSVP  VEYITYDLWE
4:HypCO27-392541    LFLVDDILEH  MSLEDGRAYN  ERLMPLFRGS  VL--PDRSVP  VEWISYDLWE
4:DalEC12-12539     LFLIDDVLED  MSFEEGTAYN  GRLMSIIRGD  EV--PDRSIP  VQYISHDLWQ
4:HypEC38-328361    LFLVDDILEH  MSLEDGRAYN  ERLMPLFRGS  VL--PDRSVP  VEWISYDLWE
4:HypEC38-80361     LFLIDDVLEN  MSFEEGTAYN  GKLMPIIRGD  EV--PNCSVP  VQKISYDLWQ
4:HypCI4A-59230     LFLIDDILEE  MSFADGEALN  NRLIELSKGP  EYATPDRSIP  AEYVIYDLWE CONSENSUS 4         SMRahDrdXA  deilEPvFtF  MraQTDXXRl  XsmXLGqYle  YReXDvGkAL
4:HypCI4A-322581    SMRAHDRIMA  DDILEPVFTF  MRAQTDSVRL  EAMDLGRYLE  YRERDVGKAL
4:HypCO27-392541    SMRAHDRDMA  DEIIEPVFTF  MWAQTDPARL  TEMGLGQYLE  YRERDVGKAL
4:DalEC12-12539     SMRAHDQRLA  DGILEPLFIF  MQAQTDKRRA  HSMSLGQYIE  YRDKDIGQAL
4:HypEC38-328361    SMRAHDRDMA  DEIIEPVFTF  MRAQTDPARL  TDMGLGQYLE  YRERDVGKAL
4:HypEC38-80361     SMRANDRELA  DGILEPLFIF  MRAQTDKRRA  HSMSLGQYLE  YRDKDIGQAL
4:HypCI4A-59230     SMRKHDLDLA  NEVLEPTFVF  MRSQTDRVRL  SIKELGEYLR  YREKDVGKAL CONSENSUS 4         LXALMRfsmX  lXvtpXXLXX  vRPXdXNCsX  HXsviNDIZS  ZEKEvlaaXt
4:HypCI4A-322581    LGALMRFSMG  LVVPPEDLAI  VRPIDFNCSR  HLSVINDIWS  FEKELLASKN
4:HypCO27-392541    LAALMRFSMA  LIVSPSDLEM  VRPVDRNCSK  HLSVINDIWS  YEKEVLAAQT
4:DalEC12-12539     LCALMRFCLD  IKLTQHELDL  VRPADVNCGI  HIAIMNDIWS  FEKEALTAAR
4:HypEC38-328361    LAALMRFSMA  LTVSPSDLEM  VRPVDRNCSK  HLSVINDIWS  YEKEVLAAQT
4:HypEC38-80361     LCALMRFCLD  IKLTQHELDI  VRPANVNCGN  HIAVINDIWS  FEKEALTATH
4:HypCI4A-59230     LSALMRYSME  LRPTAEELAA  LRPLEENCSK  HISIVNDIYS  FEKEVIAAKT CONSENSUS 4         XHeEGgvLCX  aVavlsXetX  XstdasKRvL  yXlcREWEXX  HXXlvdXll-
4:HypCI4A-322581    AHEEGGVLCS  AVSVLADQVG  ISIDGSKRIL  YYLCREWEHR  HETLVKEML-
4:HypCO27-392541    LHEEGGMLCT  AVAVLSKEAE  ISTDASKRVL  YHLCREWEDE  HRILVADIL-
4:DalEC12-12539     GHDEGGVLCN  SVAILSTETS  LSTASSKRVL  YCMCREWETK  HRRFVDELG-
4:HypEC38-328361    LHEEGGMLCT  AVAVLSKEAE  ISTDASKRVL  YHLCREWEDE  HRILVADIL-
4:HypEC38-80361     AHDEGGVLCN  SVAILSAETA  LSTASSKRVL  YCLCREWETK  HQQFVDGLG-
4:HypCI4A-59230     GHKEGSFLCS  AVKVATETA   LGISATKRVL  WSMVREWELV  HDAMCDALLL CONSENSUS 4         ----agXdtX  tlraYlqGLe  yQMSGNElWS  rtTpRYXXXX  X----  (SEQ ID NO:40)
4:HypCI4A-322581    ----QVRDTP  ALRSYVKGLE  YQMSGNEMWS  RTTMRYLAPK  D----  (SEQ ID NO:41)
4:HypCO27-392541    ----AQNDTP  VLRAYLQGLE  FQMSGNELWS  RTTLRYVQPR  P----  (SEQ ID NO:42)
4:DalEC12-12539     ----GGRDT-  TLWTYLQGLE  YQMSGNEAWS  KLTPRYQIQE  SEKL-  (SEQ ID NO:43)
4:HypEC38-328361    ----AQNDTP  VLRAYLQGLE  FQMSGNELWS  RTTLRYVQPR  P----  (SEQ ID NO:44)
4:HypEC38-80361     ----DGHDAE  TLRAYLQGLE  YQMSGNEAWS  KITPRYQIHE  SDRL-  (SEQ ID NO:45)
4:HypCI4A-59230     AASGAGTNSQ  TVRDYMRGLQ  YQMSGNELWS  CTTPRYIEAI  DQAAR  (SEQ ID NO:46)
```

FIG. 7B

CLUSTER 5

>5:HypCI4A-323210 (SEQ ID NO:51)
MVVTTRSSSFARTNGGSPQFNGKINGKANDISSKKQSRKRVSEHDFENVTKRPRVEEKTDLTRWRMLDEK
GRHTWHYLEDDQAVEKWPQSYADKWYLGLDIDLPTLPKPEKPLDAVANGLSFFEKLQLPSGQWGCEYGGP
MFLLPGVVITWYATKTPIPWYVATEIKNYLFARAHPEDGGWGLHIEGESTVFGTALNYAVLRIVGVDAEH
PVMVKARGTLHKLGGVTAGPHWAKFWLSVLGVCKWDIVNPIPTEIWLLPDWVPFAPWRWWIHIRQVFLPM
GYIYDKKWTCEETDLIRSMRQELVVEPWEKIDWAGNRNTISSIDNFHPKSWLLNTANWFLVNVWNPYLRT
KGLAQKAEDWASKLIDMEDENTDYLDLAPVNATMNTLVCYIRDGPGSYSVRRHLERLEDALWVNQEGMFC
NGTNGVQCWDTAFLIQAVIDAGLEQDARWKPMLTKALKFLDDQQIRENCKDQDVCYRQQRKGAWAFSNRD
QGYAVCDCISEALKSVILLQKSAGYPQLLEDQRIFDAIDTLLTYQNKSGACSSYEPTRGSEVLEMLNAAE
VFAKIMVEYDYVECTTAVVTALSLFQKHWPDYRTQEIKSFIGRSVKAVKSLQRPDGAWYGNWAICFTYAT
MFALESLESIGETYGNSSYSKRGCKFLISKQREDGGWSESYRSCENMVYTEHPTGSQVVMTAWALIALMK
ADYPDIEPLKKGIKLIMDRQQPNGEWKQEAIEGVFNKSCMISYPNYKFTFTMKALGMFATKYPNETVV

>5:HypCO27-37618 (SEQ ID NO:52)
MALTVCNPTADGAECKEPTWGVSTYYAPKWEIRGYPEEVSIPISCGKWEPWKLELNPFTSSLQQLLFSGV
LTISSVFLNMVTTRSGSSARANGTPQPNGKANGTISRKQPKKRASDDKLETLTKRPRLEEKTDLTRWRML
DEKGRHTWHYLEDDEAIKRWPQSYADKWYLGLDTGLPTLPKPKKPLDSVVNGLTFFEKLQLPSGQWGCEY
GGPMFLLPGVVITWYVTKTPIPWYVATEIKNYLFARANPEDGGWGLHIEGESTVFGTSLNYTVLRIVGVD
PEHPAMVKARATLHKLGGATFAPHWAKFWLSVLGVCKWDIVNPVPPEIWLLPDWVPIAPWRWWIHMRQVF
LPMSYIYEKKWTCEETDIIRGLRDELFVEQWEKIDWLGNRNSICPVDNYHPKSWLLNTVNWVLVNIWNPY
LRPNGLAQKAEDWVSKLVDMEDENTDYADLAPVNAAMNTVVCYIRDGPGAYSVRRHIERLDDAMWVNHEG
MFCNGTNGVQCWDTSFLIQAATDAGLQEDPRWKPMLTKALKFLDDQQIRENCKDQTTCYRQQRKGAWAFS
TRDQGYAVCDCISEALKSVILLQKTPGYPQLLEDRRIFDAIDTLLTYQNKSGACSSYEPTRGSELLEMLN
AAEVFGKIMVEYDYVECTTAVVTALMLFQKHWPDYRPQEIKSFIGRSVKAVKRLQRPDGSWYGNWAICFT
YATMFALESLKSIGETYNNSPYSKRGCDFLISKQREDGGWSESYRSCEKMMYIEHHTGSQVVMTAWALIG
LMKADYPDIEPLKKGIKLIMDRQQPNGEWKQEAIEGVFNKSCMISYPNYKFTFTMKALGMFAQKYPDETV
I

>5:HypEC38-80359 (SEQ ID NO:53)
MVTTRSGSSARANGTPQPNGKANGTISRKQPKKRASDDKLETITKRPRLEEKTDLTRWRMLDEKGRHTWH
YLEDDEAIKRWPQSYADKWYLGLDTGLPTLPKPKKPLDSVVNGLTFFEKLQLPSGQWGCEYGGPMFLLPG
VVITWYVTKTPIPWYVATEIKNYLFARANPEDGGWGLHIEGESTVFGTSLNYTVLRIVGVDPEHPAMVKA
RATLHKLGGATFAPHWAKFWLSVLGVCKWDIVNPVPPEIWLLPDWVPIAPWRWWIHMRQVFLPMSYIYEK
KWTCEETDIIRGLRDELFVEQWEKIDWLGNRNSICPVDNYHPKSWLLNTVNWVLVNIWNPYLRPNGLAQK
AENWVSKLVDMEDENTDYADLAPVNAAMNTVVCYIRDGPGAYSVRRHIERLDDAMWVNHEGMFCNGTNGV
QCWDTSFLIQAATDAGLQDDPRWKPMLTKALKFLDDQQIRENCKDQTTCYRQQRKGAWAFSTRDQGYAVC
DCISEALKSVILLQKTPGYPQLLEDQRIFDAIDTLLTYQNKSGACSSYEPTRGSELLEMLNAAEVFGKIM
VEYDYVECTTAVVTALMLFQKHWPDYRPQEIKSFIGRSVKAVKRLQRPDGSWYGNWAICFTYATMFALES
LKSIGETYNNSSYSKRGCDFLISKQREDGGWSESYRSCEKMMYIEHHTGSQVVMTAWALIGLMKADYPDI
EPIKKGIKLIMDRQQPNGEWKQEAIEGVFNKSCMISYPNYKFTFTMKALGMFAQKYPNETVI

>5:DalEC12-315006 (SEQ IDN NO:54)
MVVTTRSKKRVSEDAPETTVKRPRLEEKTDLRRWRMLDEKGRHTWHYLEDDEAVRKWPQSYADKWYLGLD
TGLPTLPKPQKPLDAVVNGLTFFEKLQLPSGQWGCEYGGPMFLLPGIVFTWYATKTPIPWYVATEIKNYL
FARAHPEDGGWGLHIEGESTVFGTALNYAVLRIVGLDPEHPVMVKARGTLHKLGGATYAPHWAKFWLSVL
GVCKWDIVNPVPPELWLLPDWVPFAPWRWWIHMRQVFLPMSYIYEKKWSCEETDIVRALRQELFVEPWEK
IDWLGNRNSICSVDNYHPKSWLLNTANWFLVHIWNPYLRTKGLAQKAEAWVGKLIDMEDENTDFADLAPV
NAAMNTIVCYIRDGPGSYSVRRHIERLEDSMWVNGDGMLCNGTNGVQCWDTSFLIQALTDAGLEQDPRWK
PMLNKALIFLDNQQIRENCKDQDICYRQQRKGAWAFSTRDQGYAVCDCVSEALKSVILLQHTPGFPQLLE
DQRIFDAVDTLLTYQNKSGACSSYEPTRGSELLEMLNAAEVFGKIMVEYDYVECTTAVVTALSLFQKHWP
DYRPKEIEAFIGRSVKAVKSLQQPDGSWYGNWAICYTYATMFALESLKSIGETYGNSSYSKRGCDFLISK
QREDGGWSESYRSCERMIYTEHPTGSQVVMTAWALIGLMKADYPDIKPLKKGIKLIMDRQQPNGEWKQEA
IEGVFNKSCMISYPNYKFTFTMKALGMFATKYPNETVV

FIG. 8A

| | | | | | |
|---|---|---|---|---|---|
| CONSENSUS 5 | ---------- | ---------- | ---------- | ---------- | ---------- |
| 5:HypCI4A-323210 | ---------- | ---------- | ---------- | ---------- | ---------- |
| 5:HypCO27-37618 | MALTVCNPTA | DGAECKEPTW | GVSTYYAPKW | EIRGYPEEVS | IPISCGKWEP |
| 5:HypEC38-80359 | ---------- | ---------- | ---------- | ---------- | ---------- |
| 5:DalEC12-315006 | ---------- | ---------- | ---------- | ---------- | ---------- |
| | | | | | |
| CONSENSUS 5 | ---------- | ---------- | ---------m | VTTRSXssar | angtXqX--- |
| 5:HypCI4A-323210 | ---------- | ---------- | --------MV | VTTRSSSFAR | TNGGSPQFNG |
| 5:HypCO27-37618 | WKLELNPFTS | SLQQLLFSGV | LTISSVFLNM | VTTRSGSSAR | ANGTPQP--- |
| 5:HypEC38-80359 | ---------- | ---------- | ---------M | VTTRSGSSAR | ANGTPQP--- |
| 5:DalEC12-315006 | ---------- | ---------- | --------MV | VTTRS----- | ---------- |
| | | | | | |
| CONSENSUS 5 | --ngkanXti | SXKGXkKRXS | ZZZZEtXtKR | PRlEEKTDLt | RWRMLDEKGR |
| 5:HypCI4A-323210 | KINGKANDIS | SKKQSRKRVS | EHDFENVTKR | PRVEEKTDLT | RWRMLDEKGR |
| 5:HypCO27-37618 | --NGKANGTI | SRKQPKKRAS | DDKLETLTKR | PRLEEKTDLT | RWRMLDEKGR |
| 5:HypEC38-80359 | --NGKANGTI | SRKQPKKRAS | DDKLETITKR | PRLEEKTDLT | RWRMLDEKGR |
| 5:DalEC12-315006 | ---------- | -----KKRVS | EDAPETTVKR | PRLEEKTDLR | RWRMLDEKGR |
| | | | | | |
| CONSENSUS 5 | HTWHYLEDDe | AXkXWPQSYA | DKWYLGLDtg | LPTLPKPkKP | LDXVvNGLtF |
| 5:HypCI4A-323210 | HTWHYLEDDQ | AVEKWPQSYA | DKWYLGLDID | LPTLPKPEKP | LDAVANGLSF |
| 5:HypCO27-37618 | HTWHYLEDDE | AIKRWPQSYA | DKWYLGLDTG | LPTLPKPKKP | LDSVVNGLTF |
| 5:HypEC38-80359 | HTWHYLEDDE | AIKRWPQSYA | DKWYLGLDTG | LPTLPKPKKP | LDSVVNGLTF |
| 5:DalEC12-315006 | HTWHYLEDDE | AVRKWPQSYA | DKWYLGLDTG | LPTLPKPQKP | LDAVVNGLTF |
| | | | | | |
| CONSENSUS 5 | FEKLQLPSGQ | WGCEYGGPMF | LLPGvViTWY | XTKTPIPWYV | ATEIKNYLFA |
| 5:HypCI4A-323210 | FEKLQLPSGQ | WGCEYGGPMF | LLPGVVITWY | ATKTPIPWYV | ATEIKNYLFA |
| 5:HypCO27-37618 | FEKLQLPSGQ | WGCEYGGPMF | LLPGVVITWY | VTKTPIPWYV | ATEIKNYLFA |
| 5:HypEC38-80359 | FEKLQLPSGQ | WGCEYGGPMF | LLPGVVITWY | VTKTPIPWYV | ATEIKNYLFA |
| 5:DalEC12-315006 | FEKLQLPSGQ | WGCEYGGPMF | LLPGIVFTWY | ATKTPIPWYV | ATEIKNYLFA |
| | | | | | |
| CONSENSUS 5 | RAXPEDGGWG | LHIEGESTVF | GTXLNYXVLR | IVGvDpEHPX | MVKARXTLHK |
| 5:HypCI4A-323210 | RAHPEDGGWG | LHIEGESTVF | GTALNYAVLR | IVGVDAEHPV | MVKARGTLHK |
| 5:HypCO27-37618 | RANPEDGGWG | LHIEGESTVF | GTSLNYTVLR | IVGVDPEHPA | MVKARATLHK |
| 5:HypEC38-80359 | RANPEDGGWG | LHIEGESTVF | GTSLNYTVLR | IVGVDPEHPA | MVKARATLHK |
| 5:DalEC12-315006 | RAHPEDGGWG | LHIEGESTVF | GTALNYAVLR | IVGLDPEHPV | MVKARGTLHK |
| | | | | | |
| CONSENSUS 5 | LGGaTfaPHW | AKFWLSVLGV | CKWDIVNPvP | pEiWLLPDWV | PXAPWRWWIH |
| 5:HypCI4A-323210 | LGGVTAGPHW | AKFWLSVLGV | CKWDIVNPIP | TEIWLLPDWV | PFAPWRWWIH |
| 5:HypCO27-37618 | LGGATFAPHW | AKFWLSVLGV | CKWDIVNPVP | PEIWLLPDWV | PIAPWRWWIH |
| 5:HypEC38-80359 | LGGATFAPHW | AKFWLSVLGV | CKWDIVNPVP | PEIWLLPDWV | PIAPWRWWIH |
| 5:DalEC12-315006 | LGGATYAPHW | AKFWLSVLGV | CKWDIVNPVP | PELWLLPDWV | PFAPWRWWIH |
| | | | | | |
| CONSENSUS 5 | mRQVFLPMsY | IYeKKWtCEE | TDiiRXlRXE | LfVEXWEKID | WlGNRNsIcX |
| 5:HypCI4A-323210 | IRQVFLPMGY | IYDKKWTCEE | TDLIRSMRQE | LVVEPWEKID | WAGNRNTISS |
| 5:HypCO27-37618 | MRQVFLPMSY | IYEKKWTCEE | TDIIRGLRDE | LFVEQWEKID | WLGNRNSICP |
| 5:HypEC38-80359 | MRQVFLPMSY | IYEKKWTCEE | TDIIRGLRDE | LFVEQWEKID | WLGNRNSICP |
| 5:DalEC12-315006 | MRQVFLPMSY | IYEKKWSCEE | TDIVRALRQE | LFVEPWEKID | WLGNRNSICS |

FIG. 8B-1

```
CONSENSUS 5        vDNyHPKSWL  LNTXNWXLVn  iWNPYLRXXG  LAQKAEdWvs  KLXDMEDENT
5:HypCI4A-323210   IDNFHPKSWL  LNTANWFLVN  VWNPYLRTKG  LAQKAEDWAS  KLIDMEDENT
5:HypCO27-37618    VDNYHPKSWL  LNTVNWVLVN  IWNPYLRPNG  LAQKAEDWVS  KLVDMEDENT
5:HypEC38-80359    VDNYHPKSWL  LNTVNWVLVN  IWNPYLRPNG  LAQKAENWVS  KLVDMEDENT
5:DalEC12-315006   VDNYHPKSWL  LNTANWFLVH  IWNPYLRTKG  LAQKAEAWVG  KLIDMEDENT

CONSENSUS 5        DyaDLAPVNA  aMNTXVCYIR  DGPGXYSVRR  HiERLXDamW  VNheGMfCNG
5:HypCI4A-323210   DYLDLAPVNA  TMNTLVCYIR  DGPGSYSVRR  HLERLEDALW  VNQEGMFCNG
5:HypCO27-37618    DYADLAPVNA  AMNTVVCYIR  DGPGAYSVRR  HIERLDDAMW  VNHEGMFCNG
5:HypEC38-80359    DYADLAPVNA  AMNTVVCYIR  DGPGAYSVRR  HIERLDDAMW  VNHEGMFCNG
5:DalEC12-315006   DFADLAPVNA  AMNTIVCYIR  DGPGSYSVRR  HIERLEDSMW  VNGDGMLCNG

CONSENSUS 5        TNGVQCWDTs  FLIQAatDAG  LXqDpRWKPM  LtKALkFLDd  QQIRENCKDQ
5:HypCI4A-323210   TNGVQCWDTA  FLIQAVIDAG  LEQDARWKPM  LTKALKFLDD  QQIRENCKDQ
5:HypCO27-37618    TNGVQCWDTS  FLIQAATDAG  LQEDPRWKPM  LTKALKFLDD  QQIRENCKDQ
5:HypEC38-80359    TNGVQCWDTS  FLIQAATDAG  LQDDPRWKPM  LTKALKFLDD  QQIRENCKDQ
5:DalEC12-315006   TNGVQCWDTS  FLIQALTDAG  LEQDPRWKPM  LNKALIFLDN  QQIRENCKDQ

CONSENSUS 5        XtCYRQQRKG  AWAFStRDQG  YAVCDCiSEA  LKSVILLQkt  pGyPQLLEDq
5:HypCI4A-323210   DVCYRQQRKG  AWAFSNRDQG  YAVCDCISEA  LKSVILLQKS  AGYPQLLEDQ
5:HypCO27-37618    TTCYRQQRKG  AWAFSTRDQG  YAVCDCISEA  LKSVILLQKT  PGYPQLLEDR
5:HypEC38-80359    TTCYRQQRKG  AWAFSTRDQG  YAVCDCISEA  LKSVILLQKT  PGYPQLLEDQ
5:DalEC12-315006   DICYRQQRKG  AWAFSTRDQG  YAVCDCVSEA  LKSVILLQHT  PGFPQLLEDQ

CONSENSUS 5        RIFDAiDTLL  TYQNKSGACS  SYEPTRGSEl  LEMLNAAEVF  gKIMVEYDYV
5:HypCI4A-323210   RIFDAIDTLL  TYQNKSGACS  SYEPTRGSEV  LEMLNAAEVF  AKIMVEYDYV
5:HypCO27-37618    RIFDAIDTLL  TYQNKSGACS  SYEPTRGSEL  LEMLNAAEVF  GKIMVEYDYV
5:HypEC38-80359    RIFDAIDTLL  TYQNKSGACS  SYEPTRGSEL  LEMLNAAEVF  GKIMVEYDYV
5:DalEC12-315006   RIFDAVDTLL  TYQNKSGACS  SYEPTRGSEL  LEMLNAAEVF  GKIMVEYDYV

CONSENSUS 5        ECTTAVVTAL  XLFQKHWPDY  RpqEIksFIG  RSVKAVKXLQ  rPDGsWYGNW
5:HypCI4A-323210   ECTTAVVTAL  SLFQKHWPDY  RTQEIKSFIG  RSVKAVKSLQ  RPDGAWYGNW
5:HypCO27-37618    ECTTAVVTAL  MLFQKHWPDY  RPQEIKSFIG  RSVKAVKRLQ  RPDGSWYGNW
5:HypEC38-80359    ECTTAVVTAL  MLFQKHWPDY  RPQEIKSFIG  RSVKAVKRLQ  RPDGSWYGNW
5:DalEC12-315006   ECTTAVVTAL  SLFQKHWPDY  RPKEIEAFIG  RSVKAVKSLQ  QPDGSWYGNW

CONSENSUS 5        AICfTYATMF  ALESLkSIGE  TYXNSsYSKR  GCZFLISKQR  EDGGWSESYR
5:HypCI4A-323210   AICFTYATMF  ALESLESIGE  TYGNSSYSKR  GCKFLISKQR  EDGGWSESYR
5:HypCO27-37618    AICFTYATMF  ALESLKSIGE  TYNNSPYSKR  GCDFLISKQR  EDGGWSESYR
5:HypEC38-80359    AICFTYATMF  ALESLKSIGE  TYNNSSYSKR  GCDFLISKQR  EDGGWSESYR
5:DalEC12-315006   AICYTYATMF  ALESLKSIGE  TYGNSSYSKR  GCDFLISKQR  EDGGWSESYR

CONSENSUS 5        SCEkMmYXEH  XTGSQVVMTA  WALIgLMKAD  YPDIePlKKG  IKLIMDRQQP
5:HypCI4A-323210   SCENMVYTEH  PTGSQVVMTA  WALIALMKAD  YPDIEPLKKG  IKLIMDRQQP
5:HypCO27-37618    SCEKMMYIEH  HTGSQVVMTA  WALIGLMKAD  YPDIEPLKKG  IKLIMDRQQP
5:HypEC38-80359    SCEKMMYIEH  HTGSQVVMTA  WALIGLMKAD  YPDIEPIKKG  IKLIMDRQQP
5:DalEC12-315006   SCERMIYTEH  PTGSQVVMTA  WALIGLMKAD  YPDIKPLKKG  IKLIMDRQQP

CONSENSUS 5        NGEWKQEAIE  GVFNKSCMIS  YPNYKFTFTM  KALGMFAXKY  PnETVX  (SEQ ID NO:50)
5:HypCI4A-323210   NGEWKQEAIE  GVFNKSCMIS  YPNYKFTFTM  KALGMFATKY  PNETVV  (SEQ ID NO:51)
5:HypCO27-37618    NGEWKQEAIE  GVFNKSCMIS  YPNYKFTFTM  KALGMFAQKY  PDETVI  (SEQ ID NO:52)
5:HypEC38-80359    NGEWKQEAIE  GVFNKSCMIS  YPNYKFTFTM  KALGMFAQKY  PNETVI  (SEQ ID NO:53)
5:DalEC12-315006   NGEWKQEAIE  GVFNKSCMIS  YPNYKFTFTM  KALGMFATKY  PNETVV  (SEQ ID NO:54)
```

FIG. 8B-2

NON-CLUSTERED
>N:HypCI4A-7067 (SEQ ID NO:61)
MTFFAASWWPYAPYETLEIVARLAIWFFVWDDETDPDESSAMVDNWGRVSIFRQRTVDLVRQSLTETTDP
KPLEGSSEPIIAFFGPVGEAVFRSCNKRQSNSFLEELLFYINMCGEEQKFYTTQSIPTVEEYIQTRVGSG
AARACLATVEYAYGITVPEEIMNDEMMQQLWHEAAMIIHTTNDILSFKKEISQSQVASLIPLLIPQVGSV
QLATNHAAEIVKSSIDRFDAIERQFLERYSTTPEVQEGVRKVIEGYKYACTANLNWSLITGRYKLNCESM
SGGLHITL

>N:DalEC12-24646 (SEQ ID NO:62)
MSILDTKTDFDLLLGKCIGQRVEIPDLFALCPWGLEVSPLDEKLTMEVELWRSRWINDPTSLKRNRIVES
CLFARGIAPKAALNELITLAKYQAWLFYWDDVYDFGDFNDKYEEIVSHQEQTIELLHRSLFEKDPGSIDP
AKIAPNYLTVQSIYEWASVVREKSVSSSLKIWLLKVLVDFCTATFYLQSAFDKRRILDLETYRKIRMDSS
AVFPTLGMVLFTDQVAFPPWFFDHVSIKKAAELVNIIVWVTNDIVSARQELQCKHLDNLIPLLVHHRGIT
LQEAIREASKITHQAYLDFEELEPQLMQLGENRGVVYEMQRFVASCRHVCTGIFNWTYHIKRYILWEPGM
TRSGLSTVLGEDLLKK

>N:HypCI4A-69724 (SEQ ID NO:63)
MSNSCELVGHGQTRQSVRIPDLFSSIMASKPVVNPNYFKVKAEGDRWITRIAKMDEKARAKNTRVDLCYL
VSIWAPDADEEALRMMLDWNHWVFLFDDQFDEGHLKEDLKAAQEEVDGTVAVMEEDAPLVKLEENPLRYI
FQSCWLRLKERASHAELQQRYKEQHIRFFDQLVVQVRQAAQGQILSRDVQTYIEVRRGTIGAYPAIALTE
YAQGVRLPGSVFSHNSLQECMRVSSDLVLLVNDVLSYRKDLELGVDHNLIALLIEQRMSLQQSVDKIGTM
IDNCYRRWYTALAELPPYGEEVDREVLYFVEVCRRIALGNLHWSFKTGRYLGPEGHEVHETRTMYI

>N:DalEC12-70183 (SEQ ID NO:64)
MLDSSELAEPHEGRRSVRIPDLFSSIMATKPVVNPNYFKVKAAGDRWIKRIMKMDEKASDKNSKVDFCYM
ICIWAPDADEEALRIMLDWNNWIFLFDDQFDEGHLKDDPVAAQQEVNATMAVMEDDSPLVRPEESPILYV
FQTCWLRLKQRAPTEIQQRYKERHKRYFDQLVAQVQEIARGQVLTGDVVTYLEARRRTIGVYPAITLAEY
GEGVRLSDSVLSHHSLQECMRITADLVILVNDILSYKKDLDLGVDYNLITLLMKQNLSLQESMDKIGALI
ESCYRNWYLTLAELPLYGEETDNEVLRFVEACRCVALGNLYWSFKTGRYLGSEGHDLHKTRTMYL

FIG. 9A

```
CONSENSUS 6           -----XXXsX XlXXXXXXrq svripdlfXs X---maXXpX XnXnXfkvka
N:HypCI4A-7067        ---------- ---------- ---------- ---------- ----------
N:DalEC12-24646       MSILDTKTDF DLLLGKCIGQ RVEIPDLFAL CPWGLEVSPL DEKLTMEVEL
N:HypCI4A-69724       -----MSNSC ELVGHGQTRQ SVRIPDLFSS I---MASKPV VNPNYFKVKA
N:DalEC12-70183       -----MLDSS ELAEPHEGRR SVRIPDLFSS I---MATKPV VNPNYFKVKA CONSENSUS 6           XXXrwiXXX- XXdXXXXXXn XXvdXcXfaX iwaPdAdXea LrXmXdwXXW
N:HypCI4A-7067        ---------- ---------- ----MTFFAA SWWPYAPYET LEIVARLAIW
N:DalEC12-24646       WRSRWIN--- --DPTSLKRN RIVESCLFAR GIAPKAALNE LITLAKYQAW
N:HypCI4A-69724       EGDRWITRIA KMDEKARAKN TRVDLCYLVS IWAPDADEEA LRMMLDWNHW
N:DalEC12-70183       AGDRWIKRIM KMDEKASDKN SKVDFCYMIC IWAPDADEEA LRIMLDWNNW CONSENSUS 6           XFlXDDZZDX gh---XkddX XaaqXXXXXT XaXmX-XX-X --dXXpl---
N:HypCI4A-7067        FFVWDDETDP DESSAMVDNW GRVSIFRQRT VDLVRQSLTE TTDPKPLEGS
N:DalEC12-24646       LFYWDDVYDF GD---FNDKY EEIVSHQEQT IELLHRSLFE K-DPGSID--
N:HypCI4A-69724       VFLFDDQFDE GH---LKEDL KAAQEEVDGT VAVME----- --EDAPL---
N:DalEC12-70183       IFLFDDQFDE GH---LKDDP VAAQQEVNAT MAVME----- --DDSPL---

CONSENSUS 6           ---XXpXXXp X-XXXfqscX XXXX-XX--X eXqqXXkXXh Xrff-----d
N:HypCI4A-7067        SEPIIAFFGP VGEAVFRSC- ---------N KRQSNSFLEE LLFY------I
N:DalEC12-24646       PAKIAPNYLT V-QSIYEWA- ---------S VVREKSVSSS LKIWLLKVLV
N:HypCI4A-69724       ---VKLEENP L-RYIFQSCW LRLKERASHA ELQQRYKEQH IRFF-----D
N:DalEC12-70183       ---VRPEESP I-LYVFQTCW LRLKQRAP-T EIQQRYKERH KRYF-----D CONSENSUS 6           qXXXqX---q XaaXXqXXX- dvetYiXXRr XXiXXXpaXa XXeyaXgvXl
N:HypCI4A-7067        NMCGEE---Q KFYTTQSIP- TVEEYIQTRV GSGAARACLA TVEYAYGITV
N:DalEC12-24646       DFCTATFYLQ SAFDKRRIL- DLETYRKIRM DSSAVFPTLG MVLFTDQVAF
N:HypCI4A-69724       QLVVQV---R QAAQGQILSR DVQTYIEVRR GTIGAYPAIA LTEYAQGVRL
N:DalEC12-70183       QLVAQV---Q EIARGQVLTG DVVTYLEARR RTIGVYPAIT LAEYGEGVRL CONSENSUS 6           pXsXfshXsX qXcXrXXadX vXlXNDZZSZ ZZZlXXXXdX nLIXLLiXqr
N:HypCI4A-7067        PEEIMNDEMM QQLWHEAAMI IHTTNDILSF KKEISQSQVA SLIPLLIPQV
N:DalEC12-24646       PPWFFDHVSI KKAAELVNII VWVTNDIVSA RQELQCKHLD NLIPLLVHHR
N:HypCI4A-69724       PGSVFSHNSL QECMRVSSDL VLLVNDVLSY RKDLELGVDH NLIALLIEQR
N:DalEC12-70183       SDSVLSHHSL QECMRITADL VILVNDILSY KKDLDLGVDY NLITLLMKQN CONSENSUS 6           g-slQXXXdk XXXiiXsXyr XXXXXXaXlp X-yge--evd XevXrfveXc
N:HypCI4A-7067        G-SVQLATNH AAEIVKSSID RFDAIERQFL ERYSTTPEVQ EGVRKVIEGY
N:DalEC12-24646       GITLQEAIRE ASKITHQAYL DFEELEPQLM Q-LGENRGVV YEMQRFVASC
N:HypCI4A-69724       M-SLQQSVDK IGTMIDNCYR RWYTALAELP P-YGE--EVD REVLYFVEVC
N:DalEC12-70183       L-SLQESMDK IGALIESCYR NWYLTLAELP L-YGE--ETD NEVLRFVEAC CONSENSUS 6           rXXXXgnlnW sfXtgRY-LX XegX--hglh XtXtmXX---   (SEQ ID NO:60)
N:HypCI4A-7067        KYACTANLNW SLITGRYKLN CESMS-GGLH ITL-------   (SEQ ID NO:61)
N:DalEC12-24646       RHVCTGIFNW TYHIKRYILW EPGMTRSGLS TVLGEDLLKK   (SEQ ID NO:62)
N:HypCI4A-69724       RRIALGNLHW SFKTGRY-LG PEG---HEVH ETRTMYI---   (SEQ ID NO:63)
N:DalEC12-70183       RCVALGNLYW SFKTGRY-LG SEG---HDLH KTRTMYL---   (SEQ ID NO:64)
```

FIG. 9B

| | | |
|---|---|---|
| CONSENSUS 1A | XXZZXXZX | (SEQ ID NO:71) |
| CONSENSUS 1B | ZZXXZ | (SEQ ID NO:72) |
| 1:HypCI4A-20984 | YWDDLSEK | |
| 1:HypCO27-269219 | YWDDLVEG | |
| 1:HypEC38-3887 | HWDDLVEG | |
| 1:DalEC12-25458 | YWDDLSES | |
| 2:HypCI4A-216497 | VWDDEVDA | |
| 2:HypCO27-31178 | VWDDEIDA | |
| 2:DalEC12-17536 | VWDDEVDA | |
| 2:HypEC38-200002.1 | VWDDEIDA | |
| 3:HypCI4A-6706 | FWDDEIDN | |
| 3:HypCO27-397991 | FWDDEIDT | |
| 3:DalEC12-24764 | FWDDEIDT | |
| 3:HypEC38-373976 | FWDDEIDT | |
| 4:HypCI4A-322581 | LIDDLLEY | |
| 4:HypCO27-392541 | LVDDILEH | |
| 4:DalEC12-12539 | LIDDVLED | |
| 4:HypEC38-328361 | LVDDILEH | |
| 4:HypEC38-80361 | LIDDVLEN | |
| 4:HypCI4A-59230 | LIDDILEE | |
| 5:HypCI4A-323210 | VSEHDFEN | |
| 5:HypCO27-37618 | ASDDKLET | |
| 5:HypEC38-80359 | ASDDKLET | |
| 5:DalEC12-315006 | VSEDAPET | |
| N:HypCI4A-7067 | VWDDETDP | |
| N:DalEC12-24646 | YWDDVYDF | |
| N:HypCI4A-69724 | LFDDQFDE | |
| N:DalEC12-70183 | LFDDQFDE | |

FIG. 10A

| | | |
|---|---|---|
| CONSENSUS 1C | XXZDXXZX | (SEQ ID NO:73) |
| CONSENSUS 1D | ZDXXZ | (SEQ ID NO:74) |
| 2:DalEC12-17536 | VWDDEVDA | |
| 2:HypEC38-200002.1 | VWDDEIDA | |
| 3:HypCI4A-6706 | FWDDEIDN | |
| 3:HypCO27-397991 | FWDDEIDT | |
| 3:HypEC38-373976 | FWDDEIDT | |
| 4:HypCI4A-322581 | LIDDLLEY | |
| 4:HypCO27-392541 | LVDDILEH | |
| 4:HypEC38-328361 | LVDDILEH | |
| 4:HypEC38-80361 | LIDDVLEN | |
| 5:DalEC12-315006 | VSEDAPET | |
| N:DalEC12-24646 | YWDDVYDF | |
| N:DalEC12-70183 | LFDDQFDE | |

FIG. 10B

```
CONSENSUS 2A        XZZXXXSXXZ ZXX  (SEQ ID NO:75)
CONSENSUS 2B         ZZXXXSXXZ Z    (SEQ ID NO:76)
1:HypCI4A-20984     VNDLI-SFKK EMK
1:HypCO27-269219    VNDLV-SFKK EMK
1:HypEC38-3887      VNDLI-SFKK EMK
1:DalEC12-25458     VNDLI-SFKK EMK
2:HypCI4A-216497    LNDVY-SVQK EIA
2:HypCO27-31178     LNDVY-SVQK EIA
2:DalEC12-17536     LNDVY-SVQK EIA
2:HypEC38-200002.1  LNDVY-SVQK EIA
2:HypEC38-200002.2  LNDVY-SV-- --A
3:HypCI4A-6706      LNDVL-SLQK EFR
3:HypCO27-397991    LNDVL-SLQK EFR
3:DalEC12-24764     LNDVL-SFQK EFR
3:HypEC38-373976    LNDVL-SLQK EFR
4:HypCI4A-322581    INDIW-SFEK ELL
4:HypCO27-392541    INDIW-SYEK EVL
4:DalEC12-12539     MNDIW-SFEK EAL
4:HypEC38-328361    INDIW-SYEK EVL
4:HypEC38-80361     INDIW-SFEK EAL
4:HypCI4A-59230     VNDIY-SFEK EVI
5:HypCI4A-323210    RCKFLISKQR EDG
5:HypCO27-37618     RCDFLISKQR EDG
5:HypEC38-80359     RCDFLISKQR EDG
5:DalEC12-315006    RCDFLISKQR EDG
N:HypCI4A-7067      TNDIL-SFKK EIS
N:DalEC12-24646     TNDIV-SARQ ELQ
N:HypCI4A-69724     VNDVL-SYRK DLE
N:DalEC12-70183     VNDIL-SYKK DLD
```

FIG. 11A

```
CONSENSUS 2C        XZDXXXSXXZ ZXX  (SEQ ID NO:77)
CONSENSUS 2D         ZDXXXSXXZ Z    (SEQ ID NO:78)
2:DalEC12-17536     LNDVY-SVQK EIA
2:HypEC38-200002.1  LNDVY-SVQK EIA
3:HypCI4A-6706      LNDVL-SLQK EFR
3:HypCO27-397991    LNDVL-SLQK EFR
3:HypEC38-373976    LNDVL-SLQK EFR
4:HypCI4A-322581    INDIW-SFEK ELL
4:HypCO27-392541    INDIW-SYEK EVL
4:HypEC38-328361    INDIW-SYEK EVL
4:HypEC38-80361     INDIW-SFEK EAL
5:DalEC12-315006    RCDFLISKQR EDG
N:DalEC12-24646     TNDIV-SARQ ELQ
N:DalEC12-70183     VNDIL-SYKK DLD
```

FIG. 11B

| Protein ID | SEQ ID NO: | Aspartate Rich Motif | NSE/DTE Triad |
|---|---|---|---|
| *Cluster 1* | | DDXXE | NDXXSXXKE |
| HypCI4A-20984 | 11 | GYDDLEEKLVPPEAG | IVDLIFKKEMKA |
| HypCO27-269219 | 12 | LYDDLVEGLADAAA | IVDLVFKKEMKA |
| DalEC38-3887 | 13 | LDDLVEGLADPEAA | IVDLIFKKEMKA |
| DalEC12-25458 | 14 | GYDDLEELAVDEVAA | IVDLIFKKEMKA |
| *Cluster 2* | | DDXXD | NDXXSXXKE |
| HypCI4A-216497 | 21 | IFVDDEVDAGDDVEL | ILDVYVKEIA |
| HypCO27-31178 | 22 | IFVDDEIDAGDDVE | ILDVYVKEIA |
| DalEC12-17536 | 23 | IFVDDEVDAGDDVE | ILDVYVKEIA |
| DalEC38-200002 | 24 | IFVDDEIDAGDDVE | ILDVYVKEIA |
| *Cluster 3* | | DDXXD | NDXXSXXKE |
| HypCI4A-6706 | 31 | FDDEIDGGELDDEE | LLDVLLQKEFRV |
| HypCO27-397991 | 32 | FDDEIDGGDLEDEE | LLDVLLQKEFRV |
| DalEC12-24764 | 33 | FDDEIDGGDLEDRE | LLDVLFQKEFRV |
| DalEC38-373976 | 34 | FDDEIDGGELEDEE | LLDVLLQKEFRV |
| *Cluster 4* | | DDXXE | NDXXSXXKE |
| HypCI4A-322581 | 41 | FLIDDLLEYMLEDGRAY | VIDIFKELLAEKA |
| HypCO27-392541 | 42 | FLVDDILEMMLEDGRAY | VIDIYEKEVLAAEL |
| DalEC12-12539 | 43 | FLIDDVLEDMFEEGAY | IMDIFEKEALAAEG |
| DalEC38-328361 | 44 | FLVDDILEMMLEDGRAY | VIDIYEKEVLAAEL |
| DalEC38-80361 | 45 | FLIDDVLEMMFEEGAY | VIDIFEKEALAAEA |
| HypCI4A-59230 | 49 | FLIDDILEEMFADGEAL | IVDIYFEKEVIAAKG |
| *Cluster 5* | | DDXXE | X(D/K)XXXSXXRE |
| HypCI4A-323210 | 51 | VEDDFEEVKRPRVEEE | RGEDFLIKQREDGG |
| HypCO27-37618 | 52 | ADDRLEELEKPRLEEE | RGEDFLIKQREDGG |
| DalEC38-80359 | 53 | ADDRLEEIEKPRLEEE | RGEDFLIKQRDGG |
| DalEC12-315006 | 54 | VEDAEEEVKRPRLEER | RGEDFLIKQREDGG |
| *Non-Clustered* | | DDXXD | NDXXSXXK(E/D) |
| HypCI4A-7067 | 61 | FVDDEEDPDEEEAMVD | EDILFKKEIEG |
| DalEC12-24646 | 62 | FXDDVYDFG---DFED | VDIVAQELQC |
| HypCI4A-69724 | 63 | FLFDDFDEG---LEE | LVDVLYKKDLEL |
| DalEC12-70183 | 64 | FLFDDFDEG---LKD | LVDILYKKDLDL |

FIG. 12A

| Protein ID | Major Products |
|---|---|
| *Cluster 1* | None detected |
| HypCI4A-20984 | |
| HypCO27-269219 | |
| DalEC38-3887 | |
| DalEC12-25458 | |
| *Cluster 2* | β-*cis*-ocimene, β-pinene, 1S-α-pinene,α-selinene, α-guaiene, viridiflorol, δ-guaiene, (-)-β-elemene, and (-)-alloaromadendrene |
| HypCI4A-216497 | |
| HypCO27-31178 | |
| DalEC12-17536 | |
| DalEC38-200002 | |
| *Cluster 3* | β-caryophyllene, humulen-(V1), (-)-α-neoclovene, α-gurjunene, α-selinene,α-guaiene, (+)-longifolene, thujopsene-i3,β-pinene, α-himachalene, β-cubebene, τ-gurjunene, δ-elemene, α-caryophyllene, 1S-α-pinene, aromadendrene, and (+)-valencene |
| HypCI4A-6706 | |
| HypCO27-397991 | |
| DalEC12-24764 | |
| DalEC38-373976 | |
| *Cluster 4* | β-chamigrene, β-pinene, α-limonene,2-carene, β-*cis*-ocimene, (-)-β-elemene, 4-methyl-3-(1-methylethyldene)-1-cyclohexene, (+)-valencene, τ-terpinene, α-gurjunene, (-)-alloaromadendrene, β-farnesene, β-caryophyllene, (-)-isoledene, and 1S-α-pinene |
| HypCI4A-322581 | |
| HypCO27-392541 | |
| DalEC12-12539 | |
| DalEC38-328361 | |
| DalEC38-80361 | |
| HypCI4A-59230 | |
| *Cluster 5* | τ-gurjunene, τ-muurolene, β-pinene, τ-elemene, 1S-α-pinene, α-gurjunene, β-*cis*-ocimene, α-selinene, and (-)-alloaromadendrene |
| HypCI4A-323210 | |
| HypCO27-37618 | |
| DalEC38-80359 | |
| DalEC12-315006 | |
| *Non-Clustered* | α-selinene,(-)-alloaromadendrene, τ-elemene, β-pinene, β-cubebene, β-*cis*-ocimene, α-gurjunene, 1H-cyclopropa-α-naphthalene, (-)-isoledene, β-caryophyllene, (-)-alloaromadendrene, α-gurjunene, and (+)-valencene |
| HypCI4A-7067 | |
| DalEC12-24646 | |
| HypCI4A-69724 | |
| DalEC12-70183 | |

FIG. 12B

| Cluster | Gene Name | Enzyme Function | JGI Protein ID |
|---|---|---|---|
| 2 | DalEC12-PGS | Pinene and Guaiene Synthase | 17536 |
| | DalEC38-PGS | | 200002 |
| 3 | HypC14A-CS | Caryophyllene Synthase | 6706 |
| | HypCO27-CS | | 397991 |
| | DalEC38-CS | | 373976 |
| 4 | HypC14A-CPS | Chamigrene and Pinene Synthase | 322581 |
| | HypCO27-CPS | | 392541 |
| | DalEC38-CPS | | 328361 |
| | DalEC38-GPS | Gurjunene and Pinene Synthase | 80361 |
| 5 | DalEC12-GS | Gurnunene Synthase | 315006 |
| Non-clustered | DalEC12-SS | Selinene Synthase | 24646 |
| | DalEC12-ILS | IsoLedene Synthase | 70183 |

FIG. 13

| Clusters | Compounds | EC12-GS, % of total Peak Area | | | |
|---|---|---|---|---|---|
| Cluster 5 | τ-gurnunene | 58.03 | | | |
| | τ-muurolene | 3.88 | | | |
| | β-pinene | 3.71 | | | |
| EC12-SS | α-selinene | 50.71 | | | |
| | (-)-alloaromadendrene | 8.15 | | | |
| | τ-elemene | 6.71 | | | |
| EC12-ILS | (-)-isoledene | 10.8 | | | |
| | iso-longifolene | 6.76 | | | |
| | β-caryophyllene | 6.71 | | | |
| Cluster 2 | Compounds | EC12-PGS, % of total Peak Area | EC12-PGS, % of total Peak Area | | |
| | β-pinene | 17.64 | 9.4 | | |
| | α-pinene | 16.92 | 21.04 | | |
| | β-cis-ocimene | 21.06 | 44.52 | | |
| | α-guaiene | 11.03 | 8.16 | | |
| Cluster 3 | Compounds | C14A-CS, % of total Peak Area | EC38-CS, % of total Peak Area | CO27-CS, % of total Peak Area | |
| | caryophyllene-(II) | 12.24 | 18.1 | 21.94 | |
| | β-caryophyllene | 12.75 | 13.06 | 12.46 | |
| | α-selinene | 6.74 | 7.59 | 9.81 | |
| | humulen-(vl) | 12.21 | 5.94 | 6.71 | |
| Cluster 4 | Compounds | EC38-CPS, % of total Peak Area | C14A-CPS, % of total Peak Area | EC38-GPS, % of total Peak Area | CO27-CPS, % of total Peak Area |
| | β-chamigrene | 24.38 | 61.28 | β-elemene, 4.60 | 65.35 |
| | α-gurjunene | 2-carene, 2.23 | β-cis-ocimene, 2.53 | 20.41 | β-elemene, 3.99 |
| | α-limonene | 10.23 | 3.8 | 9.83 | 3.89 |
| | β-pinene | 30.71 | 16.24 | 16.36 | 10.39 |

FIG. 14

SEQUENCE LISTING

<160> NUMBER OF SEQ ID NOS: 78

<210> SEQ ID NO 1
<211> LENGTH: 23
<212> TYPE: DNA
<213> ORGANISM: Artificial Sequence
<220> FEATURE:
<223> OTHER INFORMATION: Synthetic primer

<400> SEQUENCE: 1
gtgtggaatt gtgagcggat aac                                              23

<210> SEQ ID NO 2
<211> LENGTH: 34
<212> TYPE: DNA
<213> ORGANISM: Artificial Sequence
<220> FEATURE:
<223> OTHER INFORMATION: Synthetic primer

<400> SEQUENCE: 2
ggatccctcg agtcaattt gtctgaatgc cacg                                  34

<210> SEQ ID NO 3
<211> LENGTH: 23
<212> TYPE: DNA
<213> ORGANISM: Artificial Sequence
<220> FEATURE:
<223> OTHER INFORMATION: Synthetic primer

<400> SEQUENCE: 3
catccggctc gtataatgtg tgg                                              23

<210> SEQ ID NO 4
<211> LENGTH: 22
<212> TYPE: DNA
<213> ORGANISM: Artificial Sequence
<220> FEATURE:
<223> OTHER INFORMATION: Synthetic primer

<400> SEQUENCE: 4
gctcctcggt tcctccaaca ag                                               22

<210> SEQ ID NO 5

<400> SEQUENCE: 5

000

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000

-continued

```
<210> SEQ ID NO 9

<400> SEQUENCE: 9

000

<210> SEQ ID NO 10
<211> LENGTH: 379
<212> TYPE: PRT
<213> ORGANISM: Artificial Sequence
<220> FEATURE:
<223> OTHER INFORMATION: Consensus polypeptide sequence
<220> FEATURE:
<221> NAME/KEY: MISC_FEATURE
<222> LOCATION: (1)..(2)
<223> OTHER INFORMATION: absent or any amino acid (e.g., an amino acid
      present at a position in one of SEQ ID NOs:11-14 when optimally
      aligned with SEQ ID NO:10)
<220> FEATURE:
<221> NAME/KEY: MISC_FEATURE
<222> LOCATION: (36)..(36)
<223> OTHER INFORMATION: absent or any amino acid (e.g., an amino acid
      present at a position in one of SEQ ID NOs:11-14 when optimally
      aligned with SEQ ID NO:10)
<220> FEATURE:
<221> NAME/KEY: MISC_FEATURE
<222> LOCATION: (40)..(40)
<223> OTHER INFORMATION: absent or any amino acid (e.g., an amino acid
      present at a position in one of SEQ ID NOs:11-14 when optimally
      aligned with SEQ ID NO:10)
<220> FEATURE:
<221> NAME/KEY: MISC_FEATURE
<222> LOCATION: (46)..(47)
<223> OTHER INFORMATION: absent or any amino acid (e.g., an amino acid
      present at a position in one of SEQ ID NOs:11-14 when optimally
      aligned with SEQ ID NO:10)
<220> FEATURE:
<221> NAME/KEY: MISC_FEATURE
<222> LOCATION: (50)..(50)
<223> OTHER INFORMATION: absent or any amino acid (e.g., an amino acid
      present at a position in one of SEQ ID NOs:11-14 when optimally
      aligned with SEQ ID NO:10)
<220> FEATURE:
<221> NAME/KEY: MISC_FEATURE
<222> LOCATION: (63)..(64)
<223> OTHER INFORMATION: absent or any amino acid (e.g., an amino acid
      present at a position in one of SEQ ID NOs:11-14 when optimally
      aligned with SEQ ID NO:10)
<220> FEATURE:
<221> NAME/KEY: MISC_FEATURE
<222> LOCATION: (66)..(67)
<223> OTHER INFORMATION: absent or any amino acid (e.g., an amino acid
      present at a position in one of SEQ ID NOs:11-14 when optimally
      aligned with SEQ ID NO:10)
<220> FEATURE:
<221> NAME/KEY: MISC_FEATURE
<222> LOCATION: (73)..(73)
<223> OTHER INFORMATION: absent or any amino acid (e.g., an amino acid
      present at a position in one of SEQ ID NOs:11-14 when optimally
      aligned with SEQ ID NO:10)
<220> FEATURE:
<221> NAME/KEY: MISC_FEATURE
<222> LOCATION: (87)..(87)
<223> OTHER INFORMATION: absent or any amino acid (e.g., an amino acid
      present at a position in one of SEQ ID NOs:11-14 when optimally
      aligned with SEQ ID NO:10)
<220> FEATURE:
<221> NAME/KEY: MISC_FEATURE
<222> LOCATION: (97)..(97)
<223> OTHER INFORMATION: absent or any amino acid (e.g., an amino acid
       present at a position in one of SEQ ID NOs:11-14 when optimally
      aligned with SEQ ID NO:10)
<220> FEATURE:
<221> NAME/KEY: MISC_FEATURE
<222> LOCATION: (103)..(103)
<223> OTHER INFORMATION: absent or any amino acid (e.g., an amino acid
      present at a position in one of SEQ ID NOs:11-14 when optimally
      aligned with SEQ ID NO:10)
```

-continued

```
<220> FEATURE:
<221> NAME/KEY: MISC_FEATURE
<222> LOCATION: (105)..(105)
<223> OTHER INFORMATION: absent or any amino acid (e.g., an amino acid
      present at a position in one of SEQ ID NOs:11-14 when optimally
      aligned with SEQ ID NO:10)
<220> FEATURE:
<221> NAME/KEY: MISC_FEATURE
<222> LOCATION: (108)..(108)
<223> OTHER INFORMATION: absent or any amino acid (e.g., an amino acid
      present at a position in one of SEQ ID NOs:11-14 when optimally
      aligned with SEQ ID NO:10)
<220> FEATURE:
<221> NAME/KEY: MISC_FEATURE
<222> LOCATION: (119)..(119)
<223> OTHER INFORMATION: absent or any amino acid (e.g., an amino acid
      present at a position in one of SEQ ID NOs:11-14 when optimally
      aligned with SEQ ID NO:10)
<220> FEATURE:
<221> NAME/KEY: MISC_FEATURE
<222> LOCATION: (126)..(126)
<223> OTHER INFORMATION: absent or any amino acid (e.g., an amino acid
      present at a position in one of SEQ ID NOs:11-14 when optimally
      aligned with SEQ ID NO:10)
<220> FEATURE:
<221> NAME/KEY: MISC_FEATURE
<222> LOCATION: (131)..(135)
<223> OTHER INFORMATION: absent or any amino acid (e.g., an amino acid
      present at a position in one of SEQ ID NOs:11-14 when optimally
      aligned with SEQ ID NO:10)
<220> FEATURE:
<221> NAME/KEY: MISC_FEATURE
<222> LOCATION: (139)..(139)
<223> OTHER INFORMATION: absent or any amino acid (e.g., an amino acid
      present at a position in one of SEQ ID NOs:11-14 when optimally
      aligned with SEQ ID NO:10)
<220> FEATURE:
<221> NAME/KEY: MISC_FEATURE
<222> LOCATION: (144)..(144)
<223> OTHER INFORMATION: absent or any amino acid (e.g., an amino acid
      present at a position in one of SEQ ID NOs:11-14 when optimally
      aligned with SEQ ID NO:10)
<220> FEATURE:
<221> NAME/KEY: MISC_FEATURE
<222> LOCATION: (153)..(154)
<223> OTHER INFORMATION: absent or any amino acid (e.g., an amino acid
      present at a position in one of SEQ ID NOs:11-14 when optimally
      aligned with SEQ ID NO:10)
<220> FEATURE:
<221> NAME/KEY: MISC_FEATURE
<222> LOCATION: (158)..(158)
<223> OTHER INFORMATION: absent or any amino acid (e.g., an amino acid
      present at a position in one of SEQ ID NOs:11-14 when optimally
      aligned with SEQ ID NO:10)
<220> FEATURE:
<221> NAME/KEY: MISC_FEATURE
<222> LOCATION: (172)..(172)
<223> OTHER INFORMATION: absent or any amino acid (e.g., an amino acid
      present at a position in one of SEQ ID NOs:11-14 when optimally
      aligned with SEQ ID NO:10)
<220> FEATURE:
<221> NAME/KEY: MISC_FEATURE
<222> LOCATION: (215)..(215)
<223> OTHER INFORMATION: absent or any amino acid (e.g., an amino acid
      present at a position in one of SEQ ID NOs:11-14 when optimally
      aligned with SEQ ID NO:10)
<220> FEATURE:
<221> NAME/KEY: MISC_FEATURE
<222> LOCATION: (219)..(219)
<223> OTHER INFORMATION: absent or any amino acid (e.g., an amino acid
      present at a position in one of SEQ ID NOs:11-14 when optimally
      aligned with SEQ ID NO:10)
<220> FEATURE:
<221> NAME/KEY: MISC_FEATURE
<222> LOCATION: (232)..(232)
<223> OTHER INFORMATION: absent or any amino acid (e.g., an amino acid
      present at a position in one of SEQ ID NOs:11-14 when optimally
      aligned with SEQ ID NO:10)
<220> FEATURE:
```

```
<221> NAME/KEY: MISC_FEATURE
<222> LOCATION: (236)..(237)
<223> OTHER INFORMATION: absent or any amino acid (e.g., an amino acid
      present at a position in one of SEQ ID NOs:11-14 when optimally
      aligned with SEQ ID NO:10)
<220> FEATURE:
<221> NAME/KEY: MISC_FEATURE
<222> LOCATION: (240)..(240)
<223> OTHER INFORMATION: absent or any amino acid (e.g., an amino acid
      present at a position in one of SEQ ID NOs:11-14 when optimally
      aligned with SEQ ID NO:10)
<220> FEATURE:
<221> NAME/KEY: MISC_FEATURE
<222> LOCATION: (249)..(249)
<223> OTHER INFORMATION: absent or any amino acid (e.g., an amino acid
      present at a position in one of SEQ ID NOs:11-14 when optimally
      aligned with SEQ ID NO:10)
<220> FEATURE:
<221> NAME/KEY: MISC_FEATURE
<222> LOCATION: (272)..(272)
<223> OTHER INFORMATION: absent or any amino acid (e.g., an amino acid
      present at a position in one of SEQ ID NOs:11-14 when optimally
      aligned with SEQ ID NO:10)
<220> FEATURE:
<221> NAME/KEY: MISC_FEATURE
<222> LOCATION: (297)..(297)
<223> OTHER INFORMATION: absent or any amino acid (e.g., an amino acid
      present at a position in one of SEQ ID NOs:11-14 when optimally
      aligned with SEQ ID NO:10)
<220> FEATURE:
<221> NAME/KEY: MISC_FEATURE
<222> LOCATION: (308)..(308)
<223> OTHER INFORMATION: absent or any amino acid (e.g., an amino acid
      present at a position in one of SEQ ID NOs:11-14 when optimally
      aligned with SEQ ID NO:10)
<220> FEATURE:
<221> NAME/KEY: MISC_FEATURE
<222> LOCATION: (318)..(319)
<223> OTHER INFORMATION: absent or any amino acid (e.g., an amino acid
      present at a position in one of SEQ ID NOs:11-14 when optimally
      aligned with SEQ ID NO:10)
<220> FEATURE:
<221> NAME/KEY: MISC_FEATURE
<222> LOCATION: (331)..(333)
<223> OTHER INFORMATION: absent or any amino acid (e.g., an amino acid
      present at a position in one of SEQ ID NOs:11-14 when optimally
      aligned with SEQ ID NO:10)
<220> FEATURE:
<221> NAME/KEY: MISC_FEATURE
<222> LOCATION: (335)..(335)
<223> OTHER INFORMATION: absent or any amino acid (e.g., an amino acid
      present at a position in one of SEQ ID NOs:11-14 when optimally
      aligned with SEQ ID NO:10)
<220> FEATURE:
<221> NAME/KEY: MISC_FEATURE
<222> LOCATION: (337)..(338)
<223> OTHER INFORMATION: absent or any amino acid (e.g., an amino acid
      present at a position in one of SEQ ID NOs:11-14 when optimally
      aligned with SEQ ID NO:10)
<220> FEATURE:
<221> NAME/KEY: MISC_FEATURE
<222> LOCATION: (340)..(340)
<223> OTHER INFORMATION: absent or any amino acid (e.g., an amino acid
      present at a position in one of SEQ ID NOs:11-14 when optimally
      aligned with SEQ ID NO:10)
<220> FEATURE:
<221> NAME/KEY: MISC_FEATURE
<222> LOCATION: (342)..(353)
<223> OTHER INFORMATION: absent or any amino acid (e.g., an amino acid
      present at a position in one of SEQ ID NOs:11-14 when optimally
      aligned with SEQ ID NO:10)
<220> FEATURE:
<221> NAME/KEY: MISC_FEATURE
<222> LOCATION: (355)..(356)
<223> OTHER INFORMATION: absent or any amino acid (e.g., an amino acid
      present at a position in one of SEQ ID NOs:11-14 when optimally
      aligned with SEQ ID NO:10)
<220> FEATURE:
<221> NAME/KEY: MISC_FEATURE
```

<222> LOCATION: (358)..(360)
<223> OTHER INFORMATION: absent or any amino acid (e.g., an amino acid
      present at a position in one of SEQ ID NOs:11-14 when optimally
      aligned with SEQ ID NO:10)
<220> FEATURE:
<221> NAME/KEY: MISC_FEATURE
<222> LOCATION: (362)..(379)
<223> OTHER INFORMATION: absent or any amino acid (e.g., an amino acid
      present at a position in one of SEQ ID NOs:11-14 when optimally
      aligned with SEQ ID NO:10)

<400> SEQUENCE: 10

Xaa Xaa Met Ser Asp Tyr Asn Glu Lys Glu Leu Leu Ala Lys Arg Leu
 1               5                  10                  15

Lys Gly Gln Arg Leu Val Ile Pro Asp Met Arg Pro Ile Phe Ala His
             20                  25                  30

Trp Pro Ser Xaa Arg Asn Glu Xaa Tyr Gln Ala Val Lys Xaa Xaa Ile
         35                  40                  45

Asp Xaa Arg Leu Ala Lys Gln Thr Met Thr Asp Glu Ala Arg Xaa Xaa
     50                  55                  60

Phe Xaa Xaa Met Asn Pro Ala Leu Xaa Ala Ala Thr Trp Trp Pro Thr
 65                  70                  75                  80

Ser Ser Lys Asp His Tyr Xaa Ile Leu Val Asp Tyr Val Ile Trp Phe
                 85                  90                  95

Xaa Tyr Trp Asp Asp Leu Xaa Glu Xaa Leu Ala Xaa Asp Pro Ser Ala
            100                 105                 110

Ala Glu Asp Leu Arg Ser Xaa Thr Lys Thr Leu Val Arg Xaa Ser Leu
        115                 120                 125

Gly Leu Xaa Xaa Xaa Xaa Xaa Glu Lys Met Xaa Ile Ser Asn Pro Xaa
    130                 135                 140

Ile Leu Gly Phe Lys Asp Ile Ala Xaa Xaa Leu Cys Ser Xaa Tyr Asp
145                 150                 155                 160

Glu Glu Gln Arg Lys Val Leu Leu Gly His Phe Xaa Arg Tyr Ile Asp
                165                 170                 175

Ser Thr Leu Leu Glu Ala Glu Ala Asp Leu Ser Asp Lys Leu Pro Ser
            180                 185                 190

Leu Lys Arg Tyr Trp Glu Val Arg Ile Leu Thr Ser Gly Met Gly Thr
        195                 200                 205

Leu Leu Gly Val Thr Glu Xaa Ala Ala His Xaa Lys Leu Pro Ser Arg
    210                 215                 220

Leu Val His Ser Ala Ala Tyr Xaa Thr Leu Trp Xaa Xaa Thr Ile Xaa
225                 230                 235                 240

Ile Asn Ser Ile Val Asn Asp Leu Xaa Ser Phe Lys Lys Glu Met Lys
                245                 250                 255

Ala Gly Ser Val Leu Ser Ser Val Ala Ile Leu Tyr Gln Gln Val Xaa
            260                 265                 270

Asn Leu Asp Ala Ala Val Gln Met Ser Leu Ala His Leu Arg Ile Leu
        275                 280                 285

Val Asp Glu Phe Asp Arg Thr Ala Xaa Thr Ile Leu Ser Lys Phe Ser
    290                 295                 300

Leu Ala Pro Xaa Glu Ile Glu Pro Val Ser Lys Val Ile Xaa Xaa Leu
305                 310                 315                 320

Arg Met Val Asn Thr Gly Asn Leu Glu Trp Xaa Xaa Xaa Ala Xaa Arg
                325                 330                 335

Xaa Xaa Val Xaa Pro Xaa Xaa Xaa Xaa Xaa Xaa Xaa Xaa Xaa Xaa Xaa
            340                 345                 350

```
Xaa Asn Xaa Xaa Ile Xaa Xaa Xaa Leu Xaa Xaa Xaa Xaa Xaa
        355                 360                 365

Xaa Xaa Xaa Xaa Xaa Xaa Xaa Xaa Xaa Xaa
        370                 375
```

<210> SEQ ID NO 11
<211> LENGTH: 342
<212> TYPE: PRT
<213> ORGANISM: Hypoxylon sp. CI4A

<400> SEQUENCE: 11

```
Met Ala Tyr Ser Glu Lys Lys Leu Leu Val Lys Arg Leu Glu Gly Gln
1               5                   10                  15

Arg Tyr Thr Ile Pro Asp Met Arg Pro Ile Phe Ala His Trp Pro Ser
            20                  25                  30

Gly Gln Asn Glu His Tyr Ser Glu Val Lys Glu Ile Ile Asp Gln Arg
        35                  40                  45

Leu Ala Ser Gln Ser Met Asp Glu Glu Ala Arg Lys Ala Phe Asp Asp
    50                  55                  60

Met Asn Pro Thr Leu Leu Ala Ala Ser Arg Tyr Ser Ala Leu Val Asp
65                  70                  75                  80

Phe Val Ile Trp Phe Gly Tyr Trp Asp Asp Leu Ser Glu Lys Leu Val
                85                  90                  95

Ser Glu Pro Thr Ala Gly Ala Asp Leu Arg Ser Thr Thr Lys Leu Phe
            100                 105                 110

Val Arg Gln Ser Leu Gln Leu Ala Asn Pro Gly Lys Glu Asn Ile Ala
        115                 120                 125

Met Pro Asp Ser Leu Ile His Gly Phe Lys Ser Ile Ala Glu Lys Val
    130                 135                 140

Leu Val Ala Tyr Asp Glu Glu Gln Arg Gly Val Leu Ile Ser Asn Phe
145                 150                 155                 160

Glu Arg Tyr Ile Asp Ser Thr Glu Leu Glu Ala Glu Ala Asp Ile Ser
                165                 170                 175

Glu Glu Leu Pro Ser Leu Lys Arg Tyr Trp Glu Thr Arg Ile Met Thr
            180                 185                 190

Ser Gly Met Asp Ala Leu Leu Ala Phe Thr Glu Phe Ala Ala Glu Val
        195                 200                 205

Lys Leu Pro Leu Arg Leu Val Asn Ser Thr Leu Tyr Gln Thr Leu Trp
    210                 215                 220

Thr Thr Thr Ile Met Ile Asn Ser Ile Val Asn Asp Leu Ile Ser Phe
225                 230                 235                 240

Lys Lys Glu Met Lys Ala Gly Ser Val Leu Ser Ser Val Ala Ile Leu
                245                 250                 255

Tyr Gln Gln Val Asn Asn Leu Asp Ala Ala Val Gln Met Ser Leu Ala
            260                 265                 270

His Leu Arg Ile Met Val Asp Glu Tyr Asp Tyr Thr Ala Asn Thr Ile
        275                 280                 285

Leu Ser Glu Phe Ser Leu Asn Ser Glu Glu Thr Asp Ala Val Thr Lys
    290                 295                 300

Val Ile Asp Thr Leu Arg Thr Val Asn Thr Gly Asn Leu Glu Trp Ser
305                 310                 315                 320

Leu Gln Ala Lys Arg Tyr Gly Val Ser Pro Phe Ile Thr Gln Ala Gly
                325                 330                 335

His Ile Glu Leu Thr Leu
            340
```

<210> SEQ ID NO 12
<211> LENGTH: 351
<212> TYPE: PRT
<213> ORGANISM: Hypoxylon sp. CO27

<400> SEQUENCE: 12

Met Ile Met Ser Asp Tyr Asn Glu Lys Glu Leu Leu Ala Lys Arg Leu
1               5                   10                  15

Lys Gly Gln Arg Leu Val Ile Pro Asp Met Arg Pro Ile Phe Ala His
            20                  25                  30

Trp Pro Ser Glu Arg Asn Glu Asn Tyr Gln Ala Val Lys Asp Ala Ile
        35                  40                  45

Asp Glu Arg Leu Ala Lys Gln Thr Met Thr Asp Glu Ala Arg Thr Ser
    50                  55                  60

Phe Asn Phe Met Asn Pro Ala Leu Phe Ala Ala Thr Trp Trp Pro Thr
65                  70                  75                  80

Ser Ser Lys Asp His Tyr Arg Ile Leu Asp Tyr Val Ile Trp Phe
                85                  90                  95

Leu Tyr Trp Asp Asp Leu Val Glu Gly Leu Ala His Asp Ala Ser Ala
            100                 105                 110

Ala Glu Asp Leu Arg Ser Glu Thr Lys Thr Leu Val Arg Arg Ser Leu
        115                 120                 125

Gly Leu Gly Gly Leu Glu Glu Lys Met Thr Ile Ser Asn Pro Phe Ile
    130                 135                 140

Leu Gly Ile Lys Asp Ile Ala Lys Gly Leu Cys Ser Phe Tyr Asp Glu
145                 150                 155                 160

Glu Gln Arg Lys Val Leu Leu Gly His Phe Asp Arg Tyr Ile Asp Ser
                165                 170                 175

Thr Leu Leu Glu Ala Glu Ala Asp Leu Asn Asp Lys Leu Pro Ser Leu
            180                 185                 190

Lys Arg Tyr Trp Glu Val Arg Ile Leu Thr Ser Gly Met Gly Thr Leu
        195                 200                 205

Leu Gly Val Thr Glu Tyr Ala Ala His Ala Lys Leu Pro Ser Arg Leu
    210                 215                 220

Val His Ser Ala Ala Tyr Glu Thr Leu Trp Val Ser Thr Ile Met Ile
225                 230                 235                 240

Asn Ser Ile Val Asn Asp Leu Val Ser Phe Lys Lys Glu Met Lys Ala
                245                 250                 255

Gly Ser Val Leu Ser Ser Val Ala Ile Leu Tyr Gln Gln Val Asp Asn
            260                 265                 270

Leu Asp Ala Ala Val Gln Met Ser Leu Ala His Leu Arg Ile Leu Val
        275                 280                 285

Asp Glu Phe Asp Arg Thr Ala Thr Thr Ile Leu Ser Lys Phe Ser Leu
    290                 295                 300

Ala Pro Asn Glu Ile Glu Pro Val Ser Lys Val Ile Asn Ala Leu Arg
305                 310                 315                 320

Met Val Asn Thr Gly Asn Leu Glu Trp Arg Ser Val Leu Pro Leu Lys
                325                 330                 335

Asp Thr Tyr Ser Ala Val Ala His Leu Leu Thr Ser Tyr Thr Ala
            340                 345                 350

<210> SEQ ID NO 13
<211> LENGTH: 350
<212> TYPE: PRT

<213> ORGANISM: Hypoxylon sp. EC38

<400> SEQUENCE: 13

Met Ser Asp Tyr Asn Glu Lys Glu Leu Leu Ala Lys Arg Leu Lys Gly
1               5                   10                  15

Gln Arg Leu Val Ile Pro Asp Met Arg Ser Ile Phe Ala His Trp Pro
            20                  25                  30

Ser Ala Arg Asn Glu Asn Tyr Gln Ala Val Lys Asp Ala Val Asp Glu
        35                  40                  45

Arg Leu Ala Lys Gln Thr Met Thr Asp Glu Ala Arg Thr Ser Phe His
    50                  55                  60

Tyr Met Asn Pro Ala Leu Tyr Ala Ala Thr Trp Pro Thr Ser Ser
65                  70                  75                  80

Lys Asp His Tyr Arg Ile Leu Val Asp Tyr Val Ile Trp Phe Leu His
                85                  90                  95

Trp Asp Asp Leu Val Glu Gly Leu Ala Asp Asp Pro Ser Ala Ala Glu
            100                 105                 110

Asp Leu Arg Ser Glu Thr Lys Thr Leu Val Arg Arg Ser Leu Gly Leu
        115                 120                 125

Gly Gly Leu Asp Glu Lys Met Thr Ile Ser Asn Pro Phe Ile Leu Gly
    130                 135                 140

Phe Lys Asp Ile Ala Lys Gly Leu Cys Ser Phe Tyr Asp Glu Glu Gln
145                 150                 155                 160

Arg Lys Val Leu Leu Gly His Phe Asp Arg Tyr Ile Asp Ser Thr Leu
                165                 170                 175

Leu Glu Ala Glu Ala Asp Leu Ser Asp Lys Leu Pro Ser Leu Lys Arg
            180                 185                 190

Tyr Trp Glu Val Arg Ile Leu Thr Ser Gly Met Gly Thr Leu Leu Gly
        195                 200                 205

Val Thr Glu Tyr Ala Ala His Ala Lys Leu Pro Ser Arg Leu Val His
    210                 215                 220

Ser Ala Ala Tyr Glu Thr Leu Trp Val Ser Thr Ile Val Ile Asn Ser
225                 230                 235                 240

Ile Val Asn Asp Leu Ile Ser Phe Lys Lys Glu Met Lys Ala Gly Ser
                245                 250                 255

Val Leu Ser Ser Val Ala Ile Leu Tyr Gln Gln Val Asp Asn Leu Asp
            260                 265                 270

Ala Ala Val Gln Met Ser Leu Ala His Leu Arg Ile Leu Val Asp Glu
        275                 280                 285

Phe Asp Arg Thr Ala Thr Thr Ile Leu Ser Lys Phe Ser Leu Ala Pro
    290                 295                 300

Asn Glu Ile Glu Pro Val Ser Lys Val Ile Asn Ala Leu Arg Met Val
305                 310                 315                 320

Asn Thr Gly Asn Leu Glu Trp Ser Leu Ser Val Lys Arg Tyr Gly Val
                325                 330                 335

Gly Gln Phe Met Asn His Asn Gly Gln Ile Glu Ile Ile Leu
            340                 345                 350

<210> SEQ ID NO 14
<211> LENGTH: 375
<212> TYPE: PRT
<213> ORGANISM: Daldinia eschscholzii EC12

<400> SEQUENCE: 14

Met Pro Asn Ser Asn Glu Lys Glu Leu Val Ala Asn Ser Leu Lys Gly

```
  1               5                   10                  15
Gln Arg Leu Val Ile Pro Asp Ile Arg Pro Ile Phe Ala His Trp Pro
                 20                  25                  30
Ser Glu Glu His Glu Gln Tyr Gln Thr Val Lys Glu Ile Ile Asp Lys
                 35                  40                  45
Gln Ile Thr Glu Gln Pro Met Ser Asp Glu Ala Arg Lys Ala Phe Phe
 50                              55                  60
Asn Met Asp Pro Ser Leu Leu Ala Ala Arg Trp Trp Pro Arg Ala Ser
 65                  70                  75                  80
Lys Asp Asn Tyr Gln Val Leu Val Asp Leu Ile Ile Trp Phe Gly Tyr
                     85                  90                  95
Trp Asp Asp Leu Ser Glu Ser Leu Ala Val Asp Pro Val Ala Ala Glu
                 100                 105                 110
Asn Leu Arg Gly Ala Thr Lys Val Leu Gly Arg Gln Ala Leu Gly Leu
                 115                 120                 125
Ala Thr Ser Glu Glu Glu Val Ala Ile Ser Asn Pro Leu Ile Leu Asp
 130                         135                 140
Phe Lys Arg Ile Gly Glu Lys Ile Arg Ala Ala Tyr Asn Glu Glu Gln
 145                 150                 155                 160
Arg Arg Thr Phe Leu Gly His Phe Glu Arg Tyr Val Asp Ser Thr Val
                 165                 170                 175
Leu Glu Ala Ala Ala Asp Leu Ser Asp Thr Leu Pro Ser Leu Lys Arg
                 180                 185                 190
Tyr Trp Glu Val Arg Ile Leu Thr Ser Gly Met Gly Ile Leu Leu Gly
                 195                 200                 205
Val Thr Glu Phe Ala Ala Gly Val Lys Leu Pro Thr Ser Val Val Thr
 210                         215                 220
Ser Ala Ala Tyr Asp Thr Leu Trp Thr Thr Ala Ile Val Ile Asn Ser
 225                 230                 235                 240
Ile Val Asn Asp Leu Ile Ser Phe Lys Lys Glu Met Lys Ala Gly Ser
                 245                 250                 255
Val Leu Ser Ser Val Ala Ile Leu Tyr Ser Gln Val Asn Asn Leu Asp
                 260                 265                 270
Ala Ala Val Gln Met Ser Leu Ala His Leu Lys Ile Leu Val Ala Glu
                 275                 280                 285
Phe Asp Arg Thr Ala Asn Leu Leu Leu Thr Lys Phe Pro Leu Ser Pro
 290                     295                 300
Glu Glu Val Glu Pro Val Ser Lys Val Ile Asp Thr Leu Arg Leu Val
 305                 310                 315                 320
Asn Thr Gly Asn Leu Glu Trp Arg Phe Leu Ala Ser Lys Ala Leu Trp
                 325                 330                 335
Gly Leu Arg Leu His Leu Thr Asp Arg Thr Asp Arg Ser Asn Ser Met
                 340                 345                 350
Thr Ala Glu Leu Ala Gly Gly Tyr Thr Ile Leu Asn Ser Gly Lys Trp
                 355                 360                 365
Tyr Thr Lys Glu Trp Gln Thr
 370                 375
```

<210> SEQ ID NO 15

<400> SEQUENCE: 15

000

-continued

```
<210> SEQ ID NO 16
<400> SEQUENCE: 16
000

<210> SEQ ID NO 17
<400> SEQUENCE: 17
000

<210> SEQ ID NO 18
<400> SEQUENCE: 18
000

<210> SEQ ID NO 19
<400> SEQUENCE: 19
000

<210> SEQ ID NO 20
<211> LENGTH: 426
<212> TYPE: PRT
<213> ORGANISM: Artificial Sequence
<220> FEATURE:
<223> OTHER INFORMATION: Consensus polypeptide sequence
<220> FEATURE:
<221> NAME/KEY: MISC_FEATURE
<222> LOCATION: (2)..(2)
<223> OTHER INFORMATION: absent or any amino acid (e.g., an amino acid
      present at a position in one of SEQ ID NOs:21-25 when optimally
      aligned with SEQ ID NO:20)
<220> FEATURE:
<221> NAME/KEY: MISC_FEATURE
<222> LOCATION: (4)..(5)
<223> OTHER INFORMATION: absent or any amino acid (e.g., an amino acid
      present at a position in one of SEQ ID NOs:21-25 when optimally
      aligned with SEQ ID NO:20)
<220> FEATURE:
<221> NAME/KEY: MISC_FEATURE
<222> LOCATION: (19)..(21)
<223> OTHER INFORMATION: absent or any amino acid (e.g., an amino acid
      present at a position in one of SEQ ID NOs:21-25 when optimally
      aligned with SEQ ID NO:20)
<220> FEATURE:
<221> NAME/KEY: MISC_FEATURE
<222> LOCATION: (38)..(41)
<223> OTHER INFORMATION: absent or any amino acid (e.g., an amino acid
      present at a position in one of SEQ ID NOs:21-25 when optimally
      aligned with SEQ ID NO:20)
<220> FEATURE:
<221> NAME/KEY: MISC_FEATURE
<222> LOCATION: (48)..(51)
<223> OTHER INFORMATION: absent or any amino acid (e.g., an amino acid
      present at a position in one of SEQ ID NOs:21-25 when optimally
      aligned with SEQ ID NO:20)
<220> FEATURE:
<221> NAME/KEY: MISC_FEATURE
<222> LOCATION: (75)..(75)
<223> OTHER INFORMATION: absent or any amino acid (e.g., an amino acid
      present at a position in one of SEQ ID NOs:21-25 when optimally
      aligned with SEQ ID NO:20)
<220> FEATURE:
<221> NAME/KEY: MISC_FEATURE
<222> LOCATION: (98)..(99)
<223> OTHER INFORMATION: absent or any amino acid (e.g., an amino acid
      present at a position in one of SEQ ID NOs:21-25 when optimally
      aligned with SEQ ID NO:20)
<220> FEATURE:
<221> NAME/KEY: MISC_FEATURE
<222> LOCATION: (104)..(104)
```

```
<223> OTHER INFORMATION: absent or any amino acid (e.g., an amino acid
      present at a position in one of SEQ ID NOs:21-25 when optimally
      aligned with SEQ ID NO:20)
<220> FEATURE:
<221> NAME/KEY: MISC_FEATURE
<222> LOCATION: (133)..(133)
<223> OTHER INFORMATION: absent or any amino acid (e.g., an amino acid
      present at a position in one of SEQ ID NOs:21-25 when optimally
      aligned with SEQ ID NO:20)
<220> FEATURE:
<221> NAME/KEY: MISC_FEATURE
<222> LOCATION: (137)..(137)
<223> OTHER INFORMATION: absent or any amino acid (e.g., an amino acid
      present at a position in one of SEQ ID NOs:21-25 when optimally
      aligned with SEQ ID NO:20)
<220> FEATURE:
<221> NAME/KEY: MISC_FEATURE
<222> LOCATION: (143)..(143)
<223> OTHER INFORMATION: absent or any amino acid (e.g., an amino acid
      present at a position in one of SEQ ID NOs:21-25 when optimally
      aligned with SEQ ID NO:20)
<220> FEATURE:
<221> NAME/KEY: MISC_FEATURE
<222> LOCATION: (156)..(156)
<223> OTHER INFORMATION: absent or any amino acid (e.g., an amino acid
      present at a position in one of SEQ ID NOs:21-25 when optimally
      aligned with SEQ ID NO:20)
<220> FEATURE:
<221> NAME/KEY: MISC_FEATURE
<222> LOCATION: (190)..(190)
<223> OTHER INFORMATION: absent or any amino acid (e.g., an amino acid
      present at a position in one of SEQ ID NOs:21-25 when optimally
      aligned with SEQ ID NO:20)
<220> FEATURE:
<221> NAME/KEY: MISC_FEATURE
<222> LOCATION: (192)..(193)
<223> OTHER INFORMATION: absent or any amino acid (e.g., an amino acid
      present at a position in one of SEQ ID NOs:21-25 when optimally
      aligned with SEQ ID NO:20)
<220> FEATURE:
<221> NAME/KEY: MISC_FEATURE
<222> LOCATION: (196)..(201)
<223> OTHER INFORMATION: absent or any amino acid (e.g., an amino acid
      present at a position in one of SEQ ID NOs:21-25 when optimally
      aligned with SEQ ID NO:20)
<220> FEATURE:
<221> NAME/KEY: MISC_FEATURE
<222> LOCATION: (221)..(221)
<223> OTHER INFORMATION: absent or any amino acid (e.g., an amino acid
      present at a position in one of SEQ ID NOs:21-25 when optimally
      aligned with SEQ ID NO:20)
<220> FEATURE:
<221> NAME/KEY: MISC_FEATURE
<222> LOCATION: (246)..(246)
<223> OTHER INFORMATION: absent or any amino acid (e.g., an amino acid
      present at a position in one of SEQ ID NOs:21-25 when optimally
      aligned with SEQ ID NO:20)
<220> FEATURE:
<221> NAME/KEY: MISC_FEATURE
<222> LOCATION: (255)..(255)
<223> OTHER INFORMATION: absent or any amino acid (e.g., an amino acid
      present at a position in one of SEQ ID NOs:21-25 when optimally
      aligned with SEQ ID NO:20)
<220> FEATURE:
<221> NAME/KEY: MISC_FEATURE
<222> LOCATION: (278)..(278)
<223> OTHER INFORMATION: absent or any amino acid (e.g., an amino acid
      present at a position in one of SEQ ID NOs:21-25 when optimally
      aligned with SEQ ID NO:20)
<220> FEATURE:
<221> NAME/KEY: MISC_FEATURE
<222> LOCATION: (306)..(306)
<223> OTHER INFORMATION: absent or any amino acid (e.g., an amino acid
      present at a position in one of SEQ ID NOs:21-25 when optimally
      aligned with SEQ ID NO:20)
<220> FEATURE:
<221> NAME/KEY: MISC_FEATURE
<222> LOCATION: (351)..(351)
<223> OTHER INFORMATION: absent or any amino acid (e.g., an amino acid
```

-continued

```
       present at a position in one of SEQ ID NOs:21-25 when optimally
       aligned with SEQ ID NO:20)
<220> FEATURE:
<221> NAME/KEY: MISC_FEATURE
<222> LOCATION: (356)..(357)
<223> OTHER INFORMATION: absent or any amino acid (e.g., an amino acid
       present at a position in one of SEQ ID NOs:21-25 when optimally
       aligned with SEQ ID NO:20)
<220> FEATURE:
<221> NAME/KEY: MISC_FEATURE
<222> LOCATION: (367)..(368)
<223> OTHER INFORMATION: absent or any amino acid (e.g., an amino acid
       present at a position in one of SEQ ID NOs:21-25 when optimally
       aligned with SEQ ID NO:20)
<220> FEATURE:
<221> NAME/KEY: MISC_FEATURE
<222> LOCATION: (378)..(379)
<223> OTHER INFORMATION: absent or any amino acid (e.g., an amino acid
       present at a position in one of SEQ ID NOs:21-25 when optimally
       aligned with SEQ ID NO:20)
<220> FEATURE:
<221> NAME/KEY: MISC_FEATURE
<222> LOCATION: (381)..(381)
<223> OTHER INFORMATION: absent or any amino acid (e.g., an amino acid
       present at a position in one of SEQ ID NOs:21-25 when optimally
       aligned with SEQ ID NO:20)
<220> FEATURE:
<221> NAME/KEY: MISC_FEATURE
<222> LOCATION: (387)..(389)
<223> OTHER INFORMATION: absent or any amino acid (e.g., an amino acid
       present at a position in one of SEQ ID NOs:21-25 when optimally
       aligned with SEQ ID NO:20)
<220> FEATURE:
<221> NAME/KEY: MISC_FEATURE
<222> LOCATION: (392)..(393)
<223> OTHER INFORMATION: absent or any amino acid (e.g., an amino acid
       present at a position in one of SEQ ID NOs:21-25 when optimally
       aligned with SEQ ID NO:20)
<220> FEATURE:
<221> NAME/KEY: MISC_FEATURE
<222> LOCATION: (405)..(405)
<223> OTHER INFORMATION: absent or any amino acid (e.g., an amino acid
       present at a position in one of SEQ ID NOs:21-25 when optimally
       aligned with SEQ ID NO:20)
<220> FEATURE:
<221> NAME/KEY: MISC_FEATURE
<222> LOCATION: (408)..(408)
<223> OTHER INFORMATION: absent or any amino acid (e.g., an amino acid
       present at a position in one of SEQ ID NOs:21-25 when optimally
       aligned with SEQ ID NO:20)
<220> FEATURE:
<221> NAME/KEY: MISC_FEATURE
<222> LOCATION: (414)..(414)
<223> OTHER INFORMATION: absent or any amino acid (e.g., an amino acid
       present at a position in one of SEQ ID NOs:21-25 when optimally
       aligned with SEQ ID NO:20)
<220> FEATURE:
<221> NAME/KEY: MISC_FEATURE
<222> LOCATION: (416)..(417)
<223> OTHER INFORMATION: absent or any amino acid (e.g., an amino acid
       present at a position in one of SEQ ID NOs:21-25 when optimally
       aligned with SEQ ID NO:20)

<400> SEQUENCE: 20

Met Xaa Ser Xaa Xaa Met Met Arg Thr Thr Leu Leu Arg Leu Ala Gln
1               5                   10                  15

Arg Thr Xaa Xaa Xaa Leu Leu Ser Ile Leu Phe Pro His Ser Leu Pro
            20                  25                  30

Ala Ala Gln Glu Asp Xaa Xaa Xaa Xaa Gln Arg Ala Pro Glu Lys Xaa
        35                  40                  45

Xaa Xaa Xaa Ala Ser Ala Gln Gln Gly Leu Cys Gly Glu Ala Leu Val
    50                  55                  60

Leu Ala Ser Gln Leu Asp Gly Lys Thr Phe Xaa Leu Pro Asp Leu Trp
65                  70                  75                  80
```

```
Lys Val Phe Ser Asp Trp Pro Leu Ala Ala Asn Pro His Ala Gln Arg
                85                  90                  95

Leu Xaa Xaa Leu Val Asp Ser Xaa Leu Glu Arg Ile Ile Thr Asn Glu
            100                 105                 110

Lys Lys Leu Lys Ala Leu Lys Gln Ala Asn Phe Gly Arg Leu Ile Ser
            115                 120                 125

Leu Trp Tyr Pro Xaa Ala Glu Trp Xaa Glu Leu Glu Ile Ala Xaa Ala
130                 135                 140

Tyr Ser Val Trp Ile Phe Val Trp Asp Asp Glu Xaa Asp Ala Gly Asp
145                 150                 155                 160

Thr Asp Val Ser Asn Asp Glu Glu Leu Ser Arg Ala Tyr Tyr Gln Lys
                165                 170                 175

Ser Leu Ser Thr Ile His Asn Leu Leu Gly Leu Asp Pro Xaa Glu Xaa
            180                 185                 190

Xaa Gln Glu Xaa Xaa Xaa Xaa Xaa Glu Ser Leu His Pro Asn Met
            195                 200                 205

Ala Leu Phe Ala Asp Val Gly Arg Gly Met Arg Ala Xaa Thr Asp Arg
210                 215                 220

Ile Gln Arg Glu Arg Phe Tyr Arg Glu Leu Glu His Phe Met Ile Gln
225                 230                 235                 240

Val Gly Val Glu His Xaa His Arg Met Arg Gly Ser Ile Pro Xaa Val
                245                 250                 255

Glu Lys Tyr Ile Glu Ile Arg Ser Gly Ser Val Gly Cys Ala Pro Gln
                260                 265                 270

Ile Ala Ile Thr Asp Xaa Met Leu Lys Ile Arg Leu Pro Glu Ser Ile
            275                 280                 285

Met Glu Ser Ala Ala Met Lys Ala Leu Trp Arg Glu Thr Val Val Ile
290                 295                 300

Cys Xaa Ile Leu Asn Asp Val Tyr Ser Val Gln Lys Glu Ile Ala Gln
305                 310                 315                 320

Gly Ser Leu Leu Asn Leu Val Pro Val Met Tyr Lys Asn Cys Asp Pro
                325                 330                 335

Glu Lys Gln Ser Leu Asp Thr Val Thr Arg Asp Ile Glu Val Xaa Leu
                340                 345                 350

Gln Lys Ser Xaa Xaa Gly Phe Glu Asp Ala Ala Thr Ser Leu Xaa Xaa
            355                 360                 365

Met Ala Ser Asp Asp Ala Gln Leu Ser Xaa Xaa Asp Xaa Gln Ser Phe
370                 375                 380

Ile Lys Xaa Xaa Xaa Trp Cys Xaa Xaa Arg Tyr Phe Ile Thr Gly Val
385                 390                 395                 400

Gln Gln Trp Ser Xaa Glu Ser Xaa Arg Tyr Gly Met Ala Xaa Cys Xaa
                405                 410                 415

Xaa Glu Asp Gly Ser Leu Ser Ile Val Leu
            420                 425

<210> SEQ ID NO 21
<211> LENGTH: 402
<212> TYPE: PRT
<213> ORGANISM: Hypoxylon sp. CI4A

<400> SEQUENCE: 21

Met Ala Arg Ser Lys Arg Val Thr Thr Thr Leu Leu Asn Leu Ala Arg
1               5                   10                  15

Arg Thr His Ser Lys Leu Ser Ser Ile Leu Phe Pro Cys Pro Leu Pro
```

```
            20                  25                  30
Ala Glu Ala Ser Ser Asp Ala Val Val Gln Tyr Ala Pro Glu Lys Lys
            35                  40                  45

Lys Lys Pro Ser Ala Gln Gln His Gly Leu Cys Gly Glu Ala Leu Val
 50                  55                  60

Leu Ala Ser Gln Leu Asp Gly Gln Thr Phe Arg Leu Pro Asp Leu Trp
 65                  70                  75                  80

Lys Val Leu Ala Asp Trp Pro Met Ala Ala Asn Pro His Ala Glu Arg
                 85                  90                  95

Leu Glu Gly Leu Val Asn Ser Ile Leu Glu Arg His Ile Thr Ser Glu
                100                 105                 110

Lys Lys Leu Lys Ala Leu Lys Gln Ala Asn Phe Ala Arg Leu Ile Ser
                115                 120                 125

Leu Trp Tyr Pro Asp Ala Glu Trp Pro Glu Leu Glu Ala Ala Thr Ala
                130                 135                 140

Tyr Ser Val Trp Ile Phe Val Trp Asp Asp Glu Val Asp Ala Gly Asp
145                 150                 155                 160

Thr Asp Val Ser Leu Asp Glu Glu Leu Ser Arg Ala Tyr Tyr Lys Lys
                165                 170                 175

Ser Leu Ser Thr Ile His Arg Leu Leu Gly Leu Asp Ser Thr Ser Gly
                180                 185                 190

Asp Asp Val Ser Gly Glu Ala Glu Glu Ala Leu His Pro Asn Met
                195                 200                 205

Arg Glu Arg Phe Tyr Arg Glu Met Glu Ser Phe Met Ile Gln Val Gly
                210                 215                 220

Val Glu His Ser His Arg Met Arg Gly Ser Ile Pro Thr Val Asp Lys
225                 230                 235                 240

Tyr Met Glu Ile Arg Ser Gly Ser Val Gly Cys Ala Pro Gln Ile Ala
                245                 250                 255

Ile Thr Asp Phe Met Leu Lys Ile Arg Leu Pro Glu Ser Val Met Glu
                260                 265                 270

Ser Ala Ala Met Lys Ala Leu Trp Arg Glu Thr Val Val Ile Cys Leu
                275                 280                 285

Ile Leu Asn Asp Val Tyr Ser Val Gln Lys Glu Ile Ala Gln Gly Ser
                290                 295                 300

Leu Leu Asn Leu Val Pro Val Ile Phe Lys Asn Cys Asp Pro Lys Glu
305                 310                 315                 320

Gln Asn Leu Asp Thr Val Thr Ala Asp Ile Glu Val Ala Leu Gln Gly
                325                 330                 335

Ser Ile Arg Gly Phe Glu Asp Ala Ala Ala Ser Leu Gly Gln Met Val
                340                 345                 350

Ser Asp Asp Ala Gln Leu Asp Lys Asp Val Gln Ser Phe Val Arg Trp
                355                 360                 365

Cys Arg Tyr Phe Ile Thr Gly Val Gln Gln Trp Ser Ile Glu Ser Ala
                370                 375                 380

Arg Tyr Gly Met Ala Gln Cys Leu Gln Glu Asp Gly Ser Leu Ser Ile
385                 390                 395                 400

Val Leu

<210> SEQ ID NO 22
<211> LENGTH: 412
<212> TYPE: PRT
<213> ORGANISM: Hypoxylon sp. CO27
```

<400> SEQUENCE: 22

```
Met Lys Ser Ser Lys Met Met Arg Thr Thr Leu Leu Arg Leu Ala Gln
1               5                   10                  15
Arg Thr Arg Leu Arg Leu Leu Ser Ile Leu Phe Pro His Ser Leu Pro
            20                  25                  30
Ala Ala Gln Glu Asp Gln Arg Ala Pro Glu Lys Ala Ser Ala Gln Gln
        35                  40                  45
Gly Leu Cys Gly Glu Ala Leu Val Leu Ala Ser Gln Leu Asp Gly Lys
    50                  55                  60
Thr Phe His Leu Pro Asp Leu Trp Lys Val Phe Ser Asp Trp Pro Leu
65                  70                  75                  80
Ala Ala Asn Pro His Ala Gln Arg Leu Asp Ala Leu Val Asp Ser Leu
                85                  90                  95
Leu Glu Arg Ile Ile Thr Asn Glu Lys Lys Leu Lys Ala Leu Lys Gln
            100                 105                 110
Ala Asn Phe Gly Arg Leu Ile Ser Leu Trp Tyr Pro Asn Ala Glu Trp
        115                 120                 125
Ser Glu Leu Glu Ile Ala Ala Ala Tyr Ser Val Trp Ile Phe Val Trp
    130                 135                 140
Asp Asp Glu Ile Asp Ala Gly Asp Thr Asp Val Ser Asn Asp Glu Glu
145                 150                 155                 160
Leu Ser Arg Ala Tyr Tyr Gln Lys Ser Leu Ser Thr Ile His Asn Leu
                165                 170                 175
Leu Gly Leu Asp Pro Val Glu Asp Gly Gln Glu Pro Val Tyr Glu Asp
            180                 185                 190
Asp Glu Ser Leu His Pro Asn Met Ala Leu Phe Ala Asp Val Gly Arg
        195                 200                 205
Gly Met Arg Ala Thr Thr Asp Arg Ile Gln Arg Glu Arg Phe Tyr Arg
    210                 215                 220
Glu Leu Glu His Phe Met Ile Gln Val Gly Val Glu His Val His Arg
225                 230                 235                 240
Met Arg Gly Ser Ile Pro Ser Val Glu Lys Tyr Ile Glu Ile Arg Ser
                245                 250                 255
Gly Ser Val Gly Cys Ala Pro Gln Ile Ala Ile Thr Asp Ala Met Leu
            260                 265                 270
Lys Ile Arg Leu Pro Glu Ser Ile Met Glu Ser Ala Ala Met Lys Ala
        275                 280                 285
Leu Trp Arg Glu Thr Val Val Ile Cys Phe Ile Leu Asn Asp Val Tyr
    290                 295                 300
Ser Val Gln Lys Glu Ile Ala Gln Gly Ser Leu Leu Asn Leu Val Pro
305                 310                 315                 320
Val Met Tyr Lys Asn Cys Asp Pro Glu Lys Gln Ser Leu Asp Thr Val
                325                 330                 335
Thr Arg Asp Ile Glu Val Leu Leu Gln Lys Ser Leu Lys Gly Phe Glu
            340                 345                 350
Asp Ala Ala Thr Ser Leu Thr Gly Thr Ala Glu Lys His Glu Asn Met
        355                 360                 365
Thr Tyr His Asn Ala Gln Val Phe Ser Lys Thr Gly Ser Arg Cys Asn
    370                 375                 380
Ser Lys Val Val Thr Ala Thr Val Gly Ser His Ser Met Lys Gln Pro
385                 390                 395                 400
Gln Thr Ser Tyr Lys Ile Phe Pro Thr Glu Asp Phe
                405                 410
```

-continued

<210> SEQ ID NO 23
<211> LENGTH: 403
<212> TYPE: PRT
<213> ORGANISM: Daldinia eschscholzii EC12

<400> SEQUENCE: 23

Met Lys Ser Gln Thr Leu Ser Pro Leu Phe Arg Leu Ala Glu Leu Val
1               5                   10                  15

His Tyr Lys Leu Leu Ser Ile Phe Pro Arg Lys Pro Leu Ala Gln Thr
            20                  25                  30

Val Glu Pro Thr Ala Asn Pro Asp Leu Arg Gly Asp Ala Ser Ile Leu
        35                  40                  45

Ala Ala Gln Leu Asp Gly Lys Thr Phe Arg Leu Pro Asp Leu Trp Lys
    50                  55                  60

Val Phe Ser Glu Trp Pro Leu Ala Ala Asn Pro His Ala Lys Arg Leu
65                  70                  75                  80

Glu Gly Leu Val Asp Ser Met Leu Glu Arg Ile Ile Thr Asn Glu Lys
                85                  90                  95

Lys Leu Lys Ala Leu Lys Lys Ala Asp Phe Gly Arg Leu Met Ser Leu
            100                 105                 110

Trp Tyr Pro Asp Ala Glu Trp Pro Glu Leu Glu Ile Ala Thr Ala Tyr
        115                 120                 125

Ser Val Trp Ile Phe Val Trp Asp Asp Glu Val Asp Ala Gly Asp Thr
    130                 135                 140

Asp Val Ser Asn Asp Glu Glu Leu Ala Arg Ala Tyr Tyr Arg Lys Ser
145                 150                 155                 160

Leu Ser Thr Val His Cys Leu Leu Gly Leu Asp Glu Ser Glu Gly Ala
                165                 170                 175

Glu Glu Arg Ile Ala Arg Glu Glu Ala Ser Leu His Pro Asn Met Ala
            180                 185                 190

Leu Phe Ala Asp Val Gly Arg Gly Leu Arg Asn Ser Thr Asp Arg Ile
        195                 200                 205

Gln Arg Glu Arg Phe Tyr Arg Glu Leu Glu Asn Phe Met Ile Ser Val
    210                 215                 220

Gly Val Glu His Gly His Arg Met Arg Gly Ser Ile Pro Thr Val Glu
225                 230                 235                 240

Lys Tyr Leu His Ile Arg Ser Gly Ser Val Gly Cys Ala Pro Gln Ile
                245                 250                 255

Ala Leu Thr Asp His Met Leu Lys Ile Arg Leu Pro Glu Ser Ile Met
            260                 265                 270

Glu Cys Ala Pro Met Lys Glu Leu Trp Lys Glu Thr Val Met Cys
        275                 280                 285

Leu Ile Leu Asn Asp Val Tyr Ser Val Gln Lys Glu Ile Ala Gln Ala
    290                 295                 300

Ser Leu Phe Asn Leu Val Pro Val Met Tyr Lys Asn Cys Ser Pro Glu
305                 310                 315                 320

Lys Gln Thr Leu Asp Thr Val Thr Arg Gly Val Glu Ala Ala Leu Gln
                325                 330                 335

Glu Ser Met Arg Gly Phe Glu Asp Ala Ala Lys Ala Leu Gly Glu Met
            340                 345                 350

Ala Ser Asp Asp Ala Gln Val Ser Arg Asp Val Gln Ala Phe Ile Lys
        355                 360                 365

Trp Cys Arg Tyr Phe Ile Thr Gly Val Leu Gln Trp Ser Leu Glu Ser

```
                370               375               380
Lys Arg Tyr Gly Met Ala Asp Cys Arg His Lys Asp Gly Ser Leu Ser
385               390               395               400

Ile Val Leu

<210> SEQ ID NO 24
<211> LENGTH: 407
<212> TYPE: PRT
<213> ORGANISM: Hypoxylon sp. EC38

<400> SEQUENCE: 24

Met Met Arg Thr Thr Leu Leu Arg Leu Ala Gln Arg Thr Arg Leu Arg
1               5                  10                  15

Leu Leu Ser Ile Leu Phe Pro His Ser Leu Pro Ala Ala Gln Glu Asp
                20                  25                  30

Gln Arg Ala Pro Glu Lys Ala Ser Ala Gln Gln Gly Leu Cys Gly Glu
            35                  40                  45

Ala Leu Val Leu Ala Ser Gln Leu Asp Gly Lys Thr Phe His Leu Pro
        50                  55                  60

Asp Leu Trp Lys Val Phe Ser Asp Trp Pro Leu Ala Ala Asn Pro His
65                  70                  75                  80

Ala Gln Arg Leu Asp Ala Leu Val Asp Ser Leu Leu Glu Arg Ile Ile
                85                  90                  95

Thr Asn Glu Lys Lys Leu Lys Ala Leu Lys Gln Ala Asn Phe Gly Arg
            100                 105                 110

Leu Ile Ser Leu Trp Tyr Pro Asn Ala Glu Trp Ser Glu Leu Glu Ile
        115                 120                 125

Ala Ala Ala Tyr Ser Val Trp Ile Phe Val Trp Asp Asp Glu Ile Asp
    130                 135                 140

Ala Gly Asp Thr Asp Val Ser Asn Asp Glu Glu Leu Ser Arg Ala Tyr
145                 150                 155                 160

Tyr Gln Lys Ser Leu Ser Thr Ile His Asn Leu Leu Gly Leu Asp Pro
                165                 170                 175

Val Glu Asp Gly Gln Glu Pro Val Tyr Glu Asp Asp Glu Ser Leu His
            180                 185                 190

Pro Asn Met Ala Leu Phe Ala Asp Val Gly Arg Gly Met Arg Ala Thr
        195                 200                 205

Thr Asp Arg Ile Gln Arg Glu Arg Phe Tyr Arg Glu Leu Glu His Phe
    210                 215                 220

Met Ile Gln Val Gly Val Glu His Val His Arg Met Arg Gly Ser Ile
225                 230                 235                 240

Pro Ser Val Glu Lys Tyr Ile Glu Ile Arg Ser Gly Ser Val Gly Cys
                245                 250                 255

Ala Pro Gln Ile Ala Ile Thr Asp Ala Met Leu Lys Ile Arg Leu Pro
            260                 265                 270

Glu Ser Ile Met Glu Ser Ala Ala Met Lys Ala Leu Trp Arg Glu Thr
        275                 280                 285

Val Val Ile Cys Phe Ile Leu Asn Asp Val Tyr Ser Val Gln Lys Glu
    290                 295                 300

Ile Ala Gln Gly Ser Leu Asn Leu Val Pro Val Met Tyr Lys Asn
305                 310                 315                 320

Cys Asp Pro Glu Lys Gln Ser Leu Asp Thr Val Thr Arg Asp Ile Glu
                325                 330                 335

Val Leu Leu Gln Lys Ser Leu Lys Gly Phe Glu Asp Ala Ala Thr Ser
```

```
                    340                 345                 350
Leu Ser Glu Met Thr Ser Ser Asp Ala Lys Leu Ser Gln Asp Thr Gln
            355                 360                 365

Ser Phe Ile Lys Trp Cys Arg Tyr Phe Ile Thr Gly Val Gln Gln Trp
            370                 375                 380

Ser Leu Glu Ser Arg Arg Tyr Gly Met Ala Glu Cys Leu Asn Glu Asp
385                 390                 395                 400

Gly Ser Leu Ser Ile Val Leu
                405

<210> SEQ ID NO 25
<211> LENGTH: 403
<212> TYPE: PRT
<213> ORGANISM: Hypoxylon sp. EC38

<400> SEQUENCE: 25

Met Met Arg Thr Thr Leu Leu Arg Leu Ala Gln Arg Thr Arg Leu Arg
1               5                   10                  15

Leu Leu Ser Ile Leu Phe Pro His Ser Leu Pro Ala Ala Gln Glu Asp
            20                  25                  30

Gln Arg Ala Pro Glu Lys Ala Ser Ala Gln Gln Gly Leu Cys Gly Glu
        35                  40                  45

Ala Leu Val Leu Ala Ser Gln Leu Asp Gly Lys Thr Phe His Leu Pro
50                  55                  60

Asp Leu Trp Lys Val Phe Ser Asp Trp Pro Leu Ala Ala Asn Pro His
65                  70                  75                  80

Ala Gln Arg Leu Asp Ala Leu Val Asp Ser Leu Leu Glu Arg Ile Ile
            85                  90                  95

Thr Asn Glu Lys Lys Leu Lys Ala Leu Lys Gln Ala Asn Phe Gly Arg
            100                 105                 110

Leu Ile Ser Leu Trp Tyr Pro Asn Ala Glu Trp Ser Glu Leu Glu Ile
        115                 120                 125

Ala Ala Ala Tyr Ser Val Trp Ile Phe Val Trp Asp Asp Glu Ile Asp
130                 135                 140

Ala Gly Asp Thr Asp Val Ser Asn Asp Glu Leu Ser Arg Ala Tyr
145                 150                 155                 160

Tyr Gln Lys Ser Leu Ser Thr Ile His Asn Leu Leu Gly Leu Asp Pro
            165                 170                 175

Val Glu Asp Gly Gln Glu Pro Val Tyr Glu Asp Glu Ser Leu His
            180                 185                 190

Pro Asn Met Ala Leu Phe Ala Asp Val Gly Arg Gly Met Arg Ala Thr
        195                 200                 205

Thr Asp Arg Ile Gln Arg Glu Arg Phe Tyr Arg Glu Leu Glu His Phe
210                 215                 220

Met Ile Gln Val Gly Val Glu His Val His Arg Met Arg Gly Ser Ile
225                 230                 235                 240

Pro Ser Val Glu Lys Tyr Ile Glu Ile Arg Ser Gly Ser Val Gly Cys
            245                 250                 255

Ala Pro Gln Ile Ala Ile Thr Asp Ala Met Leu Lys Ile Arg Leu Pro
            260                 265                 270

Glu Ser Ile Met Glu Ser Ala Ala Met Lys Ala Leu Trp Arg Glu Thr
        275                 280                 285

Val Val Ile Cys Phe Ile Leu Asn Asp Val Tyr Ser Val Ala Gln Gly
        290                 295                 300
```

Ser Leu Leu Asn Leu Val Pro Val Met Tyr Lys Asn Cys Asp Pro Glu
305                 310                 315                 320

Lys Gln Ser Leu Asp Thr Val Thr Arg Asp Ile Glu Val Leu Leu Gln
            325                 330                 335

Lys Ser Leu Lys Gly Phe Glu Asp Ala Ala Thr Ser Leu Ser Glu Met
        340                 345                 350

Thr Ser Ser Asp Ala Lys Leu Ser Gln Asp Thr Gln Ser Phe Ile Lys
    355                 360                 365

Trp Cys Arg Tyr Phe Ile Thr Gly Val Gln Gln Trp Ser Leu Glu Ser
370                 375                 380

Arg Arg Tyr Gly Met Ala Glu Cys Leu Asn Glu Asp Gly Ser Leu Ser
385                 390                 395                 400

Ile Val Leu

<210> SEQ ID NO 26

<400> SEQUENCE: 26

000

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30
<211> LENGTH: 374
<212> TYPE: PRT
<213> ORGANISM: Artificial Sequence
<220> FEATURE:
<223> OTHER INFORMATION: Consensus polypeptide sequence
<220> FEATURE:
<221> NAME/KEY: MISC_FEATURE
<222> LOCATION: (7)..(7)
<223> OTHER INFORMATION: absent or any amino acid (e.g., an amino acid
      present at a position in one of SEQ ID NOs:31-34 when optimally
      aligned with SEQ ID NO:30)
<220> FEATURE:
<221> NAME/KEY: MISC_FEATURE
<222> LOCATION: (11)..(11)
<223> OTHER INFORMATION: absent or any amino acid (e.g., an amino acid
      present at a position in one of SEQ ID NOs:31-34 when optimally
      aligned with SEQ ID NO:30)
<220> FEATURE:
<221> NAME/KEY: MISC_FEATURE
<222> LOCATION: (17)..(17)
<223> OTHER INFORMATION: absent or any amino acid (e.g., an amino acid
      present at a position in one of SEQ ID NOs:31-34 when optimally
      aligned with SEQ ID NO:30)
<220> FEATURE:
<221> NAME/KEY: MISC_FEATURE
<222> LOCATION: (19)..(19)
<223> OTHER INFORMATION: absent or any amino acid (e.g., an amino acid
      present at a position in one of SEQ ID NOs:31-34 when optimally
      aligned with SEQ ID NO:30)

```
<220> FEATURE:
<221> NAME/KEY: MISC_FEATURE
<222> LOCATION: (28)..(28)
<223> OTHER INFORMATION: absent or any amino acid (e.g., an amino acid
      present at a position in one of SEQ ID NOs:31-34 when optimally
      aligned with SEQ ID NO:30)
<220> FEATURE:
<221> NAME/KEY: MISC_FEATURE
<222> LOCATION: (39)..(39)
<223> OTHER INFORMATION: absent or any amino acid (e.g., an amino acid
      present at a position in one of SEQ ID NOs:31-34 when optimally
      aligned with SEQ ID NO:30)
<220> FEATURE:
<221> NAME/KEY: MISC_FEATURE
<222> LOCATION: (47)..(47)
<223> OTHER INFORMATION: absent or any amino acid (e.g., an amino acid
      present at a position in one of SEQ ID NOs:31-34 when optimally
      aligned with SEQ ID NO:30)
<220> FEATURE:
<221> NAME/KEY: MISC_FEATURE
<222> LOCATION: (49)..(49)
<223> OTHER INFORMATION: absent or any amino acid (e.g., an amino acid
      present at a position in one of SEQ ID NOs:31-34 when optimally
      aligned with SEQ ID NO:30)
<220> FEATURE:
<221> NAME/KEY: MISC_FEATURE
<222> LOCATION: (52)..(52)
<223> OTHER INFORMATION: absent or any amino acid (e.g., an amino acid
      present at a position in one of SEQ ID NOs:31-34 when optimally
      aligned with SEQ ID NO:30)
<220> FEATURE:
<221> NAME/KEY: MISC_FEATURE
<222> LOCATION: (56)..(56)
<223> OTHER INFORMATION: absent or any amino acid (e.g., an amino acid
      present at a position in one of SEQ ID NOs:31-34 when optimally
      aligned with SEQ ID NO:30)
<220> FEATURE:
<221> NAME/KEY: MISC_FEATURE
<222> LOCATION: (65)..(65)
<223> OTHER INFORMATION: absent or any amino acid (e.g., an amino acid
      present at a position in one of SEQ ID NOs:31-34 when optimally
      aligned with SEQ ID NO:30)
<220> FEATURE:
<221> NAME/KEY: MISC_FEATURE
<222> LOCATION: (87)..(87)
<223> OTHER INFORMATION: absent or any amino acid (e.g., an amino acid
      present at a position in one of SEQ ID NOs:31-34 when optimally
      aligned with SEQ ID NO:30)
<220> FEATURE:
<221> NAME/KEY: MISC_FEATURE
<222> LOCATION: (92)..(92)
<223> OTHER INFORMATION: absent or any amino acid (e.g., an amino acid
      present at a position in one of SEQ ID NOs:31-34 when optimally
      aligned with SEQ ID NO:30)
<220> FEATURE:
<221> NAME/KEY: MISC_FEATURE
<222> LOCATION: (124)..(124)
<223> OTHER INFORMATION: absent or any amino acid (e.g., an amino acid
      present at a position in one of SEQ ID NOs:31-34 when optimally
      aligned with SEQ ID NO:30)
<220> FEATURE:
<221> NAME/KEY: MISC_FEATURE
<222> LOCATION: (140)..(140)
<223> OTHER INFORMATION: absent or any amino acid (e.g., an amino acid
      present at a position in one of SEQ ID NOs:31-34 when optimally
      aligned with SEQ ID NO:30)
<220> FEATURE:
<221> NAME/KEY: MISC_FEATURE
<222> LOCATION: (143)..(143)
<223> OTHER INFORMATION: absent or any amino acid (e.g., an amino acid
      present at a position in one of SEQ ID NOs:31-34 when optimally
      aligned with SEQ ID NO:30)
<220> FEATURE:
<221> NAME/KEY: MISC_FEATURE
<222> LOCATION: (193)..(193)
<223> OTHER INFORMATION: absent or any amino acid (e.g., an amino acid
      present at a position in one of SEQ ID NOs:31-34 when optimally
      aligned with SEQ ID NO:30)
<220> FEATURE:
```

```
<221> NAME/KEY: MISC_FEATURE
<222> LOCATION: (259)..(259)
<223> OTHER INFORMATION: absent or any amino acid (e.g., an amino acid
      present at a position in one of SEQ ID NOs:31-34 when optimally
      aligned with SEQ ID NO:30)
<220> FEATURE:
<221> NAME/KEY: MISC_FEATURE
<222> LOCATION: (269)..(269)
<223> OTHER INFORMATION: absent or any amino acid (e.g., an amino acid
      present at a position in one of SEQ ID NOs:31-34 when optimally
      aligned with SEQ ID NO:30)
<220> FEATURE:
<221> NAME/KEY: MISC_FEATURE
<222> LOCATION: (294)..(295)
<223> OTHER INFORMATION: absent or any amino acid (e.g., an amino acid
      present at a position in one of SEQ ID NOs:31-34 when optimally
      aligned with SEQ ID NO:30)
<220> FEATURE:
<221> NAME/KEY: MISC_FEATURE
<222> LOCATION: (300)..(300)
<223> OTHER INFORMATION: absent or any amino acid (e.g., an amino acid
      present at a position in one of SEQ ID NOs:31-34 when optimally
      aligned with SEQ ID NO:30)
<220> FEATURE:
<221> NAME/KEY: MISC_FEATURE
<222> LOCATION: (313)..(313)
<223> OTHER INFORMATION: absent or any amino acid (e.g., an amino acid
      present at a position in one of SEQ ID NOs:31-34 when optimally
      aligned with SEQ ID NO:30)
<220> FEATURE:
<221> NAME/KEY: MISC_FEATURE
<222> LOCATION: (329)..(329)
<223> OTHER INFORMATION: absent or any amino acid (e.g., an amino acid
      present at a position in one of SEQ ID NOs:31-34 when optimally
      aligned with SEQ ID NO:30)

<400> SEQUENCE: 30

Met Ala Pro Asp Ile Asp Xaa Ile Trp Ser Xaa Thr Ser Asp Val Ala
1               5                   10                  15

Xaa Ser Xaa Ile Asp Glu Arg Lys Asn Leu Ile Xaa Arg Ala Leu Asn
            20                  25                  30

Gln Lys Val Leu Val Pro Xaa Ile Leu Ser Leu Met Pro Glu Xaa Trp
        35                  40                  45

Xaa Ser Asp Xaa Gln Pro Asp Xaa Asp Glu Ile Asn Lys Glu Ile Asp
50                  55                  60

Xaa Trp Leu Pro Thr Val Asn Val Ala Glu Lys Lys Ala Lys His
65                  70                  75                  80

Arg Ala Arg Gly Asn Tyr Xaa Leu Leu Ala Ala Xaa Tyr Tyr Pro His
                85                  90                  95

Cys Lys Lys Asp Lys Met Leu Thr Leu Ser Lys Phe Leu Tyr Trp Ile
            100                 105                 110

Phe Phe Trp Asp Asp Glu Ile Asp Thr Gly Gly Xaa Leu Thr Glu Asp
        115                 120                 125

Glu Glu Gly Thr Leu Gln Cys Cys Gln Glu Thr Xaa Asn Cys Xaa Asp
    130                 135                 140

Asp Cys Leu Gly Pro Asn Pro Asn Tyr Thr Pro Pro Asn Ser Arg
145                 150                 155                 160

Gly Thr Val Glu Met Phe Tyr Pro Ile Leu Arg Asp Leu Arg Ala Gly
                165                 170                 175

Leu Gly Pro Val Ser Thr Glu Arg Leu Arg Leu Glu Leu His Asp Tyr
            180                 185                 190

Xaa Asn Gly Val Gly Lys Gln Gln Val Arg Gln Gly Asp His Leu
        195                 200                 205

Pro Asp Pro Trp Tyr His Phe Gln Ile Arg Ser Asp Asp Val Gly Val
    210                 215                 220
```

Ile Pro Ser Ile Thr Gln Asn Glu Tyr Ala Met Glu Phe Glu Leu Pro
225                 230                 235                 240

Glu Tyr Val Arg Arg His Glu Ala Met Glu Phe Ile Val Gln Glu Cys
            245                 250                 255

Thr Lys Xaa Thr Val Leu Leu Asn Asp Val Leu Ser Xaa Gln Lys Glu
        260                 265                 270

Phe Arg Val Ser Gln Leu Glu Asn Ile Val Leu Leu Phe Met Asn Lys
        275                 280                 285

Tyr Asn Ile Ser Leu Xaa Xaa Ala Ile Asp Lys Xaa Leu Gln Leu Ile
        290                 295                 300

Arg Glu His Tyr Ala Ile Cys Val Xaa Ala Glu Arg Leu Pro Trp
305                 310                 315                 320

Ser Lys Asp Asp Glu Lys Leu Asn Xaa Asn Ile Arg Glu Tyr Val Arg
            325                 330                 335

Gly Cys His Arg Leu Ala Thr Gly Thr Ala Phe Trp Ser Tyr Ser Cys
            340                 345                 350

Glu Arg Tyr Phe Lys Gln Thr Gln Val Asn Asp Lys Trp Glu Val Leu
            355                 360                 365

Leu Asp Leu Ser Tyr Glu
            370

<210> SEQ ID NO 31
<211> LENGTH: 373
<212> TYPE: PRT
<213> ORGANISM: Hypoxylon sp. CI4A

<400> SEQUENCE: 31

Met Ala Pro Asp Ile Asp Gln Ile Trp Ala Ser Thr Ser Asp Val Pro
1               5                   10                  15

Ala Ser Ala Val Asp Glu Arg Lys Ala Leu Ile Asn Arg Ala Leu Asn
            20                  25                  30

Gln Lys Val Leu Val Pro Asn Ile Leu Ser Leu Met Pro Thr Trp Thr
        35                  40                  45

Ser Ala Leu Gln Pro Asp Leu Asp Glu Ile Asn Lys Glu Ile Asp Glu
50                  55                  60

Trp Leu Pro Thr Val Asn Val Ala Glu Ala Lys Lys Ala Lys His Arg
65                  70                  75                  80

Ala Arg Gly Asn Tyr Ala Phe Leu Thr Ala Val Tyr Tyr Pro His Cys
                85                  90                  95

Lys Lys Asp Lys Met Leu Thr Leu Ser Lys Phe Leu Tyr Trp Ile Phe
            100                 105                 110

Phe Trp Asp Asp Glu Ile Asp Asn Gly Gly Glu Leu Thr Asp Asp Glu
        115                 120                 125

Glu Gly Thr Gln Gln Cys Cys Asp Glu Thr Asn Lys Cys Ile Asp Asp
    130                 135                 140

Cys Leu Gly Pro Asn Pro Asn Tyr Thr Pro Ser Asn Ala Arg Gly
145                 150                 155                 160

Thr Val Glu Met Phe Tyr Pro Ile Leu Arg Asp Leu Arg Ala Gly Leu
                165                 170                 175

Ser Pro Ile Ser Thr Glu Arg Leu Arg Leu Glu Leu His Asp Tyr Val
            180                 185                 190

Asn Gly Val Gly Arg Gln Gln Lys Val Arg Gln Gly Asp His Leu Pro
        195                 200                 205

Asp Pro Trp Tyr His Phe Gln Ile Arg Ser Asp Asp Val Gly Val Ile

```
                210                 215                 220
Pro Ser Ile Thr Gln Asn Glu Tyr Ala Met Glu Phe Glu Leu Pro Glu
225                 230                 235                 240

Tyr Val Arg Arg His Glu Ala Met Glu Ala Ile Val Gln Glu Cys Thr
                245                 250                 255

Lys Leu Thr Val Leu Leu Asn Asp Val Leu Ser Leu Gln Lys Glu Phe
                260                 265                 270

Arg Val Ser Gln Leu Glu Asn Ile Val Leu Leu Phe Met Asn Lys Tyr
            275                 280                 285

Asp Leu Ser Leu Gln Ala Ala Ile Asp Lys Ile Leu Asp Leu Ile Arg
    290                 295                 300

Glu His Tyr Gln Ile Cys Val Ala Ala Glu Glu Arg Leu Pro Trp Ser
305                 310                 315                 320

Lys Asp Asp Glu Lys Leu Asn Glu Asp Ile Arg Glu Tyr Val Arg Gly
                325                 330                 335

Cys Gln Arg Leu Ala Thr Gly Thr Ala Tyr Trp Ser Tyr Ser Cys Glu
                340                 345                 350

Arg Tyr Phe Lys Gln Thr Gln Val Asn Asp Lys Trp Glu Val Leu Leu
            355                 360                 365

Asp Leu Ser Tyr Glu
    370

<210> SEQ ID NO 32
<211> LENGTH: 373
<212> TYPE: PRT
<213> ORGANISM: Hypoxylon sp. CO27

<400> SEQUENCE: 32

Met Ala Pro Asp Ile Asp His Ile Trp Ser Thr Thr Ser Asp Val Ala
1               5                   10                  15

Thr Ser Ser Ile Asp Glu Arg Lys Asn Leu Ile Lys Arg Ala Leu Asn
                20                  25                  30

Gln Lys Val Leu Val Pro Ser Ile Leu Ser Leu Met Pro Glu Trp Pro
            35                  40                  45

Ser Asp Val Gln Pro Asp Val Asp Glu Ile Asn Lys Glu Ile Asp Glu
    50                  55                  60

Trp Leu Pro Thr Val Asn Val Ala Glu Lys Lys Val Lys His Arg
65                  70                  75                  80

Ala Arg Gly Asn Tyr Thr Leu Leu Ala Ala Ile Tyr Tyr Pro His Cys
                85                  90                  95

Lys Lys Asp Lys Met Leu Thr Leu Ser Lys Phe Leu Tyr Trp Ile Phe
                100                 105                 110

Phe Trp Asp Asp Glu Ile Asp Thr Gly Gly Asp Leu Thr Glu Asp Glu
            115                 120                 125

Glu Gly Thr Leu Gln Cys Cys Gln Glu Thr Leu Asn Cys Val Asp Asp
    130                 135                 140

Cys Leu Gly Pro Asn Pro Asn Tyr Thr Pro Pro Asn Ser Arg Gly
145                 150                 155                 160

Thr Val Glu Met Phe Tyr Pro Ile Leu Arg Asp Leu Arg Ala Gly Leu
                165                 170                 175

Gly Pro Val Ser Thr Glu Arg Leu Arg Leu Glu Leu His Asp Tyr Val
            180                 185                 190

Asn Gly Val Gly Lys Gln Gln Gln Val Arg Gln Gly Asp His Leu Pro
        195                 200                 205
```

```
Asp Pro Trp Tyr His Phe Gln Ile Arg Ser Asp Asp Val Gly Val Ile
    210                 215                 220

Pro Ser Ile Thr Gln Asn Glu Tyr Ala Met Glu Phe Glu Leu Pro Glu
225                 230                 235                 240

Tyr Val Arg Arg His Glu Ala Met Glu Phe Ile Val Gln Glu Cys Thr
                245                 250                 255

Lys Ile Thr Val Leu Leu Asn Asp Val Leu Ser Leu Gln Lys Glu Phe
                260                 265                 270

Arg Val Ser Gln Leu Glu Asn Ile Val Leu Leu Phe Met Asn Lys Tyr
            275                 280                 285

Asn Ile Ser Leu Ser Lys Ala Ile Asp Lys Val Leu Gln Leu Ile Arg
    290                 295                 300

Glu His Tyr Ala Ile Cys Val Glu Ala Glu Glu Arg Leu Pro Trp Ser
305                 310                 315                 320

Lys Asp Asp Glu Lys Leu Asn Asp Asn Ile Arg Glu Tyr Val Arg Gly
                325                 330                 335

Cys His Arg Leu Ala Thr Gly Thr Ala Phe Trp Ser Tyr Ser Cys Glu
                340                 345                 350

Arg Tyr Phe Lys Gln Thr Gln Val Asn Asp Lys Trp Glu Val Leu Leu
            355                 360                 365

Asp Leu Ser Tyr Glu
    370

<210> SEQ ID NO 33
<211> LENGTH: 374
<212> TYPE: PRT
<213> ORGANISM: Daldinia eschscholzii EC12

<400> SEQUENCE: 33

Met Ala Val Glu Val Gln Gln Ala Pro Ser Ala Val Lys Asp Ala Ala
1               5                   10                  15

Ser Leu Phe Lys Thr Glu Arg Asp Asn Ile Val Asn Arg Val Leu Asn
                20                  25                  30

Gln Lys Leu Arg Leu Pro Asn Val Met Ser Leu Thr Pro Glu Phe Trp
            35                  40                  45

Phe Asn Glu Ile Gln Pro Asp Leu Asp Glu Val Asn Thr Glu Ile Asp
    50                  55                  60

Lys Trp Leu Pro Ser Val Asp Val Ala Glu Glu Lys Lys Ala Lys His
65                  70                  75                  80

Arg Ser Arg Gly Asn Tyr Ala Leu Leu Ala Ala Val Thr Tyr Pro Arg
                85                  90                  95

Cys Lys Lys Glu Lys Leu Leu Thr Ile Ser Lys Phe Leu Tyr Trp Ile
                100                 105                 110

Phe Phe Trp Asp Asp Glu Ile Asp Thr Gly Gly Asp Leu Thr Glu Asp
            115                 120                 125

Arg Glu Ala Thr Leu Gln Cys Cys Lys Glu Thr Asn Glu Cys Ile Glu
        130                 135                 140

Asp Cys Phe Val Ala Ile Pro Asn Tyr Thr Pro Pro Asn Thr Arg
145                 150                 155                 160

Gly Thr Ile Ser Met Leu Tyr Pro Ile Leu Lys Glu Cys Arg Glu Gly
                165                 170                 175

Leu Gly Pro Val Ser Asn Ala Arg Leu Gln Ser Glu Leu His Ala Phe
            180                 185                 190

Ile Asn Gly Val Gly Lys Gln Gln Gln Val Arg Gln Glu Ser Leu Leu
        195                 200                 205
```

```
Pro Asp Pro Trp Tyr His Phe Gln Ile Arg Ser Asn Asp Val Gly Ala
    210                 215                 220

Leu Pro Cys Ile Thr Leu Thr Glu Tyr Ala Met Glu Phe Glu Leu Pro
225                 230                 235                 240

Glu Tyr Val Arg Arg His Glu Ala Met Glu Val Ile Ile Asp Glu Cys
                245                 250                 255

Val Lys Leu Thr Thr Leu Leu Asn Asp Val Leu Ser Phe Gln Lys Glu
                260                 265                 270

Phe Arg Val Ser Gln Leu Glu Asn Ile Val Phe Leu Phe Met Asn Lys
            275                 280                 285

Tyr Asn Ile Thr Leu Gln Ala Ala Ile Asp Lys Thr Leu Glu Leu Ile
    290                 295                 300

Arg Glu His Tyr Asn Ile Cys Ile Glu Ala Glu Lys Arg Leu Pro Trp
305                 310                 315                 320

Ser Lys Glu Asp Glu Lys Leu Asn Glu Asn Ile Arg Glu Tyr Val Lys
                325                 330                 335

Gly Cys His Leu Val Pro Ala Gly Met Val Asp Trp Ser Tyr Ser Cys
                340                 345                 350

Glu Arg Tyr Phe Asn Lys Ser Gln Val Asp Asp Asn Trp Glu Val Gln
            355                 360                 365

Leu Asp Met Ser Tyr Ala
    370

<210> SEQ ID NO 34
<211> LENGTH: 373
<212> TYPE: PRT
<213> ORGANISM: Hypoxylon sp. EC38

<400> SEQUENCE: 34

Met Ala Pro Asp Ile Asp His Ile Trp Ser Thr Thr Ser Asp Val Ala
1               5                   10                  15

Thr Ser Ser Ile Asp Glu Arg Lys Asn Leu Ile Lys Arg Ala Leu Asn
                20                  25                  30

Gln Lys Val Leu Val Pro Ser Ile Leu Ser Leu Met Pro Glu Trp Pro
            35                  40                  45

Ser Asp Val Gln Pro Asp Val Asp Glu Ile Asn Lys Glu Ile Asp Lys
        50                  55                  60

Trp Leu Pro Thr Val Asn Val Ala Glu Lys Lys Ala Lys His Arg
65                  70                  75                  80

Ala Arg Gly Asn Tyr Thr Leu Leu Ala Ala Ile Tyr Tyr Pro His Cys
                85                  90                  95

Lys Lys Asp Lys Met Leu Thr Leu Ser Lys Phe Leu Tyr Trp Ile Phe
                100                 105                 110

Phe Trp Asp Asp Glu Ile Asp Thr Gly Gly Glu Leu Thr Glu Asp Glu
            115                 120                 125

Glu Gly Thr Leu Gln Cys Cys Gln Glu Thr Leu Asn Cys Val Asp Asp
        130                 135                 140

Cys Leu Gly Pro Asn Pro Asn Tyr Thr Pro Pro Asn Ser Arg Gly
145                 150                 155                 160

Thr Val Glu Met Phe Tyr Pro Ile Leu Arg Asp Leu Arg Ala Gly Leu
                165                 170                 175

Gly Pro Val Ser Thr Glu Arg Leu Arg Leu Glu Leu His Asp Tyr Ile
            180                 185                 190

Asn Gly Val Gly Lys Gln Gln Gln Val Arg Gln Gly Asp Arg Leu Pro
```

```
                    195                 200                 205
Asp Pro Trp Tyr His Phe Gln Ile Arg Ser Asp Asp Val Gly Val Ile
    210                 215                 220

Pro Ser Ile Thr Gln Asn Glu Tyr Ala Met Glu Phe Glu Leu Pro Glu
225                 230                 235                 240

Tyr Val Arg Arg His Glu Ala Met Glu Phe Ile Val Gln Glu Cys Thr
                245                 250                 255

Lys Ile Thr Val Leu Leu Asn Asp Val Leu Ser Leu Gln Lys Glu Phe
            260                 265                 270

Arg Val Ser Gln Leu Glu Asn Ile Val Leu Leu Phe Met Asn Lys Tyr
        275                 280                 285

Asn Ile Ser Leu Ser Lys Ala Ile Asp Lys Val Leu Gln Leu Ile Arg
    290                 295                 300

Glu His Tyr Ala Ile Cys Val Ala Ala Glu Arg Leu Pro Trp Ser
305                 310                 315                 320

Lys Asp Asp Glu Lys Leu Asn Asp Asn Ile Arg Glu Tyr Val Arg Gly
                325                 330                 335

Cys His Arg Leu Ala Thr Gly Thr Ala Phe Trp Ser Tyr Ser Cys Glu
            340                 345                 350

Arg Tyr Phe Lys Gln Thr Gln Val Asn Asp Lys Trp Glu Val Leu Leu
        355                 360                 365

Asp Leu Ser Tyr Glu
    370

<210> SEQ ID NO 35

<400> SEQUENCE: 35

000

<210> SEQ ID NO 36

<400> SEQUENCE: 36

000

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

<210> SEQ ID NO 40
<211> LENGTH: 345
<212> TYPE: PRT
<213> ORGANISM: Artificial Sequence
<220> FEATURE:
<223> OTHER INFORMATION: Consensus polypeptide sequence
<220> FEATURE:
<221> NAME/KEY: MISC_FEATURE
```

```
<222> LOCATION: (1)..(12)
<223> OTHER INFORMATION: absent or any amino acid (e.g., an amino acid
      present at a position in one of SEQ ID NOs:41-46 when optimally
      aligned with SEQ ID NO:40)
<220> FEATURE:
<221> NAME/KEY: MISC_FEATURE
<222> LOCATION: (14)..(31)
<223> OTHER INFORMATION: absent or any amino acid (e.g., an amino acid
      present at a position in one of SEQ ID NOs:41-46 when optimally
      aligned with SEQ ID NO:40)
<220> FEATURE:
<221> NAME/KEY: MISC_FEATURE
<222> LOCATION: (33)..(33)
<223> OTHER INFORMATION: absent or any amino acid (e.g., an amino acid
      present at a position in one of SEQ ID NOs:41-46 when optimally
      aligned with SEQ ID NO:40)
<220> FEATURE:
<221> NAME/KEY: MISC_FEATURE
<222> LOCATION: (35)..(35)
<223> OTHER INFORMATION: absent or any amino acid (e.g., an amino acid
      present at a position in one of SEQ ID NOs:41-46 when optimally
      aligned with SEQ ID NO:40)
<220> FEATURE:
<221> NAME/KEY: MISC_FEATURE
<222> LOCATION: (38)..(38)
<223> OTHER INFORMATION: absent or any amino acid (e.g., an amino acid
      present at a position in one of SEQ ID NOs:41-46 when optimally
      aligned with SEQ ID NO:40)
<220> FEATURE:
<221> NAME/KEY: MISC_FEATURE
<222> LOCATION: (43)..(44)
<223> OTHER INFORMATION: absent or any amino acid (e.g., an amino acid
      present at a position in one of SEQ ID NOs:41-46 when optimally
      aligned with SEQ ID NO:40)
<220> FEATURE:
<221> NAME/KEY: MISC_FEATURE
<222> LOCATION: (48)..(48)
<223> OTHER INFORMATION: absent or any amino acid (e.g., an amino acid
      present at a position in one of SEQ ID NOs:41-46 when optimally
      aligned with SEQ ID NO:40)
<220> FEATURE:
<221> NAME/KEY: MISC_FEATURE
<222> LOCATION: (71)..(72)
<223> OTHER INFORMATION: absent or any amino acid (e.g., an amino acid
      present at a position in one of SEQ ID NOs:41-46 when optimally
      aligned with SEQ ID NO:40)
<220> FEATURE:
<221> NAME/KEY: MISC_FEATURE
<222> LOCATION: (81)..(81)
<223> OTHER INFORMATION: absent or any amino acid (e.g., an amino acid
      present at a position in one of SEQ ID NOs:41-46 when optimally
      aligned with SEQ ID NO:40)
<220> FEATURE:
<221> NAME/KEY: MISC_FEATURE
<222> LOCATION: (87)..(87)
<223> OTHER INFORMATION: absent or any amino acid (e.g., an amino acid
      present at a position in one of SEQ ID NOs:41-46 when optimally
      aligned with SEQ ID NO:40)
<220> FEATURE:
<221> NAME/KEY: MISC_FEATURE
<222> LOCATION: (107)..(107)
<223> OTHER INFORMATION: absent or any amino acid (e.g., an amino acid
      present at a position in one of SEQ ID NOs:41-46 when optimally
      aligned with SEQ ID NO:40)
<220> FEATURE:
<221> NAME/KEY: MISC_FEATURE
<222> LOCATION: (113)..(113)
<223> OTHER INFORMATION: absent or any amino acid (e.g., an amino acid
      present at a position in one of SEQ ID NOs:41-46 when optimally
      aligned with SEQ ID NO:40)
<220> FEATURE:
<221> NAME/KEY: MISC_FEATURE
<222> LOCATION: (117)..(117)
<223> OTHER INFORMATION: absent or any amino acid (e.g., an amino acid
      present at a position in one of SEQ ID NOs:41-46 when optimally
      aligned with SEQ ID NO:40)
<220> FEATURE:
<221> NAME/KEY: MISC_FEATURE
<222> LOCATION: (126)..(127)
```

```
<223> OTHER INFORMATION: absent or any amino acid (e.g., an amino acid
      present at a position in one of SEQ ID NOs:41-46 when optimally
      aligned with SEQ ID NO:40)
<220> FEATURE:
<221> NAME/KEY: MISC_FEATURE
<222> LOCATION: (131)..(131)
<223> OTHER INFORMATION: absent or any amino acid (e.g., an amino acid
      present at a position in one of SEQ ID NOs:41-46 when optimally
      aligned with SEQ ID NO:40)
<220> FEATURE:
<221> NAME/KEY: MISC_FEATURE
<222> LOCATION: (133)..(134)
<223> OTHER INFORMATION: absent or any amino acid (e.g., an amino acid
      present at a position in one of SEQ ID NOs:41-46 when optimally
      aligned with SEQ ID NO:40)
<220> FEATURE:
<221> NAME/KEY: MISC_FEATURE
<222> LOCATION: (159)..(159)
<223> OTHER INFORMATION: absent or any amino acid (e.g., an amino acid
      present at a position in one of SEQ ID NOs:41-46 when optimally
      aligned with SEQ ID NO:40)
<220> FEATURE:
<221> NAME/KEY: MISC_FEATURE
<222> LOCATION: (177)..(178)
<223> OTHER INFORMATION: absent or any amino acid (e.g., an amino acid
      present at a position in one of SEQ ID NOs:41-46 when optimally
      aligned with SEQ ID NO:40)
<220> FEATURE:
<221> NAME/KEY: MISC_FEATURE
<222> LOCATION: (181)..(181)
<223> OTHER INFORMATION: absent or any amino acid (e.g., an amino acid
      present at a position in one of SEQ ID NOs:41-46 when optimally
      aligned with SEQ ID NO:40)
<220> FEATURE:
<221> NAME/KEY: MISC_FEATURE
<222> LOCATION: (184)..(184)
<223> OTHER INFORMATION: absent or any amino acid (e.g., an amino acid
      present at a position in one of SEQ ID NOs:41-46 when optimally
      aligned with SEQ ID NO:40)
<220> FEATURE:
<221> NAME/KEY: MISC_FEATURE
<222> LOCATION: (194)..(194)
<223> OTHER INFORMATION: absent or any amino acid (e.g., an amino acid
      present at a position in one of SEQ ID NOs:41-46 when optimally
      aligned with SEQ ID NO:40)
<220> FEATURE:
<221> NAME/KEY: MISC_FEATURE
<222> LOCATION: (202)..(202)
<223> OTHER INFORMATION: absent or any amino acid (e.g., an amino acid
      present at a position in one of SEQ ID NOs:41-46 when optimally
      aligned with SEQ ID NO:40)
<220> FEATURE:
<221> NAME/KEY: MISC_FEATURE
<222> LOCATION: (210)..(210)
<223> OTHER INFORMATION: absent or any amino acid (e.g., an amino acid
      present at a position in one of SEQ ID NOs:41-46 when optimally
      aligned with SEQ ID NO:40)
<220> FEATURE:
<221> NAME/KEY: MISC_FEATURE
<222> LOCATION: (212)..(212)
<223> OTHER INFORMATION: absent or any amino acid (e.g., an amino acid
      present at a position in one of SEQ ID NOs:41-46 when optimally
      aligned with SEQ ID NO:40)
<220> FEATURE:
<221> NAME/KEY: MISC_FEATURE
<222> LOCATION: (212)..(212)
<223> OTHER INFORMATION: absent or any amino acid (e.g., an amino acid
      present at a position in one of SEQ ID NOs:41-46 when optimally
      aligned with SEQ ID NO:40)
<220> FEATURE:
<221> NAME/KEY: MISC_FEATURE
<222> LOCATION: (216)..(217)
<223> OTHER INFORMATION: absent or any amino acid (e.g., an amino acid
       present at a position in one of SEQ ID NOs:41-46 when optimally
      aligned with SEQ ID NO:40)
<220> FEATURE:
<221> NAME/KEY: MISC_FEATURE
<222> LOCATION: (219)..(220)
<223> OTHER INFORMATION: absent or any amino acid (e.g., an amino acid
``` present at a position in one of SEQ ID NOs:41-46 when optimally
    aligned with SEQ ID NO:40)
<220> FEATURE:
<221> NAME/KEY: MISC_FEATURE
<222> LOCATION: (224)..(224)
<223> OTHER INFORMATION: absent or any amino acid (e.g., an amino acid
    present at a position in one of SEQ ID NOs:41-46 when optimally
    aligned with SEQ ID NO:40)
<220> FEATURE:
<221> NAME/KEY: MISC_FEATURE
<222> LOCATION: (226)..(226)
<223> OTHER INFORMATION: absent or any amino acid (e.g., an amino acid
    present at a position in one of SEQ ID NOs:41-46 when optimally
    aligned with SEQ ID NO:40)
<220> FEATURE:
<221> NAME/KEY: MISC_FEATURE
<222> LOCATION: (230)..(230)
<223> OTHER INFORMATION: absent or any amino acid (e.g., an amino acid
    present at a position in one of SEQ ID NOs:41-46 when optimally
    aligned with SEQ ID NO:40)
<220> FEATURE:
<221> NAME/KEY: MISC_FEATURE
<222> LOCATION: (232)..(232)
<223> OTHER INFORMATION: absent or any amino acid (e.g., an amino acid
    present at a position in one of SEQ ID NOs:41-46 when optimally
    aligned with SEQ ID NO:40)
<220> FEATURE:
<221> NAME/KEY: MISC_FEATURE
<222> LOCATION: (239)..(239)
<223> OTHER INFORMATION: absent or any amino acid (e.g., an amino acid
    present at a position in one of SEQ ID NOs:41-46 when optimally
    aligned with SEQ ID NO:40)
<220> FEATURE:
<221> NAME/KEY: MISC_FEATURE
<222> LOCATION: (241)..(241)
<223> OTHER INFORMATION: absent or any amino acid (e.g., an amino acid
    present at a position in one of SEQ ID NOs:41-46 when optimally
    aligned with SEQ ID NO:40)
<220> FEATURE:
<221> NAME/KEY: MISC_FEATURE
<222> LOCATION: (249)..(249)
<223> OTHER INFORMATION: absent or any amino acid (e.g., an amino acid
    present at a position in one of SEQ ID NOs:41-46 when optimally
    aligned with SEQ ID NO:40)
<220> FEATURE:
<221> NAME/KEY: MISC_FEATURE
<222> LOCATION: (251)..(251)
<223> OTHER INFORMATION: absent or any amino acid (e.g., an amino acid
    present at a position in one of SEQ ID NOs:41-46 when optimally
    aligned with SEQ ID NO:40)
<220> FEATURE:
<221> NAME/KEY: MISC_FEATURE
<222> LOCATION: (260)..(260)
<223> OTHER INFORMATION: absent or any amino acid (e.g., an amino acid
    present at a position in one of SEQ ID NOs:41-46 when optimally
    aligned with SEQ ID NO:40)
<220> FEATURE:
<221> NAME/KEY: MISC_FEATURE
<222> LOCATION: (267)..(267)
<223> OTHER INFORMATION: absent or any amino acid (e.g., an amino acid
    present at a position in one of SEQ ID NOs:41-46 when optimally
    aligned with SEQ ID NO:40)
<220> FEATURE:
<221> NAME/KEY: MISC_FEATURE
<222> LOCATION: (270)..(271)
<223> OTHER INFORMATION: absent or any amino acid (e.g., an amino acid
    present at a position in one of SEQ ID NOs:41-46 when optimally
    aligned with SEQ ID NO:40)
<220> FEATURE:
<221> NAME/KEY: MISC_FEATURE
<222> LOCATION: (282)..(282)
<223> OTHER INFORMATION: absent or any amino acid (e.g., an amino acid
    present at a position in one of SEQ ID NOs:41-46 when optimally
    aligned with SEQ ID NO:40)
<220> FEATURE:
<221> NAME/KEY: MISC_FEATURE
<222> LOCATION: (289)..(290)
<223> OTHER INFORMATION: absent or any amino acid (e.g., an amino acid
    present at a position in one of SEQ ID NOs:41-46 when optimally

```
        aligned with SEQ ID NO:40)
<220> FEATURE:
<221> NAME/KEY: MISC_FEATURE
<222> LOCATION: (292)..(293)
<223> OTHER INFORMATION: absent or any amino acid (e.g., an amino acid
        present at a position in one of SEQ ID NOs:41-46 when optimally
        aligned with SEQ ID NO:40)
<220> FEATURE:
<221> NAME/KEY: MISC_FEATURE
<222> LOCATION: (297)..(297)
<223> OTHER INFORMATION: absent or any amino acid (e.g., an amino acid
        present at a position in one of SEQ ID NOs:41-46 when optimally
        aligned with SEQ ID NO:40)
<220> FEATURE:
<221> NAME/KEY: MISC_FEATURE
<222> LOCATION: (300)..(304)
<223> OTHER INFORMATION: absent or any amino acid (e.g., an amino acid
        present at a position in one of SEQ ID NOs:41-46 when optimally
        aligned with SEQ ID NO:40)
<220> FEATURE:
<221> NAME/KEY: MISC_FEATURE
<222> LOCATION: (307)..(307)
<223> OTHER INFORMATION: absent or any amino acid (e.g., an amino acid
        present at a position in one of SEQ ID NOs:41-46 when optimally
        aligned with SEQ ID NO:40)
<220> FEATURE:
<221> NAME/KEY: MISC_FEATURE
<222> LOCATION: (310)..(310)
<223> OTHER INFORMATION: absent or any amino acid (e.g., an amino acid
        present at a position in one of SEQ ID NOs:41-46 when optimally
        aligned with SEQ ID NO:40)
<220> FEATURE:
<221> NAME/KEY: MISC_FEATURE
<222> LOCATION: (337)..(345)
<223> OTHER INFORMATION: absent or any amino acid (e.g., an amino acid
        present at a position in one of SEQ ID NOs:41-46 when optimally
        aligned with SEQ ID NO:40)

<400> SEQUENCE: 40

Xaa Xaa Xaa Xaa Xaa Xaa Xaa Xaa Xaa Xaa Xaa Xaa Pro Xaa Xaa Xaa
 1               5                  10                  15

Xaa Xaa Xaa Xaa Xaa Xaa Xaa Xaa Xaa Xaa Xaa Xaa Xaa Xaa Xaa Pro
                20                  25                  30

Xaa Ser Xaa Trp Thr Xaa Leu Ile His Pro Xaa Xaa Glu Lys Val Xaa
            35                  40                  45

Arg Glu Val Asp Gly Tyr Phe Leu Gln His Trp Pro Phe Pro Asp Glu
 50                  55                  60

Asn Ser Arg Lys Lys Phe Xaa Xaa Ala Gly Phe Ser Arg Val Thr Cys
65                   70                  75                  80

Xaa Tyr Phe Pro Lys Ala Xaa Asp Asp Arg Ile His Phe Ala Cys Arg
                85                  90                  95

Leu Leu Thr Leu Leu Phe Leu Ile Asp Asp Xaa Leu Glu His Met Ser
            100                 105                 110

Xaa Glu Asp Gly Xaa Ala Tyr Asn Glu Arg Leu Met Pro Xaa Xaa Arg
        115                 120                 125

Gly Asp Xaa Leu Xaa Xaa Pro Asp Arg Ser Val Pro Val Glu Tyr Ile
130                 135                 140

Ser Tyr Asp Leu Trp Glu Ser Met Arg Ala His Asp Arg Asp Xaa Ala
145                 150                 155                 160

Asp Glu Ile Leu Glu Pro Val Phe Thr Phe Met Arg Ala Gln Thr Asp
                165                 170                 175

Xaa Xaa Arg Leu Xaa Ser Met Xaa Leu Gly Gln Tyr Leu Glu Tyr Arg
            180                 185                 190

Glu Xaa Asp Val Gly Lys Ala Leu Leu Xaa Ala Leu Met Arg Phe Ser
        195                 200                 205
```

Met Xaa Leu Xaa Val Thr Pro Xaa Xaa Leu Xaa Xaa Val Arg Pro Xaa
210                215             220

Asp Xaa Asn Cys Ser Xaa His Xaa Ser Val Ile Asn Asp Ile Xaa Ser
225             230              235                 240

Xaa Glu Lys Glu Val Leu Ala Ala Xaa Thr Xaa His Glu Gly Gly
        245                 250             255

Val Leu Cys Xaa Ala Val Ala Val Leu Ser Xaa Glu Thr Xaa Xaa Ser
        260             265             270

Thr Asp Ala Ser Lys Arg Val Leu Tyr Xaa Leu Cys Arg Glu Trp Glu
            275             280             285

Xaa Xaa His Xaa Xaa Leu Val Asp Xaa Leu Leu Xaa Xaa Xaa Xaa
        290             295             300

Ala Gly Xaa Asp Thr Xaa Thr Leu Arg Ala Tyr Leu Gln Gly Leu Glu
305         310             315             320

Tyr Gln Met Ser Gly Asn Glu Leu Trp Ser Arg Thr Pro Arg Tyr
            325             330             335

Xaa Xaa Xaa Xaa Xaa Xaa Xaa Xaa
        340             345

<210> SEQ ID NO 41
<211> LENGTH: 313
<212> TYPE: PRT
<213> ORGANISM: Hypoxylon sp. CI4A

<400> SEQUENCE: 41

Met Ser Leu Ala Pro Ser Ser Gly Asp Tyr Pro Ser Ser His Trp Thr
1               5                   10                  15

Pro Leu Ile His Pro Leu Ser Glu Lys Val Thr Arg Glu Val Asp Gly
            20                  25                  30

Tyr Tyr Leu Gln His Trp Pro Phe Pro Asp Glu Arg Ser Arg Lys Lys
        35                  40                  45

Phe Val Ala Ala Gly Phe Ser Arg Val Thr Cys Phe Tyr Phe Pro Lys
50                  55                  60

Ala Leu Asn Asp Arg Ile His Phe Ala Cys Arg Leu Leu Thr Val Leu
65                  70                  75                  80

Phe Leu Ile Asp Asp Leu Leu Glu Tyr Met Ser Leu Glu Asp Gly Lys
                85                  90                  95

Ala Tyr Asn Glu Lys Leu Ile Pro Ile Ser Arg Gly Asp Val Leu Pro
            100                 105                 110

Asp Arg Ser Val Pro Val Glu Tyr Ile Thr Tyr Asp Leu Trp Glu Ser
        115                 120                 125

Met Arg Ala His Asp Arg Ile Met Ala Asp Ile Leu Glu Pro Val
130                 135                 140

Phe Thr Phe Met Arg Ala Gln Thr Asp Ser Val Arg Leu Glu Ala Met
145                 150                 155                 160

Asp Leu Gly Arg Tyr Leu Glu Tyr Arg Glu Arg Asp Val Gly Lys Ala
                165                 170                 175

Leu Leu Gly Ala Leu Met Arg Phe Ser Met Gly Leu Val Val Pro Pro
            180                 185                 190

Glu Asp Leu Ala Ile Val Arg Pro Ile Asp Phe Asn Cys Ser Arg His
        195                 200                 205

Leu Ser Val Ile Asn Asp Ile Trp Ser Phe Glu Lys Glu Leu Leu Ala
    210                 215                 220

Ser Lys Asn Ala His Glu Glu Gly Gly Val Leu Cys Ser Ala Val Ser
225                 230                 235                 240

```
Val Leu Ala Asp Gln Val Gly Ile Ser Ile Asp Gly Ser Lys Arg Ile
                245                 250                 255

Leu Tyr Tyr Leu Cys Arg Glu Trp Glu His Arg His Glu Thr Leu Val
            260                 265                 270

Lys Glu Met Leu Gln Val Arg Asp Thr Pro Ala Leu Arg Ser Tyr Val
        275                 280                 285

Lys Gly Leu Glu Tyr Gln Met Ser Gly Asn Glu Met Trp Ser Arg Thr
    290                 295                 300

Thr Met Arg Tyr Leu Ala Pro Lys Asp
305                 310

<210> SEQ ID NO 42
<211> LENGTH: 334
<212> TYPE: PRT
<213> ORGANISM: Hypoxylon sp. CO27

<400> SEQUENCE: 42

Met Ala Pro Met Ala Glu Glu Cys Val Ser Ala Ser Pro Asn Gln Gly
1               5                   10                  15

His Ala Lys Pro Val Ala Thr Pro Met Arg Arg Ala Val His Ile Pro
            20                  25                  30

Ser Ser Glu Trp Thr Ala Gln Ile His Pro Leu His Glu Lys Val Ile
        35                  40                  45

Ala Glu Val Asp Gly Tyr Phe Leu Gln His Trp Pro Phe Pro Ser Glu
    50                  55                  60

Lys Thr Arg Lys Phe Val Ala Ala Gly Phe Ser Arg Val Thr Cys
65                  70                  75                  80

Leu Tyr Phe Pro Lys Ala Leu Asp Asp Arg Ile His Phe Ala Cys Arg
                85                  90                  95

Leu Leu Thr Leu Leu Phe Leu Val Asp Asp Ile Leu Glu His Met Ser
            100                 105                 110

Leu Glu Asp Gly Arg Ala Tyr Asn Glu Arg Leu Met Pro Leu Phe Arg
        115                 120                 125

Gly Ser Val Leu Pro Asp Arg Ser Val Pro Val Glu Trp Ile Ser Tyr
    130                 135                 140

Asp Leu Trp Glu Ser Met Arg Ala His Asp Arg Asp Met Ala Asp Glu
145                 150                 155                 160

Ile Ile Glu Pro Val Phe Thr Phe Met Trp Ala Gln Thr Asp Pro Ala
                165                 170                 175

Arg Leu Thr Glu Met Gly Leu Gly Gln Tyr Leu Glu Tyr Arg Glu Arg
            180                 185                 190

Asp Val Gly Lys Ala Leu Leu Ala Ala Leu Met Arg Phe Ser Met Ala
        195                 200                 205

Leu Ile Val Ser Pro Ser Asp Leu Glu Met Val Arg Pro Val Asp Arg
    210                 215                 220

Asn Cys Ser Lys His Leu Ser Val Ile Asn Asp Ile Trp Ser Tyr Glu
225                 230                 235                 240

Lys Glu Val Leu Ala Ala Gln Thr Leu His Glu Glu Gly Gly Met Leu
                245                 250                 255

Cys Thr Ala Val Ala Val Leu Ser Lys Glu Ala Glu Ile Ser Thr Asp
            260                 265                 270

Ala Ser Lys Arg Val Leu Tyr His Leu Cys Arg Glu Trp Glu Asp Glu
        275                 280                 285

His Arg Ile Leu Val Ala Asp Ile Leu Ala Gln Asn Asp Thr Pro Val
```

```
                        290                 295                 300

Leu Arg Ala Tyr Leu Gln Gly Leu Glu Phe Gln Met Ser Gly Asn Glu
305                 310                 315                 320

Leu Trp Ser Arg Thr Thr Leu Arg Tyr Val Gln Pro Arg Pro
                325                 330

<210> SEQ ID NO 43
<211> LENGTH: 308
<212> TYPE: PRT
<213> ORGANISM: Daldinia eschscholzii EC12

<400> SEQUENCE: 43

Met Glu Tyr Ala Gln Ser Thr Phe Thr Leu Leu Cys His Pro Arg Phe
1               5                   10                  15

Glu Val Val Glu Arg Glu Thr Asn Glu Tyr Phe Ile Ala Asn Trp Pro
            20                  25                  30

Phe Pro Asp Val Asn Ser Arg Asp Lys Phe Leu Lys Ala Gly Phe Ser
        35                  40                  45

Arg Cys Thr Cys Val Tyr Phe Pro Lys Ala Lys Asp Asp Arg Ile His
    50                  55                  60

Phe Ala Cys Arg Leu Leu Thr Leu Leu Phe Leu Ile Asp Asp Val Leu
65                  70                  75                  80

Glu Asp Met Ser Phe Glu Glu Gly Thr Ala Tyr Asn Gly Arg Leu Met
                85                  90                  95

Ser Ile Ile Arg Gly Asp Glu Val Pro Asp Arg Ser Ile Pro Val Gln
            100                 105                 110

Tyr Ile Ser His Asp Leu Trp Gln Ser Met Arg Ala His Asp Gln Arg
        115                 120                 125

Leu Ala Asp Gly Ile Leu Glu Pro Leu Phe Ile Phe Met Gln Ala Gln
    130                 135                 140

Thr Asp Lys Arg Arg Ala His Ser Met Ser Leu Gly Gln Tyr Ile Glu
145                 150                 155                 160

Tyr Arg Asp Lys Asp Ile Gly Gln Ala Leu Leu Cys Ala Leu Met Arg
                165                 170                 175

Phe Cys Leu Asp Ile Lys Leu Thr Gln His Glu Leu Asp Leu Val Arg
            180                 185                 190

Pro Ala Asp Val Asn Cys Gly Ile His Ile Ala Ile Met Asn Asp Ile
        195                 200                 205

Trp Ser Phe Glu Lys Glu Ala Leu Thr Ala Ala Arg Gly His Asp Glu
    210                 215                 220

Gly Gly Val Leu Cys Asn Ser Val Ala Ile Leu Ser Thr Glu Thr Ser
225                 230                 235                 240

Leu Ser Thr Ala Ser Ser Lys Arg Val Leu Tyr Cys Met Cys Arg Glu
                245                 250                 255

Trp Glu Thr Lys His Arg Arg Phe Val Asp Glu Leu Gly Gly Gly Arg
            260                 265                 270

Asp Thr Thr Leu Trp Thr Tyr Leu Gln Gly Leu Glu Tyr Gln Met Ser
        275                 280                 285

Gly Asn Glu Ala Trp Ser Lys Leu Thr Pro Arg Tyr Gln Ile Gln Glu
    290                 295                 300

Ser Glu Lys Leu
305

<210> SEQ ID NO 44
<211> LENGTH: 334
```

```
<212> TYPE: PRT
<213> ORGANISM: Hypoxylon sp. EC38

<400> SEQUENCE: 44

Met Ala Pro Met Val Glu Glu Tyr Val Pro Thr Ser Pro Thr Gln Asp
1               5                   10                  15

Tyr Ala Lys Pro Val Ala Thr Pro Ile Gln Arg Ala Val His Ile Pro
                20                  25                  30

Ala Ser Glu Trp Thr Ala Gln Ile His Pro Leu His Glu Lys Val Ile
            35                  40                  45

Val Glu Val Asp Gly Tyr Phe Leu Gln His Trp Pro Phe Pro Asn Glu
        50                  55                  60

Lys Ala Arg Lys Lys Phe Val Ala Ala Gly Phe Ser Arg Val Thr Cys
65                  70                  75                  80

Leu Tyr Phe Pro Lys Ala Leu Asp Asp Arg Ile His Phe Ala Cys Arg
                85                  90                  95

Leu Leu Thr Leu Leu Phe Leu Val Asp Asp Ile Leu Glu His Met Ser
            100                 105                 110

Leu Glu Asp Gly Arg Ala Tyr Asn Glu Arg Leu Met Pro Leu Phe Arg
        115                 120                 125

Gly Ser Val Leu Pro Asp Arg Ser Val Pro Val Glu Trp Ile Ser Tyr
130                 135                 140

Asp Leu Trp Glu Ser Met Arg Ala His Asp Arg Asp Met Ala Asp Glu
145                 150                 155                 160

Ile Ile Glu Pro Val Phe Thr Phe Met Arg Ala Gln Thr Asp Pro Ala
                165                 170                 175

Arg Leu Thr Asp Met Gly Leu Gly Gln Tyr Leu Glu Tyr Arg Glu Arg
            180                 185                 190

Asp Val Gly Lys Ala Leu Leu Ala Ala Leu Met Arg Phe Ser Met Ala
        195                 200                 205

Leu Thr Val Ser Pro Ser Asp Leu Glu Met Val Arg Pro Val Asp Arg
210                 215                 220

Asn Cys Ser Lys His Leu Ser Val Ile Asn Asp Ile Trp Ser Tyr Glu
225                 230                 235                 240

Lys Glu Val Leu Ala Ala Gln Thr Leu His Glu Gly Gly Met Leu
                245                 250                 255

Cys Thr Ala Val Ala Val Leu Ser Lys Glu Ala Glu Ile Ser Thr Asp
            260                 265                 270

Ala Ser Lys Arg Val Leu Tyr His Leu Cys Arg Glu Trp Glu Asp Glu
        275                 280                 285

His Arg Ile Leu Val Ala Asp Ile Leu Ala Gln Asn Asp Thr Pro Val
    290                 295                 300

Leu Arg Ala Tyr Leu Gln Gly Leu Glu Phe Gln Met Ser Gly Asn Glu
305                 310                 315                 320

Leu Trp Ser Arg Thr Thr Leu Arg Tyr Val Gln Pro Arg Pro
                325                 330

<210> SEQ ID NO 45
<211> LENGTH: 309
<212> TYPE: PRT
<213> ORGANISM: Hypoxylon sp. EC38

<400> SEQUENCE: 45

Met Glu Tyr Ala Gln Ser Thr Phe Ser Leu Leu Arg His Pro Arg Phe
1               5                   10                  15
```

```
Glu Glu Val Glu Arg Glu Thr Asn Glu Tyr Phe Leu Ala Asn Trp Pro
         20                  25                  30

Phe Pro Asp Leu Asn Ser Arg Asp Lys Phe Leu Lys Ala Gly Phe Thr
             35                  40                  45

Arg Cys Thr Cys Met Tyr Phe Pro Lys Ala Lys Asp Asp Arg Ile Gln
 50                  55                  60

Phe Ala Cys Arg Leu Leu Thr Leu Leu Phe Leu Ile Asp Asp Val Leu
 65                  70                  75                  80

Glu Asn Met Ser Phe Glu Glu Gly Thr Ala Tyr Asn Gly Lys Leu Met
                 85                  90                  95

Pro Ile Ile Arg Gly Asp Glu Val Pro Asn Cys Ser Val Pro Val Gln
            100                 105                 110

Lys Ile Ser Tyr Asp Leu Trp Gln Ser Met Arg Ala Asn Asp Arg Glu
        115                 120                 125

Leu Ala Asp Gly Ile Leu Glu Pro Leu Phe Ile Phe Met Arg Ala Gln
    130                 135                 140

Thr Asp Lys Arg Arg Ala His Ser Met Ser Leu Gly Gln Tyr Leu Glu
145                 150                 155                 160

Tyr Arg Asp Lys Asp Ile Gly Gln Ala Leu Leu Cys Ala Leu Met Arg
                165                 170                 175

Phe Cys Leu Asp Ile Lys Leu Thr Gln His Glu Leu Asp Ile Val Arg
            180                 185                 190

Pro Ala Asn Val Asn Cys Gly Asn His Ile Ala Val Ile Asn Asp Ile
        195                 200                 205

Trp Ser Phe Glu Lys Glu Ala Leu Thr Ala Thr His Ala His Asp Glu
    210                 215                 220

Gly Gly Val Leu Cys Asn Ser Val Ala Ile Leu Ser Ala Glu Thr Ala
225                 230                 235                 240

Leu Ser Thr Ala Ser Ser Lys Arg Val Leu Tyr Cys Leu Cys Arg Glu
                245                 250                 255

Trp Glu Thr Lys His Gln Gln Phe Val Asp Gly Leu Gly Asp Gly His
            260                 265                 270

Asp Ala Glu Thr Leu Arg Ala Tyr Leu Gln Gly Leu Gly Tyr Gln Met
        275                 280                 285

Ser Gly Asn Glu Ala Trp Ser Lys Ile Thr Pro Arg Tyr Gln Ile His
    290                 295                 300

Glu Ser Asp Arg Leu
305

<210> SEQ ID NO 46
<211> LENGTH: 342
<212> TYPE: PRT
<213> ORGANISM: Hypoxylon sp. CI4A

<400> SEQUENCE: 46

Met Ser Val Ala Val Glu Thr Ile Thr Ala Pro Thr Val Thr Leu Ser
 1               5                  10                  15

Thr Ser Lys Pro Leu Val Lys Glu Thr Trp Lys Ile Pro Ala Ser Gly
             20                  25                  30

Trp Thr Pro Met Ile His Pro Arg Ala Glu Glu Val Ser Arg Glu Val
             35                  40                  45

Asp Asn Tyr Phe Leu Glu His Trp Asn Phe Pro Asp Asp Asn Ala Arg
 50                  55                  60

Ser Thr Phe Leu Lys Ala Gly Phe Ser Arg Val Thr Cys Leu Tyr Phe
 65                  70                  75                  80
```

```
Pro Leu Ala Lys Asp Asp Arg Ile His Phe Ala Cys Arg Leu Leu Thr
                85                  90                  95

Val Leu Phe Leu Ile Asp Asp Ile Leu Glu Glu Met Ser Phe Ala Asp
            100                 105                 110

Gly Glu Ala Leu Asn Asn Arg Leu Ile Glu Leu Ser Lys Gly Pro Glu
        115                 120                 125

Tyr Ala Thr Pro Asp Arg Ser Ile Pro Ala Glu Tyr Val Ile Tyr Asp
    130                 135                 140

Leu Trp Glu Ser Met Arg Lys His Asp Leu Asp Leu Ala Asn Glu Val
145                 150                 155                 160

Leu Glu Pro Thr Phe Val Phe Met Arg Ser Gln Thr Asp Arg Val Arg
                165                 170                 175

Leu Ser Ile Lys Glu Leu Gly Glu Tyr Leu Arg Tyr Arg Glu Lys Asp
            180                 185                 190

Val Gly Lys Ala Leu Leu Ser Ala Leu Met Arg Tyr Ser Met Glu Leu
        195                 200                 205

Arg Pro Thr Ala Glu Glu Leu Ala Ala Leu Arg Pro Leu Glu Glu Asn
    210                 215                 220

Cys Ser Lys His Ile Ser Ile Val Asn Asp Ile Tyr Ser Phe Glu Lys
225                 230                 235                 240

Glu Val Ile Ala Ala Lys Thr Gly His Lys Glu Gly Ser Phe Leu Cys
                245                 250                 255

Ser Ala Val Lys Val Val Ala Thr Glu Thr Ala Leu Gly Ile Ser Ala
            260                 265                 270

Thr Lys Arg Val Leu Trp Ser Met Val Arg Glu Trp Glu Leu Val His
        275                 280                 285

Asp Ala Met Cys Asp Ala Leu Leu Leu Ala Ala Ser Gly Ala Gly Thr
    290                 295                 300

Asn Ser Gln Thr Val Arg Asp Tyr Met Arg Gly Leu Gln Tyr Gln Met
305                 310                 315                 320

Ser Gly Asn Glu Leu Trp Ser Cys Thr Thr Pro Arg Tyr Ile Glu Ala
                325                 330                 335

Ile Asp Gln Ala Ala Arg
            340

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50
<211> LENGTH: 846
<212> TYPE: PRT
<213> ORGANISM: Artificial Sequence
<220> FEATURE:
```

```
<223> OTHER INFORMATION: Consensus polypeptide sequence
<220> FEATURE:
<221> NAME/KEY: MISC_FEATURE
<222> LOCATION: (1)..(79)
<223> OTHER INFORMATION: absent or any amino acid (e.g., an amino acid
      present at a position in one of SEQ ID NOs:51-54 when optimally
      aligned with SEQ ID NO:50)
<220> FEATURE:
<221> NAME/KEY: MISC_FEATURE
<222> LOCATION: (86)..(86)
<223> OTHER INFORMATION: absent or any amino acid (e.g., an amino acid
      present at a position in one of SEQ ID NOs:51-54 when optimally
      aligned with SEQ ID NO:50)
<220> FEATURE:
<221> NAME/KEY: MISC_FEATURE
<222> LOCATION: (95)..(95)
<223> OTHER INFORMATION: absent or any amino acid (e.g., an amino acid
      present at a position in one of SEQ ID NOs:51-54 when optimally
      aligned with SEQ ID NO:50)
<220> FEATURE:
<221> NAME/KEY: MISC_FEATURE
<222> LOCATION: (97)..(102)
<223> OTHER INFORMATION: absent or any amino acid (e.g., an amino acid
      present at a position in one of SEQ ID NOs:51-54 when optimally
      aligned with SEQ ID NO:50)
<220> FEATURE:
<221> NAME/KEY: MISC_FEATURE
<222> LOCATION: (108)..(108)
<223> OTHER INFORMATION: absent or any amino acid (e.g., an amino acid
      present at a position in one of SEQ ID NOs:51-54 when optimally
      aligned with SEQ ID NO:50)
<220> FEATURE:
<221> NAME/KEY: MISC_FEATURE
<222> LOCATION: (112)..(112)
<223> OTHER INFORMATION: absent or any amino acid (e.g., an amino acid
      present at a position in one of SEQ ID NOs:51-54 when optimally
      aligned with SEQ ID NO:50)
<220> FEATURE:
<221> NAME/KEY: MISC_FEATURE
<222> LOCATION: (115)..(115)
<223> OTHER INFORMATION: absent or any amino acid (e.g., an amino acid
      present at a position in one of SEQ ID NOs:51-54 when optimally
      aligned with SEQ ID NO:50)
<220> FEATURE:
<221> NAME/KEY: MISC_FEATURE
<222> LOCATION: (119)..(119)
<223> OTHER INFORMATION: absent or any amino acid (e.g., an amino acid
      present at a position in one of SEQ ID NOs:51-54 when optimally
      aligned with SEQ ID NO:50)
<220> FEATURE:
<221> NAME/KEY: MISC_FEATURE
<222> LOCATION: (121)..(124)
<223> OTHER INFORMATION: absent or any amino acid (e.g., an amino acid
      present at a position in one of SEQ ID NOs:51-54 when optimally
      aligned with SEQ ID NO:50)
<220> FEATURE:
<221> NAME/KEY: MISC_FEATURE
<222> LOCATION: (127)..(127)
<223> OTHER INFORMATION: absent or any amino acid (e.g., an amino acid
      present at a position in one of SEQ ID NOs:51-54 when optimally
      aligned with SEQ ID NO:50)
<220> FEATURE:
<221> NAME/KEY: MISC_FEATURE
<222> LOCATION: (162)..(162)
<223> OTHER INFORMATION: absent or any amino acid (e.g., an amino acid
      present at a position in one of SEQ ID NOs:51-54 when optimally
      aligned with SEQ ID NO:50)
<220> FEATURE:
<221> NAME/KEY: MISC_FEATURE
<222> LOCATION: (164)..(164)
<223> OTHER INFORMATION: absent or any amino acid (e.g., an amino acid
      present at a position in one of SEQ ID NOs:51-54 when optimally
      aligned with SEQ ID NO:50)
<220> FEATURE:
<221> NAME/KEY: MISC_FEATURE
<222> LOCATION: (193)..(193)
<223> OTHER INFORMATION: absent or any amino acid (e.g., an amino acid
      present at a position in one of SEQ ID NOs:51-54 when optimally
      aligned with SEQ ID NO:50)
```

```
<220> FEATURE:
<221> NAME/KEY: MISC_FEATURE
<222> LOCATION: (231)..(231)
<223> OTHER INFORMATION: absent or any amino acid (e.g., an amino acid
      present at a position in one of SEQ ID NOs:51-54 when optimally
      aligned with SEQ ID NO:50)
<220> FEATURE:
<221> NAME/KEY: MISC_FEATURE
<222> LOCATION: (253)..(253)
<223> OTHER INFORMATION: absent or any amino acid (e.g., an amino acid
      present at a position in one of SEQ ID NOs:51-54 when optimally
      aligned with SEQ ID NO:50)
<220> FEATURE:
<221> NAME/KEY: MISC_FEATURE
<222> LOCATION: (273)..(273)
<223> OTHER INFORMATION: absent or any amino acid (e.g., an amino acid
      present at a position in one of SEQ ID NOs:51-54 when optimally
      aligned with SEQ ID NO:50)
<220> FEATURE:
<221> NAME/KEY: MISC_FEATURE
<222> LOCATION: (277)..(277)
<223> OTHER INFORMATION: absent or any amino acid (e.g., an amino acid
      present at a position in one of SEQ ID NOs:51-54 when optimally
      aligned with SEQ ID NO:50)
<220> FEATURE:
<221> NAME/KEY: MISC_FEATURE
<222> LOCATION: (290)..(290)
<223> OTHER INFORMATION: absent or any amino acid (e.g., an amino acid
      present at a position in one of SEQ ID NOs:51-54 when optimally
      aligned with SEQ ID NO:50)
<220> FEATURE:
<221> NAME/KEY: MISC_FEATURE
<222> LOCATION: (296)..(296)
<223> OTHER INFORMATION: absent or any amino acid (e.g., an amino acid
      present at a position in one of SEQ ID NOs:51-54 when optimally
      aligned with SEQ ID NO:50)
<220> FEATURE:
<221> NAME/KEY: MISC_FEATURE
<222> LOCATION: (342)..(342)
<223> OTHER INFORMATION: absent or any amino acid (e.g., an amino acid
      present at a position in one of SEQ ID NOs:51-54 when optimally
      aligned with SEQ ID NO:50)
<220> FEATURE:
<221> NAME/KEY: MISC_FEATURE
<222> LOCATION: (376)..(376)
<223> OTHER INFORMATION: absent or any amino acid (e.g., an amino acid
      present at a position in one of SEQ ID NOs:51-54 when optimally
      aligned with SEQ ID NO:50)
<220> FEATURE:
<221> NAME/KEY: MISC_FEATURE
<222> LOCATION: (379)..(379)
<223> OTHER INFORMATION: absent or any amino acid (e.g., an amino acid
      present at a position in one of SEQ ID NOs:51-54 when optimally
      aligned with SEQ ID NO:50)
<220> FEATURE:
<221> NAME/KEY: MISC_FEATURE
<222> LOCATION: (385)..(385)
<223> OTHER INFORMATION: absent or any amino acid (e.g., an amino acid
      present at a position in one of SEQ ID NOs:51-54 when optimally
      aligned with SEQ ID NO:50)
<220> FEATURE:
<221> NAME/KEY: MISC_FEATURE
<222> LOCATION: (400)..(400)
<223> OTHER INFORMATION: absent or any amino acid (e.g., an amino acid
      present at a position in one of SEQ ID NOs:51-54 when optimally
      aligned with SEQ ID NO:50)
<220> FEATURE:
<221> NAME/KEY: MISC_FEATURE
<222> LOCATION: (414)..(414)
<223> OTHER INFORMATION: absent or any amino acid (e.g., an amino acid
      present at a position in one of SEQ ID NOs:51-54 when optimally
      aligned with SEQ ID NO:50)
<220> FEATURE:
<221> NAME/KEY: MISC_FEATURE
<222> LOCATION: (417)..(417)
<223> OTHER INFORMATION: absent or any amino acid (e.g., an amino acid
      present at a position in one of SEQ ID NOs:51-54 when optimally
      aligned with SEQ ID NO:50)
<220> FEATURE:
```

-continued

```
<221> NAME/KEY: MISC_FEATURE
<222> LOCATION: (428)..(429)
<223> OTHER INFORMATION: absent or any amino acid (e.g., an amino acid
      present at a position in one of SEQ ID NOs:51-54 when optimally
      aligned with SEQ ID NO:50)
<220> FEATURE:
<221> NAME/KEY: MISC_FEATURE
<222> LOCATION: (443)..(443)
<223> OTHER INFORMATION: absent or any amino acid (e.g., an amino acid
      present at a position in one of SEQ ID NOs:51-54 when optimally
      aligned with SEQ ID NO:50)
<220> FEATURE:
<221> NAME/KEY: MISC_FEATURE
<222> LOCATION: (465)..(465)
<223> OTHER INFORMATION: absent or any amino acid (e.g., an amino acid
      present at a position in one of SEQ ID NOs:51-54 when optimally
      aligned with SEQ ID NO:50)
<220> FEATURE:
<221> NAME/KEY: MISC_FEATURE
<222> LOCATION: (475)..(475)
<223> OTHER INFORMATION: absent or any amino acid (e.g., an amino acid
      present at a position in one of SEQ ID NOs:51-54 when optimally
      aligned with SEQ ID NO:50)
<220> FEATURE:
<221> NAME/KEY: MISC_FEATURE
<222> LOCATION: (486)..(486)
<223> OTHER INFORMATION: absent or any amino acid (e.g., an amino acid
      present at a position in one of SEQ ID NOs:51-54 when optimally
      aligned with SEQ ID NO:50)
<220> FEATURE:
<221> NAME/KEY: MISC_FEATURE
<222> LOCATION: (522)..(522)
<223> OTHER INFORMATION: absent or any amino acid (e.g., an amino acid
      present at a position in one of SEQ ID NOs:51-54 when optimally
      aligned with SEQ ID NO:50)
<220> FEATURE:
<221> NAME/KEY: MISC_FEATURE
<222> LOCATION: (551)..(551)
<223> OTHER INFORMATION: absent or any amino acid (e.g., an amino acid
      present at a position in one of SEQ ID NOs:51-54 when optimally
      aligned with SEQ ID NO:50)
<220> FEATURE:
<221> NAME/KEY: MISC_FEATURE
<222> LOCATION: (661)..(661)
<223> OTHER INFORMATION: absent or any amino acid (e.g., an amino acid
      present at a position in one of SEQ ID NOs:51-54 when optimally
      aligned with SEQ ID NO:50)
<220> FEATURE:
<221> NAME/KEY: MISC_FEATURE
<222> LOCATION: (688)..(688)
<223> OTHER INFORMATION: absent or any amino acid (e.g., an amino acid
      present at a position in one of SEQ ID NOs:51-54 when optimally
      aligned with SEQ ID NO:50)
<220> FEATURE:
<221> NAME/KEY: MISC_FEATURE
<222> LOCATION: (723)..(723)
<223> OTHER INFORMATION: absent or any amino acid (e.g., an amino acid
      present at a position in one of SEQ ID NOs:51-54 when optimally
      aligned with SEQ ID NO:50)
<220> FEATURE:
<221> NAME/KEY: MISC_FEATURE
<222> LOCATION: (733)..(733)
<223> OTHER INFORMATION: absent or any amino acid (e.g., an amino acid
      present at a position in one of SEQ ID NOs:51-54 when optimally
      aligned with SEQ ID NO:50)
<220> FEATURE:
<221> NAME/KEY: MISC_FEATURE
<222> LOCATION: (758)..(758)
<223> OTHER INFORMATION: absent or any amino acid (e.g., an amino acid
      present at a position in one of SEQ ID NOs:51-54 when optimally
      aligned with SEQ ID NO:50)
<220> FEATURE:
<221> NAME/KEY: MISC_FEATURE
<222> LOCATION: (761)..(761)
<223> OTHER INFORMATION: absent or any amino acid (e.g., an amino acid
      present at a position in one of SEQ ID NOs:51-54 when optimally
      aligned with SEQ ID NO:50)
<220> FEATURE:
<221> NAME/KEY: MISC_FEATURE
```

<222> LOCATION: (838)..(838)
<223> OTHER INFORMATION: absent or any amino acid (e.g., an amino acid
present at a position in one of SEQ ID NOs:51-54 when optimally
aligned with SEQ ID NO:50)
<220> FEATURE:
<221> NAME/KEY: MISC_FEATURE
<222> LOCATION: (846)..(846)
<223> OTHER INFORMATION: absent or any amino acid (e.g., an amino acid
present at a position in one of SEQ ID NOs:51-54 when optimally
aligned with SEQ ID NO:50)

<400> SEQUENCE: 50

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Met
65                  70                  75                  80

Val Thr Thr Arg Ser Xaa Ser Ser Ala Arg Ala Asn Gly Thr Xaa Gln
                85                  90                  95

Xaa Xaa Xaa Xaa Xaa Xaa Asn Gly Lys Ala Asn Xaa Thr Ile Ser Xaa
            100                 105                 110

Lys Gly Xaa Lys Lys Arg Xaa Ser Xaa Xaa Xaa Xaa Glu Thr Xaa Thr
        115                 120                 125

Lys Arg Pro Arg Leu Glu Glu Lys Thr Asp Leu Thr Arg Trp Arg Met
    130                 135                 140

Leu Asp Glu Lys Gly Arg His Thr Trp His Tyr Leu Glu Asp Asp Glu
145                 150                 155                 160

Ala Xaa Lys Xaa Trp Pro Gln Ser Tyr Ala Asp Lys Trp Tyr Leu Gly
                165                 170                 175

Leu Asp Thr Gly Leu Pro Thr Leu Pro Lys Pro Lys Lys Pro Leu Asp
            180                 185                 190

Xaa Val Val Asn Gly Leu Thr Phe Phe Glu Lys Leu Gln Leu Pro Ser
        195                 200                 205

Gly Gln Trp Gly Cys Glu Tyr Gly Gly Pro Met Phe Leu Leu Pro Gly
    210                 215                 220

Val Val Ile Thr Trp Tyr Xaa Thr Lys Thr Pro Ile Pro Trp Tyr Val
225                 230                 235                 240

Ala Thr Glu Ile Lys Asn Tyr Leu Phe Ala Arg Ala Xaa Pro Glu Asp
                245                 250                 255

Gly Gly Trp Gly Leu His Ile Glu Gly Glu Ser Thr Val Phe Gly Thr
            260                 265                 270

Xaa Leu Asn Tyr Xaa Val Leu Arg Ile Val Gly Val Asp Pro Glu His
        275                 280                 285

Pro Xaa Met Val Lys Ala Arg Xaa Thr Leu His Lys Leu Gly Gly Ala
    290                 295                 300

Thr Phe Ala Pro His Trp Ala Lys Phe Trp Leu Ser Val Leu Gly Val
305                 310                 315                 320

Cys Lys Trp Asp Ile Val Asn Pro Val Pro Glu Ile Trp Leu Leu
                325                 330                 335

Pro Asp Trp Val Pro Xaa Ala Pro Trp Arg Trp Trp Ile His Met Arg
            340                 345                 350
```

```
Gln Val Phe Leu Pro Met Ser Tyr Ile Tyr Glu Lys Lys Trp Thr Cys
            355                 360                 365

Glu Glu Thr Asp Ile Ile Arg Xaa Leu Arg Xaa Glu Leu Phe Val Glu
370                 375                 380

Xaa Trp Glu Lys Ile Asp Trp Leu Gly Asn Arg Asn Ser Ile Cys Xaa
385                 390                 395                 400

Val Asp Asn Tyr His Pro Lys Ser Trp Leu Leu Asn Thr Xaa Asn Trp
                405                 410                 415

Xaa Leu Val Asn Ile Trp Asn Pro Tyr Leu Arg Xaa Xaa Gly Leu Ala
            420                 425                 430

Gln Lys Ala Glu Asp Trp Val Ser Lys Leu Xaa Asp Met Glu Asp Glu
        435                 440                 445

Asn Thr Asp Tyr Ala Asp Leu Ala Pro Val Asn Ala Ala Met Asn Thr
    450                 455                 460

Xaa Val Cys Tyr Ile Arg Asp Gly Pro Gly Xaa Tyr Ser Val Arg Arg
465                 470                 475                 480

His Ile Glu Arg Leu Xaa Asp Ala Met Trp Val Asn His Glu Gly Met
                485                 490                 495

Phe Cys Asn Gly Thr Asn Gly Val Gln Cys Trp Asp Thr Ser Phe Leu
            500                 505                 510

Ile Gln Ala Ala Thr Asp Ala Gly Leu Xaa Gln Asp Pro Arg Trp Lys
        515                 520                 525

Pro Met Leu Thr Lys Ala Leu Lys Phe Leu Asp Asp Gln Gln Ile Arg
    530                 535                 540

Glu Asn Cys Lys Asp Gln Xaa Thr Cys Tyr Arg Gln Arg Lys Gly
545                 550                 555                 560

Ala Trp Ala Phe Ser Thr Arg Asp Gln Gly Tyr Ala Val Cys Asp Cys
                565                 570                 575

Ile Ser Glu Ala Leu Lys Ser Val Ile Leu Gln Lys Thr Pro Gly
            580                 585                 590

Tyr Pro Gln Leu Leu Glu Asp Gln Arg Ile Phe Asp Ala Ile Asp Thr
        595                 600                 605

Leu Leu Thr Tyr Gln Asn Lys Ser Gly Ala Cys Ser Ser Tyr Glu Pro
    610                 615                 620

Thr Arg Gly Ser Glu Leu Leu Glu Met Leu Asn Ala Ala Glu Val Phe
625                 630                 635                 640

Gly Lys Ile Met Val Glu Tyr Asp Tyr Val Glu Cys Thr Thr Ala Val
                645                 650                 655

Val Thr Ala Leu Xaa Leu Phe Gln Lys His Trp Pro Asp Tyr Arg Pro
            660                 665                 670

Gln Glu Ile Lys Ser Phe Ile Gly Arg Ser Val Lys Ala Val Lys Xaa
        675                 680                 685

Leu Gln Arg Pro Asp Gly Ser Trp Tyr Gly Asn Trp Ala Ile Cys Phe
    690                 695                 700

Thr Tyr Ala Thr Met Phe Ala Leu Glu Ser Leu Lys Ser Ile Gly Glu
705                 710                 715                 720

Thr Tyr Xaa Asn Ser Ser Tyr Ser Lys Arg Gly Cys Xaa Phe Leu Ile
                725                 730                 735

Ser Lys Gln Arg Glu Asp Gly Gly Trp Ser Glu Ser Tyr Arg Ser Cys
            740                 745                 750

Glu Lys Met Met Tyr Xaa Glu His Xaa Thr Gly Ser Gln Val Val Met
        755                 760                 765

Thr Ala Trp Ala Leu Ile Gly Leu Met Lys Ala Asp Tyr Pro Asp Ile
```

```
                770               775               780
Glu Pro Leu Lys Lys Gly Ile Lys Leu Ile Met Asp Arg Gln Gln Pro
785                 790                 795                 800

Asn Gly Glu Trp Lys Gln Glu Ala Ile Glu Gly Val Phe Asn Lys Ser
                805                 810                 815

Cys Met Ile Ser Tyr Pro Asn Tyr Lys Phe Thr Phe Thr Met Lys Ala
                820                 825                 830

Leu Gly Met Phe Ala Xaa Lys Tyr Pro Asn Glu Thr Val Xaa
                835                 840                 845

<210> SEQ ID NO 51
<211> LENGTH: 768
<212> TYPE: PRT
<213> ORGANISM: Hypoxylon sp. CI4A

<400> SEQUENCE: 51

Met Val Val Thr Thr Arg Ser Ser Phe Ala Arg Thr Asn Gly Gly
1               5                   10                  15

Ser Pro Gln Phe Asn Gly Lys Ile Asn Gly Lys Ala Asn Asp Ile Ser
                20                  25                  30

Ser Lys Lys Gln Ser Arg Lys Arg Val Ser Glu His Asp Phe Glu Asn
                35                  40                  45

Val Thr Lys Arg Pro Arg Val Glu Glu Lys Thr Asp Leu Thr Arg Trp
50                  55                  60

Arg Met Leu Asp Glu Lys Gly Arg His Thr Trp His Tyr Leu Glu Asp
65                  70                  75                  80

Asp Gln Ala Val Glu Lys Trp Pro Gln Ser Tyr Ala Asp Lys Trp Tyr
                85                  90                  95

Leu Gly Leu Asp Ile Asp Leu Pro Thr Leu Pro Lys Pro Glu Lys Pro
                100                 105                 110

Leu Asp Ala Val Ala Asn Gly Leu Ser Phe Phe Glu Lys Leu Gln Leu
                115                 120                 125

Pro Ser Gly Gln Trp Gly Cys Glu Tyr Gly Gly Pro Met Phe Leu Leu
                130                 135                 140

Pro Gly Val Val Ile Thr Trp Tyr Ala Thr Lys Thr Pro Ile Pro Trp
145                 150                 155                 160

Tyr Val Ala Thr Glu Ile Lys Asn Tyr Leu Phe Ala Arg Ala His Pro
                165                 170                 175

Glu Asp Gly Gly Trp Gly Leu His Ile Glu Gly Glu Ser Thr Val Phe
                180                 185                 190

Gly Thr Ala Leu Asn Tyr Ala Val Leu Arg Ile Val Gly Val Asp Ala
                195                 200                 205

Glu His Pro Val Met Val Lys Ala Arg Gly Thr Leu His Lys Leu Gly
                210                 215                 220

Gly Val Thr Ala Gly Pro His Trp Ala Lys Phe Trp Leu Ser Val Leu
225                 230                 235                 240

Gly Val Cys Lys Trp Asp Ile Val Asn Pro Ile Pro Thr Glu Ile Trp
                245                 250                 255

Leu Leu Pro Asp Trp Val Pro Phe Ala Pro Trp Arg Trp Trp Ile His
                260                 265                 270

Ile Arg Gln Val Phe Leu Pro Met Gly Tyr Ile Tyr Asp Lys Lys Trp
                275                 280                 285

Thr Cys Glu Glu Thr Asp Leu Ile Arg Ser Met Arg Gln Glu Leu Val
                290                 295                 300
```

```
Val Glu Pro Trp Glu Lys Ile Asp Trp Ala Gly Asn Arg Asn Thr Ile
305                 310                 315                 320

Ser Ser Ile Asp Asn Phe His Pro Lys Ser Trp Leu Leu Asn Thr Ala
                325                 330                 335

Asn Trp Phe Leu Val Asn Val Trp Asn Pro Tyr Leu Arg Thr Lys Gly
            340                 345                 350

Leu Ala Gln Lys Ala Glu Asp Trp Ala Ser Lys Leu Ile Asp Met Glu
        355                 360                 365

Asp Glu Asn Thr Asp Tyr Leu Asp Leu Ala Pro Val Asn Ala Thr Met
    370                 375                 380

Asn Thr Leu Val Cys Tyr Ile Arg Asp Gly Pro Gly Ser Tyr Ser Val
385                 390                 395                 400

Arg Arg His Leu Glu Arg Leu Glu Asp Ala Leu Trp Val Asn Gln Glu
                405                 410                 415

Gly Met Phe Cys Asn Gly Thr Asn Gly Val Gln Cys Trp Asp Thr Ala
            420                 425                 430

Phe Leu Ile Gln Ala Val Ile Asp Ala Gly Leu Glu Gln Asp Ala Arg
        435                 440                 445

Trp Lys Pro Met Leu Thr Lys Ala Leu Lys Phe Leu Asp Asp Gln Gln
    450                 455                 460

Ile Arg Glu Asn Cys Lys Asp Gln Asp Val Cys Tyr Arg Gln Gln Arg
465                 470                 475                 480

Lys Gly Ala Trp Ala Phe Ser Asn Arg Asp Gln Gly Tyr Ala Val Cys
                485                 490                 495

Asp Cys Ile Ser Glu Ala Leu Lys Ser Val Ile Leu Leu Gln Lys Ser
            500                 505                 510

Ala Gly Tyr Pro Gln Leu Leu Glu Asp Gln Arg Ile Phe Asp Ala Ile
        515                 520                 525

Asp Thr Leu Leu Thr Tyr Gln Asn Lys Ser Gly Ala Cys Ser Ser Tyr
    530                 535                 540

Glu Pro Thr Arg Gly Ser Glu Val Leu Glu Met Leu Asn Ala Ala Glu
545                 550                 555                 560

Val Phe Ala Lys Ile Met Val Glu Tyr Asp Tyr Val Glu Cys Thr Thr
                565                 570                 575

Ala Val Val Thr Ala Leu Ser Leu Phe Gln Lys His Trp Pro Asp Tyr
            580                 585                 590

Arg Thr Gln Glu Ile Lys Ser Phe Ile Gly Arg Ser Val Lys Ala Val
        595                 600                 605

Lys Ser Leu Gln Arg Pro Asp Gly Ala Trp Tyr Gly Asn Trp Ala Ile
    610                 615                 620

Cys Phe Thr Tyr Ala Thr Met Phe Ala Leu Glu Ser Leu Glu Ser Ile
625                 630                 635                 640

Gly Glu Thr Tyr Gly Asn Ser Ser Tyr Ser Lys Arg Gly Cys Lys Phe
                645                 650                 655

Leu Ile Ser Lys Gln Arg Glu Asp Gly Gly Trp Ser Glu Ser Tyr Arg
            660                 665                 670

Ser Cys Glu Asn Met Val Tyr Thr Glu His Pro Thr Gly Ser Gln Val
        675                 680                 685

Val Met Thr Ala Trp Ala Leu Ile Ala Leu Met Lys Ala Asp Tyr Pro
    690                 695                 700

Asp Ile Glu Pro Leu Lys Lys Gly Ile Lys Leu Ile Met Asp Arg Gln
705                 710                 715                 720

Gln Pro Asn Gly Glu Trp Lys Gln Glu Ala Ile Glu Gly Val Phe Asn
```

```
                    725                 730                 735
Lys Ser Cys Met Ile Ser Tyr Pro Asn Tyr Lys Phe Thr Phe Thr Met
                740                 745                 750

Lys Ala Leu Gly Met Phe Ala Thr Lys Tyr Pro Asn Glu Thr Val Val
                755                 760                 765

<210> SEQ ID NO 52
<211> LENGTH: 841
<212> TYPE: PRT
<213> ORGANISM: Hypoxylon sp. CO27

<400> SEQUENCE: 52

Met Ala Leu Thr Val Cys Asn Pro Thr Ala Asp Gly Ala Glu Cys Lys
1               5                   10                  15

Glu Pro Thr Trp Gly Val Ser Thr Tyr Tyr Ala Pro Lys Trp Glu Ile
            20                  25                  30

Arg Gly Tyr Pro Glu Glu Val Ser Ile Pro Ile Ser Cys Gly Lys Trp
        35                  40                  45

Glu Pro Trp Lys Leu Glu Leu Asn Pro Phe Thr Ser Ser Leu Gln Gln
    50                  55                  60

Leu Leu Phe Ser Gly Val Leu Thr Ile Ser Ser Val Phe Leu Asn Met
65                  70                  75                  80

Val Thr Thr Arg Ser Gly Ser Ser Ala Arg Ala Asn Gly Thr Pro Gln
                85                  90                  95

Pro Asn Gly Lys Ala Asn Gly Thr Ile Ser Arg Lys Gln Pro Lys Lys
            100                 105                 110

Arg Ala Ser Asp Asp Lys Leu Glu Thr Leu Thr Lys Arg Pro Arg Leu
        115                 120                 125

Glu Glu Lys Thr Asp Leu Thr Arg Trp Arg Met Leu Asp Glu Lys Gly
    130                 135                 140

Arg His Thr Trp His Tyr Leu Glu Asp Asp Glu Ala Ile Lys Arg Trp
145                 150                 155                 160

Pro Gln Ser Tyr Ala Asp Lys Trp Tyr Leu Gly Leu Asp Thr Gly Leu
                165                 170                 175

Pro Thr Leu Pro Lys Pro Lys Lys Pro Leu Asp Ser Val Val Asn Gly
            180                 185                 190

Leu Thr Phe Phe Glu Lys Leu Gln Leu Pro Ser Gly Gln Trp Gly Cys
        195                 200                 205

Glu Tyr Gly Gly Pro Met Phe Leu Leu Pro Gly Val Val Ile Thr Trp
    210                 215                 220

Tyr Val Thr Lys Thr Pro Ile Pro Trp Tyr Val Ala Thr Glu Ile Lys
225                 230                 235                 240

Asn Tyr Leu Phe Ala Arg Ala Asn Pro Glu Asp Gly Gly Trp Gly Leu
                245                 250                 255

His Ile Glu Gly Glu Ser Thr Val Phe Gly Thr Ser Leu Asn Tyr Thr
            260                 265                 270

Val Leu Arg Ile Val Gly Val Asp Pro Glu His Pro Ala Met Val Lys
        275                 280                 285

Ala Arg Ala Thr Leu His Lys Leu Gly Gly Ala Thr Phe Ala Pro His
    290                 295                 300

Trp Ala Lys Phe Trp Leu Ser Val Leu Gly Val Cys Lys Trp Asp Ile
305                 310                 315                 320

Val Asn Pro Val Pro Pro Glu Ile Trp Leu Leu Pro Asp Trp Val Pro
                325                 330                 335
```

```
Ile Ala Pro Trp Arg Trp Trp Ile His Met Arg Gln Val Phe Leu Pro
            340                 345                 350

Met Ser Tyr Ile Tyr Glu Lys Lys Trp Thr Cys Glu Glu Thr Asp Ile
        355                 360                 365

Ile Arg Gly Leu Arg Asp Glu Leu Phe Val Glu Gln Trp Glu Lys Ile
    370                 375                 380

Asp Trp Leu Gly Asn Arg Asn Ser Ile Cys Pro Val Asp Asn Tyr His
385                 390                 395                 400

Pro Lys Ser Trp Leu Leu Asn Thr Val Asn Trp Val Leu Val Asn Ile
                405                 410                 415

Trp Asn Pro Tyr Leu Arg Pro Asn Gly Leu Ala Gln Lys Ala Glu Asp
            420                 425                 430

Trp Val Ser Lys Leu Val Asp Met Glu Asp Glu Asn Thr Asp Tyr Ala
            435                 440                 445

Asp Leu Ala Pro Val Asn Ala Ala Met Asn Thr Val Val Cys Tyr Ile
        450                 455                 460

Arg Asp Gly Pro Gly Ala Tyr Ser Val Arg Arg His Ile Glu Arg Leu
465                 470                 475                 480

Asp Asp Ala Met Trp Val Asn His Glu Gly Met Phe Cys Asn Gly Thr
                485                 490                 495

Asn Gly Val Gln Cys Trp Asp Thr Ser Phe Leu Ile Gln Ala Ala Thr
            500                 505                 510

Asp Ala Gly Leu Gln Glu Asp Pro Arg Trp Lys Pro Met Leu Thr Lys
        515                 520                 525

Ala Leu Lys Phe Leu Asp Asp Gln Gln Ile Arg Glu Asn Cys Lys Asp
    530                 535                 540

Gln Thr Thr Cys Tyr Arg Gln Arg Lys Gly Ala Trp Ala Phe Ser
545                 550                 555                 560

Thr Arg Asp Gln Gly Tyr Ala Val Cys Asp Cys Ile Ser Glu Ala Leu
                565                 570                 575

Lys Ser Val Ile Leu Leu Gln Lys Thr Pro Gly Tyr Pro Gln Leu Leu
            580                 585                 590

Glu Asp Arg Arg Ile Phe Asp Ala Ile Asp Thr Leu Leu Thr Tyr Gln
        595                 600                 605

Asn Lys Ser Gly Ala Cys Ser Ser Tyr Glu Pro Thr Arg Gly Ser Glu
    610                 615                 620

Leu Leu Glu Met Leu Asn Ala Ala Glu Val Phe Gly Lys Ile Met Val
625                 630                 635                 640

Glu Tyr Asp Tyr Val Glu Cys Thr Thr Ala Val Val Thr Ala Leu Met
                645                 650                 655

Leu Phe Gln Lys His Trp Pro Asp Tyr Arg Pro Gln Glu Ile Lys Ser
            660                 665                 670

Phe Ile Gly Arg Ser Val Lys Ala Val Lys Arg Leu Gln Arg Pro Asp
        675                 680                 685

Gly Ser Trp Tyr Gly Asn Trp Ala Ile Cys Phe Thr Tyr Ala Thr Met
    690                 695                 700

Phe Ala Leu Glu Ser Leu Lys Ser Ile Gly Glu Thr Tyr Asn Asn Ser
705                 710                 715                 720

Pro Tyr Ser Lys Arg Gly Cys Asp Phe Leu Ile Ser Lys Gln Arg Glu
                725                 730                 735

Asp Gly Gly Trp Ser Glu Ser Tyr Arg Ser Cys Glu Lys Met Met Tyr
            740                 745                 750

Ile Glu His His Thr Gly Ser Gln Val Val Met Thr Ala Trp Ala Leu
```

```
                    755                 760                 765
Ile Gly Leu Met Lys Ala Asp Tyr Pro Asp Ile Glu Pro Leu Lys Lys
            770                 775                 780

Gly Ile Lys Leu Ile Met Asp Arg Gln Gln Pro Asn Gly Glu Trp Lys
785                 790                 795                 800

Gln Glu Ala Ile Glu Gly Val Phe Asn Lys Ser Cys Met Ile Ser Tyr
                805                 810                 815

Pro Asn Tyr Lys Phe Thr Phe Thr Met Lys Ala Leu Gly Met Phe Ala
            820                 825                 830

Gln Lys Tyr Pro Asp Glu Thr Val Ile
            835                 840

<210> SEQ ID NO 53
<211> LENGTH: 762
<212> TYPE: PRT
<213> ORGANISM: Hypoxylon sp. EC38

<400> SEQUENCE: 53

Met Val Thr Thr Arg Ser Gly Ser Ser Ala Arg Ala Asn Gly Thr Pro
1               5                   10                  15

Gln Pro Asn Gly Lys Ala Asn Gly Thr Ile Ser Arg Lys Gln Pro Lys
            20                  25                  30

Lys Arg Ala Ser Asp Asp Lys Leu Glu Thr Ile Thr Lys Arg Pro Arg
        35                  40                  45

Leu Glu Glu Lys Thr Asp Leu Thr Arg Trp Arg Met Leu Asp Glu Lys
    50                  55                  60

Gly Arg His Thr Trp His Tyr Leu Glu Asp Glu Ala Ile Lys Arg
65                  70                  75                  80

Trp Pro Gln Ser Tyr Ala Asp Lys Trp Tyr Leu Gly Leu Asp Thr Gly
                85                  90                  95

Leu Pro Thr Leu Pro Lys Pro Lys Lys Pro Leu Asp Ser Val Val Asn
            100                 105                 110

Gly Leu Thr Phe Phe Glu Lys Leu Gln Leu Pro Ser Gly Gln Trp Gly
        115                 120                 125

Cys Glu Tyr Gly Gly Pro Met Phe Leu Leu Pro Gly Val Val Ile Thr
    130                 135                 140

Trp Tyr Val Thr Lys Thr Pro Ile Pro Trp Tyr Val Ala Thr Glu Ile
145                 150                 155                 160

Lys Asn Tyr Leu Phe Ala Arg Ala Asn Pro Glu Asp Gly Gly Trp Gly
                165                 170                 175

Leu His Ile Glu Gly Glu Ser Thr Val Phe Gly Thr Ser Leu Asn Tyr
            180                 185                 190

Thr Val Leu Arg Ile Val Gly Val Asp Pro Glu His Pro Ala Met Val
        195                 200                 205

Lys Ala Arg Ala Thr Leu His Lys Leu Gly Gly Ala Thr Phe Ala Pro
    210                 215                 220

His Trp Ala Lys Phe Trp Leu Ser Val Leu Gly Val Cys Lys Trp Asp
225                 230                 235                 240

Ile Val Asn Pro Val Pro Pro Glu Ile Trp Leu Leu Pro Asp Trp Val
                245                 250                 255

Pro Ile Ala Pro Trp Arg Trp Ile His Met Arg Gln Val Phe Leu
            260                 265                 270

Pro Met Ser Tyr Ile Tyr Glu Lys Lys Trp Thr Cys Glu Glu Thr Asp
        275                 280                 285
```

-continued

```
Ile Ile Arg Gly Leu Arg Asp Glu Leu Phe Val Glu Gln Trp Glu Lys
290                 295                 300
Ile Asp Trp Leu Gly Asn Arg Asn Ser Ile Cys Pro Val Asp Asn Tyr
305                 310                 315                 320
His Pro Lys Ser Trp Leu Leu Asn Thr Val Asn Trp Val Leu Val Asn
                325                 330                 335
Ile Trp Asn Pro Tyr Leu Arg Pro Asn Gly Leu Ala Gln Lys Ala Glu
                340                 345                 350
Asn Trp Val Ser Lys Leu Val Asp Met Glu Asp Glu Asn Thr Asp Tyr
                355                 360                 365
Ala Asp Leu Ala Pro Val Asn Ala Ala Met Asn Thr Val Val Cys Tyr
370                 375                 380
Ile Arg Asp Gly Pro Gly Ala Tyr Ser Val Arg Arg His Ile Glu Arg
385                 390                 395                 400
Leu Asp Asp Ala Met Trp Val Asn His Glu Gly Met Phe Cys Asn Gly
                405                 410                 415
Thr Asn Gly Val Gln Cys Trp Asp Thr Ser Phe Leu Ile Gln Ala Ala
                420                 425                 430
Thr Asp Ala Gly Leu Gln Asp Asp Pro Arg Trp Lys Pro Met Leu Thr
                435                 440                 445
Lys Ala Leu Lys Phe Leu Asp Asp Gln Gln Ile Arg Glu Asn Cys Lys
450                 455                 460
Asp Gln Thr Thr Cys Tyr Arg Gln Arg Lys Gly Ala Trp Ala Phe
465                 470                 475                 480
Ser Thr Arg Asp Gln Gly Tyr Ala Val Cys Asp Cys Ile Ser Glu Ala
                485                 490                 495
Leu Lys Ser Val Ile Leu Leu Gln Lys Thr Pro Gly Tyr Pro Gln Leu
                500                 505                 510
Leu Glu Asp Gln Arg Ile Phe Asp Ala Ile Asp Thr Leu Leu Thr Tyr
                515                 520                 525
Gln Asn Lys Ser Gly Ala Cys Ser Ser Tyr Glu Pro Thr Arg Gly Ser
530                 535                 540
Glu Leu Leu Glu Met Leu Asn Ala Ala Glu Val Phe Gly Lys Ile Met
545                 550                 555                 560
Val Glu Tyr Asp Tyr Val Glu Cys Thr Thr Ala Val Val Thr Ala Leu
                565                 570                 575
Met Leu Phe Gln Lys His Trp Pro Asp Tyr Arg Pro Gln Glu Ile Lys
                580                 585                 590
Ser Phe Ile Gly Arg Ser Val Lys Ala Val Lys Arg Leu Gln Arg Pro
                595                 600                 605
Asp Gly Ser Trp Tyr Gly Asn Trp Ala Ile Cys Phe Thr Tyr Ala Thr
                610                 615                 620
Met Phe Ala Leu Glu Ser Leu Lys Ser Ile Gly Glu Thr Tyr Asn Asn
625                 630                 635                 640
Ser Ser Tyr Ser Lys Arg Gly Cys Asp Phe Leu Ile Ser Lys Gln Arg
                645                 650                 655
Glu Asp Gly Gly Trp Ser Glu Ser Tyr Arg Ser Cys Glu Lys Met Met
                660                 665                 670
Tyr Ile Glu His His Thr Gly Ser Gln Val Val Met Thr Ala Trp Ala
                675                 680                 685
Leu Ile Gly Leu Met Lys Ala Asp Tyr Pro Asp Ile Glu Pro Ile Lys
                690                 695                 700
Lys Gly Ile Lys Leu Ile Met Asp Arg Gln Gln Pro Asn Gly Glu Trp
```

```
                705                 710                 715                 720
Lys Gln Glu Ala Ile Glu Gly Val Phe Asn Lys Ser Cys Met Ile Ser
                    725                 730                 735

Tyr Pro Asn Tyr Lys Phe Thr Phe Thr Met Lys Ala Leu Gly Met Phe
                    740                 745                 750

Ala Gln Lys Tyr Pro Asn Glu Thr Val Ile
                    755                 760

<210> SEQ ID NO 54
<211> LENGTH: 738
<212> TYPE: PRT
<213> ORGANISM: Daldinia eschscholzii EC12

<400> SEQUENCE: 54

Met Val Val Thr Thr Arg Ser Lys Lys Arg Val Ser Glu Asp Ala Pro
1               5                   10                  15

Glu Thr Thr Val Lys Arg Pro Arg Leu Glu Glu Lys Thr Asp Leu Arg
                20                  25                  30

Arg Trp Arg Met Leu Asp Glu Lys Gly Arg His Thr Trp His Tyr Leu
            35                  40                  45

Glu Asp Asp Glu Ala Val Arg Lys Trp Pro Gln Ser Tyr Ala Asp Lys
        50                  55                  60

Trp Tyr Leu Gly Leu Asp Thr Gly Leu Pro Thr Leu Pro Lys Pro Gln
65                  70                  75                  80

Lys Pro Leu Asp Ala Val Val Asn Gly Leu Thr Phe Phe Glu Lys Leu
                85                  90                  95

Gln Leu Pro Ser Gly Gln Trp Gly Cys Glu Tyr Gly Gly Pro Met Phe
            100                 105                 110

Leu Leu Pro Gly Ile Val Phe Thr Trp Tyr Ala Thr Lys Thr Pro Ile
        115                 120                 125

Pro Trp Tyr Val Ala Thr Glu Ile Lys Asn Tyr Leu Phe Ala Arg Ala
    130                 135                 140

His Pro Glu Asp Gly Gly Trp Gly Leu His Ile Glu Gly Glu Ser Thr
145                 150                 155                 160

Val Phe Gly Thr Ala Leu Asn Tyr Ala Val Leu Arg Ile Val Gly Leu
                165                 170                 175

Asp Pro Glu His Pro Val Met Val Lys Ala Arg Gly Thr Leu His Lys
            180                 185                 190

Leu Gly Gly Ala Thr Tyr Ala Pro His Trp Ala Lys Phe Trp Leu Ser
        195                 200                 205

Val Leu Gly Val Cys Lys Trp Asp Ile Val Asn Pro Val Pro Pro Glu
    210                 215                 220

Leu Trp Leu Leu Pro Asp Trp Val Pro Phe Ala Pro Trp Arg Trp Trp
225                 230                 235                 240

Ile His Met Arg Gln Val Phe Leu Pro Met Ser Tyr Ile Tyr Glu Lys
                245                 250                 255

Lys Trp Ser Cys Glu Glu Thr Asp Ile Val Arg Ala Leu Arg Gln Glu
            260                 265                 270

Leu Phe Val Glu Pro Trp Glu Lys Ile Asp Trp Leu Gly Asn Arg Asn
        275                 280                 285

Ser Ile Cys Ser Val Asp Asn Tyr His Pro Lys Ser Trp Leu Leu Asn
    290                 295                 300

Thr Ala Asn Trp Phe Leu Val His Ile Trp Asn Pro Tyr Leu Arg Thr
305                 310                 315                 320
```

-continued

```
Lys Gly Leu Ala Gln Lys Ala Glu Ala Trp Val Gly Lys Leu Ile Asp
                325                 330                 335

Met Glu Asp Glu Asn Thr Asp Phe Ala Asp Leu Ala Pro Val Asn Ala
            340                 345                 350

Ala Met Asn Thr Ile Val Cys Tyr Ile Arg Asp Gly Pro Gly Ser Tyr
        355                 360                 365

Ser Val Arg Arg His Ile Glu Arg Leu Glu Asp Ser Met Trp Val Asn
    370                 375                 380

Gly Asp Gly Met Leu Cys Asn Gly Thr Asn Gly Val Gln Cys Trp Asp
385                 390                 395                 400

Thr Ser Phe Leu Ile Gln Ala Leu Thr Asp Ala Gly Leu Glu Gln Asp
                405                 410                 415

Pro Arg Trp Lys Pro Met Leu Asn Lys Ala Leu Ile Phe Leu Asp Asn
            420                 425                 430

Gln Gln Ile Arg Glu Asn Cys Lys Asp Gln Asp Ile Cys Tyr Arg Gln
        435                 440                 445

Gln Arg Lys Gly Ala Trp Ala Phe Ser Thr Arg Asp Gln Gly Tyr Ala
    450                 455                 460

Val Cys Asp Cys Val Ser Glu Ala Leu Lys Ser Val Ile Leu Leu Gln
465                 470                 475                 480

His Thr Pro Gly Phe Pro Gln Leu Leu Glu Asp Gln Arg Ile Phe Asp
                485                 490                 495

Ala Val Asp Thr Leu Leu Thr Tyr Gln Asn Lys Ser Gly Ala Cys Ser
            500                 505                 510

Ser Tyr Glu Pro Thr Arg Gly Ser Glu Leu Leu Glu Met Leu Asn Ala
        515                 520                 525

Ala Glu Val Phe Gly Lys Ile Met Val Glu Tyr Asp Tyr Val Glu Cys
    530                 535                 540

Thr Thr Ala Val Val Thr Ala Leu Ser Leu Phe Gln Lys His Trp Pro
545                 550                 555                 560

Asp Tyr Arg Pro Lys Glu Ile Glu Ala Phe Ile Gly Arg Ser Val Lys
                565                 570                 575

Ala Val Lys Ser Leu Gln Gln Pro Asp Gly Ser Trp Tyr Gly Asn Trp
            580                 585                 590

Ala Ile Cys Tyr Thr Tyr Ala Thr Met Phe Ala Leu Glu Ser Leu Lys
        595                 600                 605

Ser Ile Gly Glu Thr Tyr Gly Asn Ser Ser Tyr Ser Lys Arg Gly Cys
    610                 615                 620

Asp Phe Leu Ile Ser Lys Gln Arg Glu Asp Gly Gly Trp Ser Glu Ser
625                 630                 635                 640

Tyr Arg Ser Cys Glu Arg Met Ile Tyr Thr Glu His Pro Thr Gly Ser
                645                 650                 655

Gln Val Val Met Thr Ala Trp Ala Leu Ile Gly Leu Met Lys Ala Asp
            660                 665                 670

Tyr Pro Asp Ile Lys Pro Leu Lys Lys Gly Ile Lys Leu Ile Met Asp
        675                 680                 685

Arg Gln Gln Pro Asn Gly Glu Trp Lys Gln Glu Ala Ile Glu Gly Val
    690                 695                 700

Phe Asn Lys Ser Cys Met Ile Ser Tyr Pro Asn Tyr Lys Phe Thr Phe
705                 710                 715                 720

Thr Met Lys Ala Leu Gly Met Phe Ala Thr Lys Tyr Pro Asn Glu Thr
                725                 730                 735

Val Val
```

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58

<400> SEQUENCE: 58

000

<210> SEQ ID NO 59

<400> SEQUENCE: 59

000

<210> SEQ ID NO 60
<211> LENGTH: 340
<212> TYPE: PRT
<213> ORGANISM: Artificial Sequence
<220> FEATURE:
<223> OTHER INFORMATION: Consensus polypeptide sequence
<220> FEATURE:
<221> NAME/KEY: MISC_FEATURE
<222> LOCATION: (1)..(8)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (10)..(11)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (13)..(18)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (29)..(29)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (31)..(34)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (37)..(38)
<223> OTHER INFORMATION: absent or any amino acid (e.g., an amino acid
      present at a position in one of SEQ ID NOs:61-64 when optimally
      aligned with SEQ ID NO:60)

-continued

```
<220> FEATURE:
<221> NAME/KEY: MISC_FEATURE
<222> LOCATION: (40)..(41)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (43)..(43)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (45)..(45)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (51)..(53)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (57)..(62)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (64)..(69)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (71)..(72)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (75)..(75)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (77)..(77)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (80)..(80)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (88)..(88)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (93)..(93)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (95)..(95)
<223> OTHER INFORMATION: absent or any amino acid (e.g., an amino acid
      present at a position in one of SEQ ID NOs:61-64 when optimally
      aligned with SEQ ID NO:60)
<220> FEATURE:
```

```
<221> NAME/KEY: MISC_FEATURE
<222> LOCATION: (98)..(99)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (101)..(105)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (107)..(109)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (111)..(115)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (120)..(130)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (132)..(132)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (135)..(136)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (138)..(139)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (141)..(141)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (145)..(149)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (152)..(154)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (156)..(159)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (161)..(161)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
```

```
<222> LOCATION: (164)..(170)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (177)..(178)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (181)..(182)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (184)..(186)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (189)..(189)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (191)..(192)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (196)..(196)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (199)..(199)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (202)..(202)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (204)..(204)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (208)..(208)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (210)..(210)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (212)..(212)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (214)..(214)
```

```
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (216)..(217)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (220)..(220)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (222)..(222)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (224)..(224)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (227)..(228)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (230)..(233)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (235)..(238)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (240)..(240)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (244)..(244)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (248)..(248)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (252)..(252)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (256)..(258)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (261)..(263)
<223> OTHER INFORMATION: absent or any amino acid (e.g., an amino acid
``` present at a position in one of SEQ ID NOs:61-64 when optimally
    aligned with SEQ ID NO:60)
<220> FEATURE:
<221> NAME/KEY: MISC_FEATURE
<222> LOCATION: (266)..(266)
<223> OTHER INFORMATION: absent or any amino acid (e.g., an amino acid
    present at a position in one of SEQ ID NOs:61-64 when optimally
    aligned with SEQ ID NO:60)
<220> FEATURE:
<221> NAME/KEY: MISC_FEATURE
<222> LOCATION: (268)..(268)
<223> OTHER INFORMATION: absent or any amino acid (e.g., an amino acid
    present at a position in one of SEQ ID NOs:61-64 when optimally
    aligned with SEQ ID NO:60)
<220> FEATURE:
<221> NAME/KEY: MISC_FEATURE
<222> LOCATION: (271)..(276)
<223> OTHER INFORMATION: absent or any amino acid (e.g., an amino acid
    present at a position in one of SEQ ID NOs:61-64 when optimally
    aligned with SEQ ID NO:60)
<220> FEATURE:
<221> NAME/KEY: MISC_FEATURE
<222> LOCATION: (278)..(278)
<223> OTHER INFORMATION: absent or any amino acid (e.g., an amino acid
    present at a position in one of SEQ ID NOs:61-64 when optimally
    aligned with SEQ ID NO:60)
<220> FEATURE:
<221> NAME/KEY: MISC_FEATURE
<222> LOCATION: (281)..(282)
<223> OTHER INFORMATION: absent or any amino acid (e.g., an amino acid
    present at a position in one of SEQ ID NOs:61-64 when optimally
    aligned with SEQ ID NO:60)
<220> FEATURE:
<221> NAME/KEY: MISC_FEATURE
<222> LOCATION: (286)..(287)
<223> OTHER INFORMATION: absent or any amino acid (e.g., an amino acid
    present at a position in one of SEQ ID NOs:61-64 when optimally
    aligned with SEQ ID NO:60)
<220> FEATURE:
<221> NAME/KEY: MISC_FEATURE
<222> LOCATION: (291)..(291)
<223> OTHER INFORMATION: absent or any amino acid (e.g., an amino acid
    present at a position in one of SEQ ID NOs:61-64 when optimally
    aligned with SEQ ID NO:60)
<220> FEATURE:
<221> NAME/KEY: MISC_FEATURE
<222> LOCATION: (294)..(294)
<223> OTHER INFORMATION: absent or any amino acid (e.g., an amino acid
    present at a position in one of SEQ ID NOs:61-64 when optimally
    aligned with SEQ ID NO:60)
<220> FEATURE:
<221> NAME/KEY: MISC_FEATURE
<222> LOCATION: (299)..(299)
<223> OTHER INFORMATION: absent or any amino acid (e.g., an amino acid
    present at a position in one of SEQ ID NOs:61-64 when optimally
    aligned with SEQ ID NO:60)
<220> FEATURE:
<221> NAME/KEY: MISC_FEATURE
<222> LOCATION: (302)..(305)
<223> OTHER INFORMATION: absent or any amino acid (e.g., an amino acid
    present at a position in one of SEQ ID NOs:61-64 when optimally
    aligned with SEQ ID NO:60)
<220> FEATURE:
<221> NAME/KEY: MISC_FEATURE
<222> LOCATION: (313)..(313)
<223> OTHER INFORMATION: absent or any amino acid (e.g., an amino acid
    present at a position in one of SEQ ID NOs:61-64 when optimally
    aligned with SEQ ID NO:60)
<220> FEATURE:
<221> NAME/KEY: MISC_FEATURE
<222> LOCATION: (318)..(318)
<223> OTHER INFORMATION: absent or any amino acid (e.g., an amino acid
    present at a position in one of SEQ ID NOs:61-64 when optimally
    aligned with SEQ ID NO:60)
<220> FEATURE:
<221> NAME/KEY: MISC_FEATURE
<222> LOCATION: (320)..(321)
<223> OTHER INFORMATION: absent or any amino acid (e.g., an amino acid
    present at a position in one of SEQ ID NOs:61-64 when optimally aligned with SEQ ID NO:60)
<220> FEATURE:
<221> NAME/KEY: MISC_FEATURE
<222> LOCATION: (324)..(326)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (331)..(331)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (333)..(333)
<223> OTHER INFORMATION: absent or any amino acid (e.g., an amino acid
      present at a position in one of SEQ ID NOs:61-64 when optimally
      aligned with SEQ ID NO:60)
<220> FEATURE:
<221> NAME/KEY: MISC_FEATURE
<222> LOCATION: (336)..(340)
<223> OTHER INFORMATION: absent or any amino acid (e.g., an amino acid
      present at a position in one of SEQ ID NOs:61-64 when optimally
      aligned with SEQ ID NO:60)

<400> SEQUENCE: 60

Xaa Xaa Xaa Xaa Xaa Xaa Xaa Ser Xaa Xaa Leu Xaa Xaa Xaa Xaa
 1               5                  10                  15

Xaa Xaa Arg Gln Ser Val Arg Ile Pro Asp Leu Phe Xaa Ser Xaa Xaa
             20                  25                  30

Xaa Xaa Met Ala Xaa Xaa Pro Xaa Xaa Asn Xaa Asn Xaa Phe Lys Val
         35                  40                  45

Lys Ala Xaa Xaa Xaa Arg Trp Ile Xaa Xaa Xaa Xaa Xaa Asp Xaa
 50                  55                  60

Xaa Xaa Xaa Xaa Xaa Asn Xaa Xaa Val Asp Xaa Cys Xaa Phe Ala Xaa
 65                  70                  75                  80

Ile Trp Ala Pro Asp Ala Asp Xaa Glu Ala Leu Arg Xaa Met Xaa Asp
             85                  90                  95

Trp Xaa Xaa Trp Xaa Xaa Xaa Xaa Pro Xaa Xaa Xaa Pro Xaa Xaa
            100                 105                 110

Xaa Xaa Xaa Phe Gln Ser Cys Xaa Xaa Xaa Xaa Xaa Xaa Xaa Xaa
            115                 120                 125

Xaa Xaa Glu Xaa Gln Gln Xaa Xaa Lys Xaa Xaa His Xaa Arg Phe Phe
        130                 135                 140

Xaa Xaa Xaa Xaa Xaa Asp Gln Xaa Xaa Xaa Gln Xaa Xaa Xaa Xaa Gln
145                 150                 155                 160

Xaa Ala Ala Xaa Xaa Xaa Gln Xaa Xaa Xaa Xaa Asp Val Glu Thr Tyr Ile
            165                 170                 175

Xaa Xaa Arg Arg Xaa Xaa Ile Xaa Xaa Xaa Pro Ala Xaa Ala Xaa Xaa
            180                 185                 190

Glu Tyr Ala Xaa Gly Val Xaa Leu Pro Xaa Ser Xaa Phe Ser His Xaa
            195                 200                 205

Ser Xaa Gln Xaa Cys Xaa Arg Xaa Xaa Ala Asp Xaa Val Xaa Leu Xaa
210                 215                 220

Asn Asp Xaa Xaa Ser Xaa Xaa Xaa Xaa Leu Xaa Xaa Xaa Xaa Asp Xaa
225                 230                 235                 240

Asn Leu Ile Xaa Leu Leu Ile Xaa Gln Arg Gly Xaa Ser Leu Gln Xaa
                245                 250                 255

Xaa Xaa Asp Lys Xaa Xaa Xaa Ile Ile Xaa Ser Xaa Tyr Arg Xaa Xaa
            260                 265                 270

```
Xaa Xaa Xaa Ala Xaa Leu Pro Xaa Xaa Tyr Gly Glu Xaa Xaa Glu
        275                 280                 285

Val Asp Xaa Glu Val Xaa Arg Phe Val Glu Xaa Cys Arg Xaa Xaa Xaa
290                 295                 300

Xaa Gly Asn Leu Asn Trp Ser Phe Xaa Thr Gly Arg Tyr Xaa Leu Xaa
305                 310                 315                 320

Xaa Glu Gly Xaa Xaa Xaa His Gly Leu His Xaa Thr Xaa Thr Met Xaa
                325                 330                 335

Xaa Xaa Xaa Xaa
        340

<210> SEQ ID NO 61
<211> LENGTH: 288
<212> TYPE: PRT
<213> ORGANISM: Hypoxylon sp. CI4A

<400> SEQUENCE: 61

Met Thr Phe Phe Ala Ala Ser Trp Trp Pro Tyr Ala Pro Tyr Glu Thr
1               5                   10                  15

Leu Glu Ile Val Ala Arg Leu Ala Ile Trp Phe Phe Val Trp Asp Asp
                20                  25                  30

Glu Thr Asp Pro Asp Glu Ser Ser Ala Met Val Asp Asn Trp Gly Arg
            35                  40                  45

Val Ser Ile Phe Arg Gln Arg Thr Val Asp Leu Val Arg Gln Ser Leu
    50                  55                  60

Thr Glu Thr Thr Asp Pro Lys Pro Leu Glu Gly Ser Ser Glu Pro Ile
65                  70                  75                  80

Ile Ala Phe Phe Gly Pro Val Gly Glu Ala Val Phe Arg Ser Cys Asn
                85                  90                  95

Lys Arg Gln Ser Asn Ser Phe Leu Glu Glu Leu Leu Phe Tyr Ile Asn
            100                 105                 110

Met Cys Gly Glu Glu Gln Lys Phe Tyr Thr Thr Gln Ser Ile Pro Thr
        115                 120                 125

Val Glu Glu Tyr Ile Gln Thr Arg Val Gly Ser Gly Ala Ala Arg Ala
130                 135                 140

Cys Leu Ala Thr Val Glu Tyr Ala Tyr Gly Ile Thr Val Pro Glu Glu
145                 150                 155                 160

Ile Met Asn Asp Glu Met Met Gln Gln Leu Trp His Glu Ala Ala Met
                165                 170                 175

Ile Ile His Thr Thr Asn Asp Ile Leu Ser Phe Lys Lys Glu Ile Ser
            180                 185                 190

Gln Ser Gln Val Ala Ser Leu Ile Pro Leu Leu Ile Pro Gln Val Gly
        195                 200                 205

Ser Val Gln Leu Ala Thr Asn His Ala Ala Glu Ile Val Lys Ser Ser
210                 215                 220

Ile Asp Arg Phe Asp Ala Ile Glu Arg Gln Phe Leu Glu Arg Tyr Ser
225                 230                 235                 240

Thr Thr Pro Glu Val Gln Glu Gly Val Arg Lys Val Ile Glu Gly Tyr
                245                 250                 255

Lys Tyr Ala Cys Thr Ala Asn Leu Asn Trp Ser Leu Ile Thr Gly Arg
            260                 265                 270

Tyr Lys Leu Asn Cys Glu Ser Met Ser Gly Gly Leu His Ile Thr Leu
        275                 280                 285

<210> SEQ ID NO 62
```

```
<211> LENGTH: 366
<212> TYPE: PRT
<213> ORGANISM: Daldinia eschscholzii EC12

<400> SEQUENCE: 62

Met Ser Ile Leu Asp Thr Lys Thr Asp Phe Asp Leu Leu Gly Lys
1               5                   10                  15

Cys Ile Gly Gln Arg Val Glu Ile Pro Asp Leu Phe Ala Leu Cys Pro
            20                  25                  30

Trp Gly Leu Glu Val Ser Pro Leu Asp Glu Lys Leu Thr Met Glu Val
        35                  40                  45

Glu Leu Trp Arg Ser Arg Trp Ile Asn Asp Pro Thr Ser Leu Lys Arg
    50                  55                  60

Asn Arg Ile Val Glu Ser Cys Leu Phe Ala Arg Gly Ile Ala Pro Lys
65              70                  75                  80

Ala Ala Leu Asn Glu Leu Ile Thr Leu Ala Lys Tyr Gln Ala Trp Leu
                85                  90                  95

Phe Tyr Trp Asp Asp Val Tyr Asp Phe Gly Asp Phe Asn Asp Lys Tyr
            100                 105                 110

Glu Glu Ile Val Ser His Gln Glu Gln Thr Ile Glu Leu Leu His Arg
        115                 120                 125

Ser Leu Phe Glu Lys Asp Pro Gly Ser Ile Asp Pro Ala Lys Ile Ala
    130                 135                 140

Pro Asn Tyr Leu Thr Val Gln Ser Ile Tyr Glu Trp Ala Ser Val Val
145                 150                 155                 160

Arg Glu Lys Ser Val Ser Ser Ser Leu Lys Ile Trp Leu Leu Lys Val
                165                 170                 175

Leu Val Asp Phe Cys Thr Ala Thr Phe Tyr Leu Gln Ser Ala Phe Asp
            180                 185                 190

Lys Arg Arg Ile Leu Asp Leu Glu Thr Tyr Arg Lys Ile Arg Met Asp
        195                 200                 205

Ser Ser Ala Val Phe Pro Thr Leu Gly Met Val Leu Phe Thr Asp Gln
    210                 215                 220

Val Ala Phe Pro Pro Trp Phe Phe Asp His Val Ser Ile Lys Lys Ala
225                 230                 235                 240

Ala Glu Leu Val Asn Ile Ile Val Trp Val Thr Asn Asp Ile Val Ser
                245                 250                 255

Ala Arg Gln Glu Leu Gln Cys Lys His Leu Asp Asn Leu Ile Pro Leu
            260                 265                 270

Leu Val His His Arg Gly Ile Thr Leu Gln Glu Ala Ile Arg Glu Ala
        275                 280                 285

Ser Lys Ile Thr His Gln Ala Tyr Leu Asp Phe Glu Glu Leu Glu Pro
    290                 295                 300

Gln Leu Met Gln Leu Gly Glu Asn Arg Gly Val Val Tyr Glu Met Gln
305                 310                 315                 320

Arg Phe Val Ala Ser Cys Arg His Val Cys Thr Gly Ile Phe Asn Trp
                325                 330                 335

Thr Tyr His Ile Lys Arg Tyr Ile Leu Trp Glu Pro Gly Met Thr Arg
            340                 345                 350

Ser Gly Leu Ser Thr Val Leu Gly Glu Asp Leu Leu Lys Lys
        355                 360                 365

<210> SEQ ID NO 63
<211> LENGTH: 346
<212> TYPE: PRT
```

<213> ORGANISM: Hypoxylon sp. CI4A

<400> SEQUENCE: 63

Met Ser Asn Ser Cys Glu Leu Val Gly His Gly Gln Thr Arg Gln Ser
1               5                   10                  15

Val Arg Ile Pro Asp Leu Phe Ser Ser Ile Met Ala Ser Lys Pro Val
            20                  25                  30

Val Asn Pro Asn Tyr Phe Lys Val Lys Ala Glu Gly Asp Arg Trp Ile
        35                  40                  45

Thr Arg Ile Ala Lys Met Asp Glu Lys Ala Arg Ala Lys Asn Thr Arg
    50                  55                  60

Val Asp Leu Cys Tyr Leu Val Ser Ile Trp Ala Pro Asp Ala Asp Glu
65                  70                  75                  80

Glu Ala Leu Arg Met Met Leu Asp Trp Asn His Trp Val Phe Leu Phe
                85                  90                  95

Asp Asp Gln Phe Asp Glu Gly His Leu Lys Glu Asp Leu Lys Ala Ala
            100                 105                 110

Gln Glu Glu Val Asp Gly Thr Val Ala Val Met Glu Asp Ala Pro
        115                 120                 125

Leu Val Lys Leu Glu Glu Asn Pro Leu Arg Tyr Ile Phe Gln Ser Cys
130                 135                 140

Trp Leu Arg Leu Lys Glu Arg Ala Ser His Ala Glu Leu Gln Gln Arg
145                 150                 155                 160

Tyr Lys Glu Gln His Ile Arg Phe Phe Asp Gln Leu Val Val Gln Val
                165                 170                 175

Arg Gln Ala Ala Gln Gly Gln Ile Leu Ser Arg Asp Val Gln Thr Tyr
            180                 185                 190

Ile Glu Val Arg Arg Gly Thr Ile Gly Ala Tyr Pro Ala Ile Ala Leu
        195                 200                 205

Thr Glu Tyr Ala Gln Gly Val Arg Leu Pro Gly Ser Val Phe Ser His
    210                 215                 220

Asn Ser Leu Gln Glu Cys Met Arg Val Ser Ser Asp Leu Val Leu Leu
225                 230                 235                 240

Val Asn Asp Val Leu Ser Tyr Arg Lys Asp Leu Glu Leu Gly Val Asp
                245                 250                 255

His Asn Leu Ile Ala Leu Leu Ile Glu Gln Arg Met Ser Leu Gln Gln
            260                 265                 270

Ser Val Asp Lys Ile Gly Thr Met Ile Asp Asn Cys Tyr Arg Arg Trp
        275                 280                 285

Tyr Thr Ala Leu Ala Glu Leu Pro Pro Tyr Gly Glu Val Asp Arg
    290                 295                 300

Glu Val Leu Tyr Phe Val Glu Val Cys Arg Arg Ile Ala Leu Gly Asn
305                 310                 315                 320

Leu His Trp Ser Phe Lys Thr Gly Arg Tyr Leu Gly Pro Glu Gly His
                325                 330                 335

Glu Val His Glu Thr Arg Thr Met Tyr Ile
            340                 345

<210> SEQ ID NO 64
<211> LENGTH: 345
<212> TYPE: PRT
<213> ORGANISM: Daldinia eschscholzii EC12

<400> SEQUENCE: 64

Met Leu Asp Ser Ser Glu Leu Ala Glu Pro His Glu Gly Arg Arg Ser

```
            1               5                   10                  15
        Val Arg Ile Pro Asp Leu Phe Ser Ser Ile Met Ala Thr Lys Pro Val
                       20                  25                  30

Val Asn Pro Asn Tyr Phe Lys Val Lys Ala Ala Gly Asp Arg Trp Ile
                       35                  40                  45

Lys Arg Ile Met Lys Met Asp Glu Lys Ala Ser Asp Lys Asn Ser Lys
                       50                  55                  60

Val Asp Phe Cys Tyr Met Ile Cys Ile Trp Ala Pro Asp Ala Asp Glu
         65                70                  75                  80

Glu Ala Leu Arg Ile Met Leu Asp Trp Asn Asn Trp Ile Phe Leu Phe
                           85                  90                  95

Asp Asp Gln Phe Asp Glu Gly His Leu Lys Asp Asp Pro Val Ala Ala
                           100                 105                 110

Gln Gln Glu Val Asn Ala Thr Met Ala Val Met Glu Asp Asp Ser Pro
                           115                 120                 125

Leu Val Arg Pro Glu Glu Ser Pro Ile Leu Tyr Val Phe Gln Thr Cys
                       130                 135                 140

Trp Leu Arg Leu Lys Gln Arg Ala Pro Thr Glu Ile Gln Gln Arg Tyr
        145                 150                 155                 160

Lys Glu Arg His Lys Arg Tyr Phe Asp Gln Leu Val Ala Gln Val Gln
                           165                 170                 175

Glu Ile Ala Arg Gly Gln Val Leu Thr Gly Asp Val Val Thr Tyr Leu
                           180                 185                 190

Glu Ala Arg Arg Arg Thr Ile Gly Val Tyr Pro Ala Ile Thr Leu Ala
                           195                 200                 205

Glu Tyr Gly Glu Gly Val Arg Leu Ser Asp Ser Val Leu Ser His His
                           210                 215                 220

Ser Leu Gln Glu Cys Met Arg Ile Thr Ala Asp Leu Val Ile Leu Val
        225                 230                 235                 240

Asn Asp Ile Leu Ser Tyr Lys Lys Asp Leu Asp Leu Gly Val Asp Tyr
                           245                 250                 255

Asn Leu Ile Thr Leu Leu Met Lys Gln Asn Leu Ser Leu Gln Glu Ser
                           260                 265                 270

Met Asp Lys Ile Gly Ala Leu Ile Glu Ser Cys Tyr Arg Asn Trp Tyr
                           275                 280                 285

Leu Thr Leu Ala Glu Leu Pro Leu Tyr Gly Glu Glu Thr Asp Asn Glu
                       290                 295                 300

Val Leu Arg Phe Val Glu Ala Cys Arg Cys Val Ala Leu Gly Asn Leu
        305                 310                 315                 320

Tyr Trp Ser Phe Lys Thr Gly Arg Tyr Leu Gly Ser Glu Gly His Asp
                           325                 330                 335

Leu His Lys Thr Arg Thr Met Tyr Leu
                           340                 345

<210> SEQ ID NO 65

<400> SEQUENCE: 65

000

<210> SEQ ID NO 66

<400> SEQUENCE: 66

000
```

```
<210> SEQ ID NO 67
<400> SEQUENCE: 67

000

<210> SEQ ID NO 68
<400> SEQUENCE: 68

000

<210> SEQ ID NO 69
<400> SEQUENCE: 69

000

<210> SEQ ID NO 70
<400> SEQUENCE: 70

000

<210> SEQ ID NO 71
<211> LENGTH: 8
<212> TYPE: PRT
<213> ORGANISM: Artificial Sequence
<220> FEATURE:
<223> OTHER INFORMATION: Consensus polypeptide sequence
<220> FEATURE:
<221> NAME/KEY: MISC_FEATURE
<222> LOCATION: (1)..(8)
<223> OTHER INFORMATION: absent or any amino acid (e.g., an amino acid
      present at a position in one of the aligned sequences present in
      FIG. 10A)

<400> SEQUENCE: 71

Xaa Xaa Xaa Xaa Xaa Xaa Xaa Xaa
1               5

<210> SEQ ID NO 72
<211> LENGTH: 5
<212> TYPE: PRT
<213> ORGANISM: Artificial Sequence
<220> FEATURE:
<223> OTHER INFORMATION: Consensus polypeptide sequence
<220> FEATURE:
<221> NAME/KEY: MISC_FEATURE
<222> LOCATION: (1)..(5)
<223> OTHER INFORMATION: absent or any amino acid (e.g., an amino acid
      present at a position in one of the aligned sequences present in
      FIG. 10A)

<400> SEQUENCE: 72

Xaa Xaa Xaa Xaa Xaa
1               5

<210> SEQ ID NO 73
<211> LENGTH: 8
<212> TYPE: PRT
<213> ORGANISM: Artificial Sequence
<220> FEATURE:
<223> OTHER INFORMATION: Consensus polypeptide sequence
<220> FEATURE:
<221> NAME/KEY: MISC_FEATURE
<222> LOCATION: (1)..(3)
<223> OTHER INFORMATION: absent or any amino acid (e.g., an amino acid
      present at a position in one of the aligned sequences present in
      FIG. 10B)
```

```
<220> FEATURE:
<221> NAME/KEY: MISC_FEATURE
<222> LOCATION: (5)..(8)
<223> OTHER INFORMATION: absent or any amino acid (e.g., an amino acid
      present at a position in one of the aligned sequences present in
      FIG. 10B)

<400> SEQUENCE: 73

Xaa Xaa Xaa Asp Xaa Xaa Xaa Xaa
1               5

<210> SEQ ID NO 74
<211> LENGTH: 5
<212> TYPE: PRT
<213> ORGANISM: Artificial Sequence
<220> FEATURE:
<223> OTHER INFORMATION: Consensus polypeptide sequence
<220> FEATURE:
<221> NAME/KEY: MISC_FEATURE
<222> LOCATION: (1)..(1)
<223> OTHER INFORMATION: absent or any amino acid (e.g., an amino acid
      present at a position in one of the aligned sequences present in
      FIG. 10B)
<220> FEATURE:
<221> NAME/KEY: MISC_FEATURE
<222> LOCATION: (3)..(5)
<223> OTHER INFORMATION: absent or any amino acid (e.g., an amino acid
      present at a position in one of the aligned sequences present in
      FIG. 10B)

<400> SEQUENCE: 74

Xaa Asp Xaa Xaa Xaa
1               5

<210> SEQ ID NO 75
<211> LENGTH: 13
<212> TYPE: PRT
<213> ORGANISM: Artificial Sequence
<220> FEATURE:
<223> OTHER INFORMATION: Consensus polypeptide sequence
<220> FEATURE:
<221> NAME/KEY: MISC_FEATURE
<222> LOCATION: (1)..(6)
<223> OTHER INFORMATION: absent or any amino acid (e.g., an amino acid
      present at a position in one of the aligned sequences present in
      FIG. 11A)
<220> FEATURE:
<221> NAME/KEY: MISC_FEATURE
<222> LOCATION: (8)..(13)
<223> OTHER INFORMATION: absent or any amino acid (e.g., an amino acid
      present at a position in one of the aligned sequences present in
      FIG. 11A)

<400> SEQUENCE: 75

Xaa Xaa Xaa Xaa Xaa Xaa Ser Xaa Xaa Xaa Xaa Xaa Xaa
1               5                   10

<210> SEQ ID NO 76
<211> LENGTH: 10
<212> TYPE: PRT
<213> ORGANISM: Artificial Sequence
<220> FEATURE:
<223> OTHER INFORMATION: Consensus polypeptide sequence
<220> FEATURE:
<221> NAME/KEY: MISC_FEATURE
<222> LOCATION: (1)..(5)
<223> OTHER INFORMATION: absent or any amino acid (e.g., an amino acid
      present at a position in one of the aligned sequences present in
      FIG. 11A)
```

```
<220> FEATURE:
<221> NAME/KEY: MISC_FEATURE
<222> LOCATION: (7)..(10)
<223> OTHER INFORMATION: absent or any amino acid (e.g., an amino acid
      present at a position in one of the aligned sequences present in
      FIG. 11A)

<400> SEQUENCE: 76

Xaa Xaa Xaa Xaa Xaa Ser Xaa Xaa Xaa Xaa
1               5                   10

<210> SEQ ID NO 77
<211> LENGTH: 13
<212> TYPE: PRT
<213> ORGANISM: Artificial Sequence
<220> FEATURE:
<223> OTHER INFORMATION: Consensus polypeptide sequence
<220> FEATURE:
<221> NAME/KEY: MISC_FEATURE
<222> LOCATION: (1)..(2)
<223> OTHER INFORMATION: absent or any amino acid (e.g., an amino acid
      present at a position in one of the aligned sequences present in
      FIG. 11B)
<220> FEATURE:
<221> NAME/KEY: MISC_FEATURE
<222> LOCATION: (4)..(6)
<223> OTHER INFORMATION: absent or any amino acid (e.g., an amino acid
      present at a position in one of the aligned sequences present in
      FIG. 11B)
<220> FEATURE:
<221> NAME/KEY: MISC_FEATURE
<222> LOCATION: (8)..(13)
<223> OTHER INFORMATION: absent or any amino acid (e.g., an amino acid
      present at a position in one of the aligned sequences present in
      FIG. 11B)

<400> SEQUENCE: 77

Xaa Xaa Asp Xaa Xaa Xaa Ser Xaa Xaa Xaa Xaa Xaa Xaa
1               5                   10

<210> SEQ ID NO 78
<211> LENGTH: 10
<212> TYPE: PRT
<213> ORGANISM: Artificial Sequence
<220> FEATURE:
<223> OTHER INFORMATION: Consensus polypeptide sequence
<220> FEATURE:
<221> NAME/KEY: MISC_FEATURE
<222> LOCATION: (1)..(1)
<223> OTHER INFORMATION: absent or any amino acid (e.g., an amino acid
      present at a position in one of the aligned sequences present in
      FIG. 11B)
<220> FEATURE:
<221> NAME/KEY: MISC_FEATURE
<222> LOCATION: (3)..(5)
<223> OTHER INFORMATION: absent or any amino acid (e.g., an amino acid
      present at a position in one of the aligned sequences present in
      FIG. 11B)
<220> FEATURE:
<221> NAME/KEY: MISC_FEATURE
<222> LOCATION: (7)..(10)
<223> OTHER INFORMATION: absent or any amino acid (e.g., an amino acid
      present at a position in one of the aligned sequences present in
      FIG. 11B)

<400> SEQUENCE: 78

Xaa Asp Xaa Xaa Xaa Ser Xaa Xaa Xaa Xaa
1               5                   10
```

TERPENE SYNTHASES FOR BIOFUEL PRODUCTION AND METHODS THEREOF

CROSS-REFERENCE TO RELATED APPLICATION

This application is a divisional of prior U.S. patent application Ser. No. 15/066,651, filed Mar. 10, 2016, and claims the benefit of U.S. Provisional Application No. 62/132,093, filed Mar. 12, 2015, each of which is hereby incorporated by reference in its entirety.

STATEMENT OF GOVERNMENT INTEREST

This invention was made with Government support under Contract No. DE-NA0003525 awarded by the United States Department of Energy/National Nuclear Security Administration. The Government has certain rights in the invention.

REFERENCE TO A SEQUENCE LISTING APPENDIX

A sequence listing appendix including an ASCII formatted file accompanies this application. The appendix includes a file named "SD13315_2_ST25.txt," created on Jul. 9, 2019 (size of 179 kilobytes), which is hereby incorporated by reference in its entirety.

FIELD OF THE INVENTION

The present invention relates to terpene synthases capable of degrading precursors into biofuel compounds, such as terpenoid compounds. In one instance, a transformed organism can include such terpene synthases, as well as vectors encoding such synthases. Methods of employing such synthases and organisms are also described herein.

BACKGROUND OF THE INVENTION

Terpenes are valuable bioproducts for use in various industries, including biofuel, pharmaceutical, healthcare, and food industry sectors. Extracting terpenes from plants can be costly with inconsistencies in yield and purity. There is a need for additional tools and processes to enable effective production of terpenes from different bioresources.

SUMMARY OF THE INVENTION

The present invention relates to terpene synthases selected to produce terpenoid compounds using a genetically modified organism (e.g., a genetically modified microbe). Such terpenoid compounds can have any useful purpose, such as for the production of high energy density fuels (e.g., aviation fuels) and chemical intermediates.

Accordingly, in one non-limiting instance, the present invention includes an isolated, genetically engineered organism (e.g., a microbial organism) including: an exogenous terpenoid precursor, an exogenous enzyme configured to synthesize a terpenoid precursor, or a nucleic acid encoding the exogenous enzyme; and an exogenous terpene synthase or a nucleic acid encoding the exogenous terpene synthase. In one embodiment, the exogenous terpene synthase is selected from the group consisting of a pinene synthase, a guaiene synthase, a pinene and guaiene synthase, a caryophyllene synthase, a chamigrene synthase, a chamigrene and pinene synthase, a gurjunene synthase, a gurjunene and pinene synthase, a gumunene synthase, a selinene synthase, and an isoledene synthase, or a bifunctional synthase of any of these.

In one non-limiting embodiment, the organism is a first microbe (e.g., a bacterium); and the exogenous terpenoid precursor, exogenous enzyme, and/or exogenous terpene synthase, as well as nucleic acids thereof encoding the polypeptide or complements thereof, are derived from a second microbe that is different than the first microbe. In one non-limiting embodiment, the first microbe is a bacterium, and the second microbe is a fungus.

In some embodiments, the organism is configured to effectively degrade the an exogenous terpenoid precursor, e.g., as compared to an organism lacking the exogenous terpenoid precursor, lacking the exogenous enzyme configured to synthesize a terpenoid precursor, and/or lacking the nucleic acid encoding the exogenous enzyme.

In some embodiments, the exogenous terpenoid precursor is selected from the group consisting of mevalonate, dimethylallyl pyrophosphate, isopentenyl pyrophosphate, farnesyl pyrophosphate, geranyl pyrophosphate, and geranylgeranyl pyrophosphate, or a salt thereof. In other embodiments, the precursor is a compound shown in FIG. 1, FIG. 21, FIG. 22, or FIG. 23.

In some embodiments, the organism is configured to produce one or more terpenoid compounds selected from the group consisting of a monoterpene, a sesquiterpene, and a diterpene. In other embodiments, the terpenoid compound is a compound shown in FIG. 3A-3E, FIG. 21, FIG. 22, or FIG. 23. In yet other embodiments, the organism is configured to produce two or more terpenoid compounds (e.g., a monoterpene and a sesquiterpene).

In some embodiments, the nucleic acid encoding the exogenous enzyme and/or the nucleic acid encoding the exogenous terpene synthase is provided as a plasmid vector.

In some embodiments, the exogenous enzyme is selected from the group consisting of acetyl-CoA acetyltransferase, HMG-CoA synthase, HMG-CoA reductase, mevalonate kinase, phosphomevalonate kinase, mevalonate diphosphate decarboxylase, isoprenyl diphosphate isomerase, and geranyl pyrophosphate synthase.

In other embodiments, the nucleic acid encoding the exogenous enzyme includes a nucleic acid sequence encoding the exogenous enzyme selected from the group consisting of acetyl-CoA acetyltransferase, HMG-CoA synthase, HMG-CoA reductase, mevalonate kinase, phosphomevalonate kinase, mevalonate diphosphate decarboxylase, isoprenyl diphosphate isomerase, and geranyl pyrophosphate synthase. In some embodiments, the nucleic acid encoding the exogenous enzyme includes a complement thereof (i.e., in which the nucleic acid encoding the exogenous enzyme includes a complement of a nucleic acid sequence encoding the exogenous enzyme selected from the group consisting of acetyl-CoA acetyltransferase, HMG-CoA synthase, HMG-CoA reductase, mevalonate kinase, phosphomevalonate kinase, mevalonate diphosphate decarboxylase, isoprenyl diphosphate isomerase, and geranyl pyrophosphate synthase).

In some embodiments, the exogenous terpene synthase is a chamigrene synthase; or the nucleic acid encoding the exogenous terpene synthase includes a nucleic acid sequence encoding the chamigrene synthase or a complement thereof. In other embodiments, the exogenous terpene synthase is a bifunctional terpene synthase (e.g., a synthase having enzymatic activity characterized by more than one type of synthase, such as a bifunctional monoterpene/sesquiterpene synthase, a bifunctional pinene/guaiene synthase, a bifunctional chamigrene/pinene synthase, a bifunctional gurjunene/pinene synthase In some embodiments, the exogenous terpene synthase includes a polypeptide sequence having at least 90% sequence identity to any one of the following: SEQ ID NO: 10, in which X at each position of SEQ ID NO:10 is an amino acid present at a position in one of SEQ ID NOs:11-14 when optimally aligned with SEQ ID NO:10; SEQ ID NO:20, in which X at each position of SEQ ID NO:20 is an amino acid present at a position in one of SEQ ID NOs:21-25 when optimally aligned with SEQ ID NO:20; SEQ ID NO:30, in which X at each position of SEQ ID NO:30 is an amino acid present at a position in one of SEQ ID NOs:31-34 when optimally aligned with SEQ ID NO:30; SEQ ID NO:40, in which X at each position of SEQ ID NO:40 is an amino acid present at a position in one of SEQ ID NOs:41-46 when optimally aligned with SEQ ID NO:40; SEQ ID NO:50, in which X at each position of SEQ ID NO:50 is an amino acid present at a position in one of SEQ ID NOs:51-54 when optimally aligned with SEQ ID NO:50; SEQ ID NO:60, in which X at each position of SEQ ID NO:60 is an amino acid present at a position in one of SEQ ID NOs:61-64 when optimally aligned with SEQ ID NO:60; or a fragment of any of these polypeptide sequences.

In some embodiments, the nucleic acid encoding the exogenous terpene synthase includes a nucleic acid sequence encoding a polypeptide sequence having at least 90% sequence identity to any polypeptide sequence described herein, or a complement thereof.

In some embodiments, the exogenous terpene synthase includes a polypeptide sequence having at least 90% sequence identity to any one of SEQ ID NOs:11-14, 21-25, 31-34, 41-46, 51-54, and 61-64, or a fragment thereof. In other embodiments, the nucleic acid encoding the exogenous terpene synthase includes a nucleic acid sequence encoding a polypeptide sequence having at least 90% sequence identity to any one of SEQ ID NOs:11-14, 21-25, 31-34, 41-46, 51-54, and 61-64, or a fragment thereof. In yet other embodiments, the nucleic acid encoding the exogenous terpene synthase includes a complement of a nucleic acid sequence encoding a polypeptide sequence having at least 90% sequence identity to any one of SEQ ID NOs:11-14, 21-25, 31-34, 41-46, 51-54, and 61-64, or a fragment thereof.

In some embodiments, the exogenous terpene synthase includes a polypeptide sequence having at least 90% sequence identity to any one of SEQ ID NOs:23, 24, 25, 31, 32, 34, 41, 42, 44, 45, 54, 62, and 64. In other embodiments, the nucleic acid encoding the exogenous terpene synthase includes a nucleic acid sequence encoding a polypeptide sequence having at least 90% sequence identity to any one of SEQ ID NOs:23, 24, 25, 31, 32, 34, 41, 42, 44, 45, 54, 62, and 64. In yet other embodiments, the nucleic acid encoding the exogenous terpene synthase includes a complement of a nucleic acid sequence encoding a polypeptide sequence having at least 90% sequence identity to any one of SEQ ID NOs:23, 24, 25, 31, 32, 34, 41, 42, 44, 45, 54, 62, and 64.

In some embodiments, the exogenous terpene synthase includes a polypeptide sequence having at least 90% sequence identity to XXZZXXZX (SEQ ID NO:71) or a fragment thereof; where X is any amino acid; and where Z is selected from the group consisting of Asp, Glu, and His. In other embodiments, the exogenous terpene synthase includes a polypeptide sequence having at least 90% sequence identity to ZZXXZ (SEQ ID NO:72); where X is any amino acid (e.g., Ala, Ser, Thr, Val, Leu, Ile, Pro, Phe, Tyr, Asp, Glu, Gln, or Lys; Ala, Val, Leu, Ile, Pro, Phe, Tyr, Glu, or Gln; or Val, Leu, Ile, or Glu); and where Z is selected from the group consisting of Asp, Glu, and His. In yet other embodiments, the exogenous terpene synthase includes a polypeptide sequence having at least 90% sequence identity to XXZDXXZX (SEQ ID NO:73); where X is selected from the group consisting of Ala, Ser, Thr, Val, Leu, Ile, Phe, Tyr, Trp, Glu, Asn, Gln, His, and Pro; and where Z is selected from the group consisting of Asp and Glu. In other embodiments, the exogenous terpene synthase includes a polypeptide sequence having at least 90% sequence identity to ZDXXZ (SEQ ID NO:74); where X is selected from the group consisting of Ala, Val, Leu, Ile, Phe, Tyr, Glu, Gln, and Pro; and where Z is selected from the group consisting of Asp and Glu.

In some embodiments, the exogenous terpene synthase includes a polypeptide sequence having at least 90% sequence identity to XZZXXXSXXZ ZXX (SEQ ID NO:75) or a fragment thereof; where X is any amino acid (e.g., Gly, Ala, Ser, Thr, Val, Leu, Ile, Met, Phe, Tyr, Trp, Asp, Glu, Gln, Lys, Arg, or absent); and where Z is selected from the group consisting of Cys, Asp, Glu, Asn, Gln, Lys, Arg, and absent. In other embodiments, the exogenous terpene synthase includes a polypeptide sequence having at least 90% sequence identity to ZDXXXSXXZZ (SEQ ID NO:76) or a fragment thereof; where X is any amino acid (e.g., Ala, Val, Leu, Ile, Phe, Tyr, Trp, Glu, Gln, Lys, Arg, or absent); and where Z is selected from the group consisting of Cys, Asp, Glu, Asn, Gln, Lys, Arg, and absent.

In yet other embodiments, the exogenous terpene synthase includes a polypeptide sequence having at least 90% sequence identity to XZDXXXSXXZZXX (SEQ ID NO:77); where X is selected from the group consisting of Gly, Ala, Thr, Val, Leu, Ile, Phe, Tyr, Trp, Asp, Glu, Gln, Lys, Arg, and absent; and where Z is selected from the group consisting of Cys, Asp, Glu, Asn, Gln, Lys, and Arg. In other embodiments, the exogenous terpene synthase includes a polypeptide sequence having at least 90% sequence identity to ZDXXXSXXZZ (SEQ ID NO:78); where X is selected from the group consisting of Ala, Val, Leu, Ile, Phe, Tyr, Trp, Glu, Gln, Lys, Arg, and absent; and where Z is selected from the group consisting of Cys, Asp, Glu, Asn, Gln, Lys, and Arg.

In another aspect, the present invention relates to a method of treating a biomass. In some embodiments, the method includes exposing the biomass to one or more organisms (e.g., any described herein); and isolating one or more terpenoid compounds.

In some embodiments, the method includes (e.g., prior to the exposing step and/or prior to the isolating step) pre-treating the biomass with one or more acids and/or enzymes.

In some embodiments, the biomass includes an alga, an amino acid, a protein, and/or a carbohydrate.

In some embodiments, the one or more terpenoid compounds is selected from the group consisting of a monoterpene, a sesquiterpene, and a diterpene. In other embodiments, the terpenoid compound is a compound shown in FIG. 3A-3E, FIG. 21, FIG. 22, or FIG. 23.

In some embodiments, the exposing step includes a first organism configured to degrade a carbohydrate in the biomass and a second organism configured to degrade a protein in the biomass.

In any embodiment herein, the exogenous terpene synthase includes a polypeptide sequence having at least 90% (e.g., 91%, 92%, 93%, 94%, 95%, 96%, 97%, 98%, 99%, or 99.9%) sequence identity to any polypeptide sequence described herein, or a fragment thereof (e.g., a fragment including 5, 6, 7, 8, 9, 10, 11, 12, 13, 14, 15, 16, 17, 18, 19, 20, 21, 2, 23, 24, 25, 30, 35, 40, 45, 50, 55, 60, 65, 70, 75, 80, 85, 90, 95, 100, or more amino acids).

In any embodiment herein, the nucleic acid encoding the exogenous terpene synthase includes a nucleic acid sequence encoding a polypeptide sequence having at least 90% (e.g., 91%, 92%, 93%, 94%, 95%, 96%, 97%, 98%, 99%, or 99.9%) sequence identity to any polypeptide sequence described herein, or a complement thereof.

In any embodiment herein, the exogenous terpene synthase is a polypeptide sequence corresponding to an enzyme identified in FIG. 2A-2C, FIG. 4A-4B, FIG. 5A-5B, FIG. 6A-6B, FIG. 7A-7B, FIG. 8A-8B, FIG. 9A-9B, or FIG. 13. In some embodiments, the nucleic acid encoding the exogenous enzyme or a complement thereof is a nucleic acid sequence encoding any polypeptide sequence described herein (e.g., as in FIG. 2, FIG. 4A-4B, FIG. 5A-5B, FIG. 6A-6B, FIG. 7A-7B, FIG. 8A-8B, FIG. 9A-9B, or FIG. 13).

In any embodiment herein, the exogenous terpene synthase is a polypeptide sequence including any sequence described herein, e.g., in FIG. 2A-2C, FIG. 4A-4B, FIG. 5A-5B, FIG. 6A-6B, FIG. 7A-7B, FIG. 8A-8B, FIG. 9A-9B, FIG. 10A-10B, FIG. 11A-11B, FIG. 12A.

In any embodiment herein, the terpenoid compound is a compound shown in FIG. 3A-3E, FIG. 14, FIG. 15A-15B, FIG. 16A-16C, FIG. 17A-17D, FIG. 18, FIG. 19A-19B, FIG. 20B, FIG. 21, FIG. 22, FIG. 23, FIG. 28, FIG. 29, FIG. 30, FIG. 31, FIG. 32, or FIG. 33.

In any embodiment herein, the nucleic encoding the exogenous enzyme and/or the nucleic acid encoding the exogenous terpene synthase is provided as a plasmid vector (e.g., as in FIG. 24, FIG. 34A, or FIG. 35A). Additional details follow.

Definitions

As used herein, the term "about" means+/−10% of any recited value. As used herein, this term modifies any recited value, range of values, or endpoints of one or more ranges.

The terms "polynucleotide" and "nucleic acid," used interchangeably herein, refer to a polymeric form of nucleotides of any length, either ribonucleotides or deoxyribonucleotides. Thus, this term includes, but is not limited to, single-stranded (e.g., sense or antisense), double-stranded, or multi-stranded ribonucleic acids (RNAs), deoxyribonucleic acids (DNAs), threose nucleic acids (TNAs), glycol nucleic acids (GNAs), peptide nucleic acids (PNAs), locked nucleic acids (LNAs), or hybrids thereof, genomic DNA, cDNA, DNA-RNA hybrids, or a polymer comprising purine and pyrimidine bases or other natural, chemically or biochemically modified, non-natural, or derivatized nucleotide bases. Polynucleotides can have any useful two-dimensional or three-dimensional structure or motif, such as regions including one or more duplex, triplex, quadruplex, hairpin, and/or pseudoknot structures or motifs.

The term "modified," as used in reference to nucleic acids, means a nucleic acid sequence including one or more modifications to the nucleobase, nucleoside, nucleotide, phosphate group, sugar group, and/or internucleoside linkage (e.g., phosphodiester backbone, linking phosphate, or a phosphodiester linkage).

The term "modified," as used in reference to amino acids, means an amino acid including one or more modifications, such as a post-translation modification (e.g., acetylation, methylation, phosphorylation, ubiquitination, sumoylation, ribosylation, glycosylation, acylation, or isomerization), or including a non-natural amino acid.

The term "modified," as used in reference to a protein, means a polypeptide sequence including one or more amino acid substitution, as compared to the reference sequence for the protein.

"Complementarity" or "complementary" or "complement" refers to the ability of a nucleic acid to form hydrogen bond(s) with another nucleic acid sequence by either traditional Watson-Crick or other non-traditional types, e.g., form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. As is known in the art, standard Watson-Crick base-pairing includes: adenine (A) pairing with thymidine (T), adenine (A) pairing with uracil (U), and guanine (G) pairing with cytosine (C). In addition, it is also known in the art that for hybridization between two RNA molecules (e.g., dsRNA), guanine (G) base pairs with uracil (U). A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" or "sufficient complementarity" as used herein refers to a degree of complementarity that is at least 60%, 65%, 70%, 75%, 80%, 85%, 90%, 95%. 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part 1, Second Chapter "Overview of principles of hybridization and the strategy of nucleic acid probe assay", Elsevier, N.Y.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence. Hybridization and washing conditions are well known and exemplified in Sambrook J, Fritsch E F, and Maniatis T, "Molecular Cloning: A Laboratory Manual," Second Edition, Cold Spring Harbor Laboratory Press, Cold Spring Harbor (1989), particularly Chapter 11 and Table 11.1 therein; and Sambrook J and Russell W, "Molecular Cloning: A Laboratory Manual," Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementation, variables well known in the art. The greater the degree of complementation between two nucleotide sequences, the greater the value of the melting temperature (Tm) for hybrids of nucleic acids having those sequences. For hybridizations between nucleic acids with short stretches of complementarity (e.g., complementarity over 35 or less, 30 or less, 25 or less, 22 or less, 20 or less, or 18 or less nucleotides) the position of mismatches becomes important (see Sambrook et al., supra, 11.7-11.8). Typically, the length for a hybridizable nucleic acid is at least about 10 nucleotides. Illustrative minimum lengths for a hybridizable nucleic acid are: at least about 15 nucleotides; at least about 20 nucleotides; at least about 22 nucleotides; at least about 25 nucleotides; and at least about 30 nucleotides). Furthermore, the skilled artisan will recognize that the temperature and wash solution salt concentration may be adjusted as necessary according to factors such as length of the region of complementation and the degree of complementation.

It is understood in the art that the sequence of polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a loop structure or hairpin structure). A polynucleotide can comprise at least 70%, at least 80%, at least 90%, at least 95%, at least 99%, or 100% sequence complementarity to a target region within the target nucleic acid sequence to which they are targeted. For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. Percent complementarity between particular stretches of nucleic acid sequences within nucleic acids can be determined routinely using BLAST programs (basic local alignment search tools) and PowerBLAST programs known in the art (Altschul S F et al., *J. Mol. Biol.* 1990; 215:403-10; Zhang J et al., *Genome Res.* 1997; 7:649-56) or by using the Gap program (Wisconsin Sequence Analysis Package, Version 8 for Unix, Genetics Computer Group, University Research Park, Madison Wis.), using default settings, which uses the algorithm of Smith T F et al., *Adv. Appl. Math.* 1981; 2(4):482-9).

By "protein," "peptide," or "polypeptide," as used interchangeably, is meant any chain of more than two amino acids, regardless of post-translational modification (e.g., glycosylation or phosphorylation), constituting all or part of a naturally occurring polypeptide or peptide, or constituting a non-naturally occurring polypeptide or peptide, which can include coded amino acids, non-coded amino acids, modified amino acids (e.g., chemically and/or biologically modified amino acids), and/or modified backbones.

The term "fragment" is meant a portion of a nucleic acid or a polypeptide that is at least one nucleotide or one amino acid shorter than the reference sequence. This portion contains, preferably, at least about 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, 1000, 1250, 1500, 1750, 1800 or more nucleotides; or 10, 20, 30, 40, 50, 60, 70, 80, 90, 100, 150, 200, 250, 300, 350, 400, 450, 500, 550, 600, 640 amino acids or more. In another example, any polypeptide fragment can include a stretch of at least about 5 (e.g., about 10, about 20, about 30, about 40, about 50, or about 100) amino acids that are at least about 40% (e.g., about 50%, about 60%, about 70%, about 80%, about 90%, about 95%, about 87%, about 98%, about 99%, or about 100%) identical to any of the sequences described herein can be utilized in accordance with the invention. In certain embodiments, a polypeptide to be utilized in accordance with the invention includes 2, 3, 4, 5, 6, 7, 8, 9, 10, or more mutations (e.g., one or more conservative amino acid substitutions, as described herein). In yet another example, any nucleic acid fragment can include a stretch of at least about 5 (e.g., about 7, about 8, about 10, about 12, about 14, about 18, about 20, about 24, about 28, about 30, or more) nucleotides that are at least about 40% (about 50%, about 60%, about 70%, about 80%, about 90%, about 95%, about 87%, about 98%, about 99%, or about 100%) identical to any of the sequences described herein can be utilized in accordance with the invention.

The term "conservative amino acid substitution" refers to the interchangeability in proteins of amino acid residues having similar side chains (e.g., of similar size, charge, and/or polarity). For example, a group of amino acids having aliphatic side chains consists of glycine (Gly, G), alanine (Ala, A), valine (Val, V), leucine (Leu, L), and isoleucine (Ile, I); a group of amino acids having aliphatic-hydroxyl side chains consists of serine (Ser, S) and threonine (Thr, T); a group of amino acids having amide containing side chains consisting of asparagine (Asn, N) and glutamine (Gln, Q); a group of amino acids having aromatic side chains consists of phenylalanine (Phe, F), tyrosine (Tyr, Y), and tryptophan (Trp, W); a group of amino acids having basic side chains consists of lysine (Lys, K), arginine (Arg, R), and histidine (His, H); a group of amino acids having acidic side chains consists of glutamic acid (Glu, E) and aspartic acid (Asp, D); and a group of amino acids having sulfur containing side chains consists of cysteine (Cys, C) and methionine (Met, M). Exemplary conservative amino acid substitution groups are valine-leucine-isoleucine, phenylalanine-tyrosine, lysine-arginine, alanine-valine, glycine-serine, glutamate-aspartate, and asparagine-glutamine.

As used herein, when a polypeptide or nucleic acid sequence is referred to as having "at least X % sequence identity" to a reference sequence, it is meant that at least X percent of the amino acids or nucleotides in the polypeptide or nucleic acid are identical to those of the reference sequence when the sequences are optimally aligned. An optimal alignment of sequences can be determined in various ways that are within the skill in the art, for instance, the Smith Waterman alignment algorithm (Smith T F et al., *J. Mol. Biol.* 1981; 147:195-7) and BLAST (Basic Local Alignment Search Tool; Altschul S F et al., *J. Mol. Biol.* 1990; 215:403-10). These and other alignment algorithms are accessible using publicly available computer software such as "Best Fit" (Smith T F et al., *Adv. Appl. Math.* 1981; 2(4):482-9) as incorporated into GeneMatcher Plus™ (Schwarz and Dayhof, "Atlas of Protein Sequence and Structure," ed. Dayhoff, M. O., pp. 353-358, 1979), BLAST, BLAST-2, BLAST-P, BLAST-N, BLAST-X, WU-BLAST-2, ALIGN, ALIGN-2, CLUSTAL, T-COFFEE, MUSCLE, MAFFT, or Megalign (DNASTAR). In addition, those skilled in the art can determine appropriate parameters for measuring alignment, including any algorithms needed to achieve optimal alignment over the length of the sequences being compared. In general, for polypeptides, the length of comparison sequences can be at least five amino acids, preferably 10, 20, 30, 40, 50, 60, 70, 80, 90, 100, 125, 150, 175, 200, 250, 300, 400, 500, 600, 700, or more amino acids, up to the entire length of the polypeptide. For nucleic acids, the length of comparison sequences can generally be at least 10, 20, 30, 40, 50, 60, 70, 80, 90, 100, 125, 150, 175, 200, 250, 300, 400, 500, 600, 700, 800, 900, 1000, 1100, 1200, 1300, 1400, 1500, 1600, 1700, 1800, 1900, 2000, 2100, or more nucleotides, up to the entire length of the nucleic acid molecule. It is understood that for the purposes of determining sequence identity when comparing a DNA sequence to an RNA sequence, a thymine nucleotide is equivalent to a uracil nucleotide.

By "substantial identity" or "substantially identical" is meant a polypeptide or nucleic acid sequence that has the same polypeptide or nucleic acid sequence, respectively, as a reference sequence, or has a specified percentage of amino acid residues or nucleotides, respectively, that are the same at the corresponding location within a reference sequence when the two sequences are optimally aligned. For example, an amino acid sequence that is "substantially identical" to a reference sequence has at least about 50%, 60%, 70%, 75%, 80%, 85%, 90%, 95%, 96%, 97%, 98%, 99%, or 100% sequence identity to the reference amino acid sequence. For polypeptides, the length of comparison sequences will generally be at least 5, 6, 7, 8, 9, 10, 11, 12, 13, 14, 15, 16, 17, 18, 19, 20, 25, 50, 75, 90, 100, 150, 200, 250, 300, or 350 contiguous amino acids (e.g., a full-length sequence). For nucleic acids, the length of comparison sequences will generally be at least 5, 10, 11, 12, 13, 14, 15, 16, 17, 18, 19, 20, 21, 22, 23, 24, or 25 contiguous nucleotides (e.g., the full-length nucleotide sequence). Sequence identity may be measured using sequence analysis software on the default setting (e.g., Sequence Analysis Software Package of the Genetics Computer Group, University of Wisconsin Biotechnology Center, 1710 University Avenue, Madison, Wis., 53705). Such software may match similar sequences by assigning degrees of homology to various substitutions, deletions, and other modifications.

A "vector" or "expression vector" is a replicon, such as plasmid, phage, virus, or cosmid, to which another nucleic acid segment, i.e., an "insert", may be attached so as to bring about the replication of the attached segment in a cell.

An "expression cassette" comprises a nucleic acid coding sequence operably linked, as defined herein, to a promoter sequence, as defined herein.

"Operably linked" or "operatively linked" or "operatively associated with," as used interchangeably, refers to a juxtaposition wherein the components so described are in a relationship permitting them to function in their intended manner. For instance, a promoter is operably linked to a coding sequence if the promoter affects its transcription or expression. A nucleic acid molecule is operatively linked or operably linked to, or operably associated with, an expression control sequence when the expression control sequence controls and regulates the transcription and translation of nucleic acid sequence. The term "operatively linked" includes having an appropriate start signal (e.g., ATG) in front of the nucleic acid sequence to be expressed and maintaining the correct reading frame to permit expression of the nucleic acid sequence under the control of the expression control sequence and production of the desired product encoded by the nucleic acid sequence. If a gene that one desires to insert into a recombinant DNA molecule does not contain an appropriate start signal, such a start signal can be inserted in front of the gene.

As used herein, the terms "top," "bottom," "upper," "lower," "above," and "below" are used to provide a relative relationship between structures. The use of these terms does not indicate or require that a particular structure must be located at a particular location in the apparatus.

Other features and advantages of the invention will be apparent from the following description and the claims.

BRIEF DESCRIPTION OF THE DRAWINGS

FIG. 4A-4B shows polypeptide sequences for TPSs in cluster 1. Provided are (A) sequences for cluster 1 (SEQ ID NOs:11-14) and (B) a comparison of sequences for cluster 1 with a consensus sequence (SEQ ID NO:10). Structural motifs are underlined, and conserved amino acids are in gray highlight. At each position, X in SEQ ID NO:10 can be an amino acid present at the aligned position in one of SEQ ID NOs:11-14.

FIGS. 5A, 5B-1, and 5B-2 shows polypeptide sequences for TPSs in cluster 2. Provided are (A) sequences for cluster 2 (SEQ ID NOs:21-25) and (B-1 and B-2) a comparison of sequences for cluster 2 with a consensus sequence (SEQ ID NO:20), in which FIG. 5B-1 and FIG. 5B-2 are taken together and referred to as FIG. 5B herein. Structural motifs are underlined, and conserved amino acids are in gray highlight. At each position, X in SEQ ID NO:20 can be an amino acid present at the aligned position in one of SEQ ID NOs:21-25.

FIG. 6A-6B shows polypeptide sequences for TPSs in cluster 3. Provided are (A) sequences for cluster 3 (SEQ ID NOs:31-34) and (B) a comparison of sequences for cluster 2 with a consensus sequence (SEQ ID NO:30). Structural motifs are underlined, and conserved amino acids are in gray highlight. At each position, X in SEQ ID NO:30 can be an amino acid present at the aligned position in one of SEQ ID NOs:31-34.

FIG. 7A-7B shows polypeptide sequences for TPSs in cluster 4. Provided are (A) sequences for cluster 4 (SEQ ID NOs:41-46) and (B) a comparison of sequences for cluster 2 with a consensus sequence (SEQ ID NO:40). Structural motifs are underlined, and conserved amino acids are in gray highlight. At each position, X in SEQ ID NO:40 can be an amino acid present at the aligned position in one of SEQ ID NOs:41-46.

FIGS. 8A, 8B-1, and 8B-2 shows polypeptide sequences for TPSs in cluster 5. Provided are (A) sequences for cluster 5 (SEQ ID NOs:51-54) and (B-1 and B-2) a comparison of sequences for cluster 2 with a consensus sequence (SEQ ID NO:50), in which FIG. 8B-1 and FIG. 8B-2 are taken together and referred to as FIG. 8B herein. Structural motifs are underlined, and conserved amino acids are in gray highlight. At each position, X in SEQ ID NO:50 can be an amino acid present at the aligned position in one of SEQ ID NOs:51-54.

FIG. 9A-9B shows polypeptide sequences for non-clustered TPSs. Provided are (A) non-clustered sequences (SEQ ID NOs:61-64) and (B) a comparison of sequences for cluster 2 with a consensus sequence (SEQ ID NO:60). Structural motifs are underlined, and conserved amino acids are in gray highlight. At each position, X in SEQ ID NO:60 can be an amino acid present at the aligned position in one of SEQ ID NOs:61-64.

FIG. 10A-10B shows consensus sequences for TPSs. Provided are (A) consensus sequence 1A (SEQ ID NO:71) and shorter consensus sequence 1B (SEQ ID NO:72); and (B) consensus sequence 1C (SEQ ID NO:73) and shorter consensus sequence 1D (SEQ ID NO:74).

FIG. 11A-11B shows consensus sequences for TPSs. Provided are (A) consensus sequence 2A (SEQ ID NO:75) and shorter consensus sequence 2B (SEQ ID NO:76); and (B) consensus sequence 2C (SEQ ID NO:77) and shorter consensus sequence 2D (SEQ ID NO:78).

FIG. 12A-12B shows (A) a protein sequence alignment of the predicted TPSs from sequenced four endophytes, which active TPSs are highlighted in gray in the first column; and (B) identified major products for the TPSs.

FIG. 13 shows a table, which provides the nomenclature of active terpene synthases in each cluster, the enzyme function, and the JGI Protein ID number.

FIG. 14 shows the most abundant terpene compounds from each cluster and TPS.

Figure 27A:
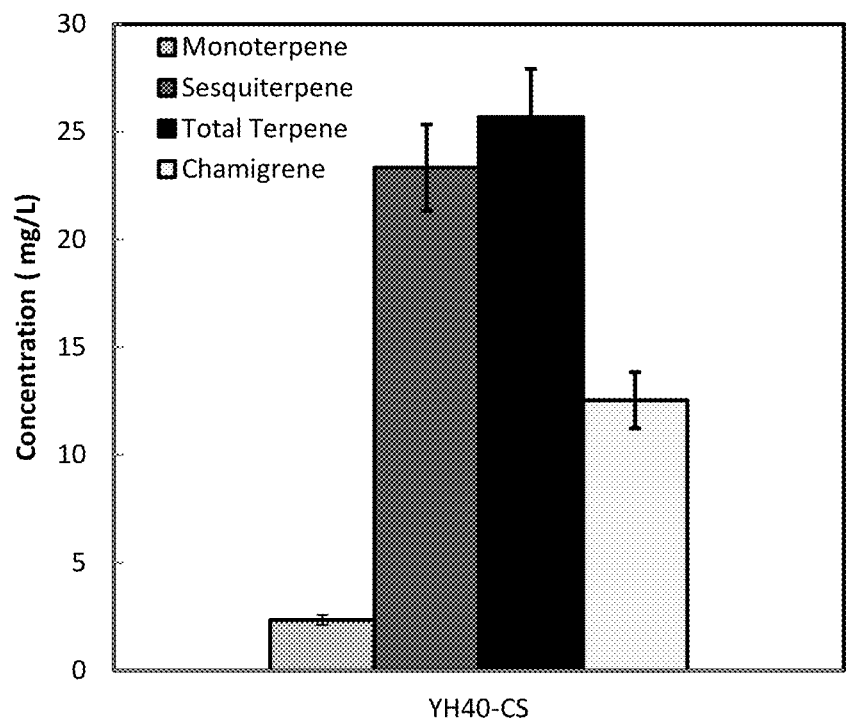
Figure 27B:
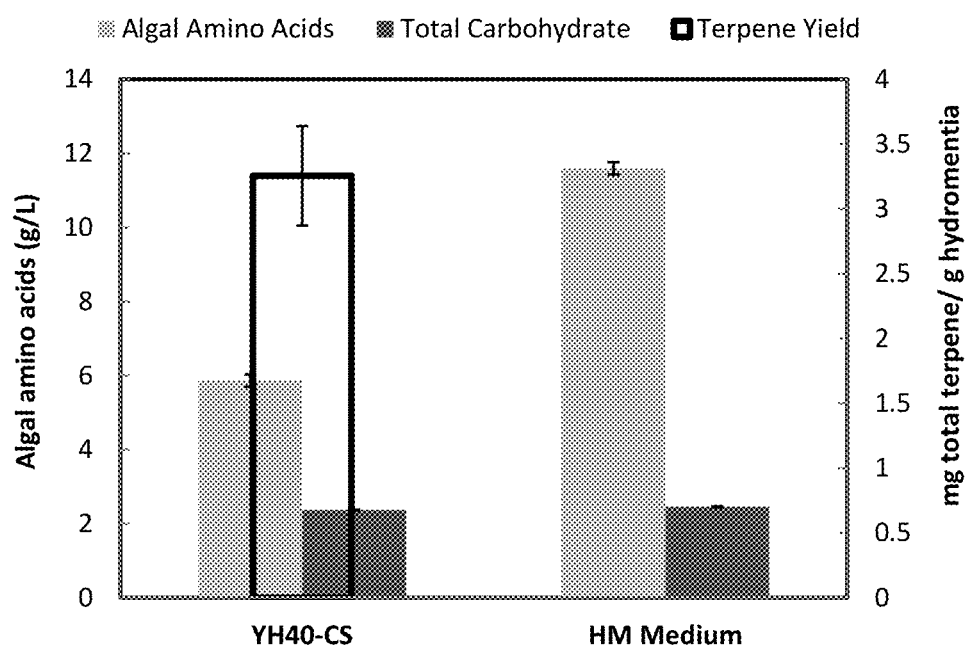

FIG. 27A-27B shows bioconversion of algal protein into terpenes using an engineered *E. coli* strain YH40-chamigrene synthase. Provided are graphs showing (A) terpene concentration produced from degrading an algal hydrolysate and (B) substrate consumption and terpene yield of the engineered *E. coli* strain YH40-chamigrene synthase (YH40-CS).

Figure 28:
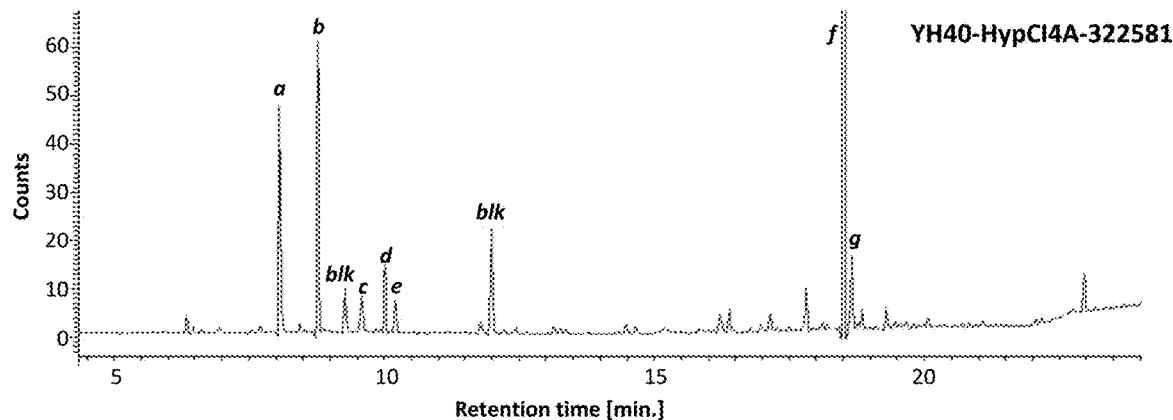

FIG. 28 shows a gas chromatograph terpene profile of YH40-HypCI4A-322581 upon degrading an amino acid mixture, in which peaks are identified in Table 13.

Figure 29:
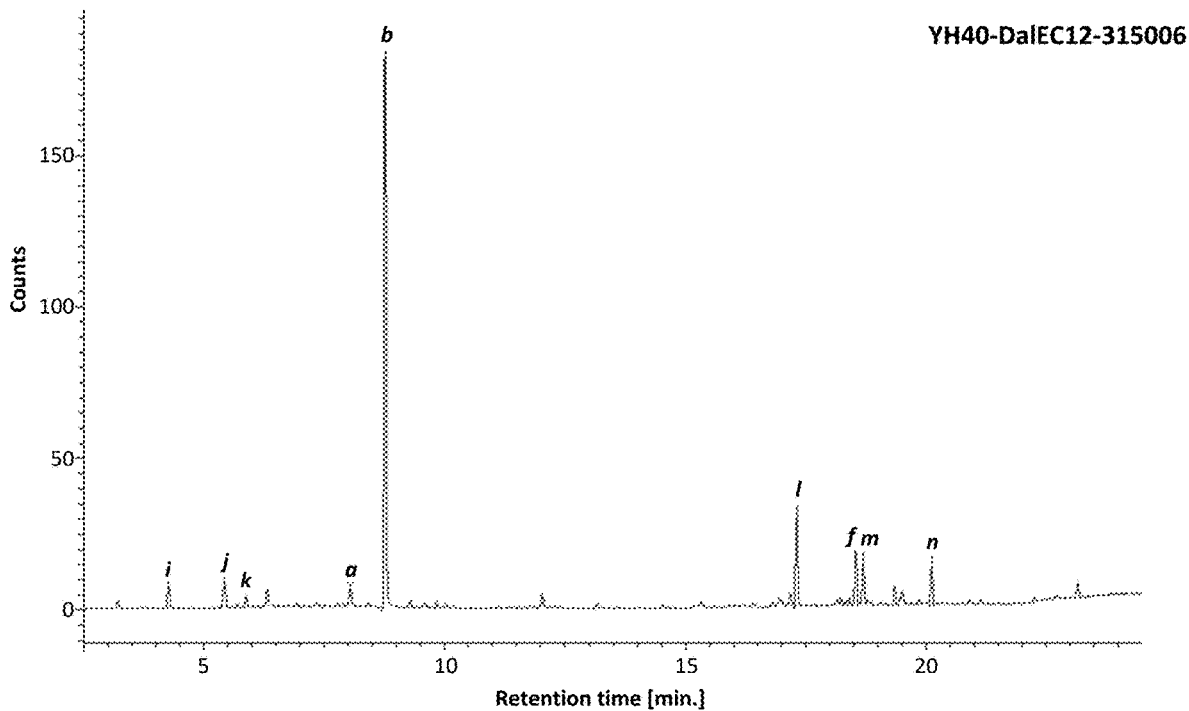

FIG. 29 shows a gas chromatograph terpene profile of YH40-DalEC12-315006 upon degrading an amino acid mixture, in which peaks are identified in Table 14.

Figure 30:
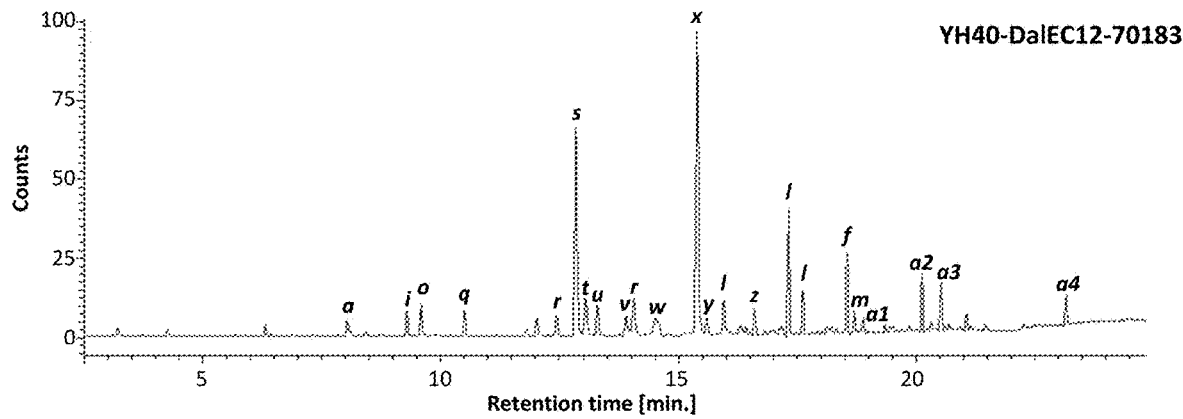

FIG. 30 shows a gas chromatograph terpene profile of YH40-DalEC12-70183 upon degrading an amino acid mixture, in which peaks are identified in Table 15.

Figure 31:
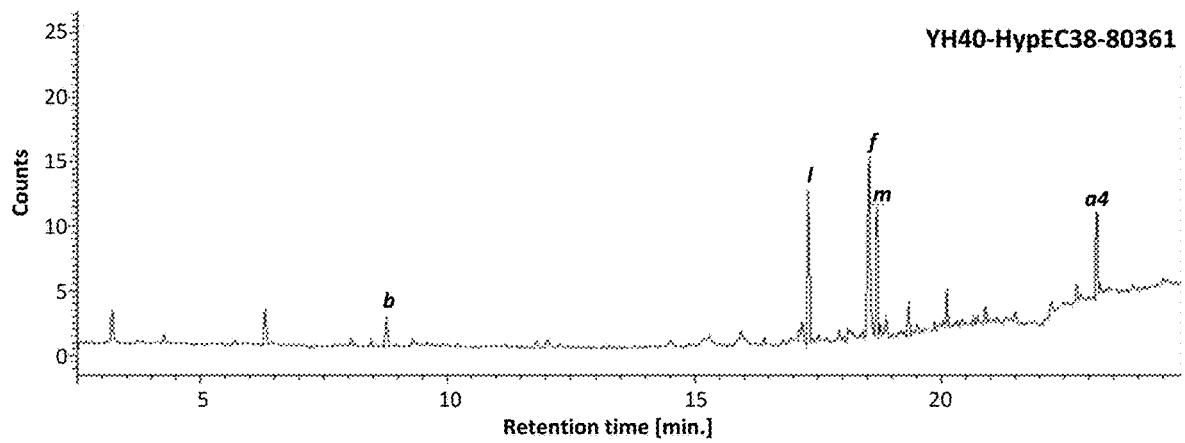

FIG. 31 shows a gas chromatograph terpene profile of YH40-HypEC38-80361 upon degrading an amino acid mixture, in which peaks are identified in Table 16.

Figure 32:
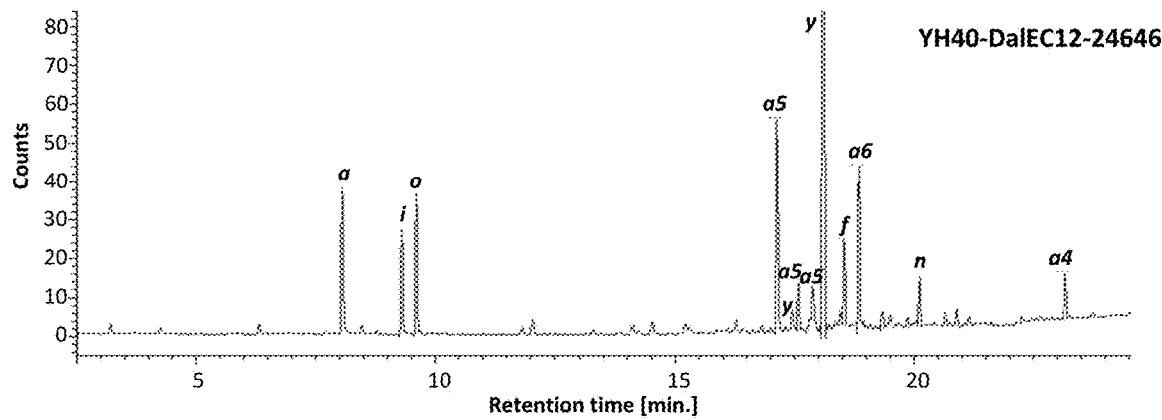

FIG. 32 shows a gas chromatograph terpene profile of YH40-DalEC12-24646 upon degrading an amino acid mixture, in which peaks are identified in Table 17.

Figure 33:
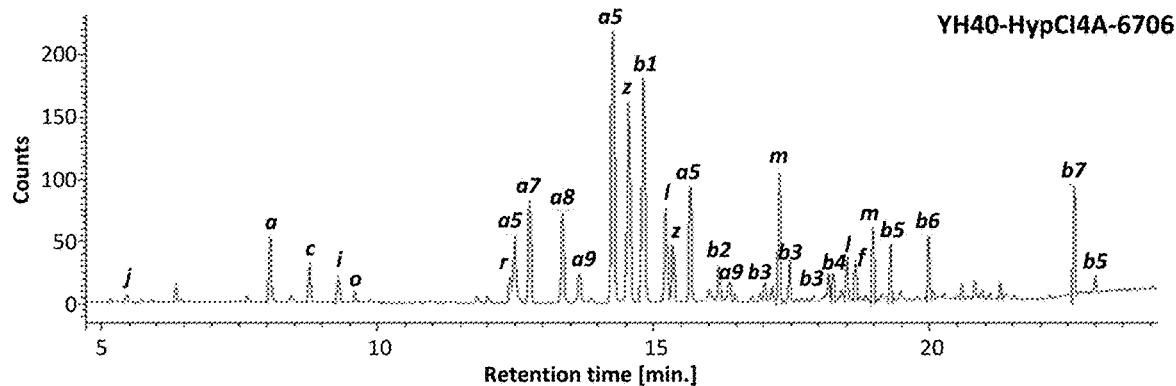

FIG. 33 shows a gas chromatograph terpene profile of YH40-HypCI4A-6706 upon degrading an amino acid mixture, in which peaks are identified in Table 18.

FIG. 34A-34D shows comprehensive conversion of algal carbohydrates and proteins into caryophyllene and other terpenes using a synthetic microbial consortium on algal hydrolysate of *Nannochloropsis* sp. Provided are (A) a caryophyllene biosynthesis pathway construct; (B) a graph showing concentration of caryophyllene and other terpenes produced by using this construct; (C) algal carbohydrate and protein consumption of the microbial consortia produced by using this construct; and (D) caryophyllene and other terpene yields based on the substrate consumption using this construct.

Figure 35A:
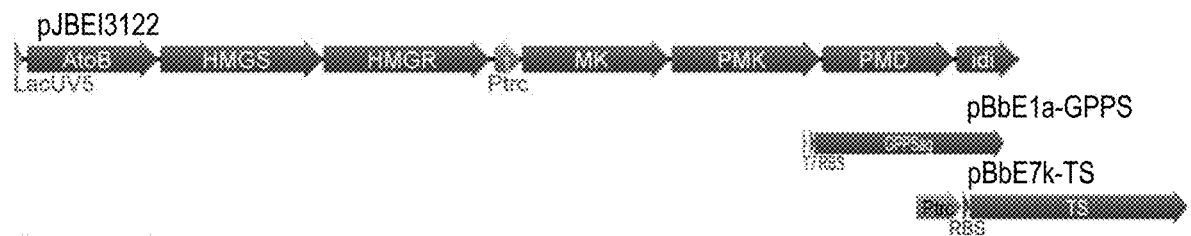
Figure 35B:
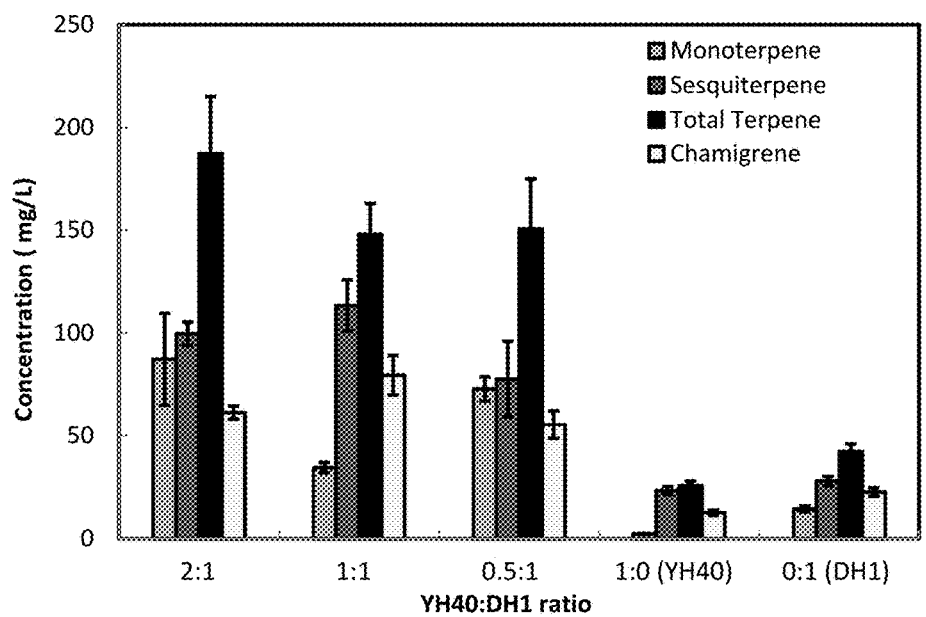
Figure 35C:
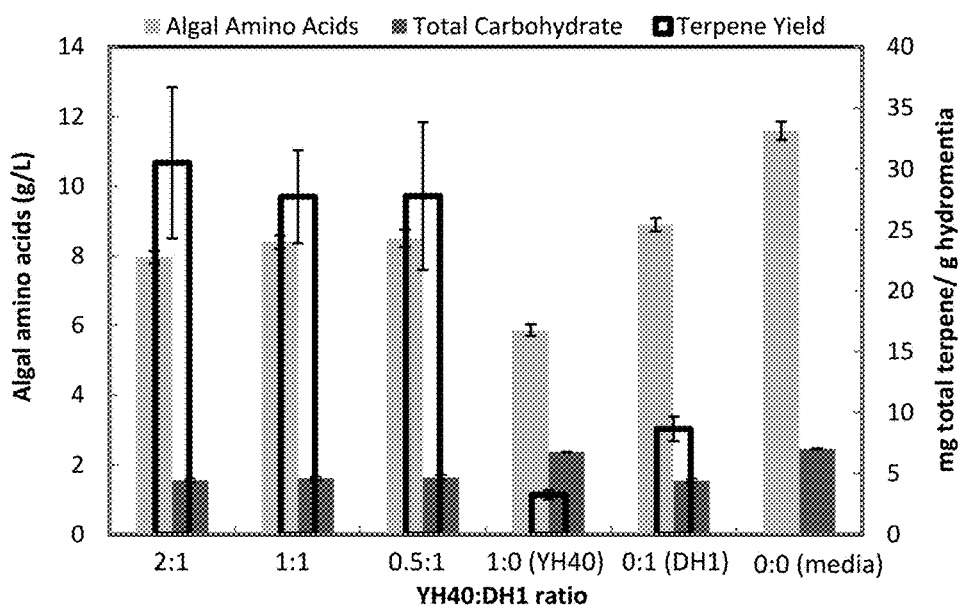

FIG. 35A-35C shows comprehensive conversion of algal carbohydrate and protein into chamigrene and other terpenes using a synthetic microbial consortium on algal hydrolysate of benthic polyculture biomass. Provided are (A) a chamigrene biosynthesis pathway construct; (B) a graph showing concentration of chamigrene and other terpenes produced by using this construct; and (C) algal carbohydrate and protein consumption and total terpene yields based on the substrate consumption by using this construct.

DETAILED DESCRIPTION OF THE INVENTION

Figure 1:
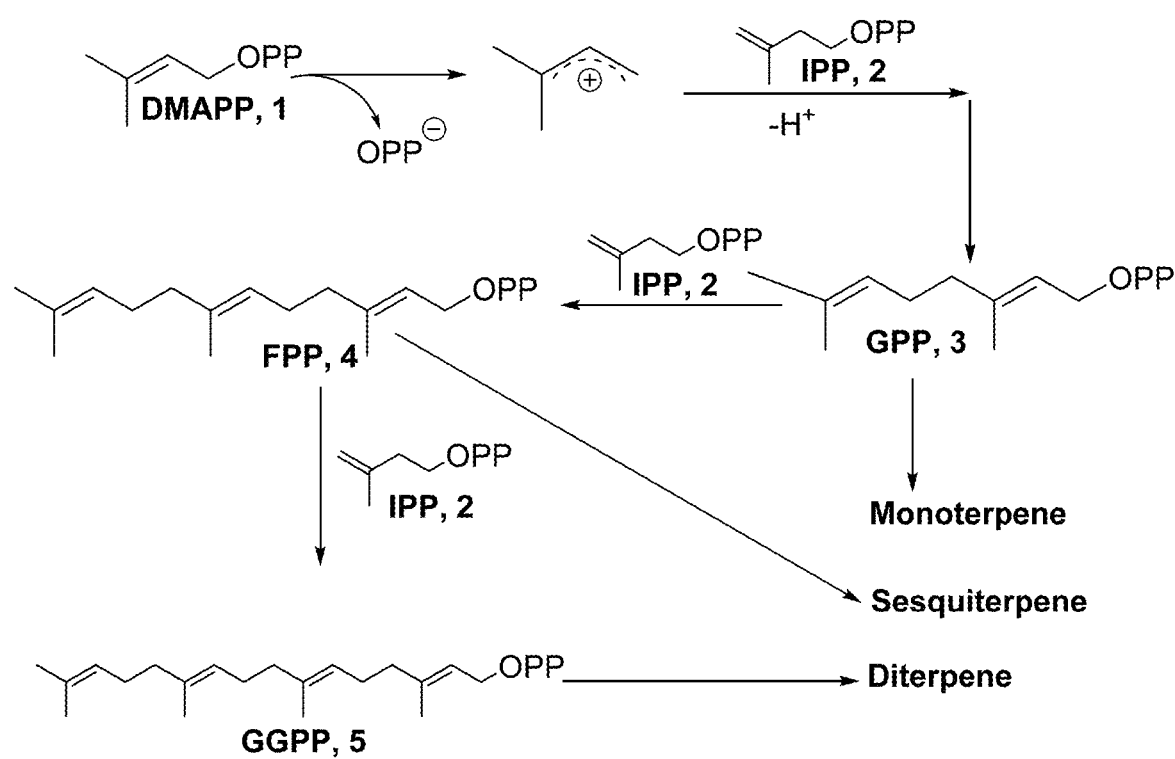
FIG. 1 shows a schematic of a biosynthetic mechanism of geranyl pyrophosphate (GPP), farnesyl pyrophosphate (FPP), geranylgeranyl pyrophosphate (GGPP), and corresponding terpene compounds (adapted from Oldfield E et al., *Angew. Chem. Int. Ed. Engl.* 2012; 51(5):1124-37).

The present invention relates to terpene synthases capable of degrading precursors into biofuel compounds, such as terpenoid compounds. Such synthases can be provided by an isolated, genetically engineered organism. In one instance, the organism includes an exogenous terpene synthase or a nucleic acid encoding the exogenous terpene synthase. As seen in FIG. 1, such synthases can assist in the production of monoterpenes, sesquiterpenes, and diterpenes by processing precursors. Exemplary terpenoid compounds include a monoterpene (e.g., a $C_{10}$ terpenoid compound or any such as camphene, carene, citral, citronellal, citronellol, halomon, limonene, linalool, myrcene, ocimene, phellandrene, pinene, sabinene, terpinene, terpinolene, and thujene), a sesquiterpene (e.g., a $C_{15}$ compound or any such as cadinene, caryophyllene, copaene, dictyophorine A, dictyophorine B, farnesene, farnesol, guaiazulene, humulene, longifolene, patchoulol, vetivazulene, and zingiberene), a diterpene (e.g., a $C_{20}$ compound or any such as abietane, cembrene A, labdane, phytane, sclarene, stemarene, stemodene, taxadiene, or taxane), or a triterpene (e.g., a $C_{30}$ compound or any such as hopane, lanostane, malabaricane, oleanane, polypodatetraene, or squalene). Other exemplary terpenoid compounds are provided in FIG. 3A-3E.

The terpene synthase can be identified in any useful manner. In one instance, naturally occurring terpene synthases can be screened to identify those that increase production of one or more terpenoid compounds (e.g., terpenoid compounds obtained by degrading a biomass, such as in the presence of one or more synthases). Exemplary synthases include those fungal terpene synthases (e.g., endophytic fungal terpene synthases, such as those for *Hypocreales* or *Xylariales*, including *Hypoxylon* and *Daldinia*). Exemplary terpene synthases are provided in FIG. 2A-2C, such as clusters described herein; and in FIG. 13, as identified by JGI Protein ID numbers, which can be accessed at genome.jgi.doe.gov/.

Furthermore, polypeptide sequences of terpene synthase are provided for cluster 1 (SEQ ID NOs:10-14 in FIGS. 4A-4B), cluster 2 (SEQ ID NOs:20-25 in FIGS. 5A-5B), cluster 3 (SEQ ID NOs:30-34 in FIGS. 6A-6B), cluster 4 (SEQ ID NOs:40-46 in FIGS. 7A-7B), cluster 5 (SEQ ID NOs:50-54 in FIGS. 8A-8B), and non-clustered (SEQ ID NOs:60-64 in FIGS. 9A-9B). The terpene synthases herein can include a consensus sequence, such as SEQ ID NO:71-74 (in FIGS. 10A-10B), SEQ ID NO:75-78 (in FIGS. 11A-11B), as well as those motifs provided in FIG. 12A.

The organism can also include proteins in one or more pathways that facilitate production of a terpenoid precursor. Thus, in some instances, the organism includes an exogenous terpenoid precursor, an exogenous enzyme configured to synthesize a terpenoid precursor, or a nucleic acid encoding the exogenous enzyme. The exogenous enzyme can include one or more in a mevalonate pathway and/or the 2-C-methyl-D-erythritol 4-phosphate/1-deoxy-D-xylulose 5-phosphate pathway (MEP/DOXP pathway). Exemplary exogenous enzymes include a acetoacetyl-CoA thiolase, HMG-CoA synthase, HMG-CoA reductase, mevalonate-5-kinase, mevalonate-3-kinase, mevalonate-3-phosphate-5-kinase, phosphomevalonate kinase, mevalonate-5-pyrophosphate decarboxylase, isopentenyl pyrophosphate isomerase, DOXP synthase, 4-diphosphocytidyl-2-C-methyl-D-erythritol synthase, 4-diphosphocytidyl-2-C-methyl-D-erythritol kinase, 2-C-methyl-D-erythritol 2,4-cyclodiphosphate synthase, HMB-PP synthase, and HMB-PP reductase.

The present invention also relates to methods of treating a biomass by exposing the biomass to one or more terpene synthases (e.g., any described herein), as well as one or more organisms configured to provide or produce such synthases. The methods can include other useful steps, including optionally pre-treating the biomass (e.g., thereby facilitating access to carbohydrates and/or proteins within the biomass) and/or isolating one or more terpenoid compounds. More than one type of terpene synthase, as well as more than one type of organism each independently including a synthase, can be employed within the method.

Biomass

Any useful biomass can be employed. Exemplary biomass include distillers grains or co-products (e.g., wet distillers grains (WDGs), dried distillers grains (DDGs), dried distillers grains with solubles (DDGS), fatty acids from oil hydrolysis, lipids from evaporation of thin stillage, syrup, distillers grains, distillers grains with or without solubles, solids from a mash before fermentation, solids from a whole stillage after fermentation, biodiesel, and acyl glycerides), oilseed meals (e.g., soybean meal or canola meal), feeds (e.g., alfalfa meal, cottonseed meal, DDGS, rice bran, or wheat bran), yeast (e.g., extracts), algae (e.g., *Nannochloropsis*, wastewater algae, or any described herein), cereal by-products (e.g., whey), etc.

The algae can include any useful organism, such as chlorophyta, diatoms, plankton, protists, and/or cyanobacteria. For instance, algae can include one or more photosynthetic organisms, including one or more microalgae, macroalgae, diatoms, green algae, yellow algae, phytoplankton, haptophytes, and/or cyanobacteria. Exemplary algae include *Achnanthes, Ankistrodesmus* (e.g., *A. falcatus* or *A. fusiformis*), *Aphanizomenon, Arthrospira* (e.g., *A. maxima*), *Bacillariophyceae, Botryococcus* (e.g., *B. braunii*), *Chlamydocapsa* (e.g., *C. bacillus*), *Chlamydomonas* (e.g., *C. perigranulata* or *C. reinhardtii*), *Chlorella* (e.g., *C. marina, C. vulgaris, C. sorokiniana, C. minutissima*, or *C. pyrenoidosa*), *Chlorococcum* (e.g., *C. infusionum, C. littorale*, or *C. humicola*), *Chlorogloeopsis* (e.g., *C. fritschii*), *Chlorophyceae, Chrysophyceae, Cyanophyceae, Dunaliella* (e.g., *D. bardawil, D. bioculata, D. primolecta, D. tertiolecta*, or *D. salina*), *Ellipsoidion, Isochrysis, Kirchneriella* (e.g., *K. lunaris*), *Nannochloropsis* (e.g., *N. salina* or *N. oculata*), *Neochloris* (e.g., *N. oleoabundans*), *Nitzschia, Phaeodactylum* (e.g., *P. tricornutum*), *Porphyridium* (e.g., *P. purpureum*), *Pyrmnesium* (e.g., *P. parvum*), *Scenedesmus* (e.g., *S. obliquus, S. quadricauda*, or *S. dimorphus*), *Schizochytrium, Skeletonema* (e.g., *S. costatum*), *Spirogyra, Spirulina* (e.g., *S. maxima* or *S. platensis*), *Synechococcus* (e.g., *S. elongatus*), and/or *Tetraselmis* (e.g., *T. maculata* or *T. suecica*). Additional algae species and organisms are described in Schneider R C S et al., "Potential production of biofuel from microalgae biomass produced in wastewater," in *Biodiesel—Feedstocks, Production and Applications*, Prof. Zhen Fang (ed.), InTech, 2012, 22 pp., which is incorporated herein by reference in its entirety.

Pre-Treatment of the Biomass

Pre-treatment can be used to convert constituents within the biomass into various biocomponents (e.g., proteins, carbohydrates, fatty acids, and/or lipids). Such biocomponents can be pre-treated to obtain more solubilized or hydrolyzed constituents, such as amino acids or sugars (e.g., glucose). For instance, carbohydrates within the biomass can be pre-treated and, thereby, be converted into a sugar and/or an alcohol, such as glucose, fucose, galactose, xylose, mannose, mannitol, ethanol, butanol, and/or pentanol. In another instance, proteins within the biomass can be treated and, thereby, hydrolyzed and converted into amino acids. Such amino acids, in turn, can be fermented to produce one or more mixed alcohols and amines. In addition, one or more extraction techniques can be applied to separate the protein/carbohydrate fraction from other constituents. Such extraction techniques can include, e.g., use of one or more ionic liquids to selectively extract a particular fraction.

Pre-treatment can include the use of one or more acids, bases, oxidizers, reducers, and/or enzymes. Exemplary pre-treatment conditions include strong and/or dilute acid hydrolysis (e.g., with $H_2SO_4$ and/or HCl), base hydrolysis or neutralization (e.g., with NaOH), heat treatment, sonication, and/or enzyme degradation (e.g., with one or more proteases, such as endoproteases, exoproteases, serine proteases (e.g., subtilisin, also known as alcalase), aminopeptidases, carboxypeptidases, endoglucanases, cellobiohydrolases, glycoside hydrolases (e.g., lysozyme), endoglucanases, glucanases, endoxyalanases, pectinases, sulfatases (e.g., arylsulfatases), cellulases, xylanases, as well as mixtures thereof, such that available as commercially available Pronase®, a mixture of proteolytic enzymes that are produced in the culture supernatant of *Streptomyces griseus* K-1).

Distillation/Extraction

The terpenoid compounds, alcohol, fermentation products, lipids, and amino acids from the biomass can be captured by distillation and solvent co-extraction. Any useful distillation and extraction techniques can be employed, including flash extraction, ionic liquid extraction, etc., to isolate one or more oils, aqueous phases, aqueous co-products, nutrients, etc.

Further distillation/extraction steps can also include any that separate liquid from solid phases, as well as separate two or more phases that can be differentiated based on solubility, miscibility, etc. (e.g., as those present in non-aqueous phases, aqueous phases, lipophilic phases, etc.) in any useful solvent (e.g., an organic solvent, an aqueous solvent, water, buffer, etc.). Phase separation techniques include flash separation (e.g., separation of liquefied mixture into biocrude oil, solid residuals, aqueous phase, and/or aqueous co-products), acid absorption (e.g., absorption of acid in a matrix to provide recovered nutrients and water for recycled use), filtration, distillation, solvent extraction, ion liquid extraction, etc. The resultant products and co-products can include one or more intermediate products that can optionally be processed to form useful end-use products.

EXAMPLES

Example 1: Rapid Discovery and Functional Characterization of Terpene Synthases from Four Endophytic Xylariaceae Endophytic fungi are ubiquitous plant endosymbionts that establish complex yet poorly understood relationships with their host organisms. Many endophytic fungi are known to produce a wide spectrum of volatile organic compounds (VOCs) with potential energy applications, which have been described as "mycodiesel." Many of these mycodiesel hydrocarbons are terpenes, a chemically diverse class of compounds produced by many plants, fungi, and bacteria. Due to their high energy densities, terpenes (e.g., pinene and bisabolene) are actively being investigated as potential "drop-in" biofuels for replacing diesel and aviation fuel. Here, we rapidly discovered and characterized 26 terpene synthases (TPSs) derived from four endophytic fungi in order to produce mycodiesel hydrocarbons. Several of the identified TPS genes were expressed in an *E. coli* strain harboring a heterologous mevalonate pathway designed to enhance terpene production, and their product profiles were determined using Solid Phase Micro-Extraction (SPME) and GC-MS. Out of the 26 TPSs profiled, 12 TPSs were identified to be particularly useful, with a majority of them exhibiting both monoterpene and sesquiterpene synthase activity.

Introduction

Endophytic fungi have evolved to live within plant tissues but without causing overt harm to their hosts. This endosymbiotic relationship involves continual interactions between host and fungi using a variety of signals, including exchange of secondary metabolites that elicit specific biological responses (see, e.g., Oldfield E et al., "Terpene biosynthesis: modularity rules," *Angew. Chem. Int. Ed. Engl.* 2012; 51(5):1124-37).

Recent studies aimed to characterize various secondary metabolites produced by endophytic fungi. In party, these studies revealed that many of these fungi emit a wide spectrum of volatile organic compounds (VOCs) while growing on plant and agricultural residues (see, e.g., Ul-Hassan S R et al., "Modulation of volatile organic compound formation in the mycodiesel-producing endophyte *Hypoxylon* sp. CI-4," *Microbiology* 2012; 158(Pt 2):465-73; Kudalkar P et al., "*Muscodor sutura*, a novel endophytic fungus with volatile antibiotic activities," *Mycoscience* 2012; 53(4):319-25; Strobel G et al., "An endophytic/pathogenic *Phoma* sp. from creosote bush producing biologically active volatile compounds having fuel potential," *FEMS Microbiol. Lett.* 2011; 320(2):87-94; Singh S K et al., "An endophytic *Phomopsis* sp. possessing bioactivity and fuel potential with its volatile organic compounds," *Microb. Ecol.* 2011; 61(4):729-39; Tomsheck A R et al., "*Hypoxylon* sp., an endophyte of *Persea indica*, producing 1,8-cineole and other bioactive volatiles with fuel potential," *Microb. Ecol.* 2010; 60(4):903-14; Strobel G A et al., "The production of myco-diesel hydrocarbons and their derivatives by the endophytic fungus *Gliocladium roseum* (NRRL 50072)," *Microbiology* 2008; 154(Pt 11):3319-28 (erratum in *Microbiology* 2010; 156(Pt 12):3830-3); Strobel G, "The story of mycodiesel," *Curr. Opin. Microbiol.* 2014; 19:52-8; and Gladden J M et al., "Tailoring next-generation biofuels and their combustion in next-generation engines," *Sandia Report No. SAND*2013-10094, 2013 (100 pp.)).

Not only do these VOCs play important roles in the biology of these fungi, they also supply a rich reservoir of potential compounds for medicinal and industrial applications. Many VOCs are hydrocarbons and other oxygenated compounds that have been referred to as "mycodiesel" due to their high energy density and near zero oxygen content, which make them compatible with the existing engines and great "drop-in" biofuel candidates. A large fraction of "mycodiesel" compounds are terpenes and their derivatives. Terpenes, or isoprenoids, are one of the most diverse class of natural products with more than 55,000 different terpenoids known (see, e.g., Ouyang Z et al., "Identification and quantification of sesquiterpenes and polyacetylenes in *Atractylodes lancea* from various geographical origins using GC-MS analysis," *Revista Brasileira de Farmacognosia [Braz. J. Pharmacognosy]* 2012; 22(5):957-63).

Terpenoids have a myriad of biological functions (e.g., as antibiotics, hormones, anticancer agents, etc.) and industrial applications (e.g., as flavorings, fragrances, and biofuels, etc.) (see, e.g., Sosa M E et al., "Insecticidal and nematicidal essential oils from Argentinean *Eupatorium* and *Baccharis* spp.," *Biochem. Syst. Ecol.* 2012; 43:132-8; Saranya J et al., "Chemical composition of leaf essential oil of *Syzygium densiflorum* wall. ex wt. & arn.—a vulnerable tree species," *J. Essential Oil Bearing Plants* 2012; 15(2):283-7; Steele C L et al., "Sesquiterpene synthases from grand fir (*Abies grandis*): comparison of constitutive and wound-induced activities, and cDNA isolation, characterization, and bacterial expression of delta-selinene synthase and gamma-humulene synthase," *J. Biol. Chem.* 1998; 273(4):2078-89; Peralta-Yahya P P et al., "Identification and microbial production of a terpene-based advanced biofuel," *Nat. Commun.* 2011; 2: Art. No. 483 (8 pp.); Rabe P et al., "Volatile terpenes from actinomycetes: a biosynthetic study correlating chemical analyses to genome data," *Chembiochem* 2013; 14(17):2345-54; Chang M C et al., "Production of isoprenoid pharmaceuticals by engineered microbes," *Nat. Chem. Biol.* 2006; 2(12):674-81; and Köksal M et al., "Taxadiene synthase structure and evolution of modular architecture in terpene biosynthesis," *Nature* 2011; 469(7328):116-20).

In one non-limiting example, mono- and sesquiterpenes are the major components of VOCs produced by the endophytes *Hypoxylon* sp. CI4A, *Hypoxylon* sp. CO27, *Hypoxylon* sp. EC38, and *Daldinia eschscholzii* EC12 when grown on potato dextrose. These organisms also produce lower levels of other non-terpene compounds, such as ketones (e.g., 11% in a CI4A culture) and alcohols (e.g., 20% in an EC12 culture) that have potential biofuel applications, indicating that there is a myriad of potential useful biosynthetic pathways present in these organisms. To make use of these compounds in industry, the biosynthetic pathways that generate them need to be elucidated, enabling them to either be manipulated in their native host to increase productivity, or to be ported into an existing industrial host where their production can be more easily controlled.

The biosynthesis of isoprenoids includes the interplay of several building blocks and terpene synthases. Universal building blocks are the $C_5$ precursors isopentenyl pyrophosphate (IPP) and dimethylallyl pyrophosphate (DMAPP). Successive condensations of DMAPP with one or more IPP in a 1,4 fashion gives rise to linear isoprenyl diphosphate compounds of various chain lengths: geranyl pyrophosphate ($C_{10}$, GPP), farnesyl pyrophosphate ($C_{15}$, FPP), and geranylgeranyl pyrophosphate ($C_{20}$, GGPP; FIG. 1). These precursors are then catalyzed by terpene synthases (TPSs) into monoterpenes ($C_{10}$), sesquiterpenes ($C_{15}$), diterpenes ($C_{20}$), and other compounds.

Most terpene synthases belong to either the terpene synthase type I or type II superfamily, which can be distinguished by distinct motifs (see, e.g., Oldfield E et al., *Angew. Chem. Int. Ed. Engl.* 2012; 51(5):1124-37; and Bogorad I W et al., "Building carbon-carbon bonds using a biocatalytic methanol condensation cycle," *Proc. Nat'l Acad. Sci. USA* 2014; 111(45):15928-33). The catalytic reaction of type I terpene synthase involves carbocation formation by abstraction of two diphosphate groups from the substrate through complexation to two highly conserved motifs: the aspartate rich motif (DDXXD) and the NSE/DTE triad ND (L/I/V) XSXXXE.

The type II terpene synthase superfamily has a highly conserved DXDD motif that facilitates the formation of a carbocation by protonation of an epoxide or olefin (see, e.g., Oldfield E et al., *Angew. Chem. Int. Ed. Engl.* 2012; 51(5): 1124-37). To date, genome sequencing has uncovered more than a thousand different genes encoding terpene synthases in bacteria (see, e.g., Haehnel-Taguchi M et al., "Afferent and motoneuron activity in response to single neuromast stimulation in the posterior lateral line of larval zebrafish," *J. Neurophysiol.* 2014; 112(6):1329-39; and He Z et al., "Global transcriptional, physiological, and metabolite analyses of the responses of *Desulfovibrio vulgaris* Hildenborough to salt adaptation," *Appl. Environ. Microbiol.* 2010; 76(5):1574-86), fungi (see, e.g., Van Dien S J et al., "Manipulation of independent synthesis and degradation of polyphosphate in *Escherichia coli* for investigation of phosphate secretion from the cell," *Appl. Environ. Microbiol.* 1997; 63(5):1689-95; and Tang Y J et al., "Investigation of carbon metabolism in *Dehalococcoides ethenogenes* strain 195 by use of isotopomer and transcriptomic analyses," *J. Bacteriol.* 2009; 191(16):5224-31), and plants (see, e.g., Khodayari A et al., "A kinetic model of *Escherichia coli* core metabolism satisfying multiple sets of mutant flux data," *Metab. Eng.* 2014; 25:50-62; Carothers J M et al., "Selecting RNA aptamers for synthetic biology: investigating magnesium dependence and predicting binding affinity," *Nucleic*

*Acids Res.* 2010; 38(8):2736-47; and Gong C M S et al., "Metabolic engineering *Deinococcus radiodurans* for actinide bioprecipitation," 227*th ACS National Meeting*, held on 28 Mar. to 1 Apr. 2004 in Anaheim, Calif., Abstract NUCL 61 (1 p.)).

Recently, endophytic fungi have also been reported to produce a diverse spectrum of terpenes, including monoterpenes, sesquiterpenes, diterpenes, and other derivatives (see, e.g., Hassan S R et al., *Microbiology* 2012; 158(Pt 2):465-73; Singh S K et al., *Microb. Ecol.* 2011; 61(4):729-39; Strobel G A et al., *Microbiology* 2008; 154(Pt 11):3319-28 (erratum in *Microbiology* 2010; 156(Pt 12):3830-3); Strobel G A et al., *Microbiology* 2008; 154(Pt 11):3319-28 (erratum in *Microbiology* 2010; 156(Pt 12):3830-3); and Strobel G et al., "Natural products from endophytic microorganisms," *J. Nat. Prod.* 2004 February; 67(2):257-68). These terpenes are not only biologically active secondary metabolites with great pharmaceutical potential, but they also have a high energy density, making them attractive renewable fossil fuel alternatives (see, e.g., Ul-Hassan S R et al., *Microbiology* 2012; 158(Pt 2):465-73; Singh S K et al., *Microb. Ecol.* 2011; 61(4):729-39; 28. Griffin M A et al., "Volatile organic compound production by organisms in the genus *Ascocoryne* and a re-evaluation of myco-diesel production by NRRL 50072," *Microbiology* 2010; 156(Pt 12):3814-29; Strobel G A et al., "Endophytic microbes embody pharmaceutical potential: specific associations of fungal endophytes with plant hosts represent a large untapped area for discovery," *ASM News* 1998; 64(5):263-8; and Strobel G A et al., "Taxol from fungal endophytes and the issue of biodiversity," *J. Indus. Microbiol.* 1996; 17(5-6):417-23). However, there are few reports describing the discovery and characterization of the terpene synthase genes that produce these compounds (see, e.g., Shaw J J et al., "Identification of a fungal 1,8-cineole synthase from *Hypoxylon* sp. with specificity determinants in common with the plant synthases," *J. Biol. Chem.* 2015; 290(13):8511-26).

Here, we undertook a systematical approach combining genome dataset mining, terpene biosynthetic pathway construction in *E. coli*, Solid Phase MicroExtraction (SPME), and GC-MS analysis to rapidly discover and characterize endophytic terpene synthases. We sequenced four endophytic fungi in the order of *Xylariales* (*Hypoxylon* sp. CI4A, *Hypoxylon* sp. CO27, *Hypoxylon* sp. EC38, and *Daldinia eschscholzii* EC12) and mined their genomes for potential TPS genes. A total of 26 putative TPS genes were identified, of which 12 were functionally expressed in *E. coli* and produced a wide array of monoterpenes and sesquiterpenes.

Discovery and Phylogenetic Tree Analysis of Putative Endophytic Terpene Synthases The putative endophyte TPS genes were identified by searching the endophyte genomes for terpene synthase Pfam functional domains. The protein sequences of the putative TPSs were downloaded from the endophyte genomes published by the Joint Genome Institute (see, e.g., U.S. Department of Energy, "MycoCosm: the fungal genomics resource—Group name: *Xylariales*," available at genome.jgi.doe.gov/Xylariales/Xylariales.info.html (last accessed Feb. 15, 2016)). Secretion signal peptides were predicted using the Signal P4.1 online tool (see, e.g., Petersen T N et al., "SignalP 4.0: discriminating signal peptides from transmembrane regions," Nat. Methods 2011; 8(10):785-6).

Figure 2A:
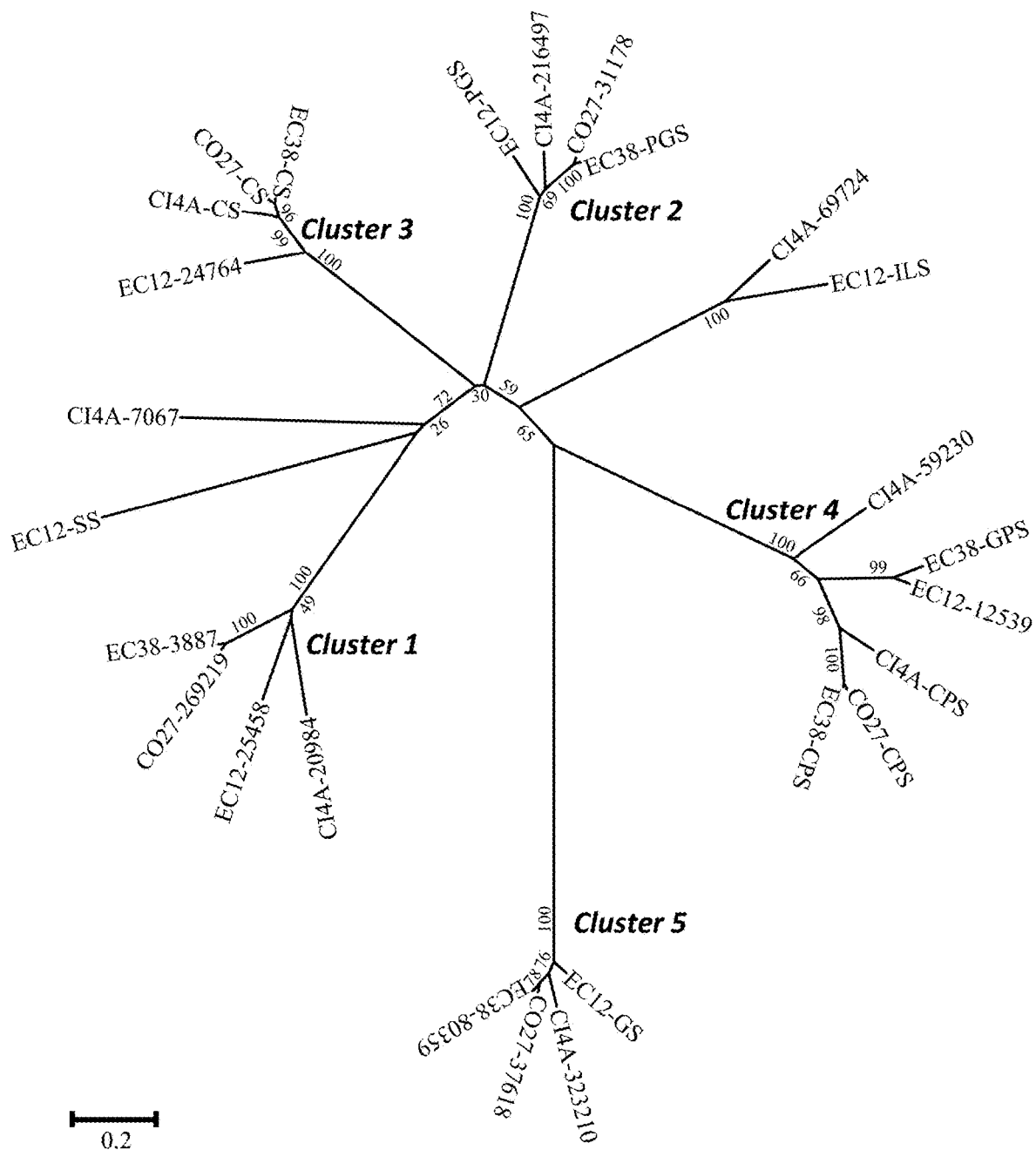
FIG. 2A-2C shows phylogenetic tree analysis of endophyte terpene synthases (TPSs). Provided are (A) a comparison of TPSs from four endophytic fungi in the genus *Hypoxylon* or *Daldinia*, in which a total of 26 TPSs from these fungi were grouped into five distinct clusters; (B) a comparison of endophyte and plant TPSs; and (C) a comparison of endophyte and other fungal TPSs.
Figure 2B:
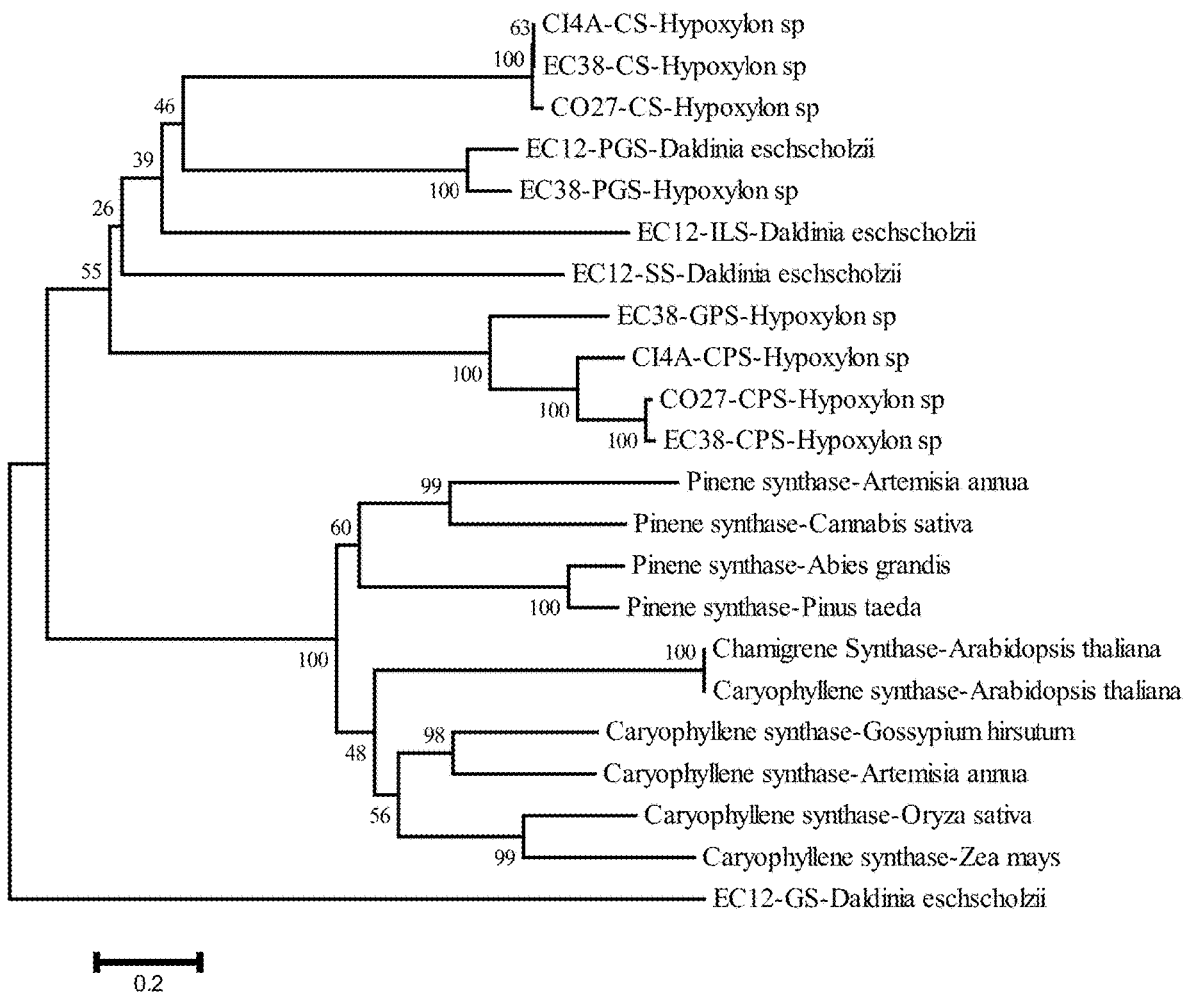
Figure 2C:
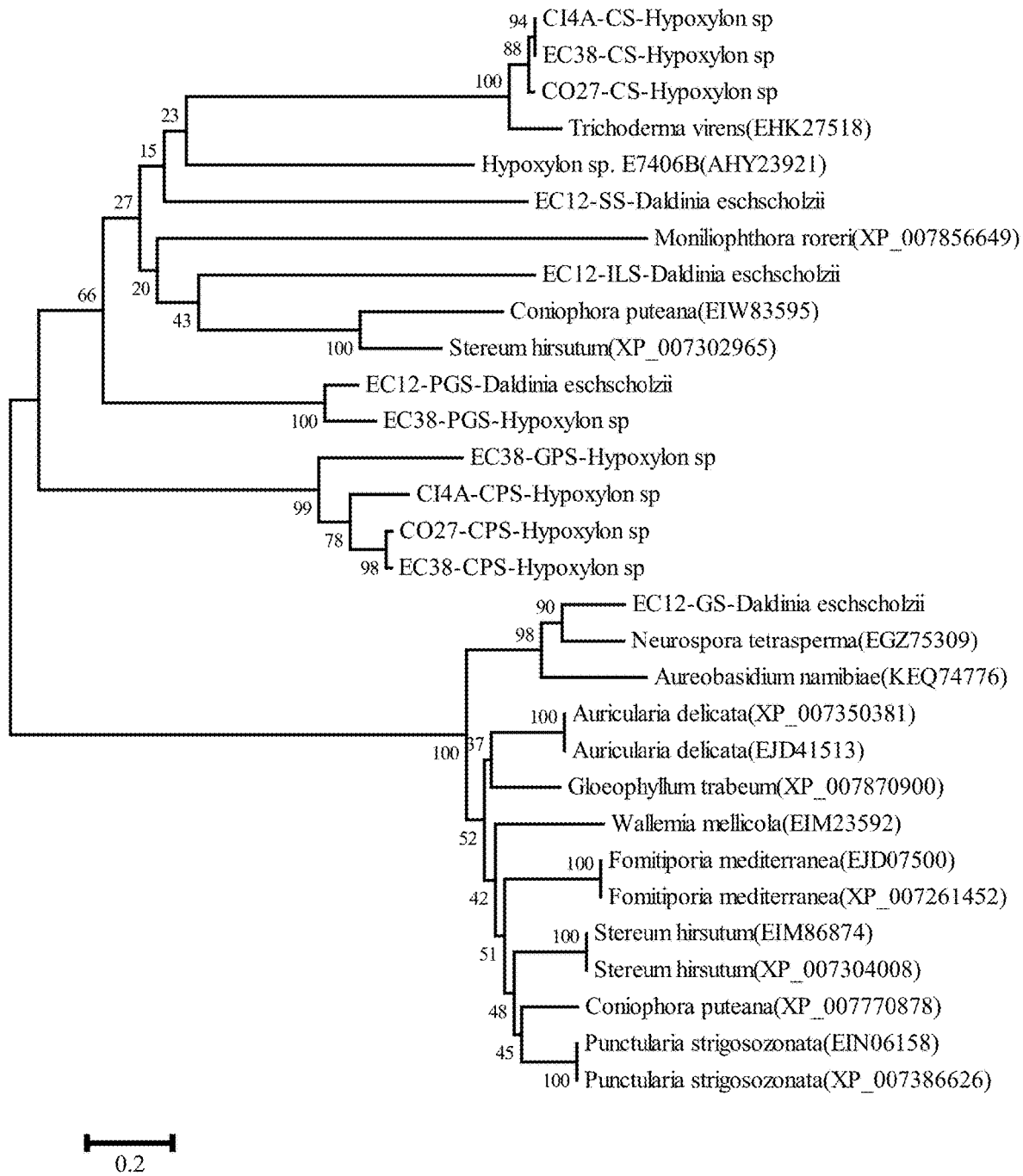

The endophytic TPS protein sequences were compared to each other and to several TPS from plants and other fungi. All protein sequences were aligned by Clustal W in MEGA 6.0 (see, e.g., Kumar S et al., "MEGA-CC: computing core of molecular evolutionary genetics analysis program for automated and iterative data analysis," *Bioinformatics* 2012; 28(20):2685-6). Neighbor joining trees were made by MEGA6.0 using the bootstrap method and Poisson model, with bar=0.2 substitutions per amino acid residue (FIG. 2A-2C). A sequence comparison of the endophytic TPSs with other plant and fungal TPSs was presented as rectangular trees, while the comparison amongst the endophytic TPSs was presented as a radiation tree.

Strains and Plasmids

*E. coli* strains DH10B and DH1 were used for cloning and production, respectively. Plasmids pJBEI-3122, pBbE1a, and pBbE2k were previously reported (see, e.g., Alonso-Gutierrez J et al., "Metabolic engineering of *Escherichia coli* for limonene and perillyl alcohol production," *Metab. Eng.* 2013; 19:33-41). Plasmid pJBEI-3122 contained genes encoding seven enzymes of the mevalonate pathway: acetoacetyl-CoA synthase (AtoB), HMG-CoA synthase (HMGS), HMG-CoA reductase (HMGR), mevalonate kinase (MK), phosphomevalonate kinase (PMK), phosphomevalonate decarboxylase (PMD), and isopentenyl diphosphate isomerase (IDI). The protein sequences of the TPSs in this study and the geranyl pyrophosphate synthase (GPPS, GenBank: AF513112.1, $GPPS_{Ag}$) from *Abies grandis* (with the chloroplast signal peptide truncated) were used to generate codon optimized genes for expression in *E. coli*. A Ribosome Binding Site (RBS) for each putative terpene gene was created and optimized using an online RBS calculator available at the Salis lab (see, e.g., salislab.net). All the DNA sequences containing the RBS site and TPS or GPPS gene, flanked by BamHI and EcoRI sites, were synthesized by Genscript.

Reconstruction of the Terpene Biosynthetic Pathway in *E. coli* Strain DH1

Each synthesized TPS ORF, including the optimized RBS, was digested by the restriction enzymes BamHI and EcoRI and ligated by T4 DNA ligase (New England BioLabs, Inc., Ipswich, Mass.) into plasmid pBbE1a to create vector pBbE1a-TPS. The synthesized $GPPS_{Ag}$ DNA fragment was digested by BamHI and EcoRI, and ligated into vector pBbE2k using T4 DNA ligase to generate the plasmid pBbE2k-$GPPS_{Ag}$. The complete terpene biosynthetic pathway was reconstructed in *E. coli* strain DH1 by co-transforming all three plasmids: pJBEI-3122, pBbE1a-TPS, and pBbE2k-$GPPS_{Ag}$. Plasmids pJBEI-3122 and pBbE2k-$GPPS_{Ag}$ were also co-transformed into strain DH1 as a negative control.

Production of Terpene Compounds in *E. coli*

Transformants containing each TPS gene were cultured in 15 mL of LB medium with 100m/L of ampicillin, 34 µg/L of chloramphenicol, and 25 µg/L of kanamycin. The cultures were incubated at 37° C. shaking at 220 rpm overnight. One mL of overnight culture was then inoculated into 20 mL of fresh EZ-rich medium (Teknova Inc., Hollister, Calif.) containing 20 g/L of glucose, as well as the three aforementioned antibiotics, and incubated at 37° C. with shaking at 220 rpm until an $OD_{600nm}$ of 0.8 was reached. Then, terpene production was induced by adding isopropyl-β-D-1-thiogalactopyranoside (IPTG) at the final concentration of 1 mM and incubating for another 20 hours at 30° C. with shaking at 180 rpm. Terpenes were extracted after 48 hours.

GC-MS Analysis of Terpene

The volatile terpene compounds in the headspace of each culture were analyzed by extracting VOCs with a preconditioned Solid-Phase Micro-Extraction (SPME) syringe consisting of 50/30 divinylbenzene/carboxen on polydimethylsiloxane on a Stable Flex fiber followed by GC-MS. The SPME fiber was explored into the headspace of each culture flask for an hour to saturate with the volatile terpene compounds produced by the various TPS-expressing strains. The syringe was then inserted into the injection port of a Varian 3800 gas chromatograph containing a 30m×0.25 mm i.d. DB waxed capillary column with a film thickness of 0.25 μm. The column temperature was programmed as follows: 60° C. for 4 min., increasing to 120° C. at 10° C./min. and holding for 5 min., then increasing to 220° C. at 20° C./min. and holding for 2 min., finally increasing to 250° C. at 50° C./min. and holding for 4 min.

The carrier gas was ultra-high purity helium at a constant flow rate of 1 mL/min, and the initial column head pressure was 50 KPa. A two minute injection time was used to desorb the terpene compounds from the sampling fiber into an injection port (splitless mode, injection temperature—220° C.) of the chromatograph coupled with a Saturn 2000 ion trap mass spectrometer. MSD parameters included an EI at 70 eV, a mass range at 30-500 Da, and a scan speed at 2 scans/sec.

GC-MS data deconvolution was performed using the Automated Mass Spectral Deconvolution and Identification System (AMDIS) spectral deconvolution software package (v. 2.70, NIST, Gaithersburg, Md.). AMDIS deconvolution settings were as follows: resolution (medium), sensitivity (low), shape requirement (medium), and component width at 10. Spectral components were searched against the NIST 2011 mass spectral library, and only components with mass spectra match factors >85% were reported as tentatively identified compounds. Compounds with peak areas >1% of the total peak area in the chromatogram are reported.

A large number of terpenes were identified by GC-MS. To confirm their identity, several commercially available terpene standards were purchased from Sigma-Aldrich and analyzed using the same methodology (Table 1 and FIG. 20B). All terpenes herein that do not appear in Table 1 are considered only to be putatively identified.

TABLE 1

GC peak analysis of terpene standards

| Compound | Retention time (min.) | % Total peak area | Match (%) | R-match (%) |
|---|---|---|---|---|
| 1R-α-pinene | 5.515 | 3.12 | 96.1 | 96.7 |
| limonene | 8.829 | 12.324 | 89.0 | 92.0 |
| β-caryophellene | 17.454 | 37.631 | 94.2 | 95.4 |
| (+)-valencene | 18.765 | 20.175 | 93.6 | 96.0 |

Figure 20A:
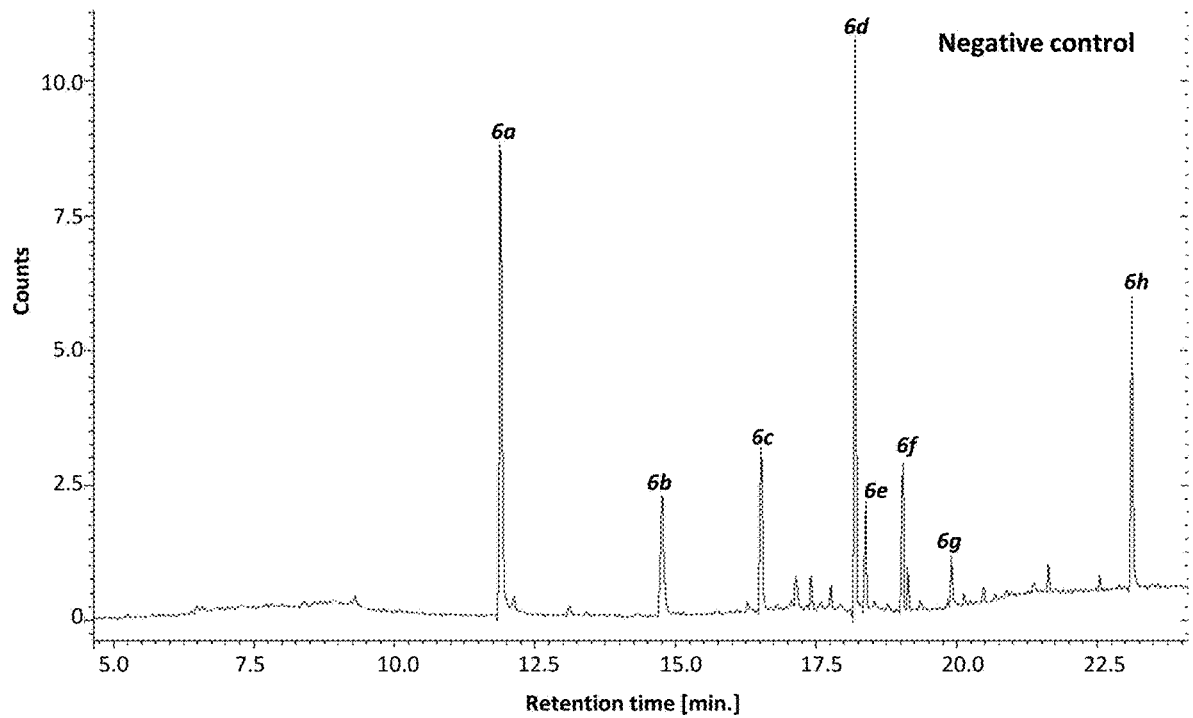
FIG. 20A-20B shows gas chromatograph compound profiles of (A) a control strain lacking TPS and (B) terpene standards.
Figure 20B:
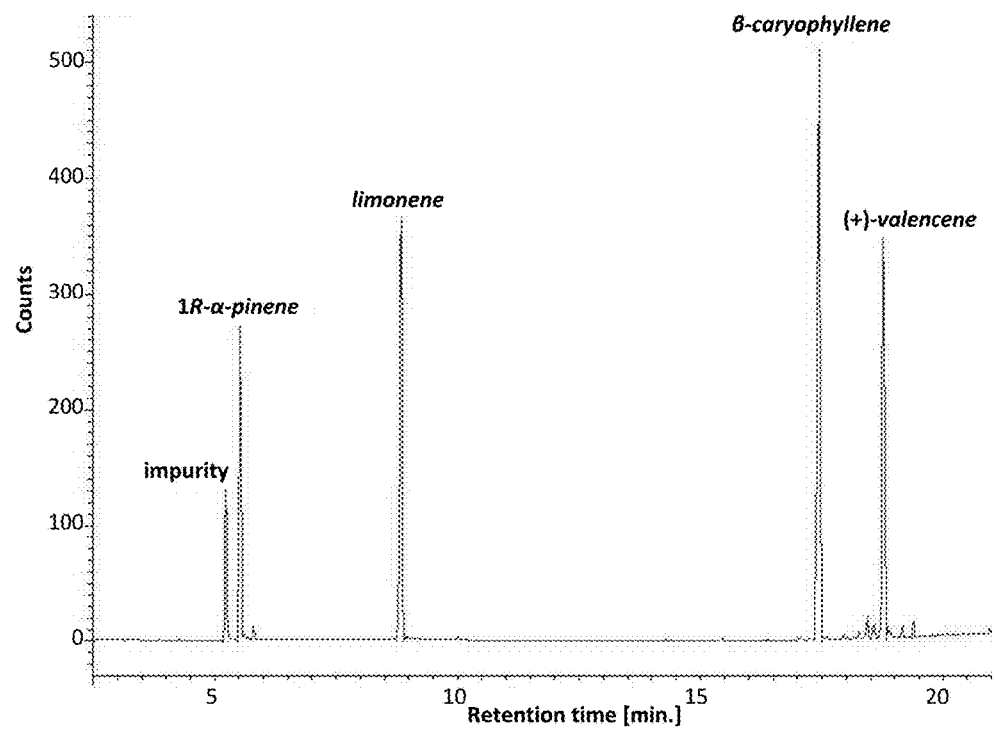

GS-MS analyses were conducted for negative control experiments, in which E. coli lacked plasmid pBbE1a-TPS that encodes an identified TPS but included plasmids pJBEI3122 and pBbE2k-GPPS$_{Ag}$ (Table 2 and FIG. 20B).

TABLE 2

GC peak analysis for negative control E. coli

| Compound (ID No. in FIG. 20B) | Retention time (min.) | % Total peak area | Match (%) | R-match (%) |
|---|---|---|---|---|
| 2-ethyl-hexanolacetate (6a) | 11.892 | 28.519 | 89 | 92.4 |
| 2-tridecanone (6d) | 18.193 | 24.846 | 94 | 94.3 |
| 5H-pyrindine (6h) | 23.114 | 14.198 | 96.2 | 96.5 |
| ethylhexanol (6b) | 14.758 | 8.15 | 96.2 | 97.4 |
| 2-undercanone (6c) | 16.525 | 7.954 | 91.7 | 92.3 |
| 3-eicosene (6f) | 19.305 | 6.869 | 94 | 95.4 |

TABLE 2-continued

GC peak analysis for negative control E. coli

| Compound (ID No. in FIG. 20B) | Retention time (min.) | % Total peak area | Match (%) | R-match (%) |
|---|---|---|---|---|
| z-5-decen-1-ol (6e) | 18.38 | 4.951 | 86.2 | 90.6 |
| 2-pentadecanone (6g) | 19.908 | 2.423 | 88.2 | 90.7 |

Identification of Terpene Synthase Genes in Four Endophytic Fungal Genomes

TPS genes were identified in the genomes of Hypoxylon sp. CI4A, Hypoxylon sp. CO27, Hypoxylon sp. EC38, and Daldinia eschscholzii (D. eschscholzii) EC12 by homology searches against conserved TPS domains. A total of 26 putative TPSs were identified in the genomes of these four endophytes, including seven TPSs from CI4A, five TPSs from CO27, six TPSs from EC38, and six TPSs from EC12. Analysis of the protein sequences determined that none of these TPS harbor a signal peptide. Protein sequence alignments with known TPSs determined that all the putative fungal TPSs fall into the type I terpene synthase superfamily and harbor a highly conserved aspartate-rich motif (DDXXD/E) (FIG. 12A). Also, all but cluster 5 TPSs (FIG. 2A) have a (N/D)DXX(S/T)XX(K/R)(D/E) NSE/DTE triad consensus sequence, which possess a X(D/K)XXXSXXRE triad (FIG. 12A).

Phylogenetic analysis of the 26 putative TPSs grouped all but four of them into five distinct clusters, suggesting that these four endophytic fungi may possess at least five distinct functional categories of terpene synthases (FIG. 2A). The endophytic TPSs were also compared to several plant and fungal TPSs and were found to have low sequence similarity with all the plant TPSs and most of the fungal TPS, except for two uncharacterized putative TPSs from Trichoderma virens (EHKY27518) and Neurospora tetraspema (EGZ75309) that shared higher sequence similarity with the three endophytic caryophyllene synthases and EC12-GS, respectively (FIG. 2B-2C). Functional characterization of each putative TPS was conducted in order to determine its catalytic activity.

Expression of Endophytic TPSs in E. coli

To determine their function, the 26 predicted TPS genes were codon optimized and expressed in E. coli along with the geranyl pyrophosphate synthase (GPPS) gene from Abies grandis (GenBank: AF513112.1, GPPS$_{Ag}$) and a plasmid harboring the entire mevalonate pathway (see, e.g., Alonso-Gutierrez J et al., Metab. Eng. 2013; 19:33-41). This plasmid was used to increase the flux of carbon through the terpene pathway with the aim of enhancing productivity and increasing the chance that even poorly expressed TPS will produce detectable levels of terpenes.

The VOC products of each TPS present in the headspace of the culture flask were extracted by SPME and analyzed with GC-MS. Of the 26 putative endophytic TPSs tested, 12 were active (FIG. 13), producing a mixture of mono- ($C_{10}$) and sesquiterpenes ($C_{15}$) (FIG. 12B and FIG. 14). In summary, no terpene compounds were produced by the TPSs in the cluster 1, and they are not discussed further. The TPSs in cluster 2 primarily produced monoterpenes, including pinene (1a, 1b), ocimene (1c), and limonene (1d), and a lower abundance (<20%) of sesquiterpenes. The TPSs in cluster 3 yielded a wide spectrum of sesquiterpenes and some monoterpenes. Caryophyllene (2d, 2e, 2g) and its isomers were the major product of these enzymes, accounting for up to 80% total peak abundance. The terpene profiles from TPSs in clusters 4 and 5 are less complex than cluster 3 TPSs, and include sesquiterpenes, e.g., chamigrene (3f), and gurjunene (2a, 2b). The non-clustered TPSs, i.e., EC12-SS (SS: Selinene Synthase) and EC12-ILS (IsoLedene Synthase), primarily produced sesquiterpenes selinene (2h) and isoledene (5a), respectively. The activity of these TPSs correlated well with the terpene products produced by their native hosts. All the major terpenes (e.g., pinene, limonene, caryophyllene, chamigrene, gurjunene, selinene, and isoledene) produced from the functional TPSs were detected in the VOC profiles of the four endophytes grown on potato dextrose. The functional endophytic TPSs had low protein sequence similarity compared to other type I TPSs from plants, but retained a conserved DDXXD motif.

An examination of other reports that describe recombinantly expressed TPS indicate that these enzymes tend to produce a single class of terpene, i.e. monoterpenes or sesquiterpenes (see, e.g., Oldfield E et al., *Angew. Chem. Int. Ed. Engl.* 2012; 51(5):1124-37; Steele C L et al., *J. Biol. Chem.* 1998; 273(4):2078-89; Degenhardt J et al., "Monoterpene and sesquiterpene synthases and the origin of terpene skeletal diversity in plants," *Phytochemistry* 2009; 70(15-16):1621-37; Chappell J et al., "Unraveling the catalytic specificity of terpene biosynthetic enzymes and engineering the biosynthesis of novel terpenes in yeast and plants," *In Vitro Cell. Dev. Biol.—Animal* 2008; 44:527 (Abstract P-26); Hyatt D C et al., "Mutational analysis of a monoterpene synthase reaction: altered catalysis through directed mutagenesis of (−)-pinene synthase from *Abies grandis*," *Arch. Biochem. Biophys.* 2005; 439(2):222-33; Schwab W et al., "Mechanism of monoterpene cyclization: stereochemical aspects of the transformation of noncyclizable substrate analogs by recombinant (−)-limonene synthase, (+)-bornyl diphosphate synthase, and (−)-pinene synthase," *Arch. Biochem. Biophys.* 2001; 392(1):123-36; Bohlmann J et al., "Monoterpene synthases from grand fir (*Abies grandis*): cDNA isolation, characterization, and functional expression of myrcene synthase, (−)-(4S)-limonene synthase, and (−)-(1S,5S)-pinene synthase," *J. Biol. Chem.* 1997; 272(35):21784-92; and Gambliel H et al., "Pinene cyclases I and II: two enzymes from sage (*Salvia officinalis*) which catalyze stereospecific cyclizations of geranyl pyrophosphate to monoterpene olefins of opposite configuration," *J. Biol. Chem.* 1984; 259(2):740-8). There are a few reports using in vitro assays that show the production of both mono- and sesquiterpenes from high concentrations of GPP or FPP substrates (see, e.g., Nagegowda D A et al., "Two nearly identical terpene synthases catalyze the formation of nerolidol and linalool in snapdragon flowers," *Plant J.* 2008; 55(2):224-39).

However, it was never demonstrated that this bifunctionality extends to an in vivo activity, so it is unclear whether or not this is a phenomenon that would actually occur in nature. Thus, this study is the first to demonstrate that TPSs can be bifunctional in vivo, producing both mono- and sesquiterpenes. It could be argued that the *E. coli* strain used in this study has artificially altered the levels of GPP and FPP, but several other TPS have been expressed in this strain that do not exhibit this characteristic. In addition, many other recombinant strains also have altered isoprenoid precursor levels, and none have had recombinant TPS that exhibit this behavior. Therefore, this phenomenon appears to be enzyme specific. It will be interesting to further investigate these enzymes to identify the structural features that enable this bifunctionality and to determine the impacts of GPP and FPP levels on product distribution. Also, it will be interesting to determine whether or not this is a widespread phenomenon that extends to the other TPS that have exhibited bifunctionality in vitro.

TPSs in the same cluster tended to produce a similar spectrum of terpene compounds. Thus, the following discussions are ordered by each cluster.

Figure 15A:
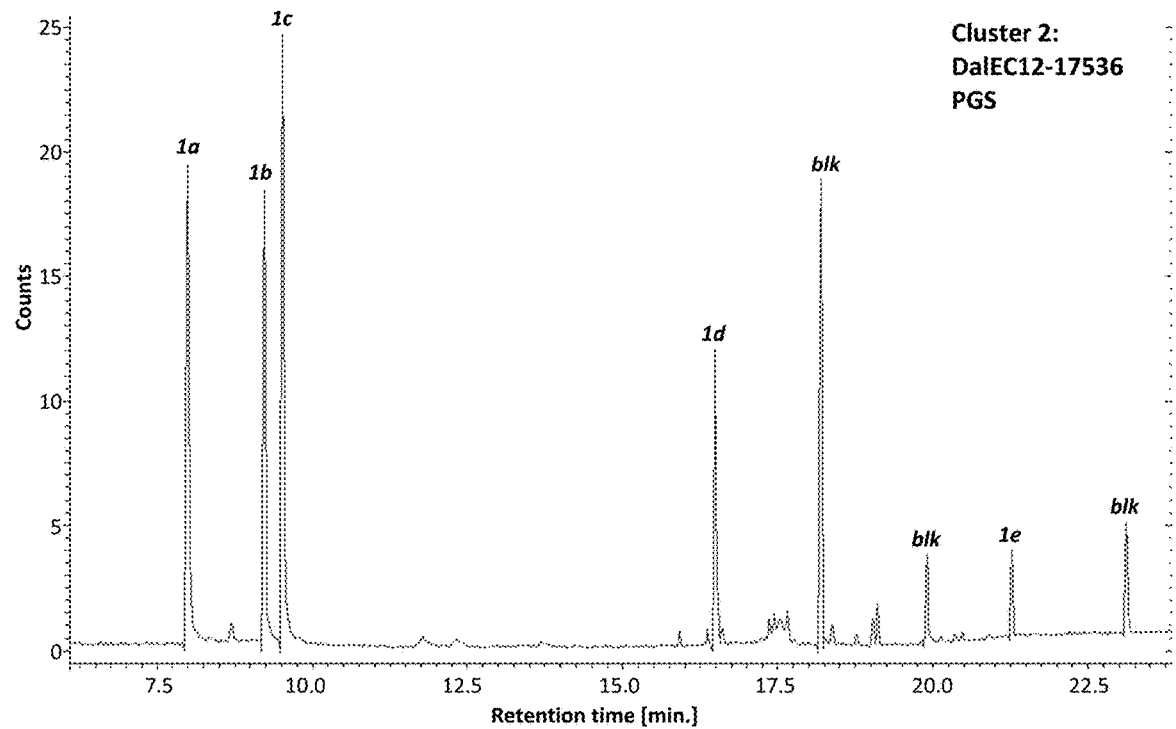
FIG. 15A-15B shows gas chromatograph terpene profiles of TPSs in the cluster 2, including (A) DalEC12-17536 (a Pinene and Guaiene Synthase or PGS) and (B) DalEC38-200002 (a PGS).
Figure 15B:
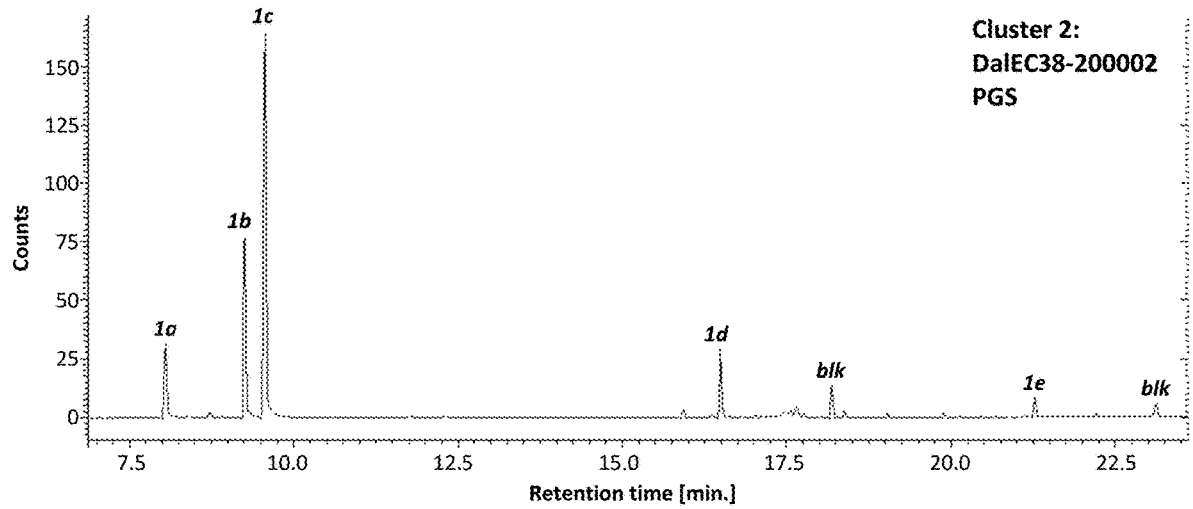

Cluster 2: Bifunctional α-, β-Pinene/α-Guaiene Synthases Cluster 2 included two enzymes having a Pinene and Guaiene Synthase (PGS) function. In cluster 2, the TPS EC12-PGS from *D. eschscholzii* EC12 and the TPS EC38-PGS from *Hypoxylon* sp. EC38 were active and produced various terpenoid compounds, including β-cis-ocimene ($C_{10}$, 1c), β-pinene ($C_{10}$, 1a), and 1s-α-pinene ($C_{10}$, 1b) as major compounds (chemical structures are provided in FIG. 3A, and GC analyses are provided in Table 3 and FIG. 15A-15B).

TABLE 3

GC peak analysis for cluster 2

TPS EC12-PGS from *D. eschscholzii* EC12

| Compound (ID No. in FIG. 15A) | Retention time (min.) | % Total peak area | Match (%)[a] | R-match (%)[b] |
|---|---|---|---|---|
| β-cis-ocimene (1c) | 9.524 | 21.06 | 94.7 | 96 |
| β-pinene (1a) | 7.994 | 17.64 | 92.5 | 93.3 |
| 1S-α-pinene (1b) | 9.225 | 16.92 | 94.3 | 96.7 |
| α-guaiene (1d) | 16.482 | 11.03 | 92.1 | 93.7 |
| viridiflorol (1e) | 21.269 | 2.385 | 88.1 | 92.6 |

TPS EC38-PGS from *Hypoxylon* sp. EC38

| Compound (ID No. in FIG. 15B) | Retention time (min.) | % Total peak area | Match (%) | R-match (%) |
|---|---|---|---|---|
| β-cis-ocimene (1c) | 9.56 | 44.52 | 93.3 | 94.8 |
| 1S-α-pinene (1b) | 9.259 | 21.04 | 95 | 96.7 |
| β-pinene (1a) | 8.041 | 9.40 | 93.9 | 94.5 |
| α-guaiene (1d) | 16.49 | 8.156 | 92.4 | 93.7 |
| viridiflorol (1e) | 21.269 | 2.076 | 89.3 | 92.6 |

[a]Match: the match factor was obtained by matching all peaks in the sample spectrum with peaks in the library. The match factor provides a sense of spectral similarity between peaks from the sample and peaks from the library.
[b]R-match: the reverse match value was obtained by ignoring all peaks that were in the sample spectrum but not in the library spectrum. The percentage value presented represents the degree of similarity between the peaks from sample and peaks from the library.

The α-pinene, β-pinene, and β-cis-ocimene accounted for 55.6% and 75% of total peak area of GC spectra from strains expressing protein EC12-PGS and EC38-PGS, respectively, which indicates that these two enzymes are pinene synthases. Additionally, the existence of two stereoisomeric products of pinene suggests that these two pinene synthases fall into class II pinene cyclases (see, e.g., Gambliel H et al., *J. Biol. Chem.* 1984; 259(2):740-8; and Dewick P M, "The biosynthesis of $C_5$-$C_{25}$ terpenoid compounds," *Nat. Prod. Rep.* 2002; 19(2):181-222).

Figure 21:
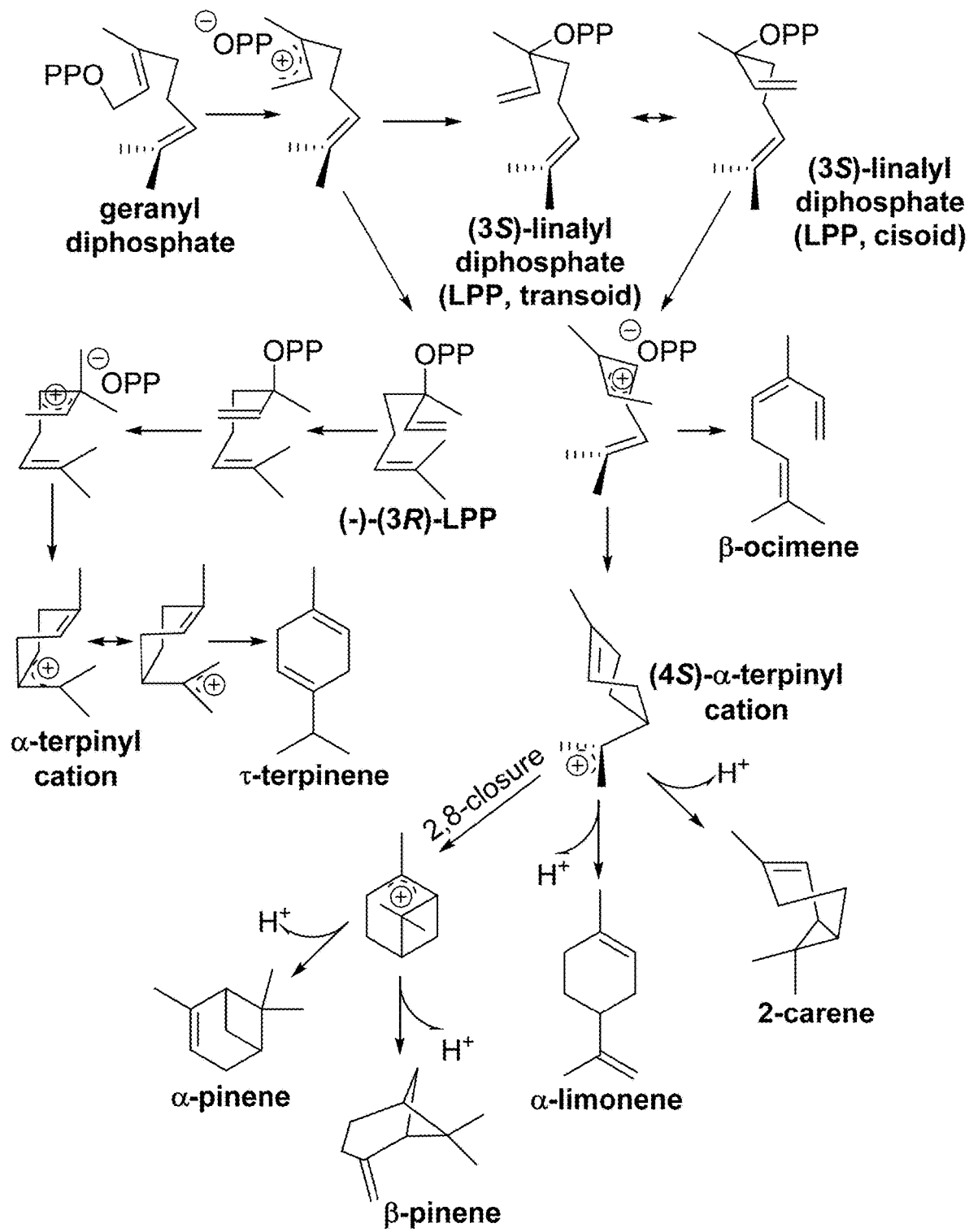
FIG. 21 shows a non-limiting schematic of a biosynthetic mechanism of monoterpenes: α-, and β-pinene, α-limonene, 2-carene, β-ocimene, and τ-terpinene (adapted from Dewick P M, *Nat. Prod. Rep.* 2002; 19(2):181-222; and Davis E M et al., *Topics Curr. Chem.* 2000; 209:53-95). The biosynthesis of pinene can be rationalized by postulating that GPP ionizes to a stable allylic cation, followed by collapse to linalyl diphosphate (LPP). The reionization of the LPP cisoid conformer followed by intramolecular electrophilic addition generates the transient α-terpinyl cation. Alternatively, an additional electrophilic attack on the newly formed cyclohexenoid double bond of α-terpinyl cation generates the pinane skeleton, which deprotonated by terpene cyclase II to form both α- and β-pinene (see, e.g., Gambliel H et al., *J. Biol. Chem.* 1984; 259(2):740-8).

FIG. 21 outlines a potential, non-limiting mechanism of pinene biosynthesis (see, e.g., Gambliel H et al., J. Biol. Chem. 1984; 259(2):740-8). Without wishing to be limited by theory, β-cis-ocimene may be the product of deprotonation followed by intramolecular electrophilic attack of a linalyl cation derived from GPP (see, e.g., Dewick P M, *Nat. Prod. Rep.* 2002; 19(2):181-222) or it is a possible artifact, as it has been reported to form in the injection port of the gas chromatography instrument used to analyze the products via thermal rearrangement of pinene (see, e.g., Stolle A et al., "Thermal rearrangements of monoterpenes and monoterpenoids," *Helvetica Chim. Acta* 2009; 92(9):1673-719). Further analysis was required to determine whether this is a bona fide TPS product or an artifact. Interestingly, a significant amount of the sesquiterpene α-guaiene ($C_{15}$, 1d) was also produced by EC12-PGS (11.026% of total peak area) and EC38-PGS (8.16% of total peak area). Other minor products were detected as well, including α-selinene ($C_{15}$, 2h), alloaromadendrene ($C_{15}$, 21) and its oxidation product viridiflorol (1e) (see, e.g., Bombarda I et al., "Spectrometric identifications of sesquiterpene alcohols from niaouli (*Melaleuca quinquenervia*) essential oil," *Anal. Chim. Acta* 2001; 447:113-23) (see Table 3).

The GPPS from *Abies grandis* used in this study was reported to specifically produce GPP, accepting only one DMAPP and one IPP co-substrates (see, e.g., Burke C et al., "Geranyl diphosphate synthase from *Abies grandis*: cDNA isolation, functional expression, and characterization," *Arch. Biochem. Biophys.* 2002; 405(1):130-6). However, the *E. coli* strain used in this study harbors a native farnesyl pyrophosphate synthase (FPPS) gene (ispA), and is therefore the likely source of the FPP used to synthesize these sesquiterpenes (see, e.g., Fujisaki S et al., "Cloning and nucleotide sequence of the ispA gene responsible for farnesyl diphosphate synthase activity in *Escherichia coli*," *J. Biochem.* 1990; 108(6):995-1000). The production of multiple monoterpenes and sesquiterpenes by these two TPSs indicates that they are bifunctional mono-/sesquiterpene synthases.

To date, the most thoroughly characterized pinene synthases are from plants, including *Pinus taeda* (see, e.g., Phillips M A et al., "cDNA isolation, functional expression, and characterization of (+)-alpha-pinene synthase and (-)-alpha-pinene synthase from loblolly pine (*Pinus taeda*): stereocontrol in pinene biosynthesis," *Arch. Biochem. Biophys.* 2003; 411(2):267-76), *Abies grandis* (see, e.g., Hyatt D C et al., *Arch. Biochem. Biophys.* 2005; 439(2):222-33; and Bohlmann J et al., *J. Biol. Chem.* 1997; 272(35):21784-92), *Artemisia annua* (see, e.g., Lu S et al., "Cloning and functional characterization of a beta-pinene synthase from *Artemisia annua* that shows a circadian pattern of expression," *Plant Physiol.* 2002; 130(1):477-86), *Cannabis sativa* (see, e.g., Günnewich N et al., "Functional expression and characterization of trichome-specific (-)-limonene synthase and (+)-α-pinene synthase from *Cannabis sativa*," *Natural Prod. Commun.* 2007; 2(3):223-32), and *Picea abies* (see, e.g., Fischbach R J et al., "Monoterpene synthase activities in leaves of *Picea abies* (L.) Karst. and *Quercus ilex* L.," *Phytochemistry* 2000; 54(3):257-65). All of these plant pinene synthases have been expressed in *E. coli*, and none of them can produce sesquiterpenes (see, e.g., Bohlmann J et al., *J. Biol. Chem.* 1997; 272(35):21784-92; Phillips M A et al., *Arch. Biochem. Biophys.* 2003; 411(2):267-76; Lu S et al., *Plant Physiol.* 2002; 130(1):477-86; Günnewich N et al., *Natural Prod. Commun.* 2007; 2(3):223-32; Fischbach R J et al., *Phytochemistry* 2000; 54(3):257-65; and Katoh S et al., "Altering product outcome in *Abies grandis* (-)-limonene synthase and (-)-limonene/(-)-alpha-pinene synthase by domain swapping and directed mutagenesis," *Arch. Biochem. Biophys.* 2004; 425(1):65-76). They primarily produced α-pinene and β-pinene, as well as lower amounts of other monoterpenes, e.g., such as limonene, camphene, myrcene, and α-terpenolen (see, e.g., Hyatt D C et al., *Arch. Biochem. Biophys.* 2005; 439(2):222-33; Bohlmann J et al., *J. Biol. Chem.* 1997; 272(35):21784-92; Phillips M A et al., *Arch. Biochem. Biophys.* 2003; 411(2):267-76; and Günnewich N et al., *Natural Prod. Commun.* 2007; 2(3):223-32).

A δ-guaiene synthase from the plant *Aquilaria crassna* has also been characterized. Like the plant pinene synthases, it only produced a single class of terpene, i.e., sesquiterpenes: δ-guaiene, α-guaiene, germacrene A, β-elemene, and α-humulene (see, e.g., Kumeta Y et al., "Genomic organization of δ-guaiene synthase genes in *Aquilaria crassna* and its possible use for the identification of *Aquilaria* species," *J. Nat. Med.* 2011; 65(3-4):508-13; Kumeta Y et al., "Characterization of δ-guaiene synthases from cultured cells of *Aquilaria*, responsible for the formation of the sesquiterpenes in agarwood," *Plant Physiol.* 2010; 154(4):1998-2007; and Lee J B et al., "Induction, cloning and functional expression of a sesquiterpene biosynthetic enzyme, δ-guaiene synthase, of *Aquilaria microcarpa* cell cultures," *Natural Prod. Commun.* 2014; 9(9):1231-5). The endophytic pinene/guaiene synthases described herein have the same DDXXD motif as the plant pinene and guaiene synthases, but otherwise have low sequence similarity to the plant TPSs.

Cluster 3: α-, β-Caryophyllene Synthases

Figure 16A:
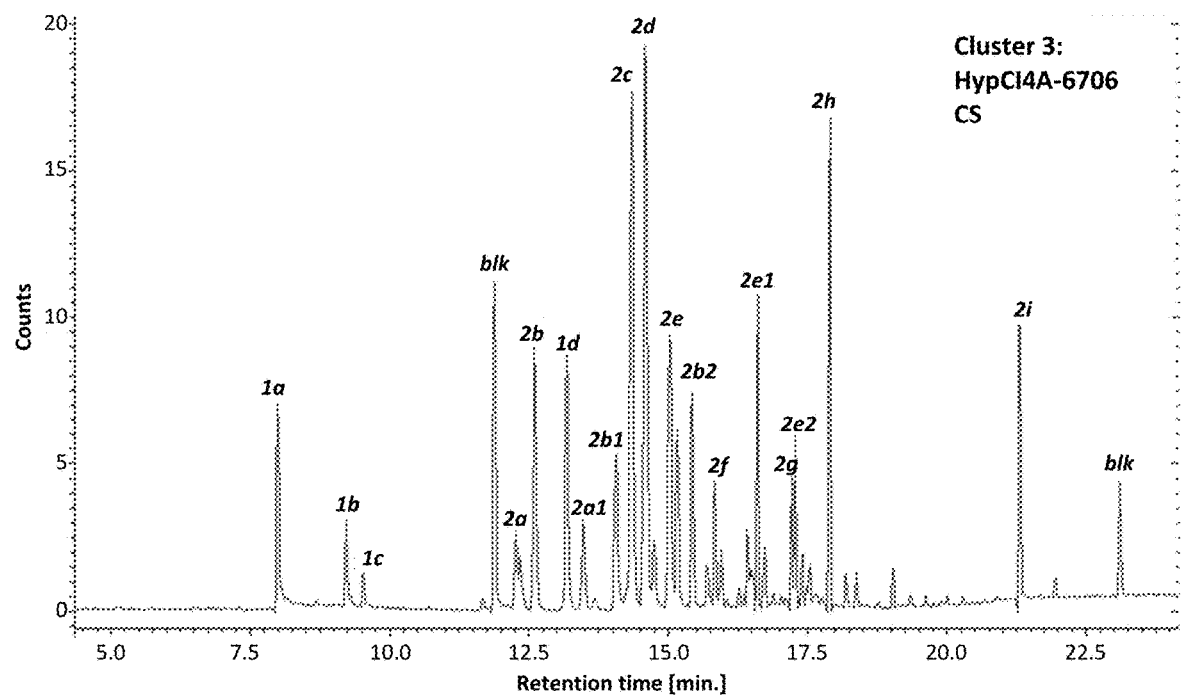
FIG. 16A-16C shows gas chromatograph terpene profiles of TPSs in the cluster 3, including (A) HypCI4A-6706 (a Caryophyllene Synthase or CS), (B) DalEC38-373976 (a CS), and (C) HypCO27-397991 (a CS).
Figure 16B:
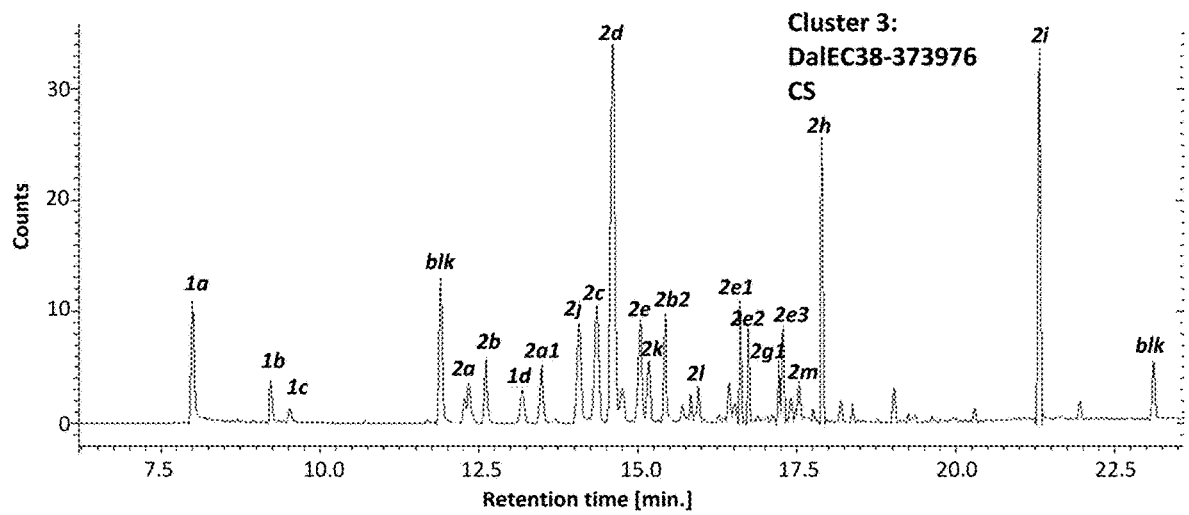
Figure 16C:
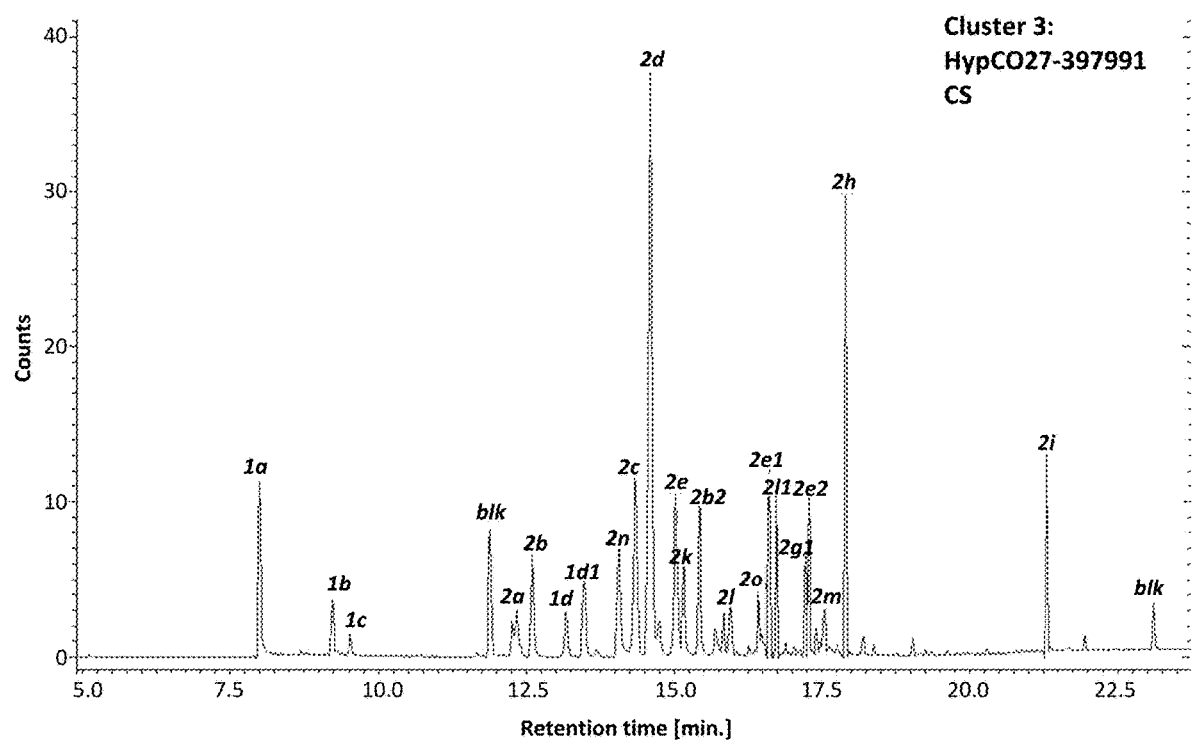

Cluster 3 included three enzymes having a Caryophyllene Synthase (CS) function. In particular, the TPSs CI4A-CS, CO27-CS, and EC38-CS were active (FIG. 14). These three TPSs produced multiple terpenes, including both mono- and sesquiterpenes, with these sesquiterpenes accounting for more than 90% of total peak area. Among these sesquiterpenes, different caryophyllene stereoisomers, such as α-caryophyllene (2g), caryophyllene-(II)(2d), humulen-(v1) (2c), and β-caryophyllene (2e) were most abundant, accounting for more than 50% of total sesquiterpene peak area (chemical structures are provided in FIG. 3B, and GC analyses are provided in Tables 4-6 and FIG. 16A-16C).

TABLE 4

GC peak analysis for TPS CI4A-CS from *Hypoxylon* sp. CI4A in cluster 3

| Compound (ID No. in FIG. 16A) | Retention time (min.) | % Total peak area | Match (%) | R-match (%) |
|---|---|---|---|---|
| caryophyllene-(II) (2d) | 14.588 | 13.24 | 88.1 | 88.5 |
| humulene-(V1) (2c) | 14.344 | 12.21 | 90.5 | 90.7 |
| α-selinene (2h) | 17.897 | 6.74 | 91.7 | 93.2 |
| β-caryophyllene (2e) | 15.026 | 6.38 | 92.9 | 93.4 |
| α-guaiene (1d) | 13.18 | 5.16 | 91.7 | 91.8 |
| α-gurjunene (2b) | 12.606 | 5.08 | 88 | 88.3 |
| thujopsene-i3 (2i) | 21.302 | 4.07 | 88.1 | 89.7 |
| β-caryophyllene (2e1) | 16.610 | 4.03 | 94 | 94.4 |
| α-gurjunene (2b1) | 14.062 | 3.71 | 89.1 | 90.8 |
| α-gurjunene (2b2) | 15.423 | 3.56 | 91.2 | 93.5 |
| β-pinene (1a) | 7.995 | 3.48 | 92.3 | 92.7 |
| β-caryophyllene (2e2) | 17.282 | 2.34 | 94.3 | 94.5 |
| τ-gurjunene (2a1) | 13.478 | 1.84 | 89.5 | 90.6 |
| δ-elemene (2f) | 15.83 | 1.78 | 85.5 | 90.1 |
| α-caryophyllene (2g) | 17.219 | 1.67 | 94.3 | 94.5 |
| τ-gurjunene (2a) | 12.263 | 1.47 | 90.5 | 92 |
| 1S-α-pinene (1b) | 9.224 | 1.12 | 94.7 | 95.9 |
| β-cis-ocimene (1c) | 9.552 | 0.56 | 91.0 | 91.4 |

TABLE 5

GC peak analysis for TPS EC38-CS from *Hypoxylon* sp. EC38 in cluster 3

| Compound (ID No. in FIG. 16B) | Retention time (min.) | % Total peak area | Match (%) | R-match (%) |
|---|---|---|---|---|
| caryophyllene-(II) (2d) | 14.604 | 18.10 | 89.2 | 89.5 |
| thujopsene-i3 (2i) | 21.308 | 10.18 | 89.4 | 91.5 |
| α-selinene (2h) | 17.898 | 7.59 | 92.6 | 93.5 |
| humulene-(V1) (2c) | 14.352 | 5.94 | 90.8 | 91.2 |
| (-)-α-neoclovene | 14.074 | 4.76 | 90 | 90.2 |

TABLE 5-continued

GC peak analysis for TPS EC38-CS from *Hypoxylon* sp. EC38 in cluster 3

| Compound (ID No. in FIG. 16B) | Retention time (min.) | % Total peak area | Match (%) | R-match (%) |
|---|---|---|---|---|
| (2j) | | | | |
| β-caryophyllene (2e) | 15.034 | 4.69 | 93.2 | 93.8 |
| β-pinene (1a) | 7.997 | 4.36 | 92.9 | 93.5 |
| α-gurjunene (2b2) | 15.426 | 3.50 | 93.1 | 94.2 |
| β-caryophyllene (2e1) | 16.609 | 3.21 | 94.5 | 94.8 |
| β-caryophyllene (2e2) | 16.735 | 2.71 | 93 | 93.3 |
| α-gurjunene (2b) | 12.612 | 2.5 | 88.6 | 89 |
| β-caryophyllene (2e3) | 17.284 | 2.45 | 93.8 | 94 |
| τ-gurjunene (2a1) | 13.485 | 2.39 | 89.3 | 90.5 |
| (+)-longifolene (2k) | 15.165 | 2.37 | 83 | 83.3 |
| τ-gurjunene (2a) | 12.275 | 1.83 | 90.1 | 91.7 |
| α-caryophyllene (2g1) | 17.22 | 1.73 | 93.5 | 94.5 |
| α-guaiene (1d) | 13.184 | 1.41 | 90.3 | 90.8 |
| 1S-α-pinene (1b) | 9.229 | 1.34 | 92.6 | 96.4 |
| (−)-alloaromadendrene (2l) | 15.952 | 1.24 | 88.7 | 90.2 |
| β-cubebene (2m) | 17.54 | 1 | 92.7 | 95.3 |
| β-cis-ocimene (1c) | 9.527 | 0.40 | 88.4 | 91 |

TABLE 6

GC peak analysis for TPS CO27-CS from *Hypoxylon* sp. CO27 in cluster 3

| Compound (ID No. in FIG. 16C) | Retention time (min.) | % Total peak area | Match (%) | R-match (%) |
|---|---|---|---|---|
| caryophyllene-(II) (2d) | 14.598 | 21.94 | 88.4 | 89 |
| α-selinene (2h) | 17.899 | 9.81 | 90.7 | 91.8 |
| humulene-(V1) (2c) | 14.346 | 6.71 | 91.5 | 92.1 |
| β-caryophyllene (2e) | 15.027 | 5.61 | 92.9 | 93.4 |
| thujopsene-i3 (2i) | 21.303 | 4.43 | 89 | 90.4 |
| β-pinene (1a) | 7.993 | 4.32 | 93.1 | 93.5 |
| cyperene (2n) | 14.068 | 4.15 | 90 | 91 |
| α-gurjunene (2b2) | 15.423 | 3.92 | 93.5 | 95.1 |
| β-caryophyllene (2e1) | 16.609 | 3.70 | 93.8 | 94.2 |
| alloaromadendrene (2l1) | 16.736 | 3.17 | 92.7 | 93 |
| β-caryophyllene (2e2) | 17.283 | 3.15 | 94.3 | 94.5 |
| α-gurjunene (2b) | 12.605 | 3.07 | 88.7 | 89 |
| (+)-longifolene (2k) | 15.159 | 2.61 | 81.7 | 82.9 |
| α-guaiene (1d1) | 13.477 | 2.48 | 89.3 | 89.9 |
| α-caryophyllene (2g1) | 17.22 | 2.12 | 93.8 | 95 |
| α-guaiene (1d) | 13.177 | 1.49 | 89.8 | 90.7 |
| β-cubebene (2m) | 17.539 | 1.27 | 90.9 | 94 |
| (−)-alloaromadendrene (2l) | 15.95 | 1.26 | 89.4 | 90.7 |
| (+)-valencene (2o) | 16.428 | 1.24 | 91.1 | 92.8 |
| 1S-α-pinene (1b) | 9.222 | 1.21 | 93.4 | 96.8 |
| τ-gurjunene (2a) | 12.268 | 0.85 | 89.5 | 91 |
| β-cis-ocimene (1c) | 9.522 | 0.51 | 88.2 | 91.5 |

Figure 3A:
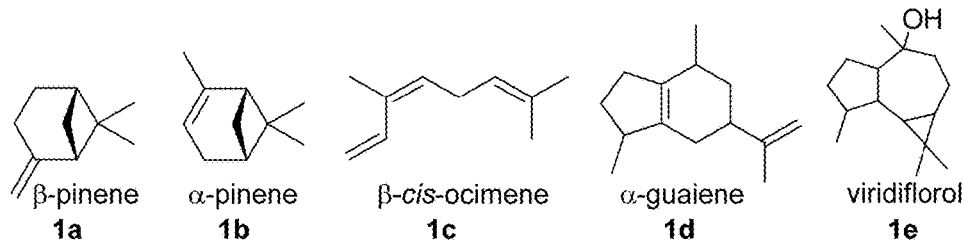
FIG. 3A-3E shows chemical structures of terpenoid compounds with terpene profiles of TPSs in (A) cluster 2, (B) cluster 3, (C) cluster 4, (D) cluster 5, and (E) non-clustered TPSs. The number and letter below each structure refers to the compounds in Tables 3-12 herein.
Figure 3B:
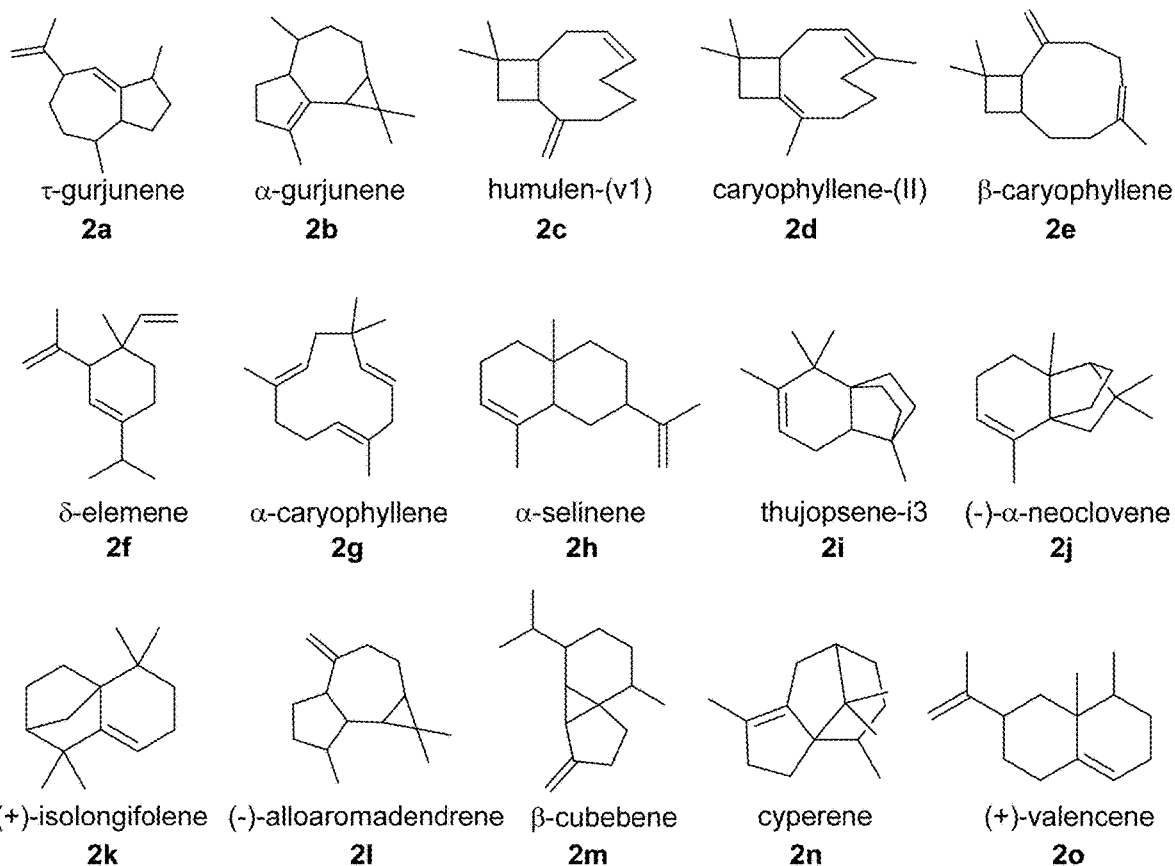
Figure 3C:
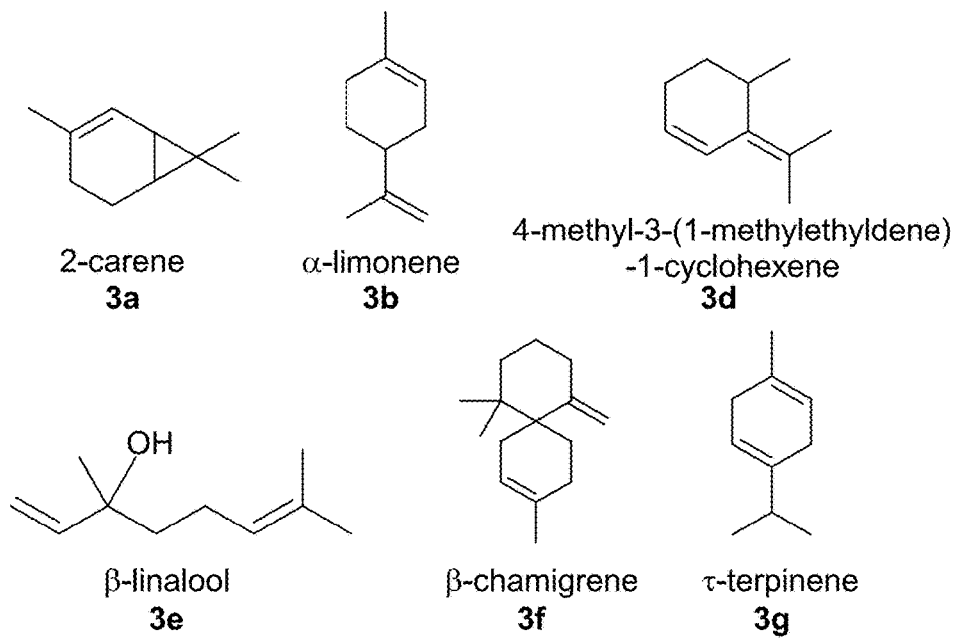
Figure 3D:
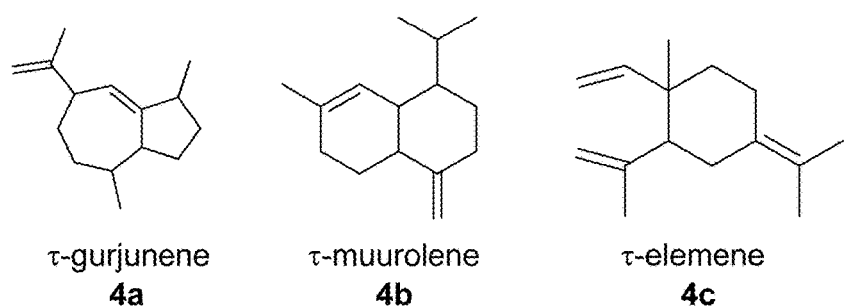
Figure 3E:
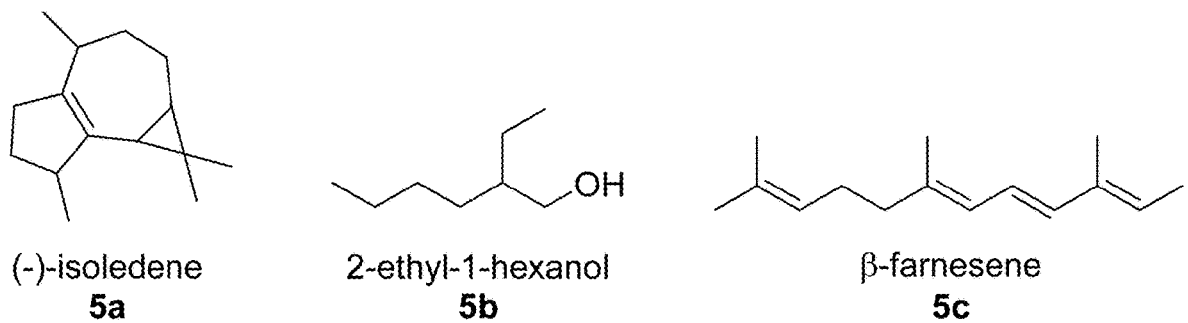
Figure 22:
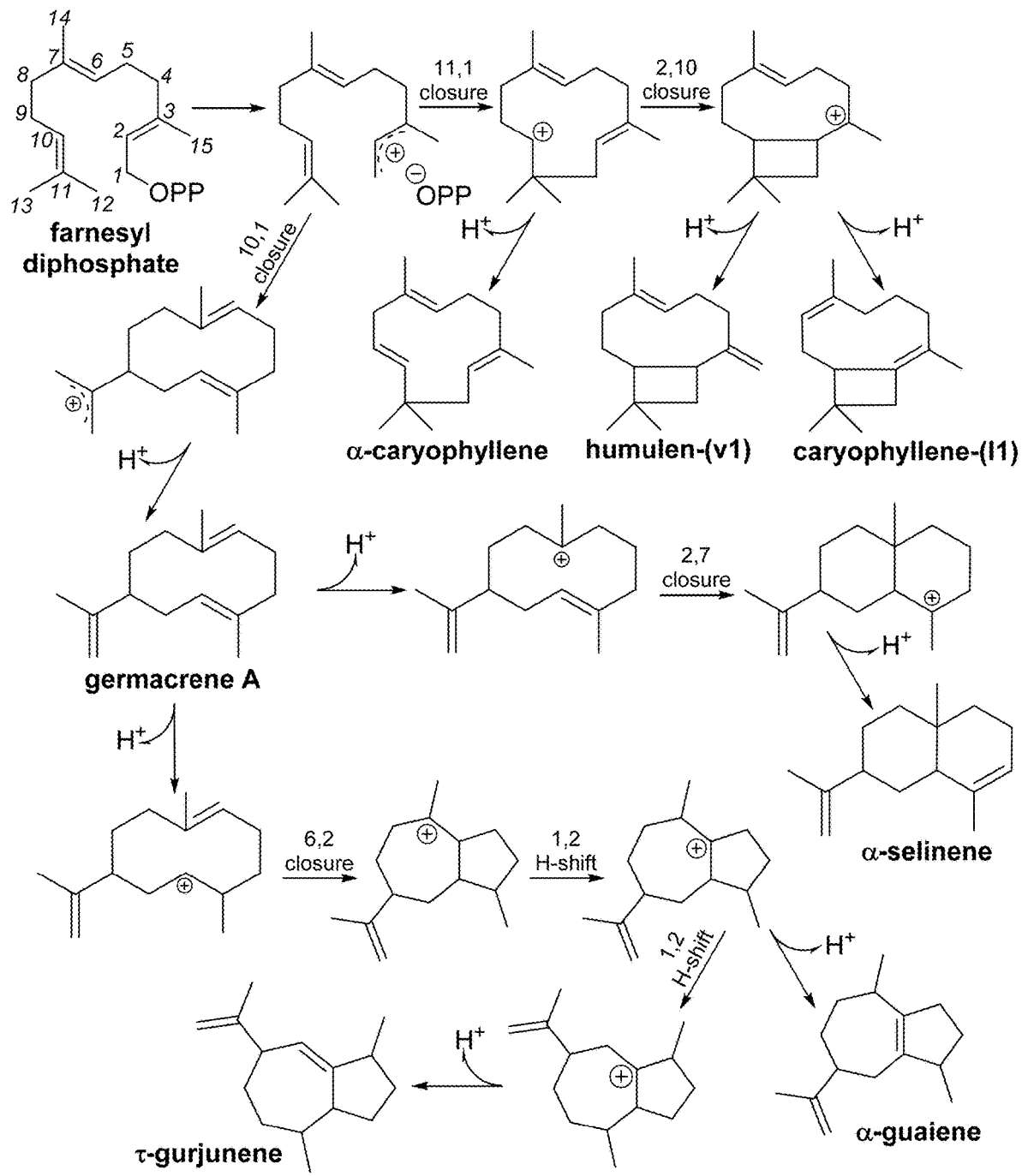
FIG. 22 shows a non-limiting schematic of a biosynthetic mechanism of sesquiterpenes: α-, and β-caryophyllene, humulen, α-selinene, α-guaiene, and τ-gurjunene (adapted from Dewick P M, *Nat. Prod. Rep.* 2002; 19(2):181-222; and Davis E M et al., *Topics Curr. Chem.* 2000; 209:53-95). Generally, FPP is ionized to generate an allylic cation, and then through a 11,1 closure to form humulyl cation and a subsequent deprotonation to yield α-caryophyllene, or through a 11,1 closure to form humulyl cation, another 2,10 closure to generate caryophyllyl cation and further deprotonated to form humulen-(v1) and β-caryophyllene. Also, FPP can be ionized and through a subsequent 10,1 closure and deprotonation, form germacrene A, which can be an intermediate for further intramolecular electrophilic attack, hydride shift, and deprotonation, yield α-selinene, α-guaiene, and τ-gurjunene.

Overall, these three TPSs appear to be primarily caryophyllene synthases. In addition to β-caryophyllene and its stereoisomers, CI4A-CS from *Hypoxylon* sp. CI4A yielded various amounts of other sesquiterpenes, including humulen-(v1) (2c), gurjunene (2a, 2b), α-guaiene (1d), α-selinene (2h), etc., as well as monoterpenes, including β-pinene (1a), 1S-α-pinene (1b), and β-cis-ocimene (1c) (FIG. 3A-3B, Table 4). EC38-CS and CO27-CS produced a similar array of terpenes, except CO27-CS produced thujopsene-i3 (2i), α/τ-neoclovene (2j) and β-cubebene (2m), while EC38-CS produced (−)-α-neoclovene (2j), β-cubebene (2m), and (+)-longifolene (2k) (Tables 5-6). Without wishing to be limited by theory, the production of multiple terpenes by each of these enzymes is likely due to various cyclization reactions of different intermediate carbocations that are formed by intramolecular electrophilic attacks and deprotonations of FPP (see, e.g., Dewick P M, *Nat. Prod. Rep.* 2002; 19(2):181-222; and Davis E M et al., "Cyclization enzymes in the biosynthesis of monoterpenes, sesquiterpenes, and diterpenes," *Topics Curr. Chem.* 2000; 209:53-95). FIG. 22 outlines a potential, non-limiting reaction mechanism of the formation of some of these terpenes.

There are no reports of fungal caryophyllene synthase, but there are several caryophyllene synthases from plants: cotton, *Artimisia annua*, maize, rice, and *Arabidopsis* (see, e.g., Huang X et al., "Identification and characterization of (E)-β-caryophyllene synthase and α/β-pinene synthase potentially involved in constitutive and herbivore-induced terpene formation in cotton," *Plant Physiol. Biochem.* 2013; 73:302-8; Shen H Y et al., "Advances in sesquiterpene synthases (cyclases) of *Artemisia annua*," Sheng Wu Gong Cheng Xue Bao [*Chinese J. Biotechnol.*] 2007; 23(6):976-81; Köllner T G et al., "A maize (E)-beta-caryophyllene synthase implicated in indirect defense responses against herbivores is not expressed in most American maize varieties," *Plant Cell* 2008; 20(2):482-94; Cheng A X et al., "The rice (E)-beta-caryophyllene synthase (OsTPS3) accounts for the major inducible volatile sesquiterpenes," *Phytochemistry* 2007; 68(12):1632-41; and Tholl D et al., "Two sesquiterpene synthases are responsible for the complex mixture of sesquiterpenes emitted from *Arabidopsis* flowers," *Plant J.* 2005; 42(5):757-71). The plant caryophyllene synthases from cotton, maize, and *Arabidopsis* use FPP as a substrate, rather than GPP, and produced several sesquiterpene compounds, including β-caryophyllene, α-humulene, (−)-α-copaene, linalool, 4,8-dimethylnona-1,3,7-triene, (E)-α-bergamotene, and (E)-β-farnesene (see, e.g., Huang X et al., *Plant Physiol. Biochem.* 2013; 73:302-8; Köllner T G et al., *Plant Cell* 2008; 20(2):482-94; and Tholl D et al., *Plant J.* 2005; 42(5):757-71).

The caryophyllene synthase from rice has similar substrate specificity, but produced more than 25 different sesquiterpene compounds, including β-caryophyllene, β-farnesene, α-bergamotene, β-elemene, etc. Many caryophyllene synthases from plants share the same DDXXD motif with the endophytic TPSs, but have different NSE/DTE triad amino acid sequences and low protein sequence similarity. As with cluster 2 TPSs, the cluster 3 caryophyllene synthases are bifunctional, producing both mono- and sesquiterpenes.

Cluster 4: Bifunctional β-Chamigrene/β-Pinene and α-Gurjunene/β-Pinene Synthases Cluster 4 included enzymes having a Chamigrene and Pinene Synthase (CPS) or a Gurjunene and Pinene Synthase (GPS) function. In cluster 4, the TPSs CI4A-CPS, CO27-CPS, EC38-CPS, and EC38-GPS were active (FIG. 14). The TPSs CI4A-CPS, CO27-CPS, and EC38-CPS produced similar terpenes, while EC38-GPS had a distinct profile. All four TPSs produced both monoterpenes and sesquiterpenes, indicating that, again, they are bifunctional mono-/sesquiterpene synthases. The TPSs CI4A-CPS, CO27-CPS, and EC38-CPS, produced β-chamigrene ($C_{15}$, 3f) as the major product (>34.8%), indicating that these three enzymes are primarily chamigrene synthases (chemical structures are provided in FIG. 3C, and GC analyses are provided in Tables 7-10 and FIG. 17A-17D).

TABLE 7

GC peak analysis for TPS EC38-CPS from
Hypoxylon sp. EC38 in cluster 4

| Compound (ID No. in FIG. 17A) | Retention time (min.) | % Total peak area | Match (%) | R-match (%) |
|---|---|---|---|---|
| β-chamigrene (3f) | 17.487 | 34.38 | 88.5 | 88.5 |
| β-pinene (1a) | 8.003 | 30.71 | 95.2 | 95.5 |
| limonene (3b) | 8.699 | 10.23 | 91.5 | 91.9 |
| 2-carene (3a) | 8.362 | 5.23 | 94.5 | 94.9 |
| β-cis-ocimene (1c) | 9.518 | 4.0 | 94.6 | 95.4 |
| 4-methyl-3-(1-methylethyldene)-1-cyclohexene (3d) | 10.121 | 1.65 | 94.4 | 95.6 |
| β-elemene (2f) | 16.475 | 1.02 | 90.7 | 91.1 |
| 1S-α-pinene (1b) | 9.225 | 1.0 | 90.3 | 96.4 |
| β-linalool (3e) | 15.905 | 0.66 | 90.2 | 90.8 |

TABLE 8

GC peak analysis for TPS CI4A-CPS from
Hypoxylon sp. CI4A in cluster 4

| Compound (ID No. in FIG. 17B) | Retention time (min.) | % Total peak area | Match (%) | R-match (%) |
|---|---|---|---|---|
| β-chamigrene (3f) | 17.502 | 61.28 | 89 | 89 |
| β-pinene (1a) | 7.995 | 16.24 | 94.6 | 94.7 |
| limonene (3b) | 8.694 | 3.80 | 91.7 | 92.3 |
| β-cis-ocimene (1c) | 9.517 | 2.53 | 95 | 95.4 |
| 2-carene (3a) | 8.355 | 1.46 | 93.8 | 94.6 |
| 1S-α-pinene (1b) | 9.223 | 0.86 | 88.9 | 95.9 |
| 4-methyl-3-(1-methylethyldene)-1-cyclohexene (3d) | 10.116 | 0.854 | 93.5 | 95.1 |

TABLE 9

GC peak analysis for TPS EC38-GPS from
Hypoxylon sp. EC38 in cluster 4

| Compound (ID No. in FIG. 17C) | Retention time (min.) | % Total peak area | Match (%) | R-match (%) |
|---|---|---|---|---|
| α-gurjunene (2b) | 17.454 | 20.41 | 92.7 | 94.2 |
| β-pinene (1a) | 7.996 | 16.36 | 92.4 | 92.8 |
| limonene (3b) | 8.698 | 9.832 | 90.8 | 91.7 |
| β-elemene (2f) | 16.478 | 4.597 | 91.1 | 92 |
| 2-ethyl-1-hexanol (5b) | 14.753 | 4.321 | 96.4 | 97.2 |
| β-cis-ocimene (1c) | 9.523 | 3.093 | 92.2 | 93.3 |
| L-alloaromadendrene (2l) | 17.142 | 2.44 | 90.4 | 92.1 |
| 4-methyl-3-(1-methylethyldene)-1-cyclohexene (3d) | 10.121 | 2.424 | 94.3 | 95.5 |
| δ-elemene (2f1) | 14.237 | 2.208 | 91.9 | 94.7 |
| β-farnesene (5c) | 17.023 | 1.697 | 91.8 | 94.5 |
| β-caryophyllene (2e) | 16.607 | 1.687 | 87.3 | 88.7 |
| (−)-alloaromadendrene (2l1) | 17.212 | 1.46 | 88.3 | 89.8 |
| (−)-isoledene (5a) | 16.662 | 1.209 | 92.1 | 93.9 |
| 1S-α-pinene (1b) | 9.225 | 1.078 | 91.7 | 93.1 |

TABLE 10

GC peak analysis for TPS CO27-CPS from
Hypoxylon sp. CO27 in cluster 4

| Compound (ID No. in FIG. 17D) | Retention time (min.) | % Total peak area | Match (%) | R-match (%) |
|---|---|---|---|---|
| β-chamigrene (3f) | 17.508 | 65.35 | 90.1 | 90.1 |
| β-pinene (1a) | 7.982 | 10.39 | 93.6 | 93.8 |
| β-elemene (2f) | 16.48 | 3.99 | 91.8 | 92 |
| limonene (3b) | 8.687 | 3.89 | 91.4 | 91.9 |
| β-cis-ocimene (1c) | 9.515 | 2.35 | 94.6 | 94.7 |
| (+)-valencene (2o) | 17.618 | 1.90 | 95.7 | 97.7 |
| τ-terpinene (3g) | 8.346 | 1.50 | 94.5 | 95.3 |
| 4-methyl-3-(1-methylethyldene)-1-cyclohexene (3d) | 10.116 | 0.883 | 94.1 | 95.6 |
| 1S-α-pinene (1b) | 9.22 | 0.59 | 90.8 | 96.4 |

Figure 23:
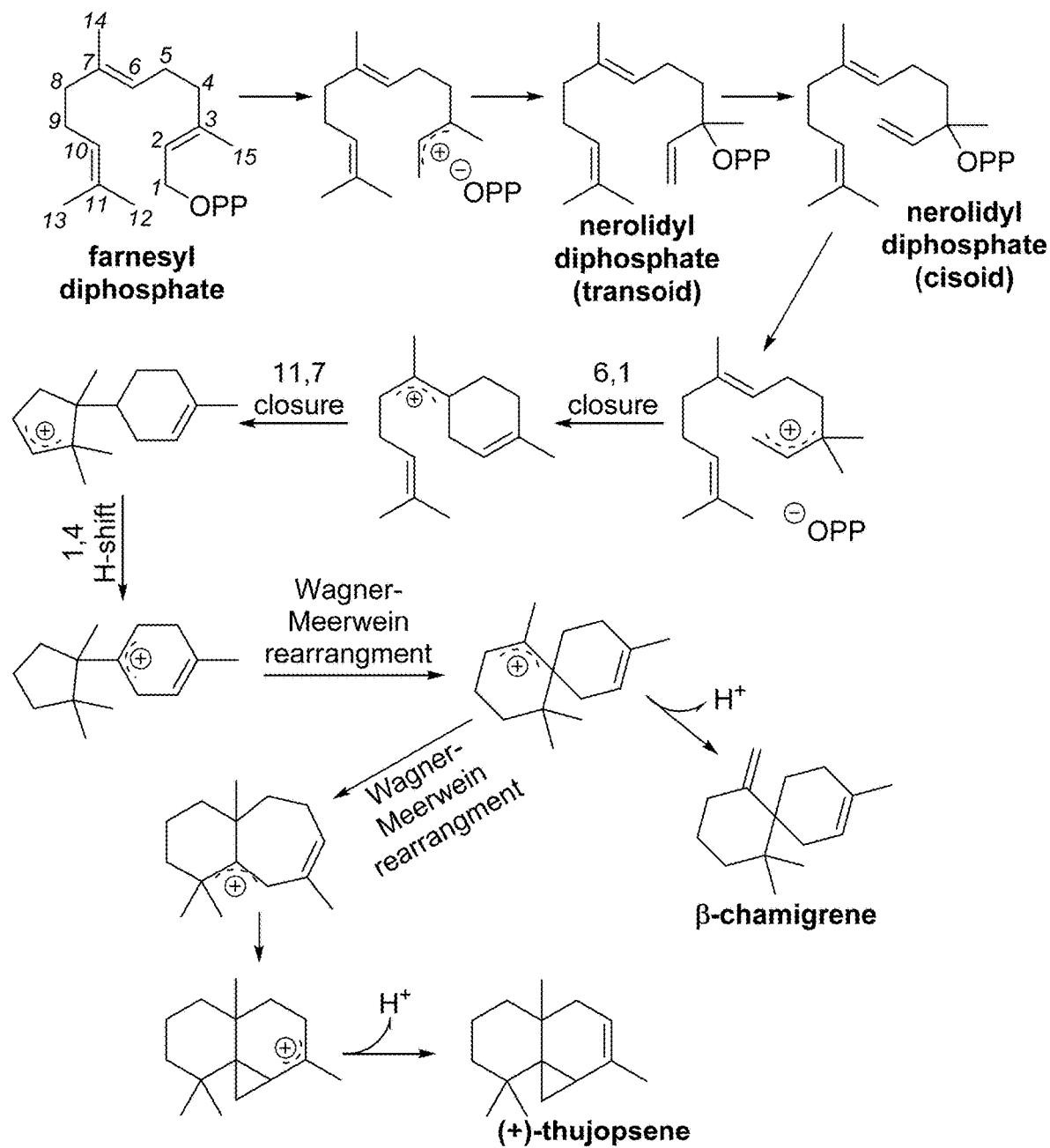
FIG. 23 shows a non-limiting schematic of a biosynthetic mechanism of sesquiterpenes: β-chamigrene and thujopsene (see, e.g., Davis E M et al., *Topics Curr. Chem.* 2000; 209:53-95; Wu S et al., "Surrogate splicing for functional analysis of sesquiterpene synthase genes," *Plant Physiol.* 2005; 138(3):1322-33). Chamigrene biosynthesis could begin with the ionization and subsequent allylic rearrangement of the diphosphate moiety of FPP, allowing for the formation of nerolidyl diphosphate (NPP, cisoid conformation). Reionization of the ciscoid conformation of NPP and subsequent intramolecular electrophilic attack would form a bisabolyl cation, which followed by a secondary intramolecular electrophilic attack and 1,4-hydride shift, would create a cuprenyl cation. A subsequent methylene migration would yield the chamigrenyl cation which could undergo a direct proton abstraction to form β-chamigrene (see, e.g., Lin P P et al., "Isobutanol production at elevated temperatures in thermophilic *Geobacillus thermoglucosidasius*," *Metab. Eng.* 2014; 24:1-8 (erratum in *Metab. Eng.* 2014; 24:192)).

FIG. 23 outlines a potential, non-limiting reaction mechanism for the biosynthesis of β-chamigrene. These three enzymes also produced lower amounts monoterpenes: β-pinene (1a), α-limonene (1d), β-cis-ocimene (1c), 4-methyl-3-(1-methylethylidene)-1-cyclohexene (3d), and α-pinene (1b), with β-pinene being the major monoterpene in each case (Table 7-10 and FIG. 17A-17D).

Other minor products included 2-carene (3a for EC38-CPS and CI4A-CPS), (−)-β-elemene (2f for EC38-CPS and CO27-CPS), (+)-valencene (2o for CO27-CPS), and τ-terpinene (3g for CO27-CPS). An exemplary, non-limiting mechanism for the biosynthesis of α-limonene, 2-carene, and τ-terpinene is represented in FIG. 21. There are no reports of a TPS producing chamigrene as the sole sesquiterpene. However, Wu et al. reported that an α-barbatene synthase from *Arabidopsis* produced a mix of α-barbatene, thujopsene, and β-chamigrene as major products but no monoterpenes (see, e.g., Wu S et al., "Surrogate splicing for functional analysis of sesquiterpene synthase genes," *Plant Physiol.* 2005; 138(3):1322-33). The endophyte TPSs shared low sequence similarity with the plant chamigrene synthase, have the same DDXXD motif, and a different NSE/DTE triad.

Figure 17A:
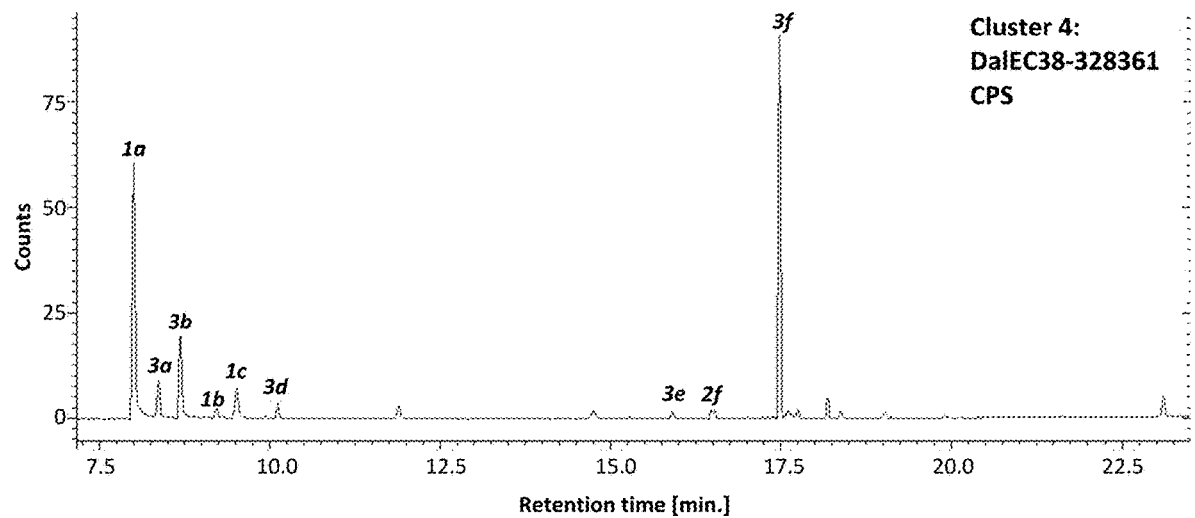
FIG. 17A-17D shows gas chromatograph terpene profiles of TPS in the cluster 4, including (A) DalEC38-328361 (a Chamigrene and Pinene Synthase or CPS), (B) HypCI4A-322581 (CPS), (C) DalEC38-80361 (Gurjunene and Pinene Synthase or GPS), and (D) HypCO27-392541 (CPS).
Figure 17B:
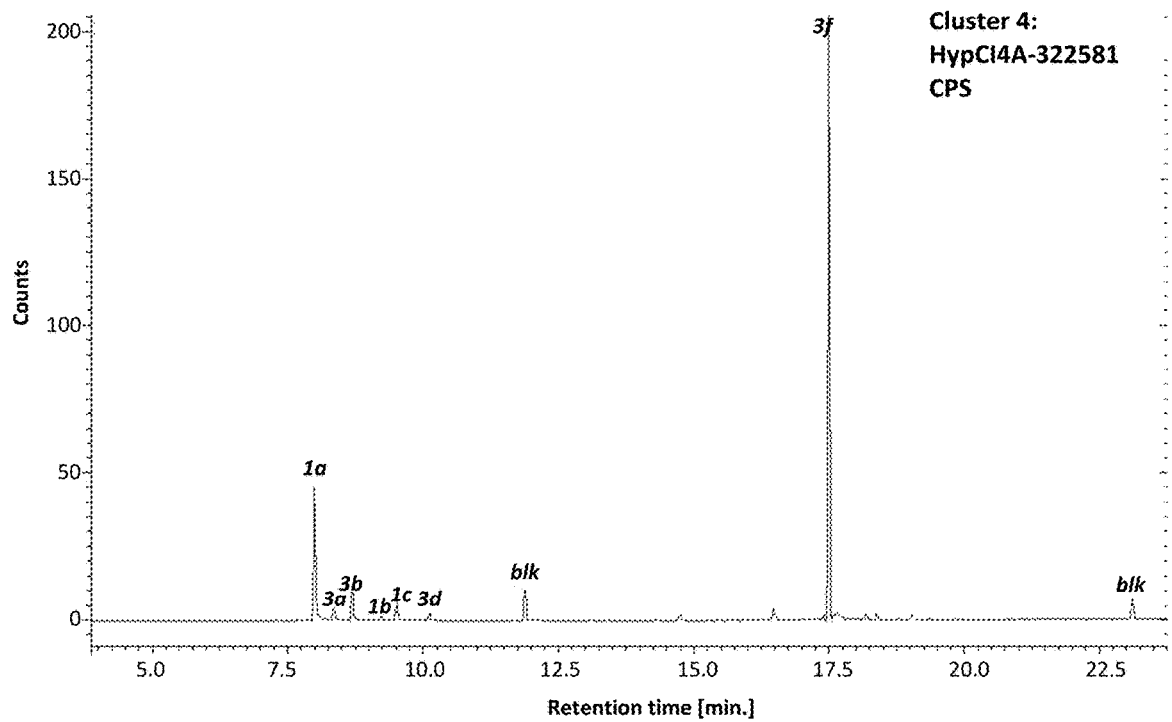
Figure 17C:
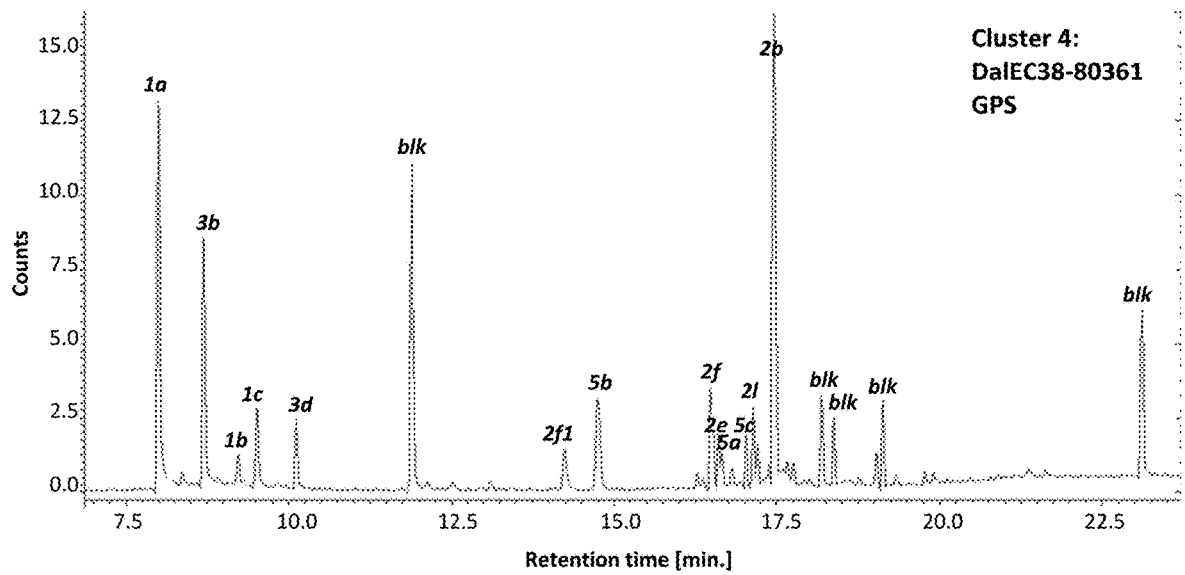
Figure 17D:
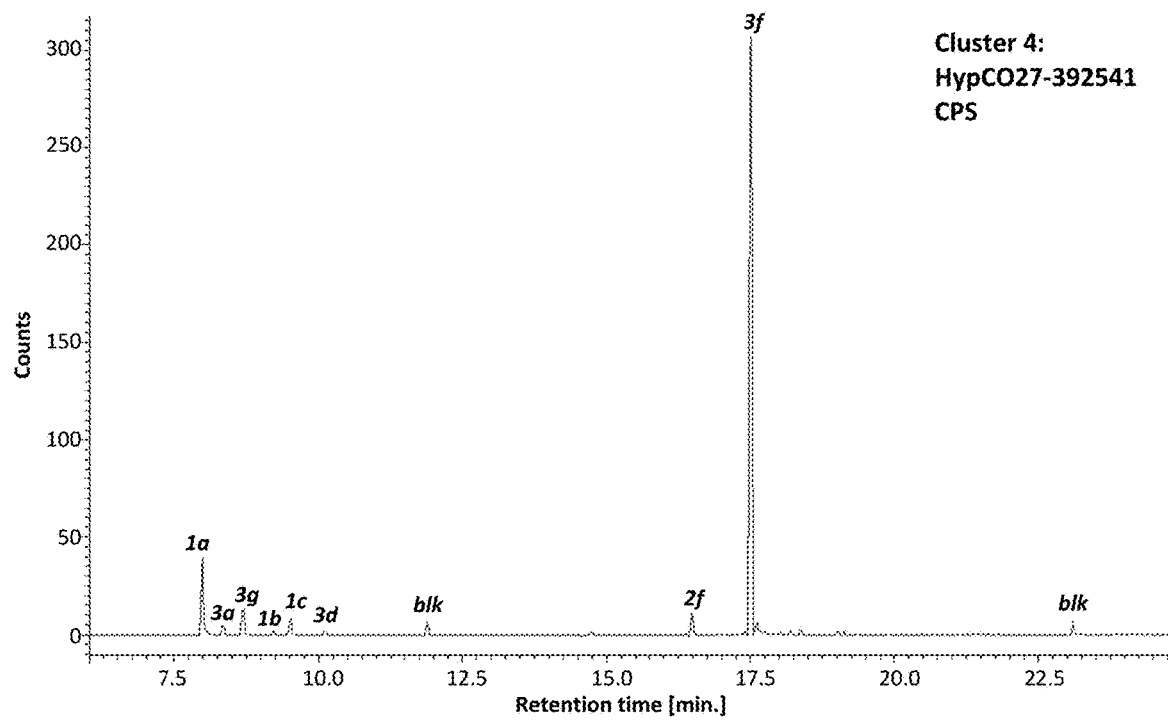

The fourth TPS in cluster 4, EC38-GPS, produced both mono- and sesquiterpenes, a common theme with the endophyte TPSs herein (Table 9 and FIG. 17C). The monoterpene β-pinene (1a) and sesquiterpene α-gurjunene (2b) were the two major products of this enzyme, accounting for 16.4% and 20.4% of total peak area, respectively. Minor products included α-limonene (3b), β-elemene (2f), L-alloaromadendrene (2l), β-cis-ocimene (1c), α-pinene (1a), β-farnesene (5c), β-caryophyllene (2d), (−)-isoledene (5a), and 4-methyl-3-(1-methylethylidene)-1-cyclohexene (3d). Schmidt et al. discovered an α-gurjunene synthase from *Solidago canadensis*, which produced germacrene D (50%), α-gurjunene (42%), γ-gurjunene (4%) as major products but no monoterpenes (see, e.g., Schmidt C O et al., "Isolation, characterization, and mechanistic studies of (−)-alpha-gurjunene synthase from *Solidago canadensis*," *Arch. Biochem. Biophys.* 1999; 364(2):167-77).

Cluster 5: τ-Gurjunene Synthase

Figure 18:
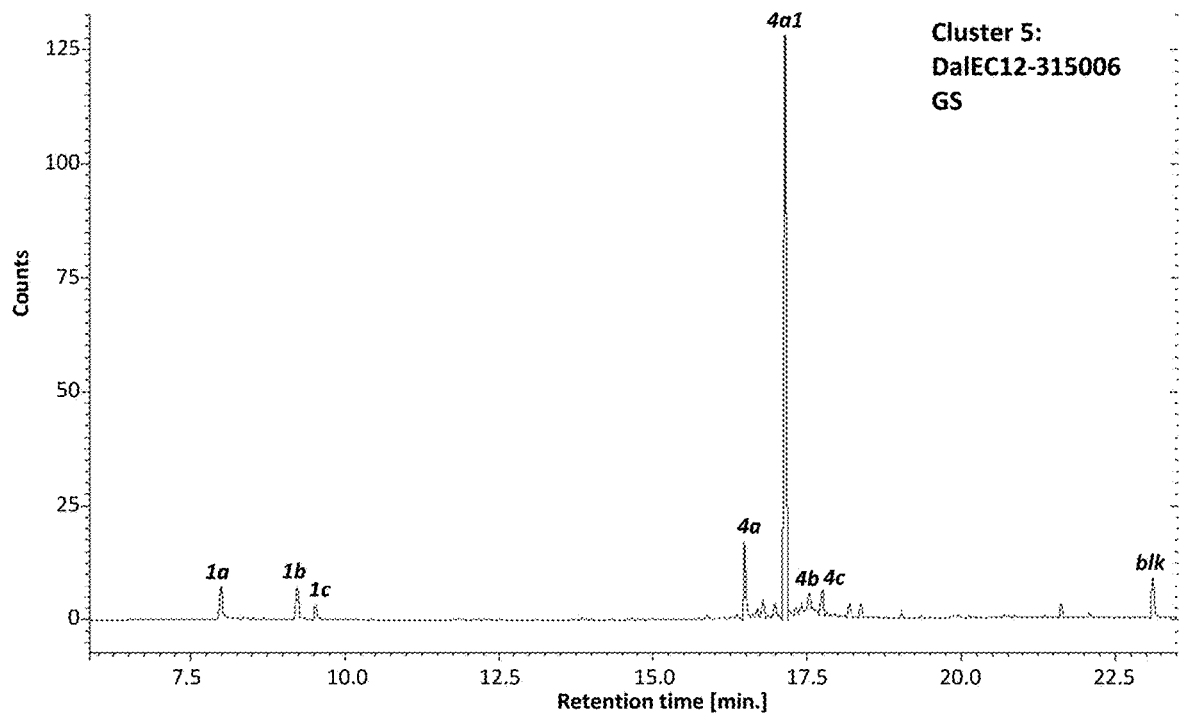
FIG. 18 shows a gas chromatograph terpene profile of a TPS in the cluster 5, DalEC12-315006 (a Gurnunene Synthase or GS).

Cluster 5 included one enzyme having Gurjunene Synthase (GC) activity: EC12-GS (FIG. 14). Its major product was the sesquiterpene τ-gurjunene (4a, 58.7% of total peak area), suggesting that it is primarily a τ-gurjunene synthase (chemical structures are provided in FIG. 3D, and GC analyses are provided in Table 11 and FIG. 18).

TABLE 11

GC peak analysis for TPS EC12-GS from
D. eschscholzii EC12 in cluster 5

| Compound (ID No. in FIG. 18) | Retention time (min.) | % Total peak area | Match (%) | R-match (%) |
|---|---|---|---|---|
| τ-gurjunene (4a1) | 17.114 | 50.07 | 90.5 | 91.9 |
| τ-gurjunene (4a) | 16.484 | 7.96 | 91.7 | 92.8 |
| τ-muurolene (4b) | 17.536 | 3.88 | 92 | 94.6 |
| β-pinene (1a) | 7.994 | 3.71 | 92.6 | 93.8 |
| τ-elemene (4c) | 17.748 | 3.44 | 91.6 | 94.4 |
| 1S-α-pinene (1b) | 9.226 | 3.38 | 93.4 | 95.4 |
| β-cis-ocimene (1c) | 9.525 | 1.71 | 92.2 | 93.6 |

EC12-GS had a broader product profile compared to the α-gurjunene synthase from *Solidago canadensis* (see, e.g., Schmidt C O et al., *Arch. Biochem. Biophys.* 1999; 364(2): 167-77), which only produced three sesquiterpenes as major products. Although gurjunene accounted for ~60% of the terpenes produced by EC12-GS, it also produced the sesquiterpenes τ-muurolene (4b), τ-elemene (4c), and the monoterpenes β-pinene (1a), α-pinene (1b), and β-cis-ocimene (1c), indicating this enzyme is a bifunctional mono-/sesquiterpene synthase. A potential, non-limiting mechanism of τ-gurjunene formation is outlined in FIG. 22.

Unclustered TPS: α-Selinene and (−)-Isoledene Synthases

Figure 19A:
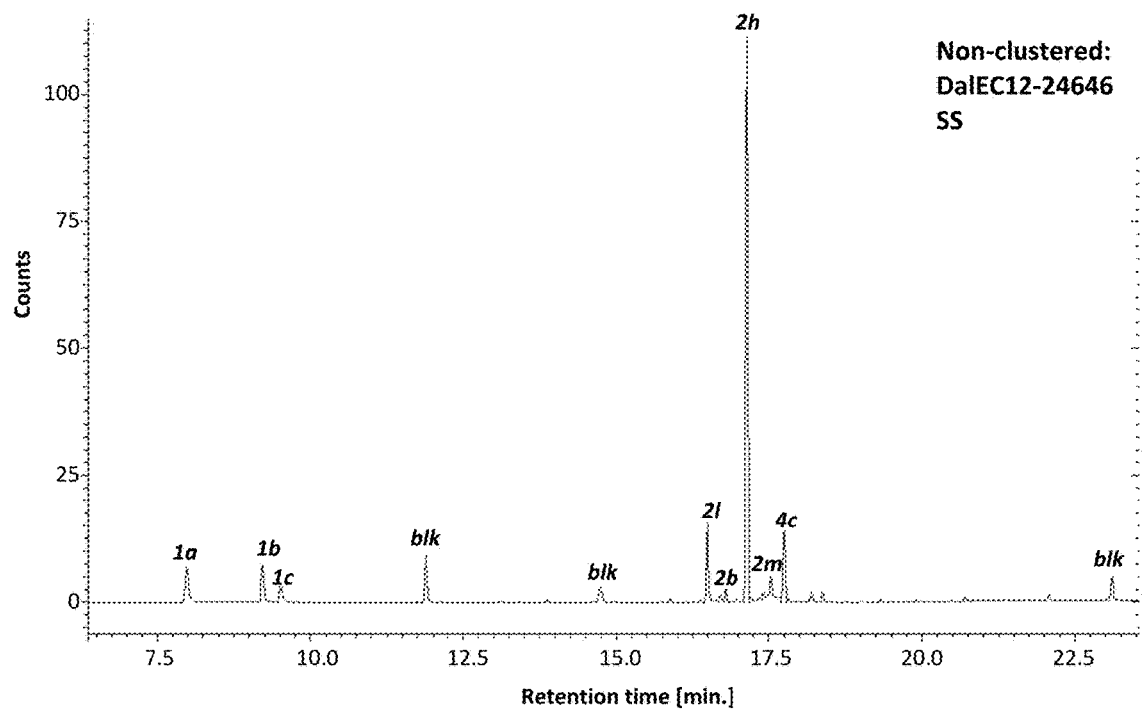
FIG. 19A-19B shows gas chromatograph terpene profiles of TPSs in a non-clustered group, including (A) DalEC12-24646 (a Selinene Synthase or SS) and (B) DalEC12-70183 (an IsoLedene Synthase or ILS).

Unclustered TPSs included Selinene Synthase (SS) and IsoLedene Synthase (ILS). Putative TPSs EC12-SS and EC12-ILS shared low sequence homology with the other predicted endophytic TPSs and did not cluster. EC12-SS produced multiple mono- and sesquiterpenes, but α-selinene (2h) was the major terpene produced (50.7% of total peak area), which suggests that this enzyme is primarily a selinene synthase (chemical structures are provided in FIG. 3B, and GC analyses are provided in Table 12 and FIG. 19A-19B).

TABLE 12

GC peak analysis for non-clustered enzymes

TPS EC12-SS from D. eschscholzii EC12

| Compound (ID No. in FIG. 19A) | Retention time (min.) | % Total peak area | Match (%) | R-match (%) |
|---|---|---|---|---|
| α-selinene (2h) | 17.142 | 50.717 | 91.2 | 93.1 |
| (−)-alloaromadendrene (2l) | 16.485 | 8.15 | 91.3 | 92.3 |
| τ-elemene (4c) | 17.746 | 6.71 | 93.5 | 96 |
| β-pinene (1a) | 7.986 | 4.43 | 94.1 | 94.4 |
| 1S-α-pinene (1b) | 9.223 | 4.24 | 94 | 94.8 |
| β-cubebene (2m) | 17.537 | 3.63 | 93.3 | 95.4 |
| β-cis-ocimene (1c) | 9.521 | 2.22 | 94 | 94.8 |
| α-gurjunene (2b) | 16.786 | 1.62 | 93.5 | 95.5 |

TPS EC12-ILS from D. eschscholzii EC12

| Compound (ID No. in FIG. 19B) | Retention time (min.) | % Total peak area | Match (%) | R-match (%) |
|---|---|---|---|---|
| (−)-isoledene (5a) | 12.652 | 10.8 | 90.5 | 91 |
| iso-longifolene (2k) | 15.622 | 6.76 | 85.7 | 86.2 |
| β-caryophyllene (2e) | 16.605 | 6.71 | 93.5 | 94.3 |
| β-elemene (2f) | 16.485 | 5.88 | 80.9 | 83.1 |
| (−)-alloaromadendrene (2l) | 13.821 | 2.24 | 85 | 85.7 |
| α-gurjunene (2b) | 12.853 | 1.90 | 85 | 85.9 |
| (+)-valencene (2o) | 16.107 | 1.5 | 86.1 | 88.3 |

Steele et al. reported the discovery of a δ-selinene synthase (ag4) from *Abies grandis* that produced more than 20 sesquiterpenes including δ-selinene (25.3%), (E,E)-germacrene B (17.4%), guaia-6,9-diene(9.7%), germacrene A (6.7%), δ-amorphene (6.4%), germacrene C (3.4%), α-selinene (1.7%), β-caryophyllene (1.5%), δ-cadinene (1.4%), and seli-3,7(11)-diene (1.2%) (see, e.g., Steele C L et al., *J. Biol. Chem.* 1998; 273(4):2078-89). Compared to this plant δ-selinene synthase, EC12-SS yielded fewer sesquiterpenes and a higher relative abundance of α-selinene (50.8%). It is also a bifunctional mono-/sesquiterpene synthase (Table 12 and FIG. 19A). FIG. 22 provides a proposed, non-limiting mechanism for selinene biosynthesis.

Figure 19B:
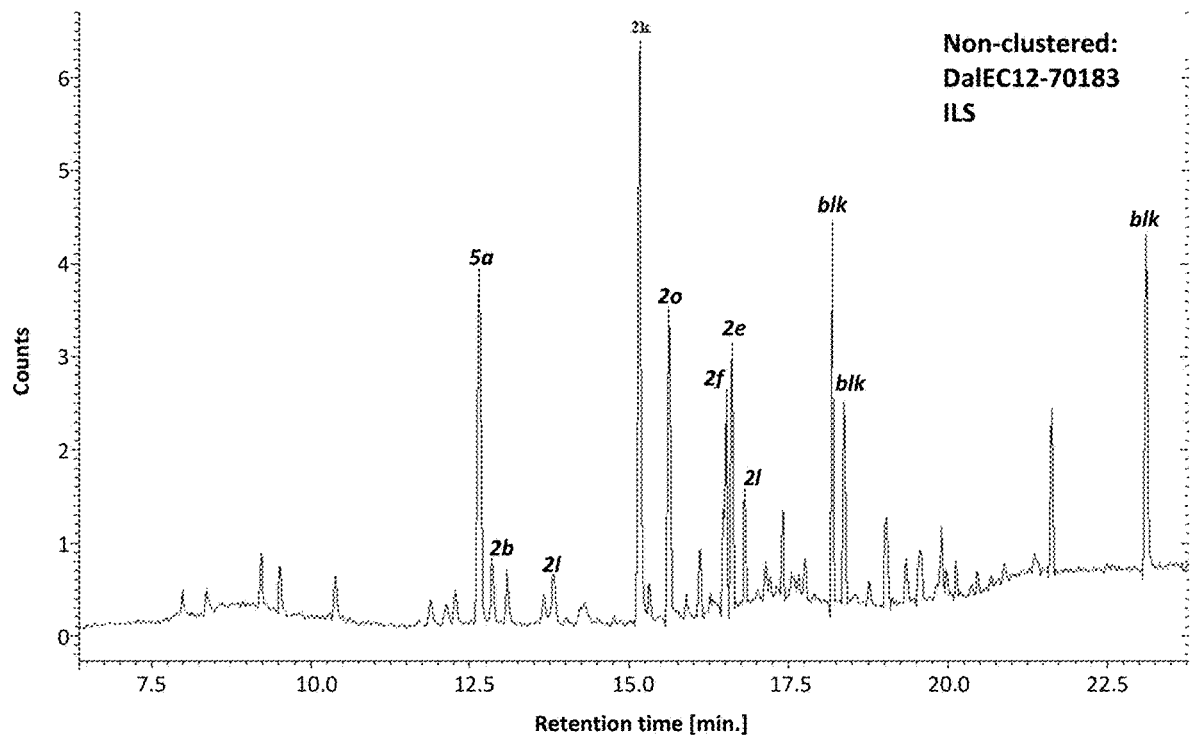

In contrast to most of the other endophyte TPS characterized, EC12-ILS produced only sesquiterpenes, with (−)-isoledene (5a) being the most abundant at 10.8% of the total peak area (Table 12 and FIG. 19B). Other terpenes were produced, including iso-longifolene (2k) and β-caryophyllene (2d) that accounted for 12.5% of total peak area. There have been other studies that reported the detection of isoledene in plants (see, e.g., Ouyang Z et al., *Revista Brasileira de Farmacognosia* [*Braz. J. Pharmacognosy*] 2012; 22(5):957-63; Sosa M E et al., *Biochem. Syst. Ecol.* 2012; 43:132-8; and Saranya J et al., *J. Essential Oil Bearing Plants* 2012; 15(2):283-7), and a putative isoledene synthase was predicted in the genome of *Eucalyptus grandis* (see, e.g., Myburg A A et al., "The genome of *Eucalyptus grandis,*" *Nature* 2014; 510(7505):356-62). However, EC12-ILS is the first isoledene synthase enzyme to be functionally characterized.

Potential Applications for Endophyte-Derived Monoterpenes and Sesquiterpenes

Next generation biofuels are expected to have high energy density and physicochemical properties compatible with current engine design, transportation systems, and/or storage infrastructure. Hydrocarbons derived from terpenes meet most of these criteria, as they are structurally similar to the compounds in petroleum distillate fuels and often have similar combustion properties (see, e.g., Edwards T et al., "Evaluation of combustion performance of alternative aviation fuels," *46th AIAA/ASME/SAE/ASEE Joint Propulsion Conference & Exhibit*, held on 25-28 Jul. 2010 in Nashville, Tenn., Art. No. AIAA 2010-7155 (21 pp.)). For example, hydrogenated pinene ($C_{10}$) dimers were reported to contain high volumetric energy similar to that of jet fuel JP-10 (see, e.g., Harvey B G et al., "High-density renewable fuels based on the selective dimerization of pinenes," *Energy Fuels* 2010; 24:267-73). The hydrogenated product of the sesquiterpene bisabolene ($C_{15}$) was shown to have better properties than D2 diesel, such as lower cloud point, a higher flash point, and a higher API gravity (see, e.g., Peralta-Yahya P P et al., *Nat. Commun.* 2011; 2: Art. No. 483 (8 pp.)).

Herein, the most abundant terpenes included pinenes and sesquiterpenes, such as guaiene, caryophyllene, chamigrene, gurjunene, and selinene. These terpenes are hydrocarbons or hydrocarbon-like compounds with a carbon content in the $C_{10}$-$C_{15}$ range, therefore being potential candidates for "drop-in" aviation fuels. Simultaneous satisfaction of combustion specifications and specifications for physical properties such as density, energy content, and viscosity often require blending of different types of hydrocarbons. The use of terpenes and terpene derivatives as blendstocks for renewable fuels for aviation and diesel applications has recently been discussed by Harvey B G et al. ("High-density renewable diesel and jet fuels prepared from multicyclic sesquiterpanes and a 1-hexene-derived synthetic paraffinic kerosene," *Energy Fuels* 2015; 29(4):2431-6). For instance, blending hydrogenated sesquiterpenes with synthetic branched paraffins could raise cetane numbers and reduce viscosity, thereby producing biosynthetic fuels that meet applicable jet and diesel specifications.

In addition to their potential use as biofuels, most of the terpenes reported herein are major components of essential oils used in the fragrance and flavoring industries (e.g., α-guaiene, β-chamigrene, α-gurjunene, etc.). Also, many have potential pharmaceutical applications, e.g., as an antitumor and anti-repression agent (see, e.g., Zhang Z et al., "Synergistic antitumor effect of α-pinene and β-pinene with paclitaxel against non-small-cell lung carcinoma (NSCLC)," *Drug Res. (Stuttg.)* 2015; 65(4):214-8; Chen W et al., "Anti-tumor effect of α-pinene on human hepatoma cell lines through inducing G2/M cell cycle arrest," *J. Pharmacol. Sci.* 2015; 127(3):332-8; and Guzmán-Gutiérrez S L et al., "Linalool and β-pinene exert their antidepressant-like activity through the monoaminergic pathway," *Life Sci.* 2015; 128:24-9). Caryophyllene, a sesquiterpene, is not only a promising high energy "drop-in" jet fuel but also has multiple potential pharmaceutical applications, such as anticancer activity, anti-inflammatory activity, life-span elongation, neuroprotection, insulin secretion moderation, acute and chronic pain attenuation, and/or alcohol dependency release characteristics (see, e.g., Nakano C et al., "Identification of the first bacterial monoterpene cyclase, a 1,8-cineole synthase, that catalyzes the direct conversion of geranyl diphosphate," *Chembiochem* 2011; 12(13):1988-91; Han L et al., "Trans-caryophyllene suppresses tumor necrosis factor (TNFα)-induced inflammation in human chondrocytes," *Eur. Food Res. Technol.* 2014; 239:1061-6; Rufino A T et al., "Evaluation of the anti-inflammatory, anti-catabolic and pro-anabolic effects of E-caryophyllene, myrcene and limonene in a cell model of osteoarthritis," *Eur. J. Pharmacol.* 2015; 750:141-50; Klauke A L et al., "The cannabinoid CB$_2$ receptor-selective phytocannabinoid beta-caryophyllene exerts analgesic effects in mouse models of inflammatory and neuropathic pain," *Eur. Neuropsychopharmacol.* 2014; 24(4):608-20; Pant A et al., "Beta-caryophyllene modulates expression of stress response genes and mediates longevity in *Caenorhabditis elegans*," *Exp. Gerontol.* 2014; 57:81-95; Liu H et al., "Neuroprotective effects of trans-caryophyllene against kainic acid induced seizure activity and oxidative stress in mice," *Neurochem. Res.* 2015; 40(1):118-23; Suijun W et al., "A role for trans-caryophyllene in the moderation of insulin secretion," *Biochem. Biophys. Res. Commun.* 2014; 444(4):451-4; Paula-Freire L I et al., "The oral administration of trans-caryophyllene attenuates acute and chronic pain in mice," *Phytomedicine* 2014; 21(3):356-62; and Al Mansouri S et al., "The cannabinoid receptor 2 agonist, β-caryophyllene, reduced voluntary alcohol intake and attenuated ethanol-induced place preference and sensitivity in mice," *Pharmacol. Biochem. Behav.* 2014; 124:260-8).

Conclusion

Previously, GC-MS was used to analyze the VOCs produced by four fungal endophytes (*Hypoxylon* sp. EC38, CI4A, CO27, and *D. eschscholzii* EC12) and hundreds of terpene compounds were detected (see, e.g., Ul-Hassan S R et al., Microbiology 2012; 158(Pt 2):465-73; Gladden J M et al., *Sandia Report No. SAND*2013-10094, 2013 (100 pp.); Banerjee D et al., "*Muscodor albus* MOW12 an Endophyte of *Piper nigrum* L. (Piperaceae) collected from north east India produces volatile antimicrobials," *Indian J. Microbiol.* 2014; 54(1):27-32; and Riyaz-Ul-Hassan S et al., "An endophytic *Nodulisporium* sp. from Central America producing volatile organic compounds with both biological and fuel potential," *J. Microbiol. Biotechnol.* 2013; 23(1):29-35). However, most of the TPS enzymes that synthesize these compounds have not been identified. Here, we leveraged an *E. coli* strain harboring a synthetic mevalonate pathway for enhanced terpene production as a synthetic biology platform to screen 26 putative TPSs from these four fungi.

TPSs were identified and characterized by a combination of genomic data mining, phylogenetic analysis, protein sequence alignment, rapid product extraction with SPME, and rapid chemical characterization with GC-MS. This approach avoided time-consuming and challenging conventional enzyme discovery routes, such as functional genomics library construction and screening, or biochemical purification of native enzymes, in addition to specific challenges for TPS enzymes, such as terpene compound purification and identification, and thereby establishes a valuable and rapid process for novel TPS discovery. Using this approach, we discovered 12 novel TPSs clustered into four homology groups that have potential uses in medicine and other industries, including the nascent biofuels sector (see, e.g., Lane J, "9 advanced molecules that could revolutionize jet and missile fuel," *Biofuels Digest*, Jun. 18, 2014 (4 pp.), available at biofuelsdigest.com/bdigest/2014/06/18/9-advanced-molecules-that-could-revolutionize-jet-and-missile-fuel/ (last accessed Feb. 15, 2016)).

Example 2: Metabolic Engineering *E. coli* to Reroute the Nitrogen Flux into Terpenes for Advanced Biofuels and Bioproducts Recent strategies for algae-based biofuels have primarily focused on biodiesel production by exploiting high algal lipid yields under nutrient stress conditions. However, under conditions supporting robust algal biomass accumulation, algal proteins typically comprise up to ~70% of the algae biomass. Therefore, economical utilization of algal biomass for production of multipurpose intermediate- to high-value bio-based products could promote scale-up of algae production and processing to commodity volumes. Terpenes are hydrocarbon and hydrocarbon-like compounds (e.g., compounds having a C:O ratio more than about 10:1) with high energy density, and are therefore promising candidates for value added bio-based chemicals and "drop-in" replacements for petroleum-based fuels.

In this Example, we demonstrate the feasibility of bioconversion of protein (e.g., using a synthetic amino acid mixture) into sesquiterpene, as well as bioconversion of algal protein hydrolysate into terpenes. To achieve this, the mevalonate pathway was reconstructed into an engineered *E. coli* YH40 with six different terpene synthases (TPSs). Strains containing various TPSs produced a spectrum of sesquiterpenes in minimal medium containing amino acids as the sole carbon source. Sesquiterpene production was optimized through three different regulation strategies, as described herein. The highest total terpene titer reached 166 mg/L, and was achieved by applying a strategy to minimize mevalonate accumulation in vivo. The highest yields of total terpene were produced under reduced IPTG induction level (0.25 mM), reduced induction temperature (25° C.), and elevated substrate concentration (20 g/L of amino acids (AAs)). The protein hydrolysate of a natural benthic algal polyculture was used as solo carbon source as well, in which the YH40-TPS strain yielded a reduced total terpene titer of about 26 mg/L due to the high salt concentration in the substrate.

This study demonstrates the feasibility of bioconversion of protein into terpenes, which are promising candidates for "drop-in" fuels in addition to various intermediate to high value bioproduct applications. The study also investigated the conversion of algal protein from waste-water derived polyculture algae biomass into various terpene compounds, which has the potential to improve the algal biofuel process feasibility through addition of high value-added products with process consolidation.

Introduction

The need for sustainable, domestically-produced replacements for petroleum has led to significant efforts for biofuels development (see, e.g., Jacobson M Z, "Review of solutions to global warming, air pollution, and energy security," *Energy Environ. Sci.* 2009; 2:148-73). Current carbon life cycle assessment suggests that production of biofuels from lignocellulosic and algae biomass provides up to ~50% greenhouse gas emission, as compared to petroleum (see, e.g., Subhadra B et al., "An integrated renewable energy park approach for algal biofuel production in United States," *Energy Policy* 2010; 38(9):4897-902; Davis R et al., "Techno-economic analysis of autotrophic microalgae for fuel production," *Appl. Energy* 2011; 88(10):3524-31; Jacobson M Z, *Energy Environ. Sci.* 2009; 2:148-73; and Scott S A et al., "Biodiesel from algae: challenges and prospects," *Curr. Opin. Biotechnol.* 2010; 21(3):277-86).

Recent strategies for algae-based biofuels have primarily focused on biodiesel production through exploiting high algal lipid yields under the nutrient stress conditions. However, nutrient stress significantly compromises the overall biomass quantity and subjects the culture to increased susceptibility to contamination and subsequent culture crashes (see, e.g., Adams C et al., "Understanding precision nitrogen stress to optimize the growth and lipid content tradeoff in oleaginous green microalgae," *Bioresour. Technol.* 2013; 131:188-94; Davis R W et al., "Multiplex fluorometric assessment of nutrient limitation as a strategy for enhanced lipid enrichment and harvesting of *Neochloris oleoabundans*," *Biotechnol. Bioeng.* 2012; 109(10):2503-12; and Sharma K K et al., "High lipid induction in microalgae for biodiesel production," *Energies* 2012; 5(5):1532-53).

Under conditions supporting robust algal biomass accumulation, proteins typically comprise up to ~70% of the ash-free dry weight of microalgae biomass (see, e.g., Becker E W, "Microalgae: biotechnology and microbiology," Cambridge University Press, Cambridge, UK, 1994 (293 pp.); Luque R et al., "Algal biofuels: the eternal promise?," *Energy Environ. Sci.* 2010; 3:254-7; and Singh J et al., "Commercialization potential of microalgae for biofuels production," *Renew. Sust. Energy Rev.* 2010; 14(9):2596-610). A significant volume of research has been pursued to convert algal lipids and carbohydrates to biodiesel (see, e.g., de la Cruz V et al., "Integrated synthesis of biodiesel, bioethanol, isobutene, and glycerol ethers from algae," *Ind. Eng. Chem. Res.* 2014; 53:14397-40; Martin M et al., "Design of an optimal process for enhanced production of bioethanol and biodiesel from algae oil via glycerol fermentation," *Appl. Energy* 2014; 135:108-14; and Sharma K K et al., *Energies* 2012; 5(5):1532-53), ethanol (see, e.g., Babujanarthanama R et al., "Simultaneous saccharification and fermentation of dilute acid pretreated red algae (*Gelidiella acerosa*) for bioethanol production," *Energy Sources A* 2014; 36(12):1305-14; Fasahati P et al., "Industrial-scale bioethanol production from brown algae: effects of pretreatment processes on plant economics," *Appl. Energy* 2015; 139:175-87; and Li K et al., "An overview of algae bioethanol production," *Int'l J. Energy Res.* 2014; 38(8):965-77), butanol (see, e.g., Anon, "Researchers convert algae to butanol," *Marine Pollution Bull.* 2011; 62(4):658), methane (see, e.g., Chen Y et al., "Inhibition of anaerobic digestion process: a review," *Bioresour. Technol.* 2008; 99(10):4044-64; and El-Mashad H M, "Biomethane and ethanol production potential of *Spirulina platensis* algae and enzymatically saccharified switchgrass," *Biochem. Eng. J.* 2015; 93:119-27), and isobutanol (see, e.g., Razeghifard R, "Algal biofuels," *Photosynth. Res.* 2013; 117(1-3):207-19).

Nonetheless, little has been reported regarding bioconversion of algal proteins. A recent work demonstrated the feasibility of converting algal protein to mixed short and medium chain fusel alcohols, such as isobutanol, 2-methyl- and 3-methy-butanol, as well as other potentially high value alcohols, including phenylethanol, acetoin, and butanediol (see, e.g., Huo Y X et al., "Conversion of proteins into biofuels by engineering nitrogen flux," *Nat. Biotechnol.* 2011; 29(4):346-51). These medium chain alcohols can present several benefits over ethanol, including >25% higher energy density, and dramatically lower hygroscopicity and corrosivity (see, e.g., Peralta-Yahya P P et al., "Microbial engineering for the production of advanced biofuels," *Nature* 2012; 488(7411):320-8). Despite the distinct advantages of these medium chain alcohols, the high oxygen content of these molecules could result in incompatibility with current engine infrastructure and with "fit for purpose" properties as "drop-in" fuels.

Isoprenoids, also referred to terpenes, are a group of natural products with over 55,000 structurally distinct chemical compounds. Compared to short and medium chain alcohols, these hydrocarbon and hydrocarbon-like compounds (e.g., compounds having a C:O ratio of greater than about 10:1), including monoterpenes (e.g., $C_{10}$ compounds), sesquiterpene (e.g., $C_{15}$ compounds), diterpene (e.g., $C_{20}$ compounds), and their derivatives, not only have various biological functionalities but also contain higher overall energy density. In particular the sesquiterpene caryophyllene has been deemed to be among the top three most promising increased energy density jet fuel compounds (see, e.g., Nakano C et al., "Identification of the first bacterial monoterpene cyclase, a 1,8-cineole synthase, that catalyzes the direct conversion of geranyl diphosphate," *Chembiochem* 2011; 12(13):1988-91). Typically biologically derived fuel molecules have very high oxygen content (e.g., a ratio of C:O of up to 2:1 for ethanol) and can introduce significant fuel cost and materials properties hurdles for blending into the petroleum-derived fuels infrastructure (see, e.g., U.S. Department of Energy, "National algal biofuels technology roadmap," May 2010 (140 pp.), available at www1.eere.energy.gov/bioenergy/pdfs/algal_biofuels_roadmap.pdf (last accessed Feb. 15, 2016). The near-zero oxygen content of terpene compounds, in addition to their high energy density, make them a particularly attractive candidate as "drop-in" fuel candidates for ground-based and aviation fuels.

Terpenes also have a variety of higher value chemical applications, e.g., as fragrances, flavoring agents, anti-fungal, and anti-viral, insect repellants, and pharmaceutical lead compounds (see, e.g., Han L et al., "Trans-caryophyllene suppresses tumor necrosis factor (TNFα)-induced inflammation in human chondrocytes," *Eur. Food Res. Technol.* 2014; 239:1061-6; Klauke A L et al., "The cannabinoid $CB_2$ receptor-selective phytocannabinoid beta-caryophyllene exerts analgesic effects in mouse models of inflammatory and neuropathic pain," *Eur. Neuropsychopharmacol.* 2014; 24(4):608-20; Liu H et al., "Neuroprotective effects of trans-caryophyllene against kainic acid induced seizure activity and oxidative stress in mice," *Neurochem. Res.*

2015; 40(1):118-23; Paula-Freire L I et al., "The oral administration of trans-caryophyllene attenuates acute and chronic pain in mice," *Phytomedicine* 2014; 21(3):356-62; Rufino A T et al., "Evaluation of the anti-inflammatory, anti-catabolic and pro-anabolic effects of E-caryophyllene, myrcene and limonene in a cell model of osteoarthritis," *Eur. J. Pharmacol.* 2015; 750:141-50; and Singh R, "Facts, growth, and opportunities in industrial biotechnology," *Org. Process Res. Dev.* 2011; 15(1):175-9). However, few studies have reported means for conversion of protein/algal protein to terpene compounds. In this study, we firstly demonstrate production of terpene compounds from synthetic amino acid mixture with an engineered *E. coli* strain harboring the reconstructed terpene biosynthesis pathway. The fermentation parameters were partially optimized to improve the terpene yield. A high protein biomass cultivated from wastewater in an Algal Turf Scrubber™ system (see, e.g., Adey W H et al., "Algal turf scrubbing: cleaning surface waters with solar energy while producing a biofuel," *BioScience* 2011; 61(6):434-41) was pretreated and investigated as sole carbon source for the terpene production with the engineered *E. coli* strain. The production of terpene as a potential "drop-in" fuel compound through the utilization of one of major biochemical components of algae biomass, algal protein, and the addition of high energy density fuel compounds with "fit for purpose" properties could foreseeably diminish the process cost and improve the feasibility of algal biofuel.

Strains and Plasmids

The mutant *E. coli* strain YH40 (BW25113/F' [traD36, proAB+, lacI$^q$ ZΔM15] ΔglnAΔgdhAΔluxSΔlsrA) was generously provided by Professor James C. Liao from University of California, Los Angeles (UCLA) (see, e.g., Huo Y X et al., *Nat. Biotechnol.* 2011; 29(4):346-51). Plasmids pJBEI3122, pBbE1a, and pBbE2k were provided courtesy of Dr. Jorge Alonso-Gutierrez from the Joint BioEnergy Institute (JBEI). Plasmid pJBEI3122 contained the mevalonate pathway genes encoding seven enzymes (see, e.g., Alonso-Gutierrez J et al., "Metabolic engineering of *Escherichia coli* for limonene and perillyl alcohol production," *Metab. Eng.* 2013; 19:33-41): acetoacetyl-CoA synthase (AtoB), HMG-CoA synthase (HMGS), HMG-CoA reductase (HMGR), mevalonate kinase (MK), phosphomevalonate kinase (PMK), phosphomevalonate decarboxylase (PMD), and isopentenyl diphosphate isomerase (IDI), except the geranyl pyrophosphate synthase (GPPS) and terpene synthase (TPS).

All six selected terpene synthase gene and the GPPS gene (GenBank: AF513112.1, GPPS$_{Ag}$) from *Abies grandis* with the chloroplast signal peptide truncated were codon optimized based on *E. coli* codon bias. The Ribosome Binding Site (RBS) for each terpene synthase gene was created and optimized by online RBS calculator developed by the Salis lab (available at salislab.net). All the gene sequences containing RBS site and restriction enzyme cutting sites were synthesized by Genscript.

Reconstruction of the Terpene Synthetic Pathway into *E. coli* Strain YH40

Each synthesized terpene synthase (TPS) and GPPS$_{Ag}$ ORF including the sequences of corresponding ribosome binding site were sub-cloned into plasmids pBbE1a and pBbE2K, respectively, under EcoRI and BamHI cutting sites to obtain vectors pBbE1a-TPS and pBbE2K-GPPS$_{Ag}$, as described before (see, e.g., Gladden J M et al., "Tailoring next-generation biofuels and their combustion in next-generation engines," *Sandia Report No. SAND*2013-10094, 2013 (100 pp.)). Plasmids pJBEI3122, pBbE1a-TPS, and pBbE2k-GPPS$_{Ag}$ were co-transformed into expression host YH40 for terpene production. Plasmids pJBEI3122 and pBbE2k-GPPS$_{Ag}$ were co-transformed into strain YH40 for use as negative controls.

The gene GPPS$_{Ag}$ was amplified (Primer 1: 5-GTG TGG AAT TGT GAG CGG ATA AC-3 (SEQ ID NO:1), Primer-2: 5-GGA TCC CTC GAG TCA ATT TTG TCT GAA TGC CAC G-3 (SEQ ID NO:2)) from the vector pBbE2K-GPPS$_{Ag}$ and subcloned into plasmid pJBEI3122, right downstream of gene isoprenyldiphosphate isomerase (idi), under the restriction cutting site BglII and XhoI, to obtain plasmid pJBEI3122-GPPS$_{Ag}$. Additionally, the amplicon of gene GPPS$_{Ag}$ was sub-cloned, under the EcoRI cutting site, into plasmid pBbE1a-TPS to obtain plasmid pBbE1a-GPPS$_{Ag}$-TPS. The right orientation of gene GPPS$_{Ag}$ was confirmed by diagnostic PCR using primer 3 (5-CAT CCG GCT CGT ATA ATG TGT GG-3 (SEQ ID NO:3)) and primer 4 (5-GCTC CTC GGT TCC TCC AAC AAG-3 (SEQ ID NO:4)). Plasmids pJBEI3122-GPPS$_{Ag}$ and pBbE1a-TPS, as well as pJBEI3122 and pBbE1a-GPPS$_{Ag}$-TPS, were co-transformed into both *E. coli* strain DH1 and YH40 for terpene production.

Production of Terpene Compounds by Engineered *E. coli* Strains

Transformants containing each terpene synthase were cultured in 15 ml of LB medium with 100m/L of ampicillin, 34 μg/L of chloramphenicol, and 25 μg/L of kanamycin. Cultures were incubated at 37° C. at 220 rpm overnight. Then, 15 ml of the overnight culture was centrifuged. Cell pellets were re-suspended twice into 4 ml of 1×M9 medium (see, e.g., Wu W, "Fuel ethanol production using novel carbon sources and fermentation medium optimization with response surface methodology," *Int. J. Agric. Biol. Eng.* 2013; 6(2):42-53) and inoculated into 30 ml of 1×M9 containing 20 g/L of amino acid mixture (Sigma-Aldrich Corp., St. Louis, Mo.) as the sole carbon source. The culture was incubated at 37° C., 220 rpm until the OD$_{600nm}$ reached 0.8, and then terpene production was induced by adding isopropyl-β-D-1-thiogalactopyranoside (IPTG) at the final concentration 1 mM. The flasks were cap-sealed and cultured for another 72 hours at 30° C., 200 rpm to allow terpene accumulation.

Terpene Production from a Synthetic Consortium of *E. coli* Strains (YH40-TPS)

ATS™ biomass samples were pretreated according to protocols from the National Renewable Energy Laboratories and hydrolyzed with 2 mg/mL Pronase® (Promega Corp., Madison, Wis.), following the manufacturer's protocol. The pretreated and hydrolyzed algal biomass was sterilized through filtration. *E. coli* strain YH40 containing the terpene biosynthesis pathway was cultured into 15 ml of LB medium, as described above. Overnight cultures were centrifuged, and cell pellets were re-suspended into 4 ml of pretreated ATS™ biomass hydrolysate. Re-suspended YH40-TPS were inoculated into the algal hydrolysate at a final concentration of 10% (v/v). Cultures were incubated at 37° C., 220 rpm and induced with 0.25 mM IPTG once the OD reached 0.8. Flasks were cap-sealed and cultured for another 72 hours at 25° C., 180 rpm for terpene production. Analytical samples were taken at the initial point of fermentation and at the end point of fermentation. Concentrations of total carbohydrate and amino acids were determined according to the established colorimetric protocols.

Terpene Analysis by GC-MS and Metabolite Analysis by LC-MS

Terpene compounds in the headspace were extracted with a preconditioned solid-phase micro-extraction (SPME) syringe consisting of 50/30 divinylbenzene/carboxen on polydimethylsiloxane on a Stable Flex fiber as described previously (see, e.g., Gladden J M et al., "Tailoring next-generation biofuels and their combustion in next-generation engines," Sandia Report No. SAND2013-10094, 2013 (100 pp.)). The SPME fiber was inserted into the headspace of each culture flask for 30 minutes to absorb the terpene compounds.

Volatile terpene compounds absorbed to the SPME fiber were analyzed by GC-MS (Varian 3800) containing a 30 mm×0.25 mm i.d. DB wax capillary column with a film thickness of 0.25 µm, as described in a previous study (see, e.g., Gladden J M et al., Sandia Report No. SAND2013-10094, 2013 (100 pp.)). The column was temperature programmed as follows: 60° C. for 4 min., increasing to 120° C. at 10° C./min. and holding for 5 min., then increasing to 220° C. at 20° C./min. and holding for 2 min., and finally increasing to 250° C. at 50° C./min. and holding for 4 min. The carrier gas was ultra-high purity helium at a constant flow rate of 1 ml/min. A two-minute injection time was used to desorb the terpene compounds from the sampling fiber into a splitless injection (220° C.) of the chromatograph coupled with a Saturn 2000 ion trap mass spectrometer. MSD parameters included an EI at 70 eV, a mass range at 30-500 Da, and a scan speed at 2 scans/sec. Spectral components were searched against the NIST 2011 mass spectral library, and only components with mass spectra match factors >85% were reported as tentatively identified compounds. Compounds with peak areas >1% of the total peak area in the chromatogram are reported herein.

Twenty-four hours after induction, cultures were centrifuged at 14,000 rpm for 10 min. and rinsed with cold DI water three times. Cell pellets were resuspended with 1 ml of methanol and placed in a bead beater apparatus for two rounds of cell disruption at 4° C. to completely break down the cells. The mixture was centrifuged, and the supernatant were transferred to new 2 ml vials. 750 µl of DI water was added into sediment lysate and vortexed vigorously at 4° C. The supernatant was then combined with methanol extract, the methanol in the mixture was blow off by $N_2$ gas, and the leftover mixture was filtrated through a 3 KDa MWCO spin column (Millipore). The metabolites were analyzed using LC-MS according to the method of Rodriguez S et al., "Production and quantification of sesquiterpenes in Saccharomyces cerevisiae, including extraction, detection and quantification of terpene products and key related metabolites," Nat. Protoc. 2014; 9(8):1980-96.

Estimation of Terpene Titer in Cultures

Serial dilutions of pinene, limonene, and caryophyllene were added into the same amount of culture media, with inoculum of negative control strain to simulate the liquid-gas phase balance of terpene compounds produced in the culture. The flasks were sealed and incubated under same conditions as terpene formation strains. Terpene compounds in the headspace were collected by SPME, as described above. The adsorption time was carefully optimized to ensure that fibers were not saturated and that amounts of absorbed terpene compounds were in linearly correlated to the standard curve. The same adsorption time was applied for all the cultures. Concentrations of terpene compounds produced in the culture were calculated by referring to the standard curve.

Terpene Production from Amino Acids Through Mevalonate Pathway Reconstruction

In nature, isoprenoids or terpenes are synthesized either by the mevalonate pathway (MEV) or by the deoxy-D-xylulose 5-phosphate pathway (DXP) in bacteria, fungi, plants, and animals (see, e.g., Anthony J R et al., "Optimization of the mevalonate-based isoprenoid biosynthetic pathway in Escherichia coli for production of the anti-malarial drug precursor amorpha-4,11-diene," Metab. Eng. 2009; 11(1):13-9; Maury J et al., "Reconstruction of a bacterial isoprenoid biosynthetic pathway in Saccharomyces cerevisiae," FEBS Lett. 2008; 582(29):4032-8; Miziorko H M, "Enzymes of the mevalonate pathway of isoprenoid biosynthesis," Arch. Biochem. Biophys. 2011; 505(2):131-43; Pitera D J et al., "Balancing a heterologous mevalonate pathway for improved isoprenoid production in Escherichia coli," Metab. Eng. 2007; 9(2):193-207; Amslinger S et al., "Biosynthesis of terpenes: preparation of (E)-1-hydroxy-2-methyl-but-2-enyl 4-diphosphate, an intermediate of the deoxyxylulose phosphate pathway," J. Org. Chem. 2002; 67(13):4590-4; Rohdich F et al., "Studies on the nonmevalonate terpene biosynthetic pathway: metabolic role of IspH (LytB) protein," Proc. Nat'l Acad. Sci. USA 2002; 99(3):1158-63; and Rohdich F et al., "Deoxyxylulose phosphate pathway of isoprenoid biosynthesis: discovery and function of ispDEFGH genes and their cognate enzymes," Pure Appl. Chem. 2003; 75(2-3):393-405).

In the mevalonate pathway, terpene biosynthesis is initiated by the condensation of two acetyl-CoA to produce acetoacetyl-CoA, in which acetyl-CoA is a critical niche in the central metabolism. Amino acids can be metabolized to form acetyl-CoA through pyruvate (Ala, Ser, Thr, Trp, Gly, Cys), through acetylacetate-CoA (Phe, Tyr, Trp, Lys, Leu), or through the TCA cycle (Pro Arg, His, Thr, Val, Ile, Met, Phe, Tyr). Both pathways share a common node: acetyl-CoA. Thus, it may be possible to produce terpenes from protein lysate through metabolic engineering of these pathways.

In this Example, our synthetic biology strategy aimed to convert amino acids to high energy density and value-added terpene products through reconstruction of the terpene biosynthesis pathway into an E. coli chassis strain, YH40 (see, e.g., Huo Y X et al., Nat. Biotechnol. 2011; 29(4):346-51). The enzymes in the mevalonate pathway diverted the metabolic flux from acetyl-CoA to the dimethylallyl pyrophosphate (DMAPP) and isopentenyl pyrophosphate (IPP) formation and further catalyzed by GPPS and TPS to produce terpene. As described herein, twelve novel terpene synthases were discovered through a synthetic biology platform.

Of the 12 novel terpene synthases, six were selected and sub-cloned downstream of the mevalonate pathway with truncated GPPS$_{Ag}$ (Abies grandis geranyl diphosphate synthase (GPPS2) mRNA, GenBank No. AF513112.1) to demonstrate terpene production from protein. These six terpene synthases included HypCI4A-6706 (SEQ ID NO:31, cluster 3, a caryophyllene synthase), HypCI4A-322581 (SEQ ID NO:41, cluster 4, a chamigrene and pinene synthase), HypEC38-80361 (SEQ ID NO:45, cluster 4, a gurjunene and pinene synthase), DalEC12-315006 (SEQ ID NO:54, cluster 5, a gurnunene synthase), DalEC12-24646 (SEQ ID NO:62, non-clustered, a selinene synthase), and DalEC12-70183 (SEQ ID NO:64, non-clustered, an isoledene synthase).

Both monoterpene and sesquiterpene were detected from the culture of strains containing these six TPSs when grown on M9 medium including an amino acid mixture as the sole carbon source. GC analyses are provided in Table 13-18 and FIGS. 28-33.

TABLE 13

GC peak analysis for YH40-HypCI4A-322581 on amino acids

| Compound (ID No. in FIG. 28) | Retention time (min.) | % Total peak area | Match (%) | R-match (%) |
|---|---|---|---|---|
| β-chamigrene (f) | 18.518 | 43.135 | 89.5 | 91.4 |
| limonene (b) | 8.777 | 3.145 | 92.3 | 92.5 |
| β-pinene (a) | 8.067 | 2.518 | 94.4 | 94.7 |
| eremophila-1(10),11-diene (g) | 18.663 | 1.051 | 94.2 | 95.8 |
| p-cymene (d) | 10.018 | 0.691 | 95.5 | 97.5 |
| τ-terpinene (c) | 9.581 | 0.469 | 89.1 | 95.6 |
| 4-methyl-3-(1-methylethylidene)-1-cyclohexene (e) | 10.203 | 0.395 | 92.9 | 95.9 |

TABLE 14

GC peak analysis for YH40-DalEC12-315006 on amino acids

| Compound (ID No. in FIG. 29) | Retention time (min.) | % Total peak area | Match (%) | R-match (%) |
|---|---|---|---|---|
| limonene (b) | 8.759 | 17.701 | 91.5 | 91.6 |
| caryophyllene (l) | 17.319 | 2.768 | 95.2 | 96.1 |
| β-chamigrene (f) | 18.547 | 1.82 | 88.9 | 90.1 |
| (+)-valencene (m) | 18.701 | 1.508 | 95.2 | 96.1 |
| butylated hydroxytoluene (n) | 20.121 | 1.303 | 91.3 | 92.6 |
| β-pinene (a) | 8.038 | 0.971 | 89.2 | 93.8 |
| 1R-α-pinene (j) | 5.428 | 0.927 | 93.2 | 96.9 |
| ethyl propanoate (i) | 4.26 | 0.86 | 88.7 | 92.2 |
| 1,3,5-cycloheptatriene (k) | 5.879 | 0.38 | 86.4 | 93.8 |

TABLE 15

GC peak analysis for YH40-DalEC12-70183 on amino acids

| Compound (ID No. in FIG. 30) | Retention time (min.) | % Total peak area | Match (%) | R-match (%) |
|---|---|---|---|---|
| 1R,4R,7R,11R-1,3,4,7-tetramethyltricyclo[5.3.1.0(4,11)]undec-2-ene (x) | 15.396 | 6.781 | 84.2 | 86.6 |
| neoisolongifolene (s) | 12.848 | 4.874 | 89.6 | 90.5 |
| β-caryophyllene (l) | 17.321 | 2.008 | 94.5 | 95.5 |
| β-chamigrene (f) | 18.551 | 1.345 | 89.9 | 90.8 |
| thujopsene-I3 (r) | 14.06 | 1.031 | 88.5 | 90 |
| cedrene-V6 (t) | 13.054 | 0.935 | 87.1 | 88.4 |
| globulol (a3) | 20.527 | 0.825 | 71.6 | 78.3 |
| 6-methyl-2,4-di-tert-butyl-phenol (a2) | 20.125 | 0.823 | 91.8 | 93.2 |
| 1-(allyloxy)-4-tert-butylbenzene (u) | 13.297 | 0.792 | 80.9 | 87.5 |
| α-gurjunene (w) | 14.523 | 0.735 | 77.8 | 82.7 |
| β-caryophyllene (l) | 17.625 | 0.712 | 90.1 | 95.1 |
| β-caryophyllene (l) | 15.953 | 0.66 | 83.3 | 86.1 |
| isolongifolene-5-ol (q) | 10.505 | 0.571 | 81.2 | 83.6 |
| β-neoclovene (v) | 13.899 | 0.508 | 87.5 | 89.9 |
| cis-β-ocimene (o) | 9.586 | 0.505 | 94 | 96.7 |
| thujopsene-I3 (r) | 12.439 | 0.483 | 88.5 | 90.5 |
| 2,4-di-tert-butylphenol (a4) | 23.165 | 0.467 | 90.3 | 93.2 |
| 1R-α-pinene (i) | 9.284 | 0.422 | 91.6 | 96.2 |
| τ-gurjunene (y) | 15.594 | 0.333 | 85.6 | 88.5 |

TABLE 15-continued

GC peak analysis for YH40-DalEC12-70183 on amino acids

| Compound (ID No. in FIG. 30) | Retention time (min.) | % Total peak area | Match (%) | R-match (%) |
|---|---|---|---|---|
| (+)-valencene (m) | 18.704 | 0.327 | 93 | 94 |
| β-pinene (a) | 8.036 | 0.277 | 90.3 | 95.9 |
| geranyl acetate (a1) | 18.892 | 0.228 | 85.9 | 92.5 |
| (+)-longifolene (z) | 16.312 | 0.195 | 83.4 | 87.8 |

TABLE 16

GC peak analysis for YH40-HypEC38-80361 on amino acids

| Compound (ID No. in FIG. 31) | Retention time (min.) | % Total peak area | Match (%) | R-match (%) |
|---|---|---|---|---|
| β-chamigrene (f) | 18.543 | 0.832 | 89.2 | 90.4 |
| β-caryophyllene (l) | 17.315 | 0.464 | 93.2 | 93.5 |
| (+)-valencene (m) | 18.7 | 0.382 | 93.1 | 94.5 |
| 2,4-di-tert-butylphenol (a4) | 23.157 | 0.28 | 87.8 | 91 |
| limonene (b) | 8.764 | 0.097 | 83.1 | 90.6 |

TABLE 17

GC peak analysis for YH40-DalEC12-24646 on amino acids

| Compound (ID No. in FIG. 32) | Retention time (min.) | % Total peak area | Match (%) | R-match (%) |
|---|---|---|---|---|
| τ-gurjunene (y) | 18.111 | 17.055 | 89.5 | 89.6 |
| α-gurjunene (a5) | 17.145 | 2.29 | 90.9 | 91.2 |
| τ-elemene (a6) | 18.853 | 1.557 | 91.9 | 92.4 |
| β-pinene (a) | 8.054 | 1.482 | 94.8 | 95.4 |
| cis-β-ocimene (o) | 9.596 | 1.359 | 96.3 | 96.7 |
| 1S-α-pinene (i) | 9.295 | 0.943 | 93.7 | 96.5 |
| β-chamigrene (f) | 18.547 | 0.863 | 89.2 | 90.6 |
| α-gurjunene (a5) | 17.891 | 0.842 | 92.1 | 94.4 |
| α-gurjunene (a5) | 17.589 | 0.66 | 93.7 | 95.7 |
| butylated hydroxytoluene (n) | 20.119 | 0.435 | 89.8 | 92.2 |
| 2,4-di-tert-butylphenol (a4) | 23.161 | 0.416 | 92.2 | 94.6 |
| τ-gurjunene (y) | 17.459 | 0.352 | 91.3 | 94.3 |

TABLE 18

GC peak analysis for YH40-HypCI4A-6706 on Amino Acids

| Compound (ID No. in FIG. 33) | Retention time (min.) | % Total peak area | Match (%) | R-match (%) |
|---|---|---|---|---|
| α-gurjunene (a5) | 14.264 | 12.082 | 88.2 | 89.3 |
| caryophyllene-(I1) (b1) | 14.815 | 10.418 | 88.1 | 88.8 |
| longifolene-(V4) (z) | 14.554 | 8.853 | 90.8 | 91.5 |
| (−)-α-gurjunene (a5) | 15.664 | 4.076 | 94.2 | 94.7 |
| β-maaliene (a7) | 12.764 | 3.763 | 88.2 | 88.8 |
| (−)-alloaromadendrene (b3) | 17.283 | 3.654 | 92.8 | 93.7 |
| β-caryophyllene (l) | 15.228 | 3.601 | 93.9 | 94.7 |
| 2-isopropenyl-4a,8-dimethyl-1,2,3,4,4a,5,6,7-octahydronaphthalene (a8) | 13.354 | 3.387 | 90 | 90.3 |
| α-selinene (b5) | 22.629 | 3.092 | 89 | 91.1 |
| α-gurjunene (a5) | 12.494 | 2.601 | 89.2 | 90 |
| β-pinene (a) | 8.061 | 2.294 | 95 | 95.7 |

TABLE 18-continued

GC peak analysis for YH40-HypCI4A-6706 on Amino Acids

| Compound (ID No. in FIG. 33) | Retention time (min.) | % Total peak area | Match (%) | R-match (%) |
|---|---|---|---|---|
| α-selinene (b5) | 18.973 | 2.214 | 90.7 | 92.8 |
| (+)-longifolene (z) | 15.353 | 2.111 | 80.8 | 81.7 |
| 5β,7β-H,10α-eudesm-11-en-1α-ol (b7) | 19.986 | 1.906 | 85.3 | 87 |
| 2-tridecanone (b6) | 19.294 | 1.702 | 92.4 | 93.7 |
| β-chamigrene (f) | 18.508 | 1.272 | 89.8 | 90.2 |
| thujopsene-(I2) (a9) | 13.662 | 1.236 | 88.6 | 91 |
| (+)-valencene (m) | 18.66 | 1.23 | 94.7 | 95.8 |
| limonene (c) | 8.773 | 1.22 | 91.8 | 93 |
| (−)-alloaromadendrene (b3) | 17.469 | 1.191 | 92.9 | 94.1 |
| thujopsene-(I2) (a9) | 16.184 | 1.163 | 83.5 | 85.3 |
| thujopsene-I3 (r) | 12.413 | 0.954 | 89.5 | 90.9 |
| α-humulene (b4) | 18.176 | 0.835 | 89.8 | 95.9 |
| β-caryophyllene (l) | 18.256 | 0.787 | 93.2 | 95.3 |
| 1S-α-pinene (i) | 9.294 | 0.749 | 91.6 | 96.9 |
| (+)-valencene (m) | 17.019 | 0.661 | 88.6 | 93 |
| 1,2,3,6-tetramethylbicyclo[2.2.2]octa-2,5-diene (b2) | 16.011 | 0.576 | 78.5 | 89.3 |
| β-cis-ocimene (o) | 9.594 | 0.436 | 90.6 | 95.9 |
| (−)-alloaromadendrene (b3) | 16.934 | 0.361 | 86.6 | 92.3 |
| 1R-α-pinene (j) | 5.458 | 0.272 | 84.6 | 95.6 |

No terpene compounds were detected in the negative control strains. Among the six TPSs, five of them produced sesquiterpene as the most abundant compounds in the culture headspace, except TPS-315006 (YH40-DalEC12-315006) that produced limonene (17.70% of total peak area) as the major product along with minor amounts of other sesquiterpene compounds: caryophyllene, chamigrene, valencene, pinene, and others. Surprisingly, this TPS was identified as a τ-gurjunene synthase (see, e.g., Gladden J M et al., Sandia Report No. SAND2013-10094, 2013 (100 pp.)), which produced τ-gurjunene as the most abundant compound (accounting for 58.03% of total peak area) when the strain DH1-TPS-315006 grew on EZ-rich medium; and no obvious limonene was detected other than pinene. Compared to the host E. coli DH1 strain, the YH40 strain is a derivative of E. coli BW25113 and was specifically engineered to boost amino acid utilization (see, e.g., Huo Y X et al., Nat. Biotechnol. 2011; 29(4):346-51).

The YH40 strains containing TPS-70183 and TPS-6706 produced the widest spectrum of terpene compounds, as compared to the other four TPSs. More than 15 terpene compounds were detected from cultures of each strain. The terpene compounds produced in the order of abundance included the following: 1R,4R,7R,11R-1,3,4,7-tetramethyltricyclo[5.3.1.0(4,11)]undec-2-ene (6.8%), neoisolongifolene (4.9%), β-caryophyllene (2.0%), β-chamigrene (1.35%), and thujopsene-I3(1.0%). By comparing the substrate dependence of the strain containing TPS-70183, isoledene was the most abundant compound produced from glucose as the carbon source, but this compound was not detected from a culture with amino acids. Instead, 1R,4R,7R,11R-1,3,4,7-tetramethyltricyclo [5.3.1.0(4,11)]undec-2-ene (6.8%) was the major terpene product. Additionally, β-chamigrene and thujopsene-I3 were detected, which wasn't produced using a glucose-based fermentation broth.

Different carbon sources can provide different products, even when the same TPS is employed. In one instance, the product profile difference between two different carbon sources indicates that TPSs in two strains grown on two different media can have different catalytic reaction mechanisms. The variation in the terpene profile was also observed for TPS-6706 and other terpene synthases, in which strains incubated with an amino acid-based medium instead of glucose. TPS-6706 was identified as caryophyllene synthase and yielded caryophyllene (40% of total peak area) as the most abundant compound when the strain was grown on glucose. However, α-gurjunene was produced as the most abundant terpene compound (12.08% of total peak area) when grown on amino acids, followed by caryophyllene (10.42% of total peak area). Similar to DH1-6706 grown on glucose, YH40-6706 produced multiple sesquiterpene compounds, as well as several monoterpene compounds. Compared to the caryophyllene synthase isolated from cotton (see, e.g., Huang X et al., "Identification and characterization of (E)-β-caryophyllene synthase and α/β-pinene synthase potentially involved in constitutive and herbivore-induced terpene formation in cotton," Plant Physiol. Biochem. 2013; 73:302-8), which yielded a small number of sesquiterpenes, the caryophyllene synthases in this study produced more than 20 sesquiterpene compounds, as well as monoterpene compounds.

TPS-322581 was identified as chamigrene synthase, which produced chamigrene as the major product when grown on glucose. Similarly, the strain YH40-322581 produced chamigrene as the most abundant terpene (43% of total peak area) when cultured on amino acids. Besides chamigrene, the additional monoterpenes limonene and pinene were also detected but with abundance less than 3.2% of total peak area. Compared to TPS-6706, this enzyme tends to produce a single sesquiterpene compound, suggesting its distinct catalytic mechanism from TPS-6706.

For TPS-80361 the three most abundant terpene compounds were β-chamigrene, β-caryophyllene, and (+)-valencene, indicating the enzyme is a sesquiterpene synthase. Similar differences in the terpene profile were observed for this enzyme as well. TPS-80361 was determined to be a α-gurjunene synthase, which produced α-gurjunene as a major product from glucose. Various monoterpenes were present in less abundant amounts, where such monoterpenes included pinene, limonene, and its isomers. When grown on amino acids, however, the strain produced three major sesquiterpene compounds mentioned above and monoterpenes were barely detected.

TPS-24646 was identified as α-selinene synthase, which produced α-selinene (50.7% of total peak area) as the most abundant compound from glucose. However, when cultured on protein as the sole carbon source, gurjunene was detected as the major product (21.2% of total peak area). Besides gurjunene, β-chamigrene and other monoterpenes (e.g., such as elemene, pinene and ocimene) were also detected in the headspace of the culture, which is similar to the terpene profile from glucose.

Optimization of Terpene Production Through Different Metabolic Flux Regulations

Figure 24:
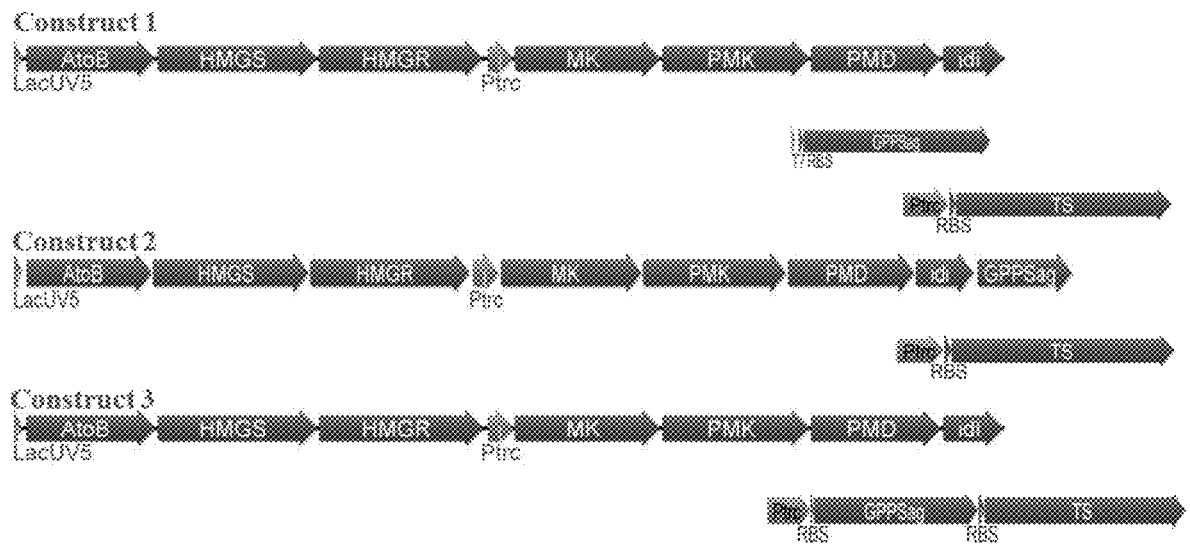
FIG. 24 shows an exemplary approach for optimization of terpene production through different pathway enzyme regulation strategies. Provided are schematics of Construct 1: GPPS and terpene synthase (TS) were expressed in separate plasmids under strong promoters, mevalonate pathway enzymes were expressed under medium strength promoter LacUV5 and strong promoter Ptrc, respectively, to optimize flux to GGP; Construct 2: mevalonate pathway enzymes and GPPS$_{Ag}$ were expressed under medium strength promoter LacUV5 and strong promoter Ptrc, respectively, to optimize flux to GGP, TPS was regulated by a strong promoter T7; and Construct 3: GPPS$_{Ag}$ and TPS were tandem expressed under a strong promoter Ptrc, mevalonate pathway enzymes were expressed under medium strength promoter LacUV5 and strong promoter Ptrc, respectively, to optimize flux to GGP.

TPS-322581 (a chamigrene synthase) was chosen as an example for metabolic flux optimization since this enzyme produces chamigrene as the sole sesquiterpene compound. To achieve maximal metabolic flux for terpene production, three regulation strategies were designed and constructed, as shown in FIG. 24. In the first construct (construct 1 in FIG. 24), all mevalonate pathway enzymes were cloned into one vector pJBEI3122 under two promoters with different strength. The first three enzymes (AtoB, HMGS, and HMGR) were cloned under a medium strength promoter lacUV5, whereas the last four enzymes (MK, PMK, PMD, and idi) were expressed downstream of a strong promoter Ptrc to obtain maximal metabolic flux to GPPS. The signal peptide (truncated GPPS$_{Ag}$) and chamigrene synthase (TS) were expressed into two separate plasmids under strong promoters, T7 and Ptrc, respectively, to generate a large metabolic flux driving force toward the final products. These three plasmids were co-transformed into strain YH40 as an engineered host for terpene production.

In the second construct (construct 2 in FIG. 24), the GPPS$_{Ag}$ peptide was cloned downstream of the enzyme idi under the Ptrc promoter in the plasmid pJBEI3122 to achieve the homologous expression of the intermediate pathway enzymes, while the chamigrene synthase was expressed in a separate plasmid under the strong promoter Ptrc. Both plasmids were co-transformed into strain YH40.

In the third design (construct 3 in FIG. 24), the GPPS$_{Ag}$ peptide was cloned into the same plasmid with TPS under the strong promoter Ptrc but ahead of the TPS. Plasmid pJBEI3122 and plasmid-GPPS$_{Ag}$-TPS were co-transformed into YH40.

Figure 25A:
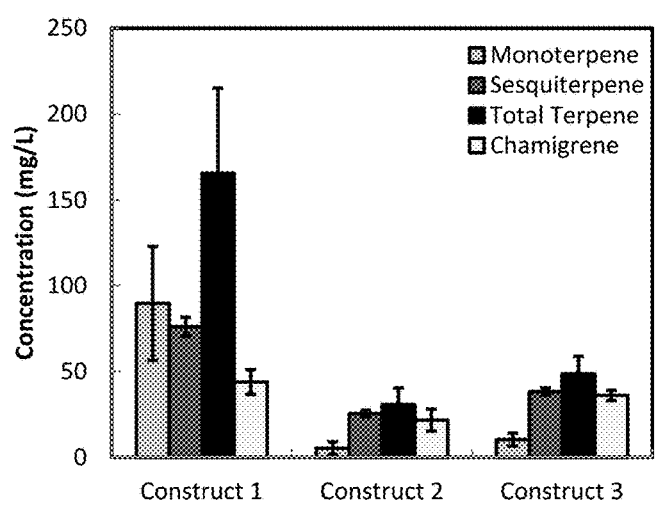
FIG. 25A-25B shows (A) terpene concentrations produced from different constructs in FIG. 24; and (B) in vivo metabolite mevalonate concentrations from different constructs in FIG. 24.

Strains containing different constructs were cultured in a M9 medium containing 20 g/L of an amino acid mixture, which included equal molar quantities of each amino acid, to determine the terpene yield. Construct 1 produced the highest terpene concentration, up to 166.6 mg/L, including 89.6 mg/L of monoterpene and 76 mg/L sesquiterpene (44 mg/L of chamigrene); and a terpene concentration was detected with construct 3 (49 mg/L of total terpene) and construct 2 (31 mg/L of total terpene) (FIG. 25A).

Compared to construct 1 that produced higher monoterpene than sesquiterpene, constructs 2 and 3 produced 3.8 and 2.7 fold higher concentrations of sesquiterpene than monoterpene, respectively. Interestingly, constructs 2 and 3 produced a lower amount of chamigrene than construct 1, but the percentage of chamigrene in sesquiterpene from construct 1 was the least (58%), compared to 85% and 94% from construct 2 and construct 3, respectively.

Figure 25B:
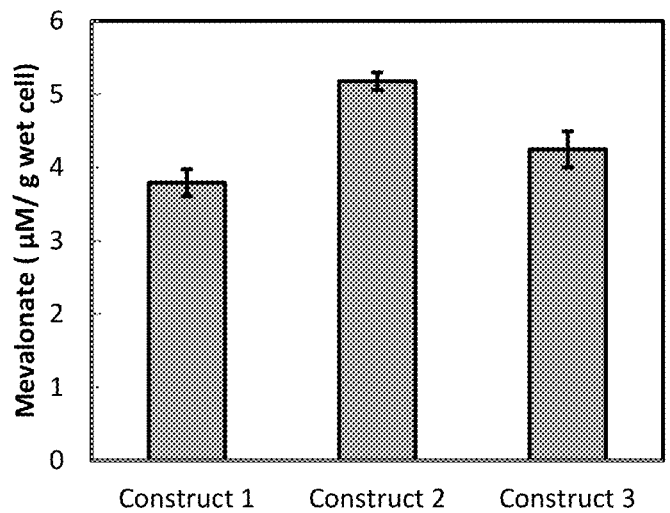

To further elucidate metabolic flux flow with the different constructs, various intermediate pathway metabolites were extracted and analyzed by the LC-MS. The results were consistent with the terpene concentrations obtained from the different regulation strategies. Only mevalonate accumulation was detected among all the intermediate metabolites, and the concentrations were inversely related to the terpene yield. As seen in FIG. 25B, construct 1 accumulated the least amount of mevalonate at 3.79 µM/g cell, followed by construct 3 (4.25 µM/g cell), and construct 2 (5.18 µM/g cell), respectively. The lower concentration of mevalonate suggests that higher metabolic flux was more effectively diverted to product formation using construct 1, as compared to the other two regulation strategies provided by constructs 2 and 3. Additionally, mevalonate was identified as the most likely toxic intermediate metabolite to cell growth (see, e.g., Martin V J et al., "Engineering a mevalonate pathway in *Escherichia coli* for production of terpenoids," *Nat. Biotechnol.* 2003; 21(7):796-802; and Pitera D J et al., *Metab. Eng.* 2007; 9(2):193-207). The consumption of mevalonate most likely minimized toxicity, further improving the terpene production.

Optimization of Amino Acid Degradation and Terpene Synthesis

Various conditions were altered to optimize terpene synthesis. Exemplary conditions include use of a transcription inducer, as well varying concentrations of the inducer; variation of the amino acid concentration in the fermentation broth; and/or variation of the fermentation temperature. Additional details follow.

Figure 26A:
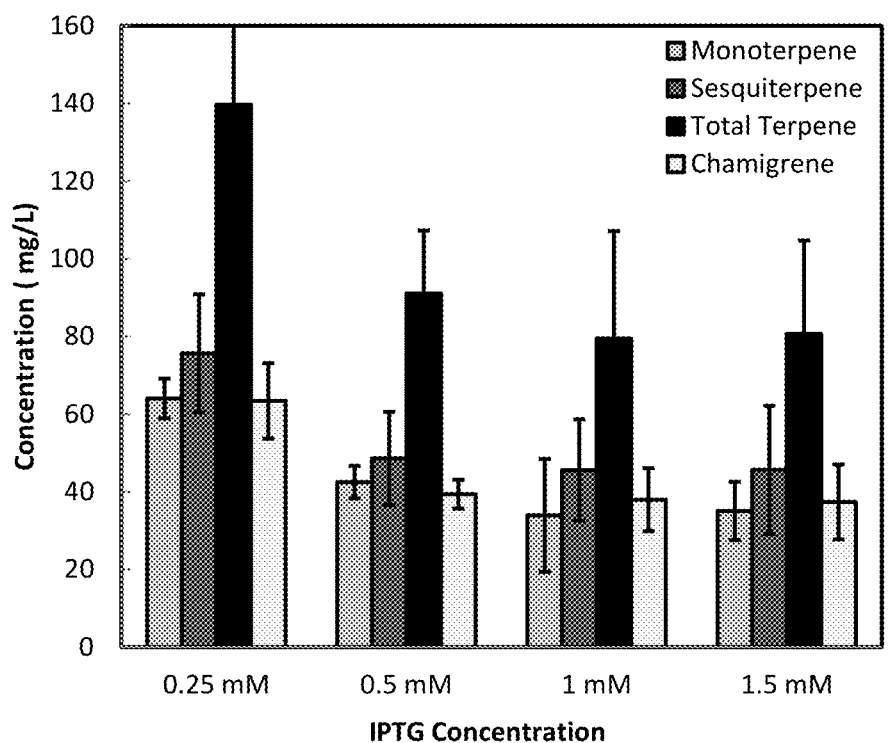
FIG. 26A-26C shows optimization of the terpene formation from construct 1. Provided are graphs showing (A) induction with different concentrations of isopropyl-β-D-1- thiogalactopyranoside (IPTG); (B) terpene production in construct 1 induced with 0.25 mM IPTG under variable amino acid concentrations; and (C) terpene formation in construct 1 induced with 0.25 mM IPTG under variable temperature.

The final terpene concentration is not only regulated by the transcriptional and translational rates but also by the thermodynamics of the pathway enzymes. IPTG was used as a common inducer for transcription of all of the terpene biosynthesis pathway genes in this work. The proper induction strength will optimize the transcriptional rate of pathway genes, which consequently results in the optimal enzyme concentrations that produce the maximum concentration of the target terpene compounds. From the experimental results, 0.25 mM of IPTG yielded the highest total terpene concentration, up to 140 mg/L, including 64 mg/L monoterpene and 75 mg/L of sesquiterpene, as shown in FIG. 26A. The strain induced at 0.5 mM of IPTG produced 91 mg/L of total terpene, which was about 36% less than that produced at 0.25 mM IPTG. Similar concentrations of total terpene were detected when the strains were induced at 1 mM and 1.5 mM, which were ~53% of the total terpene produced when induced by 0.25 mM of IPTG.

Substrate inhibition is believed to be a significant factor affecting product yield during fermentation (see, e.g., Wu W et al., "A general inhibition kinetics model for ethanol production using a novel carbon source: sodium gluconate," Bioprocess Biosyst. Eng. 2013; 36(11):1631-40). The amino acid substrate mixture contained charged amino acids (Arg, Lys, Asp, and Glu) and other polar amino acids. A high concentration of amino acids in the fermentation medium may increase the ionic strength of the medium, thereby resulting in the low cell growth. Therefore, the effects of amino acid concentration on terpene yield were also investigated in the study.

Figure 26B:
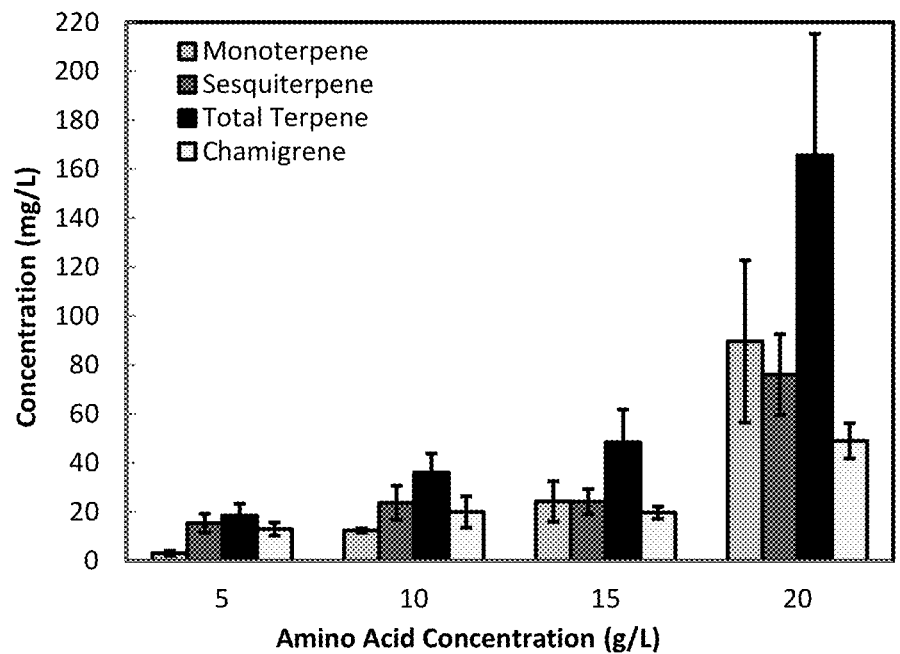

The results showed that the terpene yield increased with the elevation of the amino acid concentration in the medium, as shown in FIG. 26B. At 20 g/L of amino acids, the strain produced the highest terpene titer, up to 166.6 mg/L of total terpene while only 18 mg/L of total terpene was produced when the medium contained 5 g/L of amino acids. Contrarily, the ratio of sesquiterpene to monoterpene was the highest in the culture on 5 g/L of amino acids, up to a factor of ~5. This ratio decreased with increasing amino acid concentrations in the medium. At 20 g/L of amino acid, the strain produced more monoterpene than sesquiterpene. Accordingly, shifts in the terpene profile can be modified by changing the concentration of amino acids in the medium.

Figure 26C:
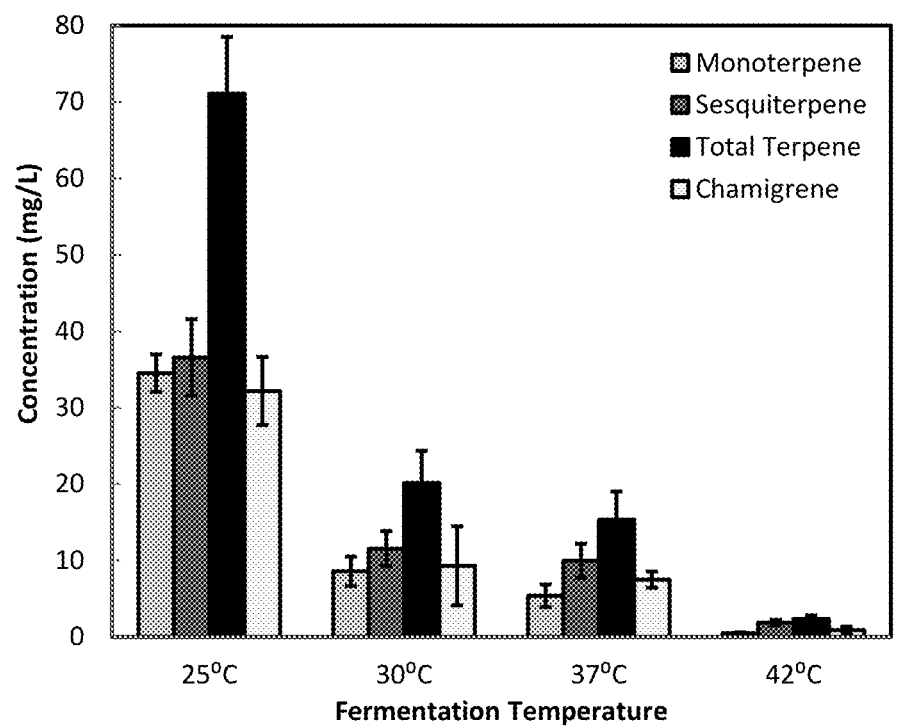

The concentration of produced terpenes can be dependent on the reaction rate, which in turn can be determined by properties of various pathway enzymes, their concentrations, and the reaction temperature. According to the Arrhenius equation, the chemical reaction rate increases with increases in temperature. However, in terms of the enzymatic reaction, there exists an optimal reaction temperature at which the enzyme has maximal catalytic ability. Based on the experimental results, terpene concentrations (up to 71 mg/L) reached the highest value when the strain was induced at 25° C. (FIG. 26C). When the induction temperature rose to 30° C. and 37° C., the strain produced only 28% (20 mg/L) and 21% (15 mg/L) of the terpene yielded at 25° C. The strain produced only very small quantities of terpene at 42° C.

Bioconversion of Algal Protein for Terpene Production

It is commonly speculated that in fuels process including an algae, the algal carbohydrate can be bio-converted into ethanol, but algal proteins can be used in animal feeds or other non-fuel applications (see, e.g., Li K et al., *Int'l J. Energy Res.* 2014; 38(8):965-77; Moody J W et al., "Global evaluation of biofuel potential from microalgae," *Proc. Nat'l Acad. Sci. USA* 2014; 111(23):8691-6; Razeghifard R, *Photosynth. Res.* 2013; 117(1-3):207-19; and Weaver L J et al., "A kinetic-based approach to understanding heterologous mevalonate pathway function in *E. coli*," *Biotechnol. Bioeng.* 2015; 112(1):111-9).

To improve technoeconomic feasibility of using algae as a fuel source, algal biofuel processing options can be improved by adding high value-added petroleum replacements and fuel compounds that are compatible with current fuel engine infrastructure. With an engineered *E. coli* strain (YH40-TPS), we successfully demonstrated bioconversion of algal proteins into terpene compounds as a next generation fuel concept (see FIG. 27A-27B). Chamigrene synthase (CS) was chosen as a representative TPS due to its relatively simple profile. The terpene biosynthetic pathway was constructed in an *E. coli* strain YH40, which was randomly mutated to boost amino acid consumption as solo carbon source to support its growth.

As seen in FIG. 27A, terpene yield reached 26 mg/L of total terpene, including 2.4 mg/L of monoterpene, 23.4 mg/L of sesquiterpene, as well as 12.6 mg/L of chamigrene. The low terpene yields indicated the relatively inefficient bioconversion of algal biomass. In fact, strain YH40-CS only used approximately half of the algal amino acids in the medium while algal carbohydrate consumption was minimal (3.8% of total carbohydrate). Increased yield of terpenoid compounds may be obtained, e.g., by including an organism that preferentially consumes carbohydrates.

Additionally, the benthic algae polyculture of HydroMentia contained up to 70% ash, which yielded high ion strength in the algal biomass hydrolysate that used as the fermentation medium. This high ion strength in the culture media may be another major reason responsible for low yield of terpenes. Optionally strategies for optimizing terpene synthesis could be pretreating the algal biomass, and then separation the solid ash component prior to fermentation with terpene synthase(s). Composition analysis indicated that carbohydrate and protein accounts for 74.2% of the mixed benthic biomass ash free dry weight (HydroMentia, Inc). Based on these data, the strain YH40-TPS produced 3.3 mg terpene/g algae (0.33%), as shown in FIG. 27B, which is comparable to the current state-of-art essential oil extraction yields from plant tissues that are ranged between 0.1% to 0.8% of plant tissue biomass (see, e.g., Gong H Y et al., "Analysis of essential oils of *Origanum vulgare* from six production areas of China and Pakistan," *Revista Brasileira de Farmacognosia* [*Braz. J. Pharmacognosy*] 2014; 24(1): 25-32; and Moncada J et al., "Techno-economic and environmental assessment of essential oil extraction from Oregano (*Origanum vulgare*) and Rosemary (*Rosmarinus officinalis*) in Colombia," *J. Cleaner Production* 2016; 112 (1):172-81).

Discussion

First generation biofuels encountered severe criticism because the feedstocks were common food crops, which raised concerns about global food security, especially with regards to the most vulnerable regions of the global economy. As recently reviewed (see, e.g., Yen H W et al., "Microalgae-based biorefinery—from biofuels to natural products," *Bioresour. Technol.* 2013; 135:166-74), microalgae-based biofuels have been recognized as an important feedstock for second generation biofuels in addition to lignocellulosic biomass.

Techno-economic analysis suggests that a viable algal biofuel process will require high algae biomass productivity, inexpensive harvesting and biomass pretreatment methods, as well as co-production of high value products in addition to conventional fuel compounds such as ethanol and diesel. Leveraging the development of high value products, such as terpenes, with the comprehensive use of algae biomass through heterotrophic fermentation has several advantages in terms of process cost reduction. Terpenes as hydrocarbon or hydrocarbon-like compounds have only recently been considered as a next generation fuel (see, e.g., Griffin MA et al., "Volatile organic compound production by organisms in the genus Ascocoryne and a re-evaluation of myco-diesel production by NRRL 50072," *Microbiology* 2010; 156(Pt 12):3814-29; Lane J, "9 advanced molecules that could revolutionize jet and missile fuel," *Biofuels Digest*, Jun. 18, 2014 (4 pp.), available at www.biofuels.com; Strobel G, "The story of mycodiesel," *Curr. Opin. Microbial.* 2014; 19:52-8; and Strobel GA et al., "The production of mycodiesel hydrocarbons and their derivatives by the endophytic fungus *Gliocladium roseum* (NRRL 50072)," *Microbiology* 2008; 154(Pt 11):3319-28 (erratum in *Microbiology* 2010; 156(Pt 12):3830-3). Via photosynthetic pathways, algae microorganisms are able to produce large amount of proteins (e.g., about 40-60%), carbohydrates (e.g., about 25-40%), and lipids (e.g., about 10-20%) under non-stressed conditions. Therefore, efficient use of algae biomass for conversion to fuels requires processes to convert both of the major algal biochemical pools (i.e., proteins and carbohydrates) to high energy density and low oxygen liquid fuels, thereby enabling viable algal biofuel process and generating effective petroleum replacements.

For terpene production, biosynthesis can be achieved either through the mevalonate or DXP pathways, for which the metabolic flux is diverted from acetyl-CoA and pyruvate, respectively, to the final products (see, e.g., Gräwert T et al., "Biochemistry of the nonmevalonate isoprenoid pathway," *Cell. Mol. Life Sci.* 2011; 68(23):3797-814; Illarionova V et al., "Nonmevalonate terpene biosynthesis enzymes as anti-infective drug targets: substrate synthesis and high-throughput screening methods," *J. Org. Chem.* 2006; 71(23):8824-34; Kim S W et al., "Metabolic engineering of the nonmevalonate isopentenyl diphosphate synthesis pathway in *Escherichia coli* enhances lycopene production," *Biotechnol. Bioeng.* 2001; 72(4):408-15; Lee T S et al., "Metabolic engineering of mevalonate pathway," 239*th ACS National Meeting & Exposition*, held on 21-25 Mar. 2010 in San Francisco, Calif. (abstract, 1 p.); and Martin V J et al., *Nat. Biotechnol.* 2003; 21(7):796-802).

Correspondingly, both carbohydrate and amino acid assimilation can yield pyruvate and acetyl-CoA as common building blocks in the central metabolism although the catabolism of amino acids has more diverse pathways than that of glucose. These facts enable terpene production through comprehensive utilization of algal carbohydrates and proteins through a strain engineering approach. Algal carbohydrate has been reported to be converted into pinene in previous study (see, e.g., Scullin C et al., "Optimization of renewable pinene production from the conversion of macroalgae *Saccharina latissimi*," *Bioresour. Technol.* 2015; 184:415-20), while algal protein are barely studied for high value-added terpene compound production. Here, we firstly demonstrated the feasibility of bioconversion of protein into various terpene compounds using a synthetic amino acid mixture as solo carbon source in the culture. The algal proteins from natural benthic algal polyculture (ATS™ biomass provided by Hydromentia, Inc., Ocala, Fla.) was further used as real substrate in the culture and was effectively converted to the sesquiterpene chamigrene as well as several monoterpene compounds. The highest titer of total terpene was achieved up to 165 mg/L from 20 g/L of an amino acid mixture, including 90 mg/L of monoterpene and 76 mg/L of sesquiterpene (FIG. 26B). However, the terpene yield from algal protein was dramatically reduced to 26 mg/L, corresponding to 3.3 mg terpene/g algae.

Compared to the recent reported ~40 mg/L of sabinene produced from glycerol in shaker flasks (see, e.g., Zhang H et al., "Microbial production of sabinene—a new terpene-based precursor of advanced biofuel," *Microb. Cell Fact.* 2014; 13: Art. No. 20 (10 pp.)), the terpene titer from algal protein was lower. Nonetheless, the constructs herein can be employ different amino acid (e.g., 13 amino acids), and carbon sources can be selected to be those including high protein concentrations or those separated to provide a high-protein fraction. In addition, employing microbial fermentation of algae biomass cultivated from waste-water as opposed to conventional terpene production methods, e.g., mechanical and solvent-based extraction of agricultural products, avoided several energetically and environmentally-intensive unit operations, especially including avoidance of arable land that can sustain other crops (e.g., edible crops), as well as minimal use of water, fertilizer, and solvents.

In terms of the potential for terpene yield improvement, terpene biosynthesis can be limited by transcriptional and translational regulation, as well as the enzyme kinetics or reaction thermodynamics. To optimize the expression of proteins in the mevalonate pathway and generate the optimal metabolic flux to the desired final products, all the pathway genes were expressed under the control of different promoter combinations with different transcriptional and translational regulations. In construct 1, the first three enzymes of MEV pathway (AtoB, HMGS, and HMGR) were regulated under a medium strength promoter LacUV5 to achieve the medium level of mevalonate accumulation, which was able to minimize the toxicity of mevalonate to cell growth. In contrast, the last four enzymes (MK, PMK, PMD, and IDI) were expressed under a strong promoter Ptrc to divert maximal flux to the IPP and DMAPP, as well as to efficiently consume the toxic intermediate metabolite mevalonate (see, e.g., Anthony J R et al., *Metab. Eng.* 2009; 11(1):13-9; Ma S M et al., "Optimization of a heterologous mevalonate pathway through the use of variant HMG-CoA reductases," *Metab. Eng.* 2011; 13(5):588-97; Pitera D J et al., *Metab. Eng.* 2007; 9(2):193-207; and Weaver L J et al., *Biotechnol. Bioeng.* 2015; 112(1):111-9). In addition, to drive the resulting metabolic flux to the final terpene products, both downstream enzymes $GPPS_{Ag}$ and chamigrene synthase were over-expressed under strong promoters T7 and Ptrc, respectively.

From our shaker flask experiments, the strain containing construct 1 yielded ~166.6 mg/L total terpene, including 89.6 mg/L monoterpene and 76 mg/L sesquiterpene with chamigrene as the major product. Compared to construct 1, both construct 2 and construct 3 displayed less transcriptional and translational efficiency of downstream enzymes including $GPPS_{Ag}$ and chamigrene synthase, indicated by higher mevalonate levels in vivo which diminished the cell growth as well as the final terpene yields.

IPTG was employed as a common inducer for the LacUV5, T7, and Ptrc promoters to initiate protein expression and subsequent catalysis of the metabolic reactions to terpene generation. The concentration of the IPTG was optimized for maximal terpene production. At low concentrations of IPTG (0.25 mM), the strain yielded the highest terpene concentration, up to 140 mg/L. Terpene yield decreased with elevation of the IPTG concentrations. The decreased terpene yield at higher induction levels in this study is likely due to the different induction efficiencies of promoters LacUV5, T7, and Ptrc, which may result in induction competition among the different promoters, which can further lead to imbalance of the metabolic flux, thereby resulting in reduced product yield (see, e.g., Anderson J C et al., "BglBricks: A flexible standard for biological part assembly," *J. Biol. Eng.* 2010; 20; 4(1):1 (12 pp.); and Lee T S et al., "BglBrick vectors and datasheets: A synthetic biology platform for gene expression." *J. Biol. Eng.* 2011; 5: Art. No. 12 (14 pp.)). Additionally, at high concentrations IPTG can be toxic to cell growth, which could further compromise terpene formation.

The terpene yield was also subjected to changes in environmental fermentation factors, such as temperature and substrate concentration. The YH40-TPS strain produced higher terpene yield at lower temperature and produced negligible terpene quantities at 42° C. Without wishing to be limited by mechanism, this may have occurred as lower temperatures can initiate an optimal translation rate of terpene pathway enzymes to achieve optimal fully functional pathway enzymes concentrations in vivo, which catalyzed the maximum metabolic flux to the terpene formation (see, e.g., Rosano G L et al., "Recombinant protein expression in *Escherichia coli*: advances and challenges," *Front. Microbiol.* 2014; 5: Art. No. 172 (17 pp.)).

Terpene yield may also be subject to the effect of substrate inhibition during the fermentation. In this experiment, the terpene yields on amino acid concentrations above 20 g/L were not investigated due to the limited solubility of amino acids, especially those with aromatic side chains. Within the concentration range of 5-20 g/L of amino acids, the terpene yield increased with higher amino acid concentrations. At the low concentration of amino acids, the strain utilized the majority of amino acids for cell growth and maintenance instead of terpene production.

Regarding the multiple terpene products yielded from each strain, all six selected TSPs are type I terpene cyclase, which contained two highly conserved motifs: the aspartate rich motif (DDXXD) and the NSE triad (ND(L/I/V) XSXXXE) (see, e.g., Miller D J et al., "Sesquiterpene synthases: passive catalysts or active players?," *Nat. Prod. Rep.* 2012; 29(1):60-71; and Oldfield E et al., "Terpene biosynthesis: modularity rules," *Angew. Chem. Int. Ed. Engl.* 2012; 51(5):1124-37). These TSPs are involved in binding of substrate precursors (e.g., GPP and FPP) and catalyzing terpene formation. Without wishing to be limited by mechanism, monoterpene formation generally starts from the ionization of geranyl diphosphate to form geranyl cation followed by isomerization to several different carbocations. The resulting carbocations undergo a range of cyclization, hydride shifts, methyl shifts, and conformation rearrangements before the reaction is quenched by deprotonation or water capture (see, e.g., Croteau R et al., "[44] Monoterpene and sesquiterpene cyclases," *Methods in Enzymology* 1985; 110:383-405; Degenhardt J et al., "Monoterpene and sesquiterpene synthases and the origin of terpene skeletal diversity in plants," *Phytochemistry* 2009; 70(15-16):1621-37; and Oldfield E et al., *Angew. Chem. Int. Ed. Engl.* 2012; 51(5):1124-37).

Without wishing to be limited by mechanism, sesquiterpene formation can be similar to monoterpene, but with higher complexity due to the higher complexation state of FPP than that of GPP, which involves multiple isomerations of carbocations and cyclization reactions. The different intermediate carbocations can undergo different cyclization reactions, hydride or methyl shifts, and conformation rearrangements, which is most likely the reason of multiple products formation from each terpene synthase. Additionally, the product profile is not only determined by the catalyzing properties of terpene synthase but also the reaction environment since the reaction is also terminated by deprotonation or water capture. The YH40-TPS strains were grown on the M9 medium containing a mixture of amino acids which has higher ion strength and lower pH than that of EZ-rich medium, which may contribute to different terpene profiles even when the same TSP is employed but with different growth media.

Conclusion

Algae-based biofuels production has primarily focused on biodiesel production through transesterification of algal lipids. Under robust algal biomass accumulation conditions, carbohydrate and proteins typically include up to ~80% of the ash-free dry weight of algae biomass. Therefore, a comprehensive process for bioconversion of algal carbohydrates and proteins to high energy density fuels and value-added bioproducts should significantly improve the algal fuel process feasibility. In this study, we engineered the E. coli strain harboring the terpene biosynthesis pathway and firstly demonstrated the feasibility of bioconversion of algal proteins to terpenes, which are attractive candidates for high energy density aviation fuels and other intermediate to high value bio-based chemicals applications. The terpene yield achieved was 3.3 mg/g algae, which is comparable to the current essential oil extraction yield from plant tissues. The results indicate high potential for terpene product from renewable algae biomass and offer a versatile path forward for the production of fuels and active bioproducts from algae.

Example 3: One-Pot Bioconversion of Algae Biomass into Terpenes for Advanced Biofuels and Bioproducts Under robust algae growth conditions, algal carbohydrates and proteins typically comprise up to ~80% of the ash-free dry weight of microalgae biomass. Therefore, production of algal biofuel through comprehensive use of all algal components and the addition of high energy density fuel compounds with "fit for purpose" properties or high-value bioproducts can both diminish the process cost and improve the overall process feasibility. In this Example, we firstly demonstrated the concept of a "one-pot" bioconversion of algal carbohydrate and protein into value-added terpene compounds (e.g., as advanced biofuel and high value bioproducts), thereby improving the feasibility of developing an engineered microbial consortium. The consortium for caryophyllene production yielded the highest titer of total terpene, up to 507.4 mg/L, including 471 mg/L of sesquiterpene, 36.4 mg/L of monoterpene, and 124.4 mg/L of caryophyllene on algal hydrolysate from Nannochloropsis sp. Additionally, the consortium expressing chamigrene synthase produced 187 mg/L of total terpene, including 87 mg/L of monoterpene, 100 mg/L of sesquiterpene, and 62 mg/L of chamigrene using a hydrolysate from a benthic polyculture biomass as the carbon source. Compared to the yields of terpene extracted from plant tissue, both consortia increased the terpene yield about 3-40 times.

Introduction

Rising demand for transportation fuels and the concerns with fossil fuel derived environmental pollution, as well as the green-house gas emission derived climate change, have resulted in the compelling need for alternative, sustainable energy sources (see, e.g., Lynd L R et al., "Consolidated bioprocessing of cellulosic biomass: an update," Curr. Opin. Biotechnol. 2005; 16(5):577-83). Algae-based biofuels have been considered as a promising alternative to fossil fuels (see, e.g., Moody J W et al., "Global evaluation of biofuel potential from microalgae," Proc. Nat'l Acad. Sci. USA 2014; 111(23):8691-6; Razeghifard R, "Algal biofuels," Photosynth. Res. 2013; 117(1-3):207-19; and Luque R, "Algal biofuels: the eternal promise?," Energy Environ. Sci. 2010; 3:254-7).

Current state-of-the-art of algal biofuel technologies have primarily focused on biodiesel production through prompting high algal lipid yields under the nutrient stress conditions. There has been less emphasis on using algae-based carbohydrates and proteins as carbon sources for the fermentative production of liquid fuel compounds or other high-value bioproducts (see, e.g., El-Mashad H M, "Biomethane and ethanol production potential of Spirulina platensis algae and enzymatically saccharified switchgrass," Biochem. Eng. J. 2015; 93:119-27; Babujanarthanama R et al., "Simultaneous saccharification and fermentation of dilute acid pretreated red algae (Gelidiella acerosa) for bioethanol production," Energy Sourc. A 2014; 36(12):1305-14; and Huo Y X et al., "Conversion of proteins into biofuels by engineering nitrogen flux," Nat. Biotechnol. 2011; 29(4): 346-51). However, under robust algae growth conditions, algal carbohydrate and proteins typically comprise up to ~80% of the ash-free dry weight of microalgae biomass (see, e.g., Wang H et al., "Growth and biochemical composition of filamentous microalgae Tribonema sp. as potential biofuel feedstock," Bioprocess Biosyst. Eng. 2014; 37(12):2607-13; and Chen C Y et al., "Microalgae-based carbohydrates for biofuel production," Biochem. Eng. J. 2013; 78:1-10). Therefore, production of algal biofuel through comprehensive use of all algae biochemical components can both diminish processing cost and improve overall process feasibility.

Terpenes are a group of natural products with over 55,000 structurally similar chemical compounds. Compared to biodiesel and other short- and medium-chain alcohols, these molecules contain near zero oxygen content, have various biological functionalities (see, e.g., Zhang Z et al., "Synergistic antitumor effect of α-pinene and β-pinene with paclitaxel against non-small-cell lung carcinoma (NSCLC)," Drug Res. (Stuttg.) 2015; 65(4):214-8; Rufino A T et al., "Evaluation of the anti-inflammatory, anti-catabolic and pro-anabolic effects of E-caryophyllene, myrcene and limonene in a cell model of osteoarthritis," Eur. J. Pharmacol. 2015; 750:141-50; Kovač J et al., "Antibiotic resistance modulation and modes of action of (−)-α-pinene in Campylobacter jejuni," PLoS One 2015; 10(4):e0122871 (14 pp.); Han L et al., "Trans-caryophyllene suppresses tumor necrosis factor (TNFα)-induced inflammation in human chondrocytes," Eur. Food Res. Technol. 2014; 239(6):1061-6; and Guo K et al., "Trans-caryophyllene suppresses hypoxia-induced neuroinflammatory responses by inhibiting NF-κB activation in microglia," J. Mol. Neurosci. 2014; 54(1):41-8) and have high energy density, making them particularly attractive candidates as "drop-in" fuel candidates for aviation fuels (see, e.g., Strobel G, "The story of mycodiesel," Curr. Opin. Microbiol. 2014; 19:52-8; Riyaz-Ul-Hassan S et al., "An endophytic Nodulisporium sp. from Central America producing volatile organic compounds with both biological and fuel potential," J. Microbiol. Biotechnol. 2013; 23(1):29-35; Gladden J M et al., "Tailoring next-generation biofuels and their combustion in next-generation engines," Sandia Report No. SAND2013-10094, 2013 (100 pp.); Strobel G et al., "An endophytic/pathogenic Phoma sp. from creosote bush producing biologically active volatile compounds having fuel potential," FEMS Microbiol. Lett. 2011; 320(2):87-94; Strobel G A et al., "The production of myco-diesel hydrocarbons and their derivatives by the endophytic fungus *Gliocladium roseum* (NRRL 50072)," *Microbiology* 2008; 154(Pt 11):3319-28 (erratum in Microbiology 2010; 156(Pt 12):3830-3); and Griffin M A et al., "Volatile organic compound production by organisms in the genus *Ascocoryne* and a re-evaluation of myco-diesel production by NRRL 50072," *Microbiology* 2010; 156(Pt 12):3814-29). In this Example, we demonstrate the concept of "one-pot" bioconversion of algal carbohydrates and proteins into terpenes, e.g., for use as advanced biofuel compounds and high value bioproducts.

Results and Discussion

Caryophyllene and chamigrene, natural bicyclic sesquiterpene ($C_{15}$) compounds, are common components present in the essential oils from various plants (see, e.g., Malingré T et al., "The essential oil of *Cannabis sativa*," *Planta Med.* 1975; 28(1):56-61; Kpadonou Kpoviessi B G et al., "Chemical variation of essential oil constituents of *Ocimum gratissimum* L. from Benin, and impact on antimicrobial properties and toxicity against *Artemia salina* leach," *Chem. Biodivers.* 2012; 9(1):139-50; Rodrigues F F et al., "Chemical composition, antibacterial and antifungal activities of essential oil from *Cordia verbenacea* DC leaves," *Pharmacognosy Res.* 2012; 4(3):161-5; and Meccia G et al., "Chemical composition and antibacterial activity of the essential oil of *Cordia verbenacea* from the Venezuelan Andes," *Nat. Prod. Commun.* 2009; 4(8):1119-22).

A recent study suggested that the blending of hydrogenated sesquiterpanes (in particular carophyllanes), which have a moderate cetane number and only moderately high viscosity, with synthetic branched paraffins to raise cetane and reduce viscosity, could produce biosynthetic fuels that meet applicable jet fuel and diesel specifications (see, e.g., Harvey B G et al., "High-density renewable diesel and jet fuels prepared from multicyclic sesquiterpanes and a 1-hexene-derived synthetic paraffinic kerosene," *Energy Fuels* 2015; 29(4):2431-6). Therefore, caryophyllene and its isomers have been deemed to be among the top three most promising candidates for jet fuel with high energy density (see, e.g., Nakano C et al., "Identification of the first bacterial monoterpene cyclase, a 1,8-cineole synthase, that catalyzes the direct conversion of geranyl diphosphate," *Chembiochem* 2011; 12(13):1988-91). As described herein, we discovered and functionally characterized caryophyllene and chamigrene synthases from endophytes (see, e.g., Wu W et al., "Rapid discovery and functional characterization of terpene synthases from four endophytic *Xylariaceae*," *PLoS One* 2016; 11(2):e0146983 (19 pp.)). Furthermore, we demonstrated the feasibility of bioconversion of algal protein into terpene through terpene biosynthesis reconstruction into mutant *E. coli* YH40 strain.

Figure 34A:
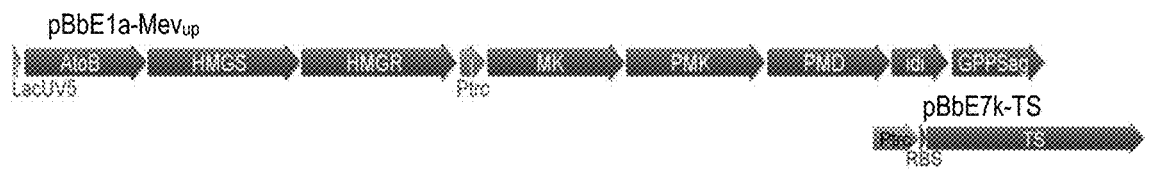
Figure 34B:
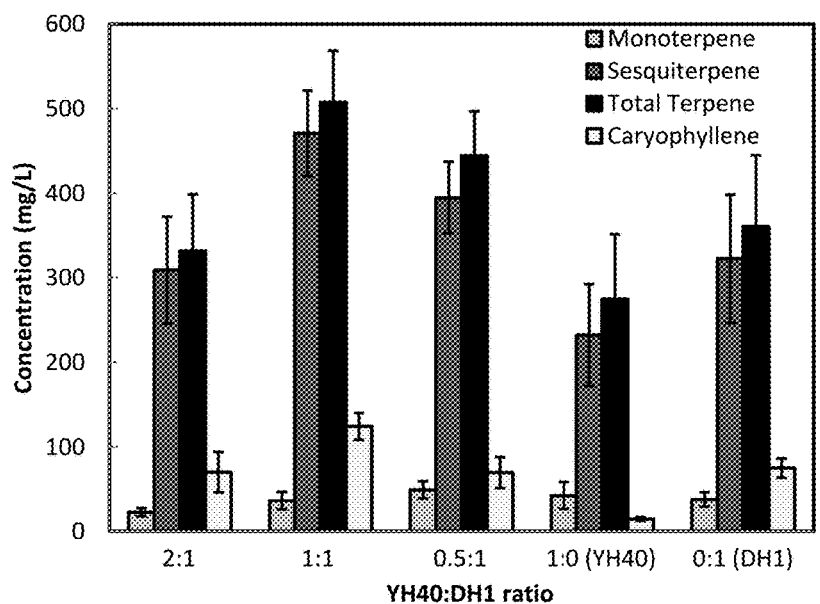

Based on the previous studies, we developed a synthetic microbial consortium and investigated the production of caryophyllene, chamigrene, and other terpene products in one-pot fermentation using algal hydrolysate of microalgae monocultures from strain *Nannochloropsis* sp. as well as natural benthic algal assemblages cultivated from wastewater. To achieve this, the terpene biosynthesis pathway was reconstructed into *E. coli* YH40 strain (see, e.g., Huo Y X et al., *Nat. Biotechnol.* 2011; 29(4):346-51), designated for the conversion of algal protein into caryophyllene or chamigrene, and into *E. coli* DH1 strain, designated for the conversion of algal carbohydrate into caryophyllene or chamigrene, respectively (FIG. 34A).

Caryophyllene and chamigrene yields were investigated under three different combinations of inoculum YH40-CI4A-CS/DH1-CI4A-CS at ratios of 2:1 (consortia R2), 1:1 (consortia R1), and 0.5:1 (consortia R0.5), as well as the single strains YH40-CI4A-CS or DH1-CI4A-CS alone. As shown FIG. 34B, when co-culture of the two strains containing caryophyllene synthases were grown on algal hydrolysate from *Nannochloropsis* sp. at an inoculum ratio 1:1 (consortia R1), the consortia produced the highest titer of total terpene, up to 507.4 mg/L, including 471 mg/L of sesquiterpene, 36.4 mg/L of monoterpene, and 124.4 mg/L of caryophyllene.

Figure 34C:
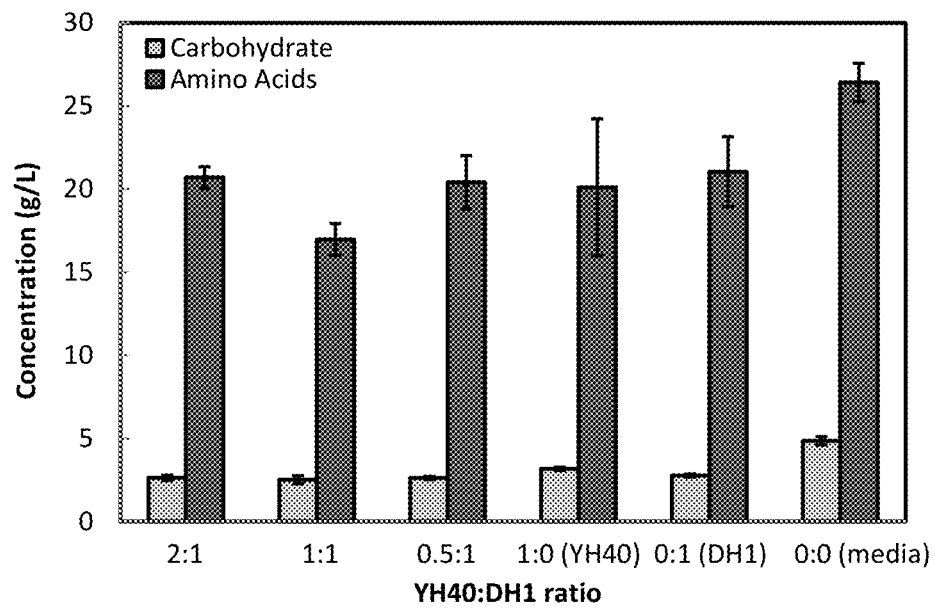

Correspondingly, the consortia R1 consumed the highest amount of algal carbohydrates and proteins, which accounted for 48.2% of total algal carbohydrates and 36% of total algal proteins in the media (FIG. 34C). Compared to the consortia R1, the consortia R2 and R0.5 consumed a significantly lower fraction of the total algal biomass, with correspondingly lower concentrations of terpenes.

Figure 34D:
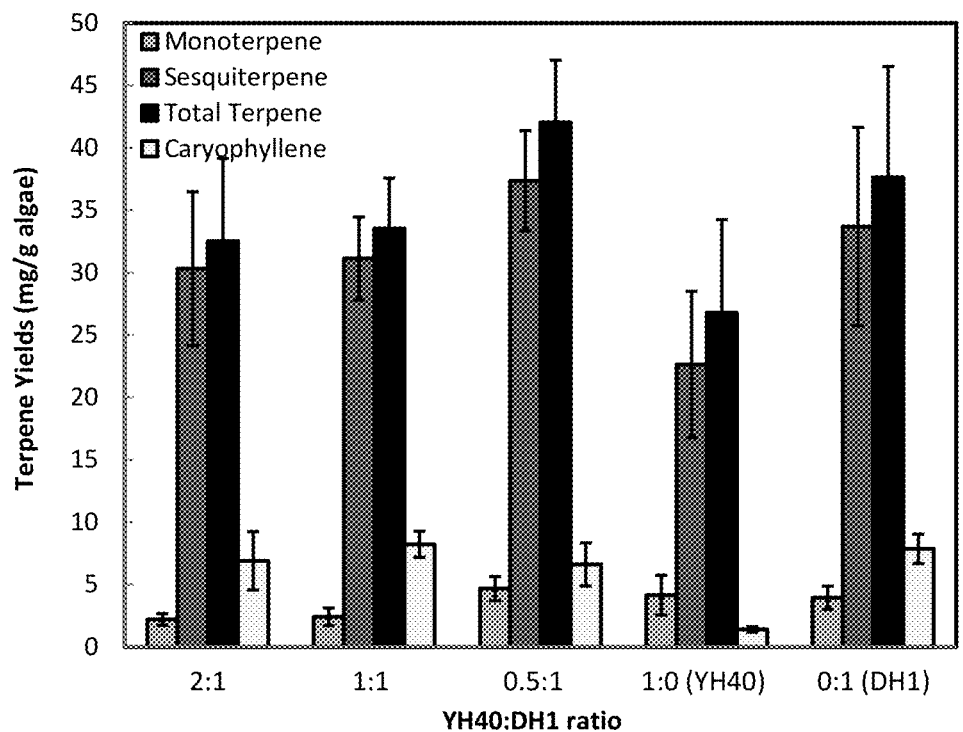

The strain YH40-CI4A-CS alone produced the least amount of total terpene (274.7 mg/L), sesquiterpene (232.1 mg/L), and caryophyllene (14.4 mg/L). In contrast, DH1-CI4A-CS yielded 30% higher sesquiterpene and total terpene than strain YH40-CI4A-CS, as well as four times higher titer of caryophyllene (75.2 mg/L). Compositional analysis of the *Nannochloropsis* sp. biomass indicated that the biomass was 20% carbohydrates and 58% protein. Based on these data, the highest terpene yield that was achieved corresponded to ~42 mg total terpene/g algae from consortia R0.5 with 37.4 mg sesquiterpene/g algae and 6.6 mg caryophyllene/g algae, as shown in FIG. 34D.

For co-culture of the two engineered strains containing chamigrene on the hydrolysate of benthic algal assemblages, the experimental results showed that the terpene yield reached 187 mg/L of total terpene at the 2:1 ratio (YH40-CI4A-CPS/DH1-CI4A-CPS), including 87 mg/L of monoterpene and 100 mg/L of sesquiterpene, and chamigrene was the major product accumulated up to 62 mg/L. The synthetic microbial consortia produced similar total terpene at the 1:1 and 0.5:1 ratios of YH40-CI4A-CPS/DH1-CI4A-CPS, which were ~150 mg/L of total terpene. The microbial consortium at ratio 1 yielded the highest concentration of sesquiterpene (113 mg/L) as well as chamigrene (80 mg/L) among three consortia, while the monoterpene yield was the lowest (34.5 mg/L).

The YH40-TS and DH1-TS strains alone produced only 26 and 43 mg/L of total terpene, respectively, indicating relatively inefficient bioconversion of algal biomass. Compared to a single bioconversion strain, the synthetic microbial consortia produced 2.5-6.2 times higher total terpene concentration, suggesting that both algal carbohydrate and protein can be more effectively converted in the single-pot process.

In terms of algal carbohydrate and amino acid consumption, none of the synthetic consortia were able to completely consume the algal carbohydrates and amino acids. The 2:1 consortium ratio utilized the highest amount of algal biomass, corresponding to 36.8% of total carbohydrates and 31.3% of algal amino acids. The other two consortia ratios consumed similar amount of the total carbohydrates and algal amino acids, which were 10-15% less than the 2:1 consortium. Strain YH40-CI4A-CPS used approximately half of the algal amino acids in the medium but algal carbohydrate consumption was minimal (3.8% of total carbohydrate). Strain DH1-TS consumed both algal carbohydrates (37.8% of total carbohydrate) and amino acids (23.3% of algal amino acids) in the medium.

Compositional analysis indicated that carbohydrate and protein accounts for 74.2% of the mixed benthic biomass ash free dry weight (HydroMentia, Inc.). Based on these data, the 2:1 consortium ratio produced the highest terpene yield at 30.5 mg terpene/g algae while the 1:1 and 1:2 consortium ratios yielded 27.0 and 28.5 mg terpene/g algae, respectively. The strain YH40-CI4A-CPS only produced 3.3 mg terpene/g algae, which was lower than 8.7 mg terpene/g algae yielded by strain DH1-CI4A-CPS, as shown in FIG. 35C.

Compared to total terpene yield produced from the benthic polyculture biomass in our previous study, the consortium employing *Nannochloropsis* sp. monoculture produced more than 2-fold higher titer of total terpene.

In the consortium used for bioconversion of the benthic polyculture biomass, the chamigrene synthase (JGI protein ID 322581) gene was expressed as the last enzyme in the terpene biosynthesis pathway. Compared to the multiple sesquiterpene produced by caryophyllene synthase in this study, chamigrene synthase only produces a single sesquiterpene (chamigrene) with a limited number of monoterpenes, which was likely a reason for the higher yield of total terpene from *Nannochloropsis* sp.

Furthermore, the ash content of the benthic polyculture was more than 50% of total biomass, compared to 5.9% of *Nannochloropsis* sp. The higher ash content of the benthic polyculture biomass resulted in higher ionic strength in the final algal hydrolysates (fermentation medium), which retarded the cell growth and compromised the terpene yield.

Additionally, according to the techno-economic analysis of current state-of-the-art of essential oil production, the extraction yield of essential oil ranged from 0.1% to 1% of plant tissue, corresponding to 1 mg-10 mg essential oil/g plant tissue (see, e.g., Moncada J et al., "Techno-economic and environmental assessment of essential oil extraction from Oregano (*Origanum vulgare*) and Rosemary (*Rosmarinus officinalis*) in Colombia," *J. Cleaner Prod.* 2016; 112(1):172-81; and Gong H Y et al., "Analysis of essential oils of *Origanum vulgare* from six production areas of China and Pakistan," *Revista Brasileira de Farmacognosia* [*Braz. J. Pharmacognosy*] 2014; 24(1):25-32) based on the relatively low concentration of essential oils in plant tissue (see, e.g., Iijima Y et al., "The biochemical and molecular basis for the divergent patterns in the biosynthesis of terpenes and phenylpropenes in the peltate glands of three cultivars of basil," *Plant Physiol.* 2004; 136(3):3724-36). Compared to the extraction yield of essential oil from plant tissue, the engineered strains in this study increased the terpene yield about 3-40 times, which makes it a promising alternative pathway for terpene production.

Strains and Plasmids

The *E. coli* strain DH1 was obtained from Joint BioEnergy Institute (JBEI). The mutant *E. coli* strain YH40 (BW25113/F' [traD36, proAB+, lacI$^q$ ZΔM15] ΔglnAΔgdhAΔluxSΔlsrA) was generously provided by Professor James C. Liao from University of California, Los Angeles (UCLA). Plasmid pBbE1a-MEVup containing the terpene biosynthesis pathway, as well as plasmids pBbE1a-GPPS and pBbE7k-TS were constructed as described in prior Examples. Plasmids containing the whole terpene biosynthesis pathway were co-transformed into strains DH1 and YH40, respectively.

Terpene Production from a Microbial Consortium on Algal Hydrolysates

Algal biomass samples from both sources were pretreated according to protocols from the National Renewable Energy Laboratories and hydrolyzed with 2 mg/mL Pronase® (Promega Corp., Madison, Wis.) following the manufacturer's protocol. Pretreated and hydrolyzed algal biomass was sterilized through filtration.

*E. coli* strains DH1 and YH40 each containing the terpene biosynthesis pathway were cultured into 15 ml of LB medium as described in the previous study. Overnight cultures were centrifuged and the cell pellets were re-suspended into 4 ml of pretreated algal hydrolysate. Various ratios (2:1, 1:1, and 1:2) of engineered YH40 to DH1 were inoculated into the algal hydrolysate at a final concentration of 10% v/v. Cultures were incubated at 37° C., 220 rpm and induced with 1 mM IPTG once the OD reached 0.8. Flasks were cap-sealed and cultured for another 72 hours at 25° C., 180 rpm for terpene production.

Analytical samples were taken at the initial and end point of fermentation. The concentrations of total carbohydrate and amino acids were determined according to the established colorimetric protocols. The terpene profile and concentration was determined as described in the previous study (see, e.g., Gladden J M et al., "Tailoring next-generation biofuels and their combustion in next-generation engines," *Sandia Report No. SAND*2013-10094, 2013 (100 pp.); and Wu W et al., "Rapid discovery and functional characterization of terpene synthases from four endophytic Xylariaceae," *PLoS One* 2016; 11(2):e0146983 (19 pp.)). Each run was performed in triplicate. The data presented in the figures were the mean values and the errors were calculated as the standard deviation of the triplicates.

Conclusion

Algae-based biofuels production has primarily focused on biodiesel production through transesterification of algal lipids. Under robust algal biomass accumulation conditions, carbohydrate and proteins typically comprise up to ~80% of the ash-free dry weight of algae biomass. Therefore, a comprehensive process for bioconversion of algal carbohydrates and proteins to high energy density fuels and value-added bioproducts should significantly improve the algal fuel process feasibility.

Here, we demonstrated simultaneous bioconversion of algal carbohydrates and proteins to terpenes which are attractive candidates for high energy density aviation fuels and other intermediate to high value bio-based chemicals applications. Using an engineered microbial consortium, greater than 30% of the carbohydrates and proteins from both a wastewater-based mixed algal feedstock and monoculture of strain *Nannochloropsis* sp. were converted to terpenes, including both monoterpenes and sesquiterpenes. This microbial consortium concept for comprehensive utilization of algal biomass offers a versatile path forward for the production of fuels and active bioproducts from algae.

Other Embodiments

All publications, patents, and patent applications, including U.S. Provisional Application No. 62/132,093, filed Mar. 12, 2015, mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. A method of treating a biomass, the method comprising:
    exposing the biomass to one or more organisms of an isolated, genetically engineered organism, wherein the organism comprises:
        an exogenous terpenoid precursor, an exogenous enzyme configured to synthesize a terpenoid precursor, or a nucleic acid encoding the exogenous enzyme; and
        an exogenous terpene synthase or a nucleic acid encoding the exogenous terpene synthase, wherein the exogenous terpene synthase is selected from the group consisting of a pinene synthase, a guaiene synthase, a pinene and guaiene synthase, a caryophyllene synthase, a chamigrene synthase, a chamigrene and pinene synthase, a gurjunene synthase, a gurjunene and pinene synthase, a gumunene synthase, a selinene synthase, and an isoledene synthase, or a bifunctional synthase of any of these; and
    isolating one or more terpenoid compounds.

2. The method of claim 1, wherein the exogenous terpenoid precursor is selected from the group consisting of mevalonate, dimethylallyl pyrophosphate, isopentenyl pyrophosphate, farnesyl pyrophosphate, geranyl pyrophosphate, and geranylgeranyl pyrophosphate, or a salt thereof.

3. The method of claim 1, wherein the organism is configured to produce one or more terpenoid compounds selected from the group consisting of a monoterpene, a sesquiterpene, and a diterpene.

4. The method of claim 1, wherein the nucleic acid encoding the exogenous enzyme and/or the nucleic acid encoding the exogenous terpene synthase is provided as a plasmid vector.

5. The method of claim 1, wherein the exogenous enzyme is selected from the group consisting of acetyl-CoA acetyltransferase, HMG-CoA synthase, HMG-CoA reductase, mevalonate kinase, phosphomevalonate kinase, mevalonate diphosphate decarboxylase, isoprenyl diphosphate isomerase, and geranyl pyrophosphate synthase.

6. The method of claim 5, wherein the nucleic acid encoding the exogenous enzyme comprises a nucleic acid sequence encoding the exogenous enzyme selected from the group consisting of acetyl-CoA acetyltransferase, HMG-CoA synthase, HMG-CoA reductase,
    mevalonate kinase, phosphomevalonate kinase, mevalonate diphosphate decarboxylase, isoprenyl diphosphate isomerase, and geranyl pyrophosphate synthase.

7. The method of claim 1, wherein the exogenous terpene synthase is a chamigrene synthase; or wherein the nucleic acid encoding the exogenous terpene synthase comprises a nucleic acid sequence encoding the chamigrene synthase.

8. The method of claim 1, wherein the exogenous terpene synthase comprises a polypeptide sequence having at least 90% sequence identity to any one of the following SEQ ID NOs or wherein the nucleic acid encoding the exogenous endophytic fungal terpene synthase comprises a nucleic acid sequence encoding a polypeptide sequence having at least 90% sequence identity to any one of the following SEQ ID NOs:
    SEQ ID NO: 10, in which X at each position of SEQ ID NO: 10 is an amino acid present at a position in one of SEQ ID NOs: 11-14 when optimally aligned with SEQ ID NO:10;
    SEQ ID NO:20, in which X at each position of SEQ ID NO:20 is an amino acid present at a position in one of SEQ ID NOs:21-25 when optimally aligned with SEQ ID NO:20;
    SEQ ID NO:30, in which X at each position of SEQ ID NO:30 is an amino acid present at a position in one of SEQ ID NOs:31-34 when optimally aligned with SEQ ID NO:30;
    SEQ ID NO:40, in which X at each position of SEQ ID NO:40 is an amino acid present at a position in one of SEQ ID NOs:41-46 when optimally aligned with SEQ ID NO:40;
    SEQ ID NO:50, in which X at each position of SEQ ID NO:50 is an amino acid present at a position in one of SEQ ID NOs:51-54 when optimally aligned with SEQ ID NO:50; or
    SEQ ID NO:60, in which X at each position of SEQ ID NO:60 is an amino acid present at a position in one of SEQ ID NOs:61-64 when optimally aligned with SEQ ID NO: 60.

9. The method of claim 1, wherein the nucleic acid encoding the exogenous terpene synthase comprises a nucleic acid sequence encoding a polypeptide sequence having at least 90% sequence identity to any one of the following:
    SEQ ID NO: 10, in which X at each position of SEQ ID NO: 10 is an amino acid present at a position in one of SEQ ID NOs: 11-14 when optimally aligned with SEQ ID NO:10;
    SEQ ID NO:20, in which X at each position of SEQ ID NO:20 is an amino acid present at a position in one of SEQ ID NOs:21-25 when optimally aligned with SEQ ID NO:20;
    SEQ ID NO:30, in which X at each position of SEQ ID NO:30 is an amino acid present at a position in one of SEQ ID NOs:31-34 when optimally aligned with SEQ ID NO:30;
    SEQ ID NO:40, in which X at each position of SEQ ID NO:40 is an amino acid present at a position in one of SEQ ID NOs:41-46 when optimally aligned with SEQ ID NO:40;
    SEQ ID NO:50, in which X at each position of SEQ ID NO:50 is an amino acid present at a position in one of SEQ ID NOs:51-54 when optimally aligned with SEQ ID NO:50; or
    SEQ ID NO:60, in which X at each position of SEQ ID NO:60 is an amino acid present at a position in one of SEQ ID NOs:61-64 when optimally aligned with SEQ ID NO: 60.

10. The method of claim 1, wherein the exogenous terpene synthase comprises a polypeptide sequence having at least 90% sequence identity to any one of SEQ ID NOs: 11-14, 21-25, 31-34, 41-46, 51-54, and 61-64; or wherein the nucleic acid encoding the exogenous terpene synthase comprises a nucleic acid sequence encoding a polypeptide sequence having at least 90% sequence identity to any one of SEQ ID NOs: 11-14, 21-25,31-34,41-46,51-54, and 61-64.

11. The method of claim 10, wherein the exogenous terpene synthase comprises a polypeptide sequence having at least 90% sequence identity to any one of SEQ ID NOs:23, 24, 25, 31, 32, 34, 41, 42, 44, 45, 54, 62, and 64; or wherein the nucleic acid encoding the exogenous terpene synthase comprises a nucleic acid sequence encoding a polypeptide sequence having at least 90% sequence identity to any one of SEQ ID NOs:23, 24, 25, 31, 32, 34, 41, 42, 44, 45, 54, 62, and 64.

12. The method of claim 1, wherein the exogenous terpene synthase comprises a polypeptide sequence having at least 90% sequence identity to XXZZXXZX (SEQ ID NO:71); wherein X is any amino acid; and wherein Z is selected from the group consisting of Asp, Glu, and His.

13. The method of claim 12, wherein the exogenous terpene synthase comprises a polypeptide sequence having at least 90% sequence identity to XXZDXXZX (SEQ ID NO:73); wherein X is selected from the group consisting of Ala, Ser, Thr, Val, Leu, Ile, Phe, Tyr, Trp, Glu, Asn, Gln, His, and Pro; and wherein Z is selected from the group consisting of Asp and Glu.

14. The method of claim 1, wherein the exogenous terpene synthase comprises a polypeptide sequence having at least 90% sequence identity to XZZXXXSXXZ ZXX (SEQ ID NO:75); wherein X is any amino acid; and wherein Z is selected from the group consisting of Cys, Asp, Glu, Asn, Gln, Lys, Arg, and absent.

15. The method of claim 14, wherein the exogenous terpene synthase comprises a polypeptide sequence having at least 90% sequence identity to XZDXXXSXXZZXX (SEQ ID NO:77); wherein X is selected from the group consisting of Gly, Ala, Thr, Val, Leu, Ile, Phe, Tyr, Trp, Asp, Glu, Gln, Lys, Arg, and absent; and wherein Z is selected from the group consisting of Cys, Asp, Glu, Asn, Gln, Lys, and Arg.

16. The method of claim 1, further comprising, prior to the exposing step:
pre-treating the biomass with one or more acids and/or enzymes.

17. The method of claim 1, wherein the biomass comprises an alga, an amino acid, a protein, and/or a carbohydrate.

18. The method of claim 1, wherein the one or more terpenoid compounds is selected from the group consisting of a monoterpene, a sesquiterpene, and a diterpene.

19. The method of claim 1, wherein the exposing step comprises a first organism configured to degrade a carbohydrate in the biomass and a second organism configured to degrade a protein in the biomass.

20. The method of claim 1, wherein the exogenous terpene synthase is an exogenous endophytic fungal terpene synthase.

* * * * *